(12) United States Patent  (10) Patent No.: US 8,501,713 B2
Wynne et al.  (45) Date of Patent: Aug. 6, 2013

(54) DRUG COMBINATIONS FOR THE TREATMENT OF DUCHENNE MUSCULAR DYSTROPHY

(75) Inventors: Graham Michael Wynne, Bicester (GB); Stephen Paul Wren, Aylesbury (GB); Peter David Johnson, Oxford (GB); Paul Damien Price, Higher Bebington (GB); Olivier De Moor, Oxford (GB); Gary Nugent, Sutton (GB); Richard Storer, Folkestone (GB); Richard Joseph Pye, Kidlington (GB); Colin Richard Dorgan, Abingdon (GB)

(73) Assignee: Summit Corporation PLC, Abingdon (GB)

( * ) Notice: Subject to any disclaimer, the term of this patent is extended or adjusted under 35 U.S.C. 154(b) by 191 days.

(21) Appl. No.: 12/600,242

(22) PCT Filed: Aug. 1, 2008

(86) PCT No.: PCT/GB2008/050648
§ 371 (c)(1),
(2), (4) Date: Nov. 30, 2010

(87) PCT Pub. No.: WO2009/019504
PCT Pub. Date: Feb. 12, 2009

(65) Prior Publication Data
US 2011/0195932 A1    Aug. 11, 2011

(30) Foreign Application Priority Data
Aug. 3, 2007 (GB) .................................. 0715088.1
Apr. 21, 2008 (GB) .................................. 0807216.7

(51) Int. Cl.
*A01N 57/00* (2006.01)
*A61K 31/675* (2006.01)
*C07F 9/28* (2006.01)
*C07D 209/48* (2006.01)
*C07D 307/00* (2006.01)

(52) U.S. Cl.
USPC .............. 514/80; 548/113; 548/511; 549/469

(58) Field of Classification Search
USPC ............ 514/80, 171; 548/113, 511; 549/469
See application file for complete search history.

(56) References Cited

U.S. PATENT DOCUMENTS

| 3,185,698 A | 5/1965 | Koch et al. |
| 3,993,659 A | 11/1976 | Meyer |
| 4,110,246 A | 8/1978 | Frischkorn et al. |
| 4,245,007 A | 1/1981 | Guglielmetti |
| 4,447,350 A | 5/1984 | Martini et al. |
| 4,791,205 A | 12/1988 | Schinzel et al. |
| 4,831,152 A | 5/1989 | Itoh et al. |
| 5,015,565 A | 5/1991 | Wolff |
| 5,302,704 A | 4/1994 | Adam et al. |
| 5,567,843 A | 10/1996 | Lysenko |
| 5,583,178 A | 12/1996 | Oxman et al. |
| 5,585,091 A | 12/1996 | Pelzer et al. |
| 5,596,025 A | 1/1997 | Oxman et al. |
| 5,645,948 A | 7/1997 | Shi et al. |
| 5,914,213 A | 6/1999 | Grasshoff et al. |
| 5,977,101 A | 11/1999 | Ali et al. |
| 6,004,719 A | 12/1999 | Gaudiana et al. |
| 6,110,638 A | 8/2000 | Boggs et al. |
| 6,177,572 B1 | 1/2001 | Wang |
| 6,222,044 B1 | 4/2001 | Lysenko |
| 6,248,311 B1 | 6/2001 | Candau |
| 6,251,373 B1 | 6/2001 | Candau |
| 6,296,835 B1 | 10/2001 | Candau |
| 6,312,822 B1 | 11/2001 | Irick et al. |
| 6,372,736 B1 | 4/2002 | Kemp et al. |
| 6,436,558 B1 | 8/2002 | Sato et al. |
| 6,541,423 B1 | 4/2003 | Mayer et al. |
| 6,565,987 B2 | 5/2003 | Irick |
| 6,589,915 B1 | 7/2003 | Mayer et al. |
| 6,716,413 B1 | 4/2004 | Achilefu et al. |
| 7,097,888 B2 | 8/2006 | Shukla et al. |
| 7,147,935 B2 | 12/2006 | Kamatani et al. |
| 7,361,678 B2 | 4/2008 | Mjalli et al. |

(Continued)

FOREIGN PATENT DOCUMENTS

| CA | 1018173 A | 9/1977 |
| CH | 616544 G | 4/1980 |

(Continued)

OTHER PUBLICATIONS

Merlini et al. (Muscle Nerve, 27, 222-227, 2003).*
Remington (Science and Practice of Pharmacy, Nineteenth edition, vol. 1, p. 806, 1995, p. 1-4).*
Corticosteroids—Mayo Clinic (Mayo Clinic, Prednisone and other corticosteroids Balance the risks and benefits, 2010).*
Drugcite document (Deflazacort, 2012).*
Science Daily (Science Daily, New Guideline: Corticosteroids Recommended for Duchenne Muscular Dystrophy) 2005.*
NINDS Muscular Dystrophy Information Page, 2012.*
Mayo Clinic, Muscular Dystrophy, 2012.*
Allamand, et al., Human Molecular Genetics, 2000, 9(16), 2459-67.
Bulfield, et al., Proc. Natl. Acad. Sci. USA, 1984, 81, 1189-92.

(Continued)

*Primary Examiner* — Sreeni Padmanabhan
*Assistant Examiner* — Uma Ramachandran
(74) *Attorney, Agent, or Firm* — Heslin Rothenberg Farley & Mesiti P.C.

(57) ABSTRACT

Combinations comprising (or consisting essentially of) one or more compounds of formula (1) with one or more ancillary agents, to processes for preparing the combinations, and to various therapeutic uses of the combinations. Also provided are pharmaceutical compositions containing the combinations as well as a method of treatment of Duchenne muscular dystrophy, Becker muscular dystrophy or cachexia using the combinations.

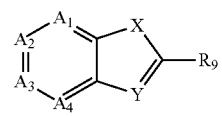

(1)

6 Claims, 3 Drawing Sheets

U.S. PATENT DOCUMENTS

| | | |
|---|---|---|
| 2004/0082542 A1 | 4/2004 | Mjalli et al. |
| 2004/0214896 A1 | 10/2004 | Konno et al. |
| 2004/0242673 A1 | 12/2004 | Lockhart et al. |
| 2005/0026811 A1 | 2/2005 | Mjalli et al. |
| 2005/0107399 A1 | 5/2005 | Boman et al. |
| 2005/0113283 A1 | 5/2005 | Solow-Cordero et al. |
| 2005/0129874 A1 | 6/2005 | Shukla et al. |
| 2005/0260126 A1 | 11/2005 | Kudo et al. |
| 2005/0261298 A1 | 11/2005 | Solow-Cordero et al. |
| 2005/0267093 A1 | 12/2005 | Lehmann-Lintz et al. |
| 2006/0038484 A1 | 2/2006 | Noh et al. |
| 2006/0223849 A1 | 10/2006 | Mjalli et al. |
| 2006/0287344 A1 | 12/2006 | Albers et al. |
| 2007/0032564 A1 | 2/2007 | Callant et al. |
| 2007/0072113 A1 | 3/2007 | Taguchi et al. |
| 2007/0125712 A1 | 6/2007 | Little et al. |
| 2007/0176542 A1 | 8/2007 | Ragini et al. |
| 2007/0178332 A1 | 8/2007 | Ragini et al. |
| 2007/0185176 A1 | 8/2007 | Van Gelder et al. |
| 2007/0267959 A1 | 11/2007 | Ragini et al. |
| 2008/0114022 A1 | 5/2008 | Bala et al. |

FOREIGN PATENT DOCUMENTS

| | | |
|---|---|---|
| FR | 2757389 A | 6/1998 |
| FR | 2818142 A | 6/2002 |
| GB | 2353038 A | 2/2001 |
| JP | 1265259 A | 10/1989 |
| JP | 08015917 A | 1/1996 |
| JP | 08175992 A | 7/1996 |
| JP | 8183771 A | 7/1996 |
| JP | 10002862 A | 1/1998 |
| JP | 11171881 A | 6/1999 |
| JP | 03069292 A | 5/2000 |
| JP | 2001/039034 A | 2/2001 |
| JP | 2001/261664 A | 9/2001 |
| JP | 2002/047278 A | 2/2002 |
| JP | 2003/005356 A | 1/2003 |
| JP | 2004/034438 A | 2/2004 |
| JP | 2004/250411 A | 9/2004 |
| JP | 2007/238540 A | 9/2007 |
| WO | 99/16761 | 4/1999 |
| WO | WO00/37501 A1 | 6/2000 |
| WO | WO01/58896 A1 | 8/2001 |
| WO | WO02/16333 A2 | 2/2002 |
| WO | WO03/062392 A2 | 7/2003 |
| WO | WO2004/041277 A1 | 5/2004 |
| WO | WO2004/069394 A2 | 8/2004 |
| WO | WO2004/098494 A2 | 11/2004 |
| WO | WO2006/015959 A2 | 2/2006 |
| WO | WO2006/042391 A2 | 4/2006 |
| WO | WO2006/044503 A2 | 4/2006 |
| WO | WO2006/051410 A1 | 5/2006 |
| WO | WO2006/069155 A2 | 6/2006 |
| WO | WO2006/091862 A2 | 8/2006 |
| WO | 2006/094236 | 9/2006 |
| WO | WO2006/094235 A1 | 9/2006 |
| WO | WO2006/124780 A2 | 11/2006 |
| WO | 2007/019417 | 2/2007 |
| WO | WO2007/017602 A2 | 2/2007 |
| WO | WO2007/019344 A1 | 2/2007 |
| WO | WO2007/052985 A1 | 5/2007 |
| WO | WO2007/058990 A2 | 5/2007 |
| WO | WO2007/091106 A2 | 8/2007 |
| WO | WO2007/096362 A1 | 8/2007 |
| WO | WO2007/146712 A2 | 12/2007 |
| WO | 2009/019504 | 2/2009 |

OTHER PUBLICATIONS

Khurana, et al., Nature Reviews Drug Discovery, 2003, 2, 379-90.
Nicolaus, Decision Making in Drug Research, 1983, pp. 173-186, Raven Press, New York.
Perkins, et al., Neuromuscular Disorders, 2002, 12, S78-S89.
International Search Report, mailed Jan. 15, 2008, International Application No. PCT/GB2007/050055.
Written Opinion of the International Search Authority, mailed Jan. 15, 2008, International Application No. PCT/GB2007/050055.
International Preliminary Report on Patentability, issued Aug. 12, 2008, International Application No. PCT/GB2007/050055.
Caira, "Crystalline Polymorphism of Organic Compounds," Topic in Current Chemistry, Springer Verlag, Berlin Heidelberg, vol. 198, pp. 163-208 (1998).
DeLuca et al., Tetrahedron, vol. 53, No. 2, pp. 457-464 (1997).
Kumar et al., Synlett, No. 9, pp. 1401-1404 (2005).
Pottorf et al., Tetrahedron Letters, vol. 44, No. 1, pp. 175-178 (2003).
Razavi et al., Angew. Chem. Int. Ed., vol. 42, pp. 2758-2761 (2003).
International Preliminary Report on Patentability for International Application No. PCT/GB2008/050648, issued Feb. 9, 2010.
International Search Report for International Application No. PCT/GB2008/050648, mailed Dec. 10, 2008.

* cited by examiner

Figure 1 Dose dependent luciferase induction
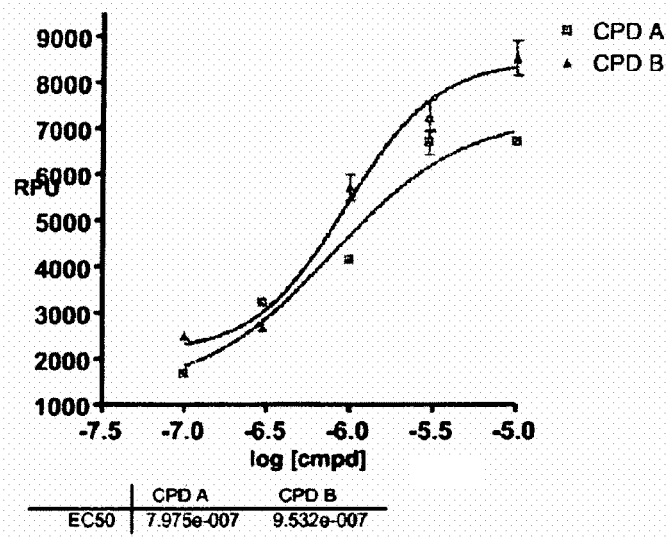
CPD A - 5-amino-2-(5,6-dimethylbenzo[d]oxazol-2-yl)phenol
CPD B - 2-(4-(diethylamino)phenyl)-6-methyl-2H-benzo[d][1,2,3]triazol-5-amine
Figure 2 An example of TA muscle sections stained with antibody specific for mouse utrophin
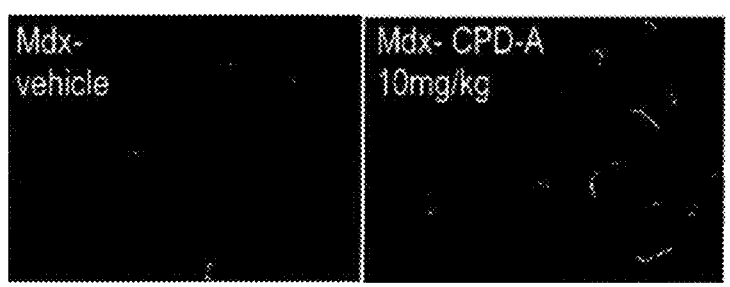

Figure 3 Mice exposed to CPD-A (V2 and V3) showed increased levels of utrophin expression compared to control:
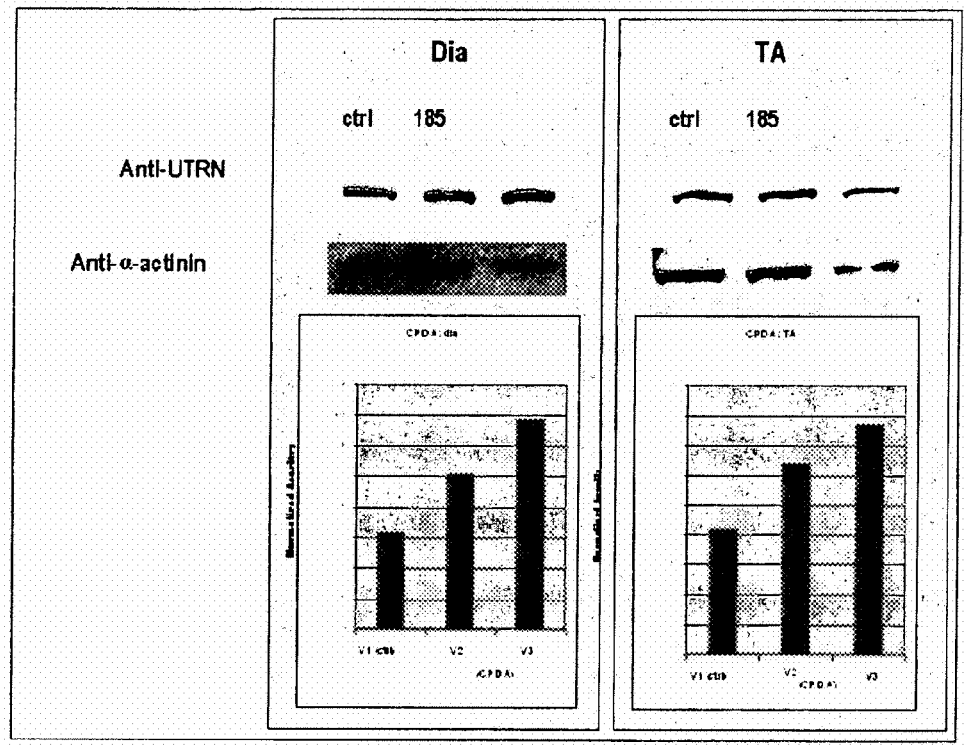

Figure 4 Synergy with prednisone in fatigue reduction test
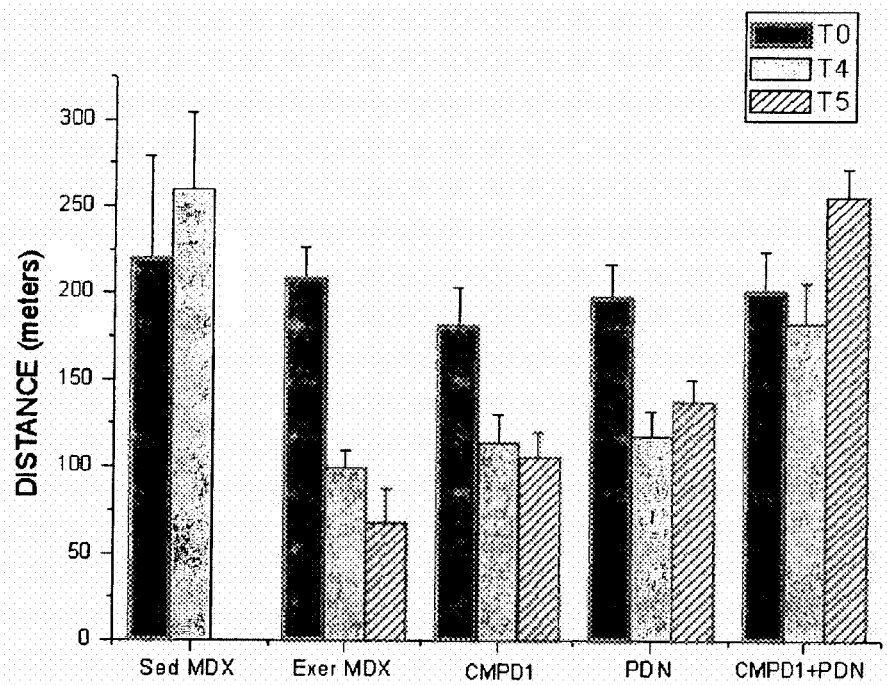
Resistance to treadmill running, expressed as maximal distance run (in meters) at T0, after 4 (T4) and 5 weeks (T5). Each bar is the mean ± S.E.M. from 3-7 animals.

DRUG COMBINATIONS FOR THE TREATMENT OF DUCHENNE MUSCULAR DYSTROPHY

TECHNICAL FIELD

This invention relates to combinations comprising (or consisting essentially of) one or more compounds of the formula (1) as defined herein with one or more ancillary agents, to processes for preparing the combinations, and to various therapeutic uses of the combinations. Also provided are pharmaceutical compositions containing the combinations as well as a method of treatment of Duchenne muscular dystrophy, Becker muscular dystrophy or cachexia using the combinations.

BACKGROUND OF THE INVENTION

Duchenne muscular dystrophy (DMD) is a common, genetic neuromuscular disease associated with the progressive deterioration of muscle function, first described over 150 years ago by the French neurologist, Duchenne de Boulogne, after whom the disease is named. DMD has been characterized as an X-linked recessive disorder that affects 1 in 3,500 males caused by mutations in the dystrophin gene. The gene is the largest in the human genome, encompassing 2.6 million base pairs of DNA and containing 79 exons. Approximately 60% of dystrophin mutations are large insertion or deletions that lead to frameshift errors downstream, whereas approximately 40% are point mutations or small frameshift rearrangements. The vast majority of DMD patients lack the dystrophin protein. Becker muscular dystrophy is a much milder form of DMD caused by reduction in the amount, or alteration in the size, of the dystrophin protein. The high incidence of DMD (1 in 10,000 sperm or eggs) means that genetic screening will never eliminate the disease, so an effective therapy is highly desirable.

A number of natural and engineered animal models of DMD exist, and provide a mainstay for preclinical studies (Allamand, V. & Campbell, K. P. Animal models for muscular dystrophy: valuable tools for the development of therapies. *Hum. Mol. Genet.* 9, 2459-2467 (2000).) Although the mouse, cat and dog models all have mutations in the DMD gene and exhibit a biochemical dystrophinopathy similar to that seen in humans, they show surprising and considerable variation in terms of their phenotype. Like humans, the canine (Golden retriever muscular dystrophy and German shorthaired pointer) models have a severe phenotype; these dogs typically die of cardiac failure. Dogs offer the best phenocopy for human disease, and are considered a high benchmark for preclinical studies. Unfortunately, breeding these animals is expensive and difficult, and the clinical time course can be variable among litters.

The mdx mouse is the most widely used model due to availability, short gestation time, time to mature and relatively low cost (Bulfield, G., Siller, W. G., Wight, P. A. & Moore, K. J. X chromosome-linked muscular dystrophy (mdx) in the mouse. *Proc. Natl Acad. Sci. USA* 81, 1189-1192 (1984)).

Since the discovery of the DMD gene about 20 years ago, varying degrees of success in the treatment of DMD have been achieved in preclinical animal studies, some of which are being followed up in humans. Present therapeutic strategies can be broadly divided into three groups: first, gene therapy approaches; second, cell therapy; and last, pharmacological therapy. Gene- and cell-based therapies offer the fundamental advantage of obviating the need to separately correct secondary defects/pathology (for example, contractures), especially if initiated early in the course of the disease. Unfortunately, these approaches face a number of technical hurdles. Immunological responses against viral vectors, myoblasts and newly synthesized dystrophin have been reported, in addition to toxicity, lack of stable expression and difficulty in delivery.

Pharmacological approaches for the treatment of muscular dystrophy differ from gene- and cell-based approaches in not being designed to deliver either the missing gene and/or protein. In general, the pharmacological strategies use drugs/molecules in an attempt to improve the phenotype by means such as decreasing inflammation, improving calcium homeostasis and increasing muscle progenitor proliferation or commitment. These strategies offer the advantage that they are easy to deliver systemically and can circumvent many of the immunological and/or toxicity issues that are related to vectors and cell-based therapies. Although investigations with corticosteroids and sodium cromoglycate, to reduce inflammation, dantrolene to maintain calcium homeostasis and clenbuterol to increase muscle strength, have produced promising results none of these potential therapies alone has yet been shown to be effective in treating DMD.

An alternative pharmacological approach is upregulation therapy. Upregulation therapy is based on increasing the expression of alternative genes to replace a defective gene and is particularly beneficial when an immune response is mounted against a previously absent protein. Upregulation of utrophin, an autosomal paralogue of dystrophin has been proposed as a potential therapy for DMD (Perkins & Davies, Neuromuscul Disord, S1: S78-S89 (2002), Khurana & Davies, Nat Rev Drug Discov 2:379-390 (2003)). When utrophin is overexpressed in transgenic mdx mice it localizes to the sarcolemma of muscle cells and restores the components of the dystrophin-associated protein complex (DAPC), which prevents the dystrophic development and in turn leads to functional improvement of skeletal muscle. Adenoviral delivery of utrophin in the dog has been shown to prevent pathology. Commencement of increased utrophin expression shortly after birth in the mouse model can be effective and no toxicity is observed when utrophin is ubiquitously expressed, which is promising for the translation of this therapy to humans. Upregulation of endogenous utrophin to sufficient levels to decrease pathology might be achieved by the delivery of small diffusible compounds.

Ancillary Agents

A wide variety of ancillary agents find application in the combinations of the invention, as described in detail below.

SUMMARY OF THE INVENTION

We have now found a group of compounds which upregulate endogenous utrophin in predictive screens and, thus, may be useful in the treatment of DMD.

According to the invention, we provide a combination comprising (or consisting essentially of) an ancillary agent and a compound of Formula (I)

in which $A_1$, $A_2$, $A_3$ and $A_4$, which may be the same or different, represent N or $CR_1$, X is a divalent group selected from O, $S(O)_n$, C=W, $NR_4$, $NC(=O)R_5$ and $CR_6R_7$, W is O, S, $NR_{20}$, Y is N or $CR_8$, one of $R_4$, $R_5$, $R_6$, $R_8$, $R_9$ and $NR_{20}$ represents -L-$R_3$, in which L is a single bond or a linker group, additionally, $R_3$-$R_9$, which may be the same or different, independently represent hydrogen or a substituent and $R_{20}$ represents hydrogen, hydroxyl, alkyl optionally substituted by aryl, alkoxy optionally substituted by aryl, aryl, CN, optionally substituted alkoxy, optionally substituted aryloxy, optionally substitute alkanoyl, optionally substituted aroyl, $NO_2$, $NR_{30}R_{31}$, in which $R_{30}$ and $R_{31}$, which may be the same or different, represent hydrogen, optionally substituted alkyl or optionally substituted aryl; additionally, one of $R_{30}$ and $R_{31}$ may represent optionally substituted alkanoyl or optionally substituted aroyl, n represents an integer from 0 to 2, in addition, when an adjacent pair of $A_1$-$A_4$ each represent $CR_1$, then the adjacent carbon atoms, together with their substituents may form a ring B, when X is $CR_6R_7$, $R_6$ and $R_7$, together with the carbon atom to which they are attached may form a ring C, when one of $A_1$-$A_4$ is $CR_1$, and $R_1$ represents $COR_{16}$, $R_{16}$ is preferably alkoxy or $NR_{10}R_{11}$, or a pharmaceutically acceptable salt thereof (optionally for the therapeutic and/or prophylactic treatment of Duchenne muscular dystrophy, Becker muscular dystrophy or cachexia).

BRIEF DESCRIPTION OF THE DRAWINGS

FIG. 1 shows the pharmacological dose response of compounds of the invention in a luciferase assay.

FIG. 2 shows an example of TA muscle sections stained with antibody specific for mouse utrophin.

FIG. 3 illustrates a Western blot and antibody staining showing utorphin expression in mouse muscle tissue.

FIG. 4 shows the results of a mouse treadmill exercise test with and without compounds of the invention, alone and in combination with prednisolone.

Compounds of formula I may exist in tautomeric, enantiomeric and diastereomeric forms, all of which are included within the scope of the invention. All of the compounds of formula may be made by conventional methods. Methods of making heteroaromatic ring systems are well known in the art. In particular, methods of synthesis are discussed in Comprehensive Heterocyclic Chemistry, Vol. 1 (Eds.: A R Katritzky, C W Rees), Pergamon Press, Oxford, 1984 and Comprehensive Heterocyclic Chemistry II: A Review of the Literature 1982-1995 The Structure, Reactions, Synthesis, and Uses of Heterocyclic Compounds, Alan R. Katritzky (Editor), Charles W. Rees (Editor), E. F. V. Scriven (Editor), Pergamon Pr, June 1996. Other general resources which would aid synthesis of the compounds of interest include March's Advanced Organic Chemistry: Reactions, Mechanisms, and Structure, Wiley-Interscience; 5th edition (Jan. 15, 2001). Of particular relevance are the synthetic methods discussed in WO 2006/044503. Some general methods of synthesis are as follows.

Benzoxazoles of formula I or pharmaceutically acceptable salts thereof may be prepared from compounds of formula II.

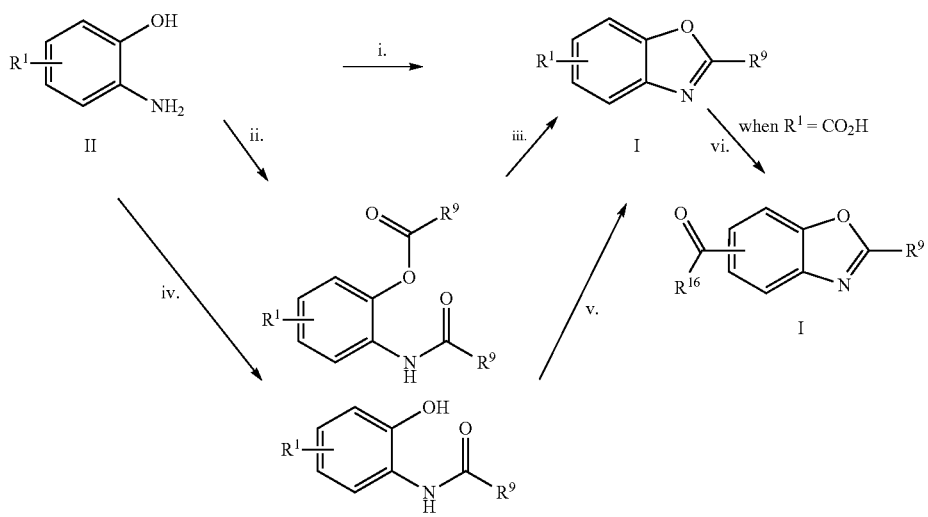

Scheme 1

Reaction conditions:
i. $R^9CO_2H$ (or $R^9COCl$), PPA, heat; or $R^9COCl$, dioxane, μwave, then NaOH
ii. $R^9COCl$, pryidine, rt
iii. TsOH, xylenes
iv. $R^9CO_2H$, HATU, pyridine, DMF
v. PPA, heat
vi. HATU, DMF, $^iPr_2Net$, alkylNH$_2$, rt Formation of the benzoxazole I can be carried out in a variety of ways, as illustrated above.

For example, reaction of the compound of formula II with an acyl derivative, such as the acid or the acid chloride, and heating in an appropriate solvent and an appropriate temperature in the presence of an acid catalyst, for example polyphosphoric acid. This is illustrated above as step (i).

The reaction may be carried out in an aprotic solvent, preferably a polar, aprotic solvent, for example tetrahydrofuran, and a temperature of from −10° C. to +150° C. Generally the reaction may be carried on at the reflux temperature of the solvent at normal pressure.

the presence of an appropriate coupling reagent occurs, for example, in DMF in the presence of a nucleophilic catalyst such as pyridine.

When $R^1$=$CO_2H$, this acid may be coupled with an amine as shown by step (vi). Suitable coupling conditions include use of HATU in DMF in the presence of $^iPr_2NEt$, $R^{16}NH_2$ at room temperature.

Compounds in which the six membered ring is substituted with an amide derivative are of particular interest. These may be produced from an intermediate amine derivative III.

Scheme 2

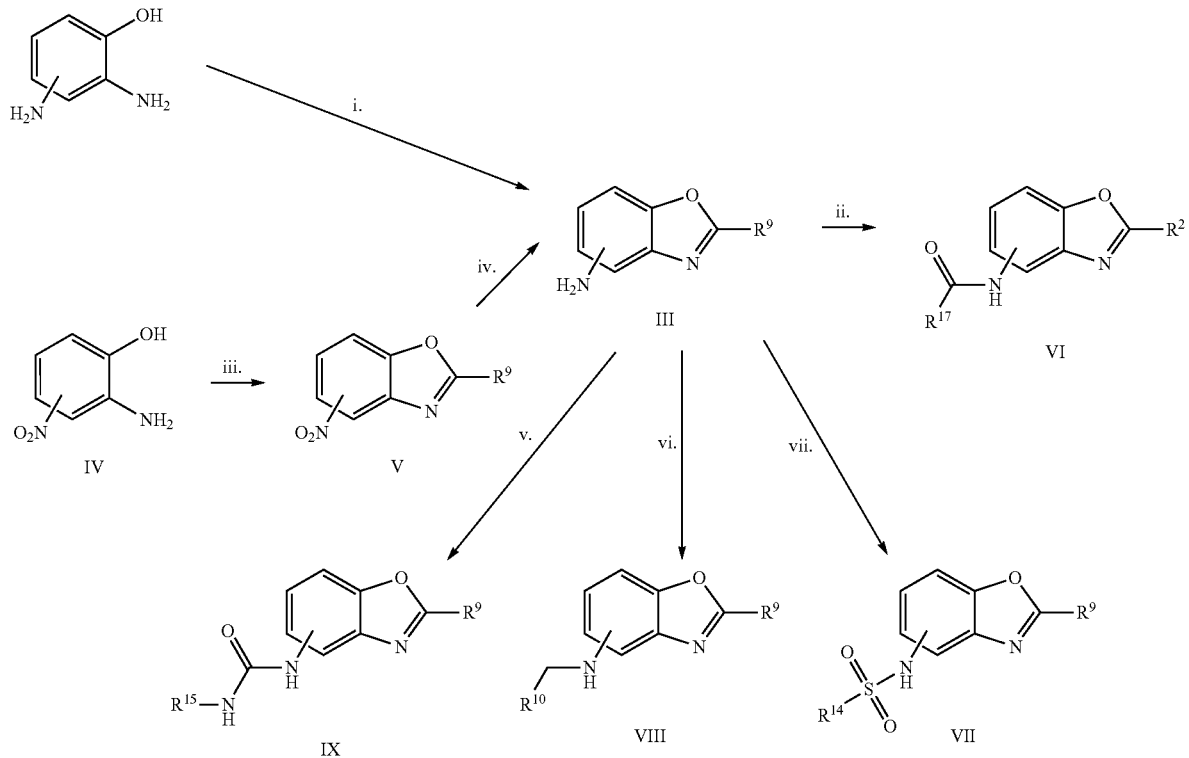

Reaction conditions:
i. As for (i); Scheme 1
ii. $R^{17}COCl$, pyridine (or $NEt_3$, DCM); or $R^9CO_2H$, HATU, pyridine, DMF
iii. As for (i); Scheme 1
iv. $SnCl_2$, EtOH, heat; or Pd/C, $H_2$, IMS; or Fe, $NH_4Cl$, IMS/water, heat
v. $R^9NCO$, DCM, rt
vi. $NaBH(OAc)_3$, $R^{10}CHO$, DCE, rt
vii. $R^{14}SO_2Cl$, pyridine, DCM, rt Alternatively, the compound of formula II may first be reacted with an excess of an acyl derivative $R^9COX$ (where X is for example Cl), such that acylation takes place on both oxygen and nitrogen. This can be brought about by, for example, reaction in pyridine at room temperature (step ii). Ring closure to form the compound of formula II can then occur in a subsequent ring closure step in which, for example, the doubly acylated product is heated in xylenes in the presence of an acid catalyst such as a sulphonic acid (step iii).

Another illustrative example of formation of a compound of formula I is shown by steps iv and v. First the amine is coupled to an acid using a peptide coupling reagent. Available coupling reagents are well known to those skilled in the art, and include HBTU, TBTU and HATU. Amide formation in Intermediate amine III may be synthesised either by using the method outlined in scheme 1, step (i) wherein $R^1$=$NH_2$, or alternatively, in a two step process as defined by steps (iii) and (iv) of scheme 2. Nitro substituted benzoxazole derivative V is produced from nitro substituted phenyl derivative IV, also in a method analogous to that illustrated by scheme 1, step 1, and then the nitro-benzoxazole derivative V is reduced in a subsequent step to give intermediate amine III. The skilled person is well aware of suitable methods to reduce a nitro group to give an amine. Selective methods for reducing $NO_2$ to $NH_2$ include Sn/HCl, or $H_2$/Pd/C in a suitable solvent, e.g. ethanol at a temperature of from 0° to 80° C. or heating in the presence of iron, $NH_4Cl$ in industrial methylated spirits/water.

Intermediate amine III can then be coupled as required.

Amide derivatives of formula VI can be produced by coupling amine III with an acyl derivative. This can be achieved by, for example, reaction of an appropriate acid chloride in either pyridine, or in $CH_2Cl_2$ (step ii).

Sulfonamide derivatives VII can be produced by reaction of amine III with an appropriate sulfonyl chloride in, for example, $CH_2Cl_2$ in the presence of pyridine at room temperature.

Amine derivatives VIII can be produced by use of an appropriate reductive amination strategy. Methods of reductive amination are well known in the art. They include, for example, reaction of the amine with an appropriate aldehyde and sodium triacetoxyborohydride in 1,2-dichloroethane.

Urea derivatives of formula IX can be produced, for example, by reaction of amine III with the appropriate isocyanate, for example, at room temperature in $CH_2Cl_2$.

Benzothiazoles of formula X or pharmaceutically acceptable salts thereof may be prepared from compounds of formula XI.

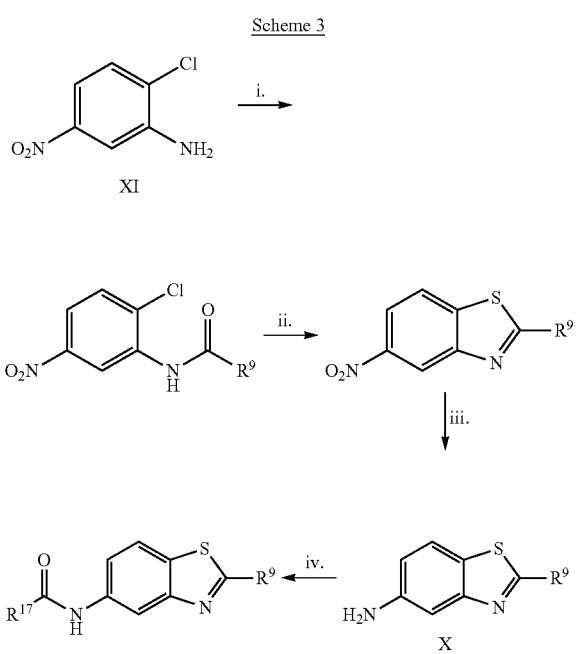

Scheme 3

Reaction conditions:
i. $R^9COCl$, pyridine, rt
ii. $Na_2S$, $S_8$, IMS, heat
iii. Fe, $NH_4Cl$, IMS, heat
iv. $R^{17}COCl$, pyridine (or $NEt_3$, DCM); or $R^{17}CO_2H$, HATU, pyridine, DMF The compounds of formula XI can be converted to the corresponding amide by, for example, reaction with the appropriate acid chloride in pyridine (step (i)), or by using an appropriate peptide coupling reagent. Such methods are well known to the person skilled in the art as discussed hereinabove.

The amide can then be converted to the nitro-benzothiazole of formula XII in a one-pot procedure involving reaction with $Na_2S$, $S_8$ at elevated temperature in industrial methylated spirit. Nitro derivative XII can be reduced as discussed previously and the resulting primary amine manipulated in an analogous manner to the primary amine in scheme 2 steps (ii), (v), (vi) and (vii).

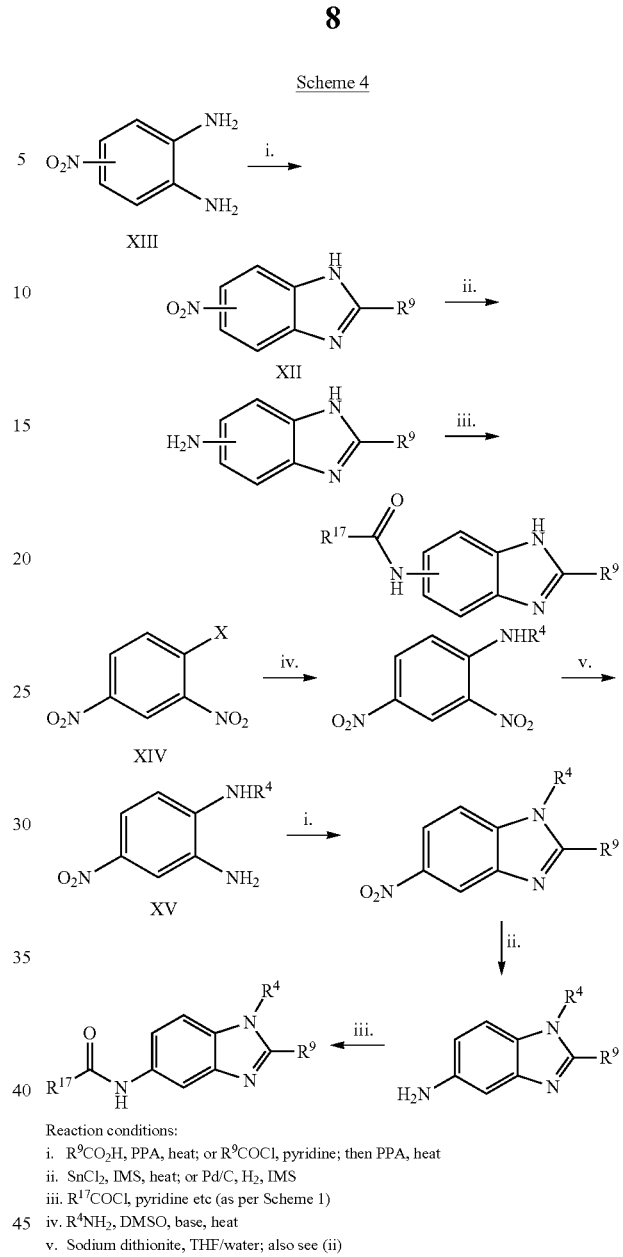

Scheme 4

Reaction conditions:
i. $R^9CO_2H$, PPA, heat; or $R^9COCl$, pyridine; then PPA, heat
ii. $SnCl_2$, IMS, heat; or Pd/C, $H_2$, IMS
iii. $R^{17}COCl$, pyridine etc (as per Scheme 1)
iv. $R^4NH_2$, DMSO, base, heat
v. Sodium dithionite, THF/water; also see (ii)

Benzimidazoles of formula XII can be produced according to scheme 4. Reaction of a diaminophenyl derivative of formula XIII with an acyl derivative, such as an acid or an acid chloride in an appropriate solvent and at an appropriate temperature in the presence of an acid catalyst, for example polyphosphoric acid, produces a benzimidazole derivative of formula XII. This is illustrated above as step (i). The nitro group may then be reduced and manipulated to produce other functionality as discussed hereinabove.

Alternatively, benzimidazoles may be produced by reacting a di-nitro compound of formula XIV, wherein X represents a leaving group, preferably a halogen such as chlorine or fluorine, with an amine, for example, in DMSO at elevated temperature in the presence of a base. Subsequent selective reduction of one nitro group using sodium dithionite in THF/water can then take place to give a diamine of formula XV. Ring closure to form a benzimidazoles, and manipulation of the nitro group can then proceed as illustrated and discussed previously.

Scheme 5

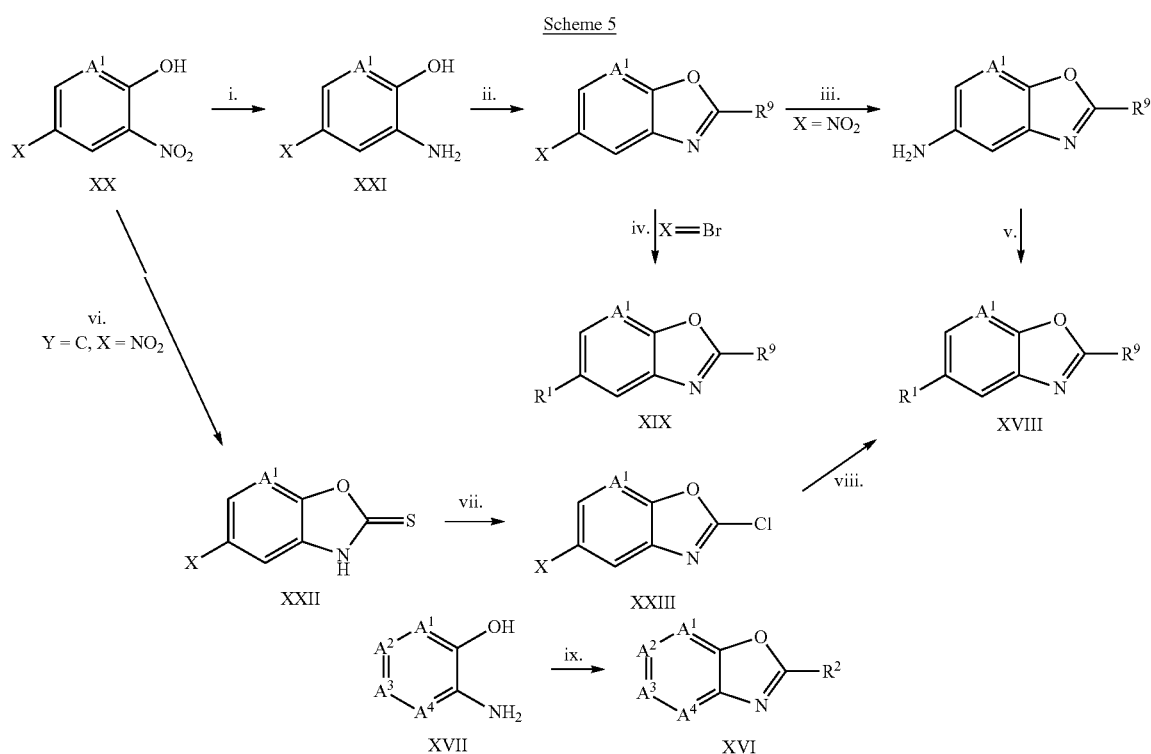

Reaction conditions:
i.   Na$_2$S hydrate, MeOH, NH$_4$Cl, water; or Na$_2$S$_2$O$_4$/EtOH; or SnCl$_2$, EtOH
ii.  As for (i), Scheme 1; or R$^9$COCl, pyridine; then PPA, heat
iii. SnCl$_2$, EtOH, heat
iv.  R$^1$B(OH)$_2$, Pd(PPh$_3$)$_4$, K$_2$CO$_3$, dioxane/water, μwave
v.   R$^{17}$COCl, pyridine, rt
vi.  EtOC(S)SK, pyridine, heat
vii. SOCl$_2$; or POCl$_3$
viii. R$^3$B(OH)$_2$, Pd(PPh$_3$)$_4$, K$_2$CO$_3$, solvent
ix.  PPA, R$^2$CO$_2$H heat Benzoxazoles of formula XVI can be made by methods analogous to those discussed previously. For example the method illustrated above (ix) involves heating a compound of formula XVII in an appropriate solvent in the presence of acid catalyst and an appropriate acyl derivative eg a carboxylic acid.

Benzoxazoles of formula XVIII and XIX can be synthesised from the appropriate nitro compound of formula XX. Reduction of the nitro compound XX gives the corresponding amino alcohol XXI (for example using Sn/HCl, or any of the other appropriate methods well known to the person skilled in the art). Benzoxazole formation via reaction of the amino alcohol with an appropriate acyl derivative can then be achieved using any of the methods disclosed hereinabove.

For oxazoles of formula XXIII in which X=Br, a Suzuki coupling reaction can then be used to give further derivatives. An example of appropriate conditions are R$^1$B(OH)$_2$, Pd(PPh$_3$)$_4$, K$_2$CO$_3$, dioxane/water, μwave, in which a benzoxazole of formula XIX results. The person skilled in the art is familiar with Suzuki coupling reactions and could easily manipulate the conditions to produce a wide variety of compounds.

For oxazoles produced by step (ii) in which X=NO$_2$, the nitro group can be reduced to the corresponding amine, using any of the methods well known to the person skilled in the art discussed hereinabove. The amine may then be manipulated using, for example, any of the methods discussed in scheme 2 above, to give, for example, a compound of formula XVIII.

Alternatively, benzoxazoles of formula XVIII can be made, also from a compound of formula XX, via thiocarbamate XXII, which is produced by heating a compound of formula XX with EtOC(S)SK in pyridine. The compound of formula XXII can be converted to the chloride of formula XXIII for example by use of well known reagents such as SOCl$_2$ or POCl$_3$. A Suzuki coupling using, for example, conditions illustrated by step viii above gives a benzoxazole of formula XVIII.

In the above processes it may be necessary for any functional groups, e.g. hydroxy or amino groups, present in the starting materials to be protected, thus it may be necessary to remove one or more protective groups to generate the compound of formula I.

Suitable protecting groups and methods for their removal are, for example, those described in "Protective Groups in Organic Synthesis" by T. Greene and P. G. M. Wutts, John Wiley and Sons Inc., 1991. Hydroxy groups may, for example, be protected by arylmethyl groups such as phenylmethyl, diphenylmethyl or triphenylmethyl; acyl groups such as acetyl, trichloroacetyl or trifluoroacetyl; or as tetrahydropyranyl derivatives. Suitable amino protecting groups include arylmethyl groups such as benzyl, (R,S)-α-phenylethyl, diphenylmethyl or triphenylmethyl, and acyl groups such as acetyl, trichloroacetyl or trifluoroacetyl. Conventional methods of deprotection may be used including hydrogenolysis, acid or base hydrolysis, or photolysis. Arylmethyl groups may, for example, be removed by hydrogenolysis in the presence of a metal catalyst e.g. palladium on charcoal. Tetrahydropyranyl groups may be cleaved by hydrolysis under acidic conditions. Acyl groups may be removed by hydrolysis with a base such as sodium hydroxide or potassium carbonate, or a group such as trichloroacetyl may be removed by reduction with, for example, zinc and acetic acid.

The compounds of formula I, and salts thereof, may be isolated from their reaction mixtures using conventional techniques.

Salts of the compounds of formula I may be formed by reacting the free acid, or a salt thereof, or the free base, or a salt or derivative thereof, with one or more equivalents of the appropriate base or acid. The reaction may be carried out in a solvent or medium in which the salt is insoluble or in a solvent in which the salt is soluble, e.g. ethanol, tetrahydrofuran or diethyl ether, which may be removed in vacuo, or by freeze drying. The reaction may also be a metathetical process or it may be carried out on an ion exchange resin.

Pharmaceutically acceptable salts of the compounds of formula I include alkali metal salts, e.g. sodium and potassium salts; alkaline earth metal salts, e.g. calcium and magnesium salts; salts of the Group III elements, e.g. aluminium salts; and ammonium salts. Salts with suitable organic bases, for example, salts with hydroxylamine; lower alkylamines, e.g. methylamine or ethylamine; with substituted lower alkylamines, e.g. hydroxy substituted alkylamines; or with monocyclic nitrogen heterocyclic compounds, e.g. piperidine or morpholine; and salts with amino acids, e.g. with arginine, lysine etc, or an N-alkyl derivative thereof; or with an aminosugar, e.g. N-methyl-D-glucamine or glucosamine. The non-toxic physiologically acceptable salts are preferred, although other salts are also useful, e.g. in isolating or purifying the product.

Diastereoisomers may be separated using conventional techniques, e.g. chromatography or fractional crystallisation. The various optical isomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation.

Substituents that alkyl may represent include methyl, ethyl, butyl, eg sec butyl. Halogen may represent F, Cl, Br and I, especially Cl.

Examples of substituents that $R_3$ in the compound of formula I may represent include alkyl, alkoxy or aryl, each optionally substituted by one or more, preferably one to three substituents, $R_2$, which may be the same or different.

In addition, when L is single bond, $R_3$ may represent thioalkyl optionally substituted by alkyl or optionally substituted aryl, thioaryl, in which the aryl is optionally substituted, optionally substituted aryl, hydroxyl, $NO_2$, CN, $NR_{10}R_{11}$, halogen, $SO_2R_{12}$, $NR_{13}SO_2R_{14}$, C(=W)$R_{16}$, OC(=W)$NR_{10}R_{11}$, $NR_{15}$C(=W)$R_{17}$, P(=O)$OR_{40}R_{41}$, $R_{10}$, $R_{11}$, $R_{12}$, $R_{13}$, $R_{14}$, $R_{15}$, $R_{16}$, $R_{17}$, $R_{40}$ and $R_{41}$, which may be the same or which may be the same or different, represent hydrogen, alkyl optionally substituted by optionally substituted aryl, optionally substituted aryl, in addition, $NR_{10}R_{11}$ together with the nitrogen to which they are attached may form a ring, $R_{12}$ may have the same meaning as $NR_{10}R_{11}$, when $R_{17}$ represents $NR_{10}R_{11}$, that $R_{10}$ and $R_{11}$, which may be the same or different, may represent hydrogen, COalkyl and CO optionally substituted aryl, $R_{16}$ and $R_{17}$, which may be the same or different, may each represent alkyl substituted by one or more of halogen, alkoxy optionally substituted aryl or optionally substituted aryl, optionally substituted aryloxy, aryl or $NR_{10}R_{11}$, and when $R_{16}$ or $R_{17}$ represents $NR_{10}R_{11}$, one of $R_{10}$ and $R_{11}$, may additionally represent CO alkyl optionally substituted or COaryl optionally substituted, and in addition to the definitions shared with $R_{17}$, $R_{16}$ may represent hydroxy.

Examples of substituents that $R_1$ and $R_2$, which may be the same or different, may represent include:

alkyl optionally substituted by one or more halogen, alkoxy or optionally substituted aryl, thioaryl or aryloxy,alkoxy optionally substituted by optionally by alkyl or optionally substituted aryl,hydroxyl, OC(=W)$NR_{10}R_{11}$, optionally substituted aryl,thioalkyl optionally substituted by alkyl or optionally substituted aryl,thioaryl, in which the aryl is optionally substituted, $NO_2$, CN, $NR_{10}R_{11}$, halogen, $SO_2R_{12}$, $NR_{13}SO_2R_{14}$, C(=W)$R_{16}$, $NR_{15}$C(=W)$R_{17}$, $R_{10}$, $R_{11}$, $R_{12}$, $R_{13}$, $R_{14}$, $R_{15}$, $R_{16}$ and $R_{17}$, which may be the same or different, represent hydrogen, alkyl optionally substituted by optionally substituted aryl, optionally substituted aryl, in addition, $NR_{10}R_{11}$ together with the nitrogen to which they are attached may form a ring, $R_{12}$ may have the same meaning as $NR_{10}R_{11}$, when $R_{17}$ represents $NR_{10}R_{11}$, that $R_{10}$ and $R_{11}$, which may be the same of different, may represent hydrogen, COalkyl and CO optionally substituted aryl, $R_{16}$ may represent hydroxy, alkoxy, or $NR_{10}R_{11}$, $R_{17}$ may represent alkyl substituted by one or more of halogen, alkoxy, optionally substituted aryl or $NR_{10}R_{11}$ and when $R_{17}$ represents $NR_{10}R_{11}$, that $NR_{10}R_{11}$ may represent hydrogen, COalkyl and CO optionally substituted aryl.

When L represents a linker group, examples of linker groups that L may represent include:

O, S, (CO)$_n$NR$_{18}$, alkylene, alkenylene, alkynylene, each of which may be optionally interrupted by one or more of O, S, NR$_{18}$, or one or more C—C single, double or triple bonds, a —N—N— single or double bond, $R_{18}$ represents hydrogen, alkyl, COR$_{16}$.

When L is (CO)$_n$NR$_{18}$, n may represent 0, 1 or 2, when n is 1 or 2, $R_{18}$ preferably represents hydrogen.

Although the scope for variation of $R_4$, $R_5$, $R_6$, $R_7$ and $R_8$ is large, preferably $R_4$, $R_5$, $R_6$, $R_7$ and $R_8$, represent hydrogen, alkyl or optionally substituted aryl.

Preferably Y represents N and X represents O, S or NR$_4$. That is preferably the compound according to formula I is a benzoxazole, a benzthiazole or a benzimidazole.

Although any one of $R_4$, $R_6$, $R_8$ or $R_9$ may represent -L-$R_3$—, in preferred compounds $R_9$ represents -L-$R_3$.

Alkyl may represent any alkyl chain. Alkyl includes straight and branched, saturated and unsaturated alkyl, as well as cyclic alkyl, such as cyclopropyl, cyclobutyl, cyclopentyl, cyclohexyl and cycloheptyl. However, preferably, when any of the substituents represents alkyl, alkyl is saturated, linear or branched and has from 1 to 10 carbon atoms, preferably from 1 to 8 carbon atoms and more preferably from 1 to 6 carbon atoms. When any of the substituents represents alkyl, a particularly preferred group is cycloalkyl, for example cyclopropyl, cyclobutyl, cyclopentyl, cyclohexyl and cycloheptyl.

Aryl may represent any aromatic system. Preferably, in the compounds of formula I, aryl is an aromatic hydrocarbon or a 5 to 10 membered aromatic heterocycle containing 1 to 4 hetero atoms selected from an oxygen atom, a sulphur atom and a nitrogen atom as a ring constituent besides carbon. We prefer heterocycles which contain one or two heteroatoms. Aromatic heterocycles that may be mentioned include furan, thiophene, pyrrole, pyridine.

Particularly preferably, when aryl is an aromatic hydrocarbon, aryl represents a 6 to 10 membered monocyclic or bicyclic system, for example phenyl or naphthalene.

Saturated and unsaturated heterocycles that may be mentioned include those containing 4 to 7 ring atoms, preferably 5 or 6 ring atoms, preferably containing one to two heteroatoms selected from N, S and O. Heterocycles that may be mentioned include pyrrolidine, piperidine, tetrahydrofuran, piperazine and morpholine. N-containing heterocycles are particularly preferred, eg when $NR_{10}R_{11}$ forms a heterocyclic ring.

As detailed above, when an adjacent pair of $A_1$-$A_4$ each represent $CR_1$, the adjacent carbon atoms, together with their substituents may form a ring ring B. Also, when X is $CR_6R_7$, $R_6$ and $R_7$, together with the carbon to which they are attached may form a ring C. Preferably ring B and/or ring C is a saturated or unsaturated 3 to 10 membered carbocylic or heterocyclic ring.

Particularly preferably ring B is benzene ring.

Particularly preferably ring C is a 3-10 membered saturated or unsaturated carbocylic ring.

We particularly prefer compounds in which at least one $R_1$ represents $NR_{15}C(=W)R_{17}$, more particularly the group $NR_{15}COR_{17}$.

We also prefer compounds in which at least one $R_1$ represents $CONR_{10}R_{11}$.

For one group of particularly preferred compounds at least one $R_1$ represents an amide group $NHCOR_{17}$ wherein $R_{17}$ is selected from:
alkyl $C_1$-$C_6$,
alkyl $C_1$-$C_6$ substituted by phenyl
alkyl $C_1$-$C_6$ substituted by alkoxy $C_1$-$C_6$,
haloalkyl $C_1$-$C_6$,
perfluoroalkyl $C_1$-$C_6$,
phenyl optionally substituted by one or more of halogen, alkyl $C_1$-$C_6$, alkoxy $C_1$-$C_6$, amino, (alkyl $C_1$-$C_6$)amino, di(alkyl $C_1$-$C_6$) amino or phenyl,
CH:CH phenyl,
naphthyl, pyridinyl, thiophenyl and furanyl.

We prefer compounds in which one or both of $R_1$ and $R_2$ are other than —COOH.

For another group of particularly preferred compounds at least one $R_1$ represents a group $NR_{16}CONR_{10}R_{11}$, then in which $R_{10}$ and $R_{11}$, which may be the same or different, are selected from optionally substituted aryl, alkyl and COaryl optionally substituted. A particularly preferred group which at least one of $R_1$ may represent is $NHCONFIR_{15}$ and $R_{15}$ is selected from phenyl, alkyl $C_1$ to $C_6$ and COphenyl optionally substituted by one or more halogen.

For another group of particularly preferred compounds at least one $R_1$ represents alkyl C1 to C6, optionally substituted by phenyl or a 5 or 6-membered saturated or unsaturated heterocycle containing one to two heteroatoms selected from N, S and O.

For another group of particularly preferred compounds at least one $R_1$ represents $COR_{16}$ and $R_{16}$ is alkoxy $C_1$-$C_6$, amino, (alkyl $C_1$-$C_6$)amino or di(alkyl $C_1$-$C_6$) amino.

For another group of particularly preferred compounds at least one $R_1$ represents:
$NO_2$,
halogen,
amino or (alkyl $C_1$-$C_6$)amino or di(alkyl $C_1$-$C_6$) amino in which the alkyl $C_1$ to $C_6$ is optionally substituted by phenyl or a 5 or 6 membered saturated or unsaturated heterocycle,
$NHSO_2$alkyl $C_1$-$C_6$, $NHSO_2$phenyl,
$SO_2$alkyl $C_1$-$C_6$,
phenyl optionally substituted by $C_1$ to $C_6$ alkoxy C1-C6,
a 5-10 membered, saturated or unsaturated, mono- or bi-cyclic heterocycle containing from 1-3 heteroatoms selected from N, S and O.

There is also wide scope for variation of the group $R_3$. Preferably $R_3$ represents aryl and is optionally substituted by one to three substituents, $R_2$, which may be the same or different. Particularly preferably, $R_3$ is a 5-10 membered aromatic mono- or bi-cyclic system, especially a hydrocarbon 5-10 membered aromatic mono- or bi-cyclic system, for example benzene or naphthalene. Alternatively, the 5-10 membered aromatic mono- or bi-cyclic system, may be a heterocyclic system containing up to three heteroatoms selected from N, O and S, for example a thiophene, furan, pyridine or pyrrole.

Preferably the substituent(s) $R_2$ is/are selected from:
alkyl $C_1$-$C_6$, optionally substituted by thiophenyl or phenoxy, each optionally substituted by halogen,
alkoxy $C_1$-$C_6$
phenyl,
thioalkyl $C_1$-$C_6$
thiophenyl, optionally substituted by halogen,
$NO_2$,
CN
$NR_{10}R_{11}$, in which $R_{10}$ and $R_{11}$, which may be the same or different represent hydrogen, alkyl $C_1$-$C_6$, or together with the nitrogen to which they are attached form a 5 to 7 membered ring which may contain one or more additional heteroatoms selected from N, O and S,
halogen
$SO_2R_{12}$, in which $R^{12}$ represents a 5 to 7 membered ring which may contain one or more additional heteroatoms selected from N, O and S
$NHCOR_{17}$, in which $R_{17}$ represents
alkyl $C_1$-$C_6$, optionally substituted by:
phenyl or halogen, or
phenyl optionally substituted by alkoxy $C_1$-$C_6$, carboxy or halogen,
or
a 5 or 6 membered saturated or unsaturated heterocycle,
phenyl or a 5 or 6 membered saturated or unsaturated heterocycle optionally substituted by halogen, alkoxy $C_1$ to $C_6$, carboxy or a group $SO_2NR_{10}R_{11}$,
Particularly preferably when $R_2$ represents $NR_{10}R_{11}$, $NR_{10}R_{11}$ represents N-pyrrole, N-piperidine, N'($C_1$-$C_6$) alkyl N piperazine or N-morpholine.

Preferably the linker group L represents:
—NH.NH—
—CH=CH
—$NCOR_{16}$ in which $R_{16}$ represents phenyl or a 5 or 6 membered saturated or unsaturated heterocycle optionally substituted by halogen, alkoxy C1 to C6, carboxy.

$A_1$-$A_4$ may represent N or $CR_1$. Consequently, the benzoxazole six membered ring may contain 1, 2, 3 or 4 nitrogen atoms. Embodiments of the invention exist in which two of $A_1$-$A_4$ represent nitrogen, one of $A_1$-$A_4$ represents nitrogen and in which all of $A_1$-$A_4$ represents $CR_1$.

In a particularly preferred group of compounds:

$A_1$, $A_2$, $A_3$ and $A_4$, which may be the same or different, represent N or $CR_1$, X is a divalent group selected from O, $S(O)_n$, C=W, $NR_4$, NC(=O)$R_6$ and $CR_6R_7$, W is O, S, $NR_{20}$, Y is N or $CR_8$, one of $R_4$, $R_5$, $R_6$, $R_8$, $R_9$ and $NR_{20}$ represents -L-$R_3$, in which L is a single bond or a linker group, additionally, $R_4$-$R_9$, which may be the same or different, independently represent hydrogen or a substituent and $R_{20}$ represents hydrogen, hydroxyl, alkyl optionally substituted by aryl, alkoxy optionally substituted by aryl, aryl, CN, optionally substituted alkoxy, optionally substituted aryloxy, optionally substitute alkanoyl, optionally substituted aroyl, $NO_2$, $NR_{30}R_{31}$, in which $R_{30}$ and $R_{31}$, which may be the same or different, represent hydrogen, optionally substituted alkyl or optionally substituted aryl; additionally, one of $R_{30}$ and $R_{31}$ may represent optionally substituted alkanoyl or optionally substituted aroyl, n represents an integer from 0 to 2, $R_3$ represents alkyl, alkoxy or aryl, each optionally substituted by one to three substitutents, $R_2$, which may be the same or different $R_1$ and $R_2$, which may be the same or different, represent:

alkyl optionally substituted by one or more halogen, alkoxy or optionally substituted aryl, thioaryl or aryloxy, alkoxy optionally substituted by optionally by alkyl or optionally substituted aryl, hydroxyl,

OC(=W)$NR_{10}R_{11}$ optionally substituted aryl, thioalkyl optionally substituted by alkyl or optionally substituted aryl, thioaryl, in which the aryl is optionally substituted, $NO_{21}$

CN, $NR_{10}R_{11}$, halogen, $SO_2R_{12}$, $NR_{13}SO_2R_{14}$,

C(=W)$R_{16}$, $NR_{15}$C(=W)$R_{17}$, $R_{10}$, $R_{11}$, $R_{12}$, $R_{13}$, $R_{14}$, $R_{15}$, $R_{16}$ and $R_{17}$, which may be the same or different, represent hydrogen, alkyl optionally substituted by optionally substituted aryl, optionally substituted aryl, in addition, $NR_{10}R_{11}$ together with the nitrogen to which they are attached may form a ring, $R_{12}$ may have the same meaning as $NR_{10}R_{11}$, when $R_{17}$ represents $NR_{10}R_{11}$, that $NR_{10}R_{11}$ may represent hydrogen, COalkyl and CO optionally substituted aryl, $R_{16}$ may represent hydroxy, alkoxy, or $NR_{10}R_{11}$, $R_{17}$ may represent alkyl substituted by one or more of halogen, alkoxy, optionally substituted aryl or $NR_{10}R_{11}$, and when $R_{17}$ represents $NR_{10}R_{11}$, that $NR_{10}R_{11}$ may represent hydrogen, COalkyl and CO optionally substituted aryl, and in addition, when an adjacent pair of $A_1$-$A_4$ each represent $CR_1$, then the adjacent carbon atoms, together with their substituents may form a ring B, when X is $CR_6R_7$, $R_6$ and $R_7$, together with the carbon atom to which they are attached may form a ring C, or a pharmaceutically acceptable salt thereof, optionally for the therapeutic and/or prophylactic treatment of Duchenne muscular dystrophy, Becker muscular dystrophy or cachexia.

We also provide a method for the treatment or prophylaxis of Duchenne muscular dystrophy, Becker muscular dystrophy or cachexia in a patient in need thereof, comprising administering to the patient an effective amount of a combination of the invention.

General Preferences and Definitions

The combinations of the invention may produce a therapeutically efficacious effect relative to the therapeutic effect of the individual compounds when administered separately.

The term "efficacious" includes advantageous effects such as additivity, synergism, reduced side effects, reduced toxicity, increased time to disease progression, increased time of survival, sensitization or resensitization of one agent to another, or improved response rate. Advantageously, an efficacious effect may allow for lower doses of each or either component to be administered to a patient, thereby decreasing the toxicity of chemotherapy, whilst producing and/or maintaining the same therapeutic effect.

A "synergistic" effect in the present context refers to a therapeutic effect produced by the combination which is larger than the sum of the therapeutic effects of the components of the combination when presented individually.

An "additive" effect in the present context refers to a therapeutic effect produced by the combination which is larger than the therapeutic effect of any of the components of the combination when presented individually.

A "pharmaceutical composition" is a solid or liquid composition in a form, concentration and level of purity suitable for administration to a patient (e.g. a human or animal patient) upon which administration it can elicit the desired physiological changes. Pharmaceutical compositions are typically sterile and/or non-pyrogenic. The term non-pyrogenic as applied to the pharmaceutical compositions of the invention defines compositions which do not elicit undesirable inflammatory responses when administered to a patient.

As used herein, the terms mobilizing agent and mobilization are terms of art referring to agents and treatments which serve to promote the migration of CD34', stem, progenitor and/or precursor cells from the marrow to the peripheral blood (for a review, see e.g. Cottler-Fox et al. (2003)*Stem cell mobilization Hematology:* 419-437). Current standard agents for mobilization suitable for use according to the invention include G-CSF (Filgrastim™, Amgen), GM-CSF (Sargramostim™, Berlex, Richmond, Calif.) and erythropoietin (which has some mobilizing activity w.r.t. $CD34^+$ cells). Alternative agents include stem cell factor (SCF) (which is particularly effective when used in combination with G-CSF) and various derivatives of G-CSF (Pegfilgrastim™ Amgen) and erythropoietin (Darbopoietin®, Amgen). The latter agents benefit from extended half-lives and so increase the temporal window available for collection. AMD3100 (AnorMed™, Vancouver, Canada), which is a reversible inhibitor of the binding of stromal derived factor (SDF-1a) to its cognate receptor CXCR4, is currently in clinical trials as a mobilizing agent. Other agents include docetaxel (see e.g. Prince et al. (2000) Bone Marrow Transplantation 26: 483-487).

The term "upregulation of utrophin" as used herein includes elevated expression or over-expression of utrophin, including gene amplification (i.e. multiple gene copies) and increased expression by a transcriptional effect, and hyperactivity and activation of utrophin, including activation by mutations. The term "utrophin upregulating agent" is to be interpreted accordingly. Thus, upregulation of utrophin covers increasing utrophin activity at the level of the encoding DNA as well as the transcriptional, translational or post-translational level. Preferred compounds of formula (I) are utrophin upregulators (as disclosed herein).

As used herein, the term "combination", as applied to two or more compounds and/or agents (also referred to herein as the components), is intended to define material in which the two or more compounds/agents are associated. The terms "combined" and "combining" in this context are to be interpreted accordingly.

The association of the two or more compounds/agents in a combination may be physical or non-physical. Examples of physically associated combined compounds/agents include:

compositions (e.g. unitary formulations) comprising the two or more compounds/agents in admixture (for example within the same unit dose);

compositions comprising material in which the two or more compounds/agents are chemically/physicochemically linked (for example by crosslinking, molecular agglomeration or binding to a common vehicle moiety);

compositions comprising material in which the two or more compounds/agents are chemically/physicochemically co-packaged (for example, disposed on or within lipid vesicles, particles (e.g. micro- or nanoparticles) or emulsion droplets);

pharmaceutical kits, pharmaceutical packs or patient packs in which the two or more compounds/agents are co-packaged or co-presented (e.g. as part of an array of unit doses);

Examples of non-physically associated combined compounds/agents include material (e.g. a non-unitary formulation) comprising at least one of the two or more compounds/agents together with instructions for the extemporaneous association of the at least one compound/agent to form a physical association of the two or more compounds/agents;

material (e.g. a non-unitary formulation) comprising at least one of the two or more compounds/agents together with instructions for combination therapy with the two or more compounds/agents;

material comprising at least one of the two or more compounds/agents together with instructions for administration to a patient population in which the other(s) of the two or more compounds/agents have been (or are being) administered;

material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The combinations of the invention may produce a therapeutically efficacious effect relative to the therapeutic effect of the individual compounds/agents when administered separately.

The term "ancillary agent" as used herein may define a compound/agent which yields an efficacious combination (as herein defined) when combined with a compound of the formula (1) as defined herein. The ancillary agent may therefore act as an adjunct to the compound of the formula (1) as defined herein, or may otherwise contribute to the efficacy of the combination (for example, by producing a synergistic or additive effect or improving the response rate, as herein defined).

As used herein, the term "antibody" defines whole antibodies (including polyclonal antibodies and monoclonal antibodies (Mabs)). The term is also used herein to refer to antibody fragments, including F(ab), F(ab'), F(ab')2, Fv, Fc3 and single chain antibodies (and combinations thereof), which may be produced by recombinant DNA techniques or by enzymatic or chemical cleavage of intact antibodies. The term "antibody" is also used herein to cover bispecific or bifunctional antibodies which are synthetic hybrid antibodies having two different heavy/light chain pairs and two different binding sites. Bispecific antibodies can be produced by a variety of methods including fusion of hybridomas or linking of Fab' fragments. Also covered by the term "antibody" are chimaeric antibodies (antibodies having a human constant antibody immunoglobulin domain coupled to one or more non-human variable antibody immunoglobulin domain, or fragments thereof). Such chimaeric antibodies therefore include "humanized" antibodies. Also covered by the term "antibody" are minibodies (see WO 94/09817), single chain Fv-Fc fusions and human antibodies antibodies produced by transgenic animals The term "antibody" also includes multimeric antibodies and higher-order complexes of proteins (e.g. heterodimeric antibodies).

Ancillary Agents for Use According to the Invention

Any of a wide variety of ancillary agents may be used in the combinations of the invention. Preferably, the ancillary agents for use in the combinations of the invention as described herein are selected from the following classes:
1. Antiinflammatory agents;
2. Protease inhibitors;
3. Myostatin antagonists;
4. Cytokines and mobilizing agents;
5. Corticosteroids;
6. Anabolic steroids;
7. TGF-β antagonists;
8. Antioxidants and mitochondrial supporting agents;
9. Dystrophin expression enhancing agents;
10. Gene replacement/repair agents;
11. Cell-based compositions;
12. Creatine;
13. anti-osteoporotic agents;
14. auxiliary utrophin upregulating agents;
15. cGMP signalling modulators; and
16. a combination of two or more of the foregoing classes.

A reference to a particular ancillary agent herein is intended to include ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof).

1. Antinflammatory Agents

Muscles affected by DMD show signs of inflammation, including an abundance of macrophages. Thus, a wide range of antiinflammatory agents can be used in the treatment of muscular dystrophies, as discussed below.

1.1 Beta2-Adrenergic Receptor Agonists

In one embodiment of the invention, the ancillary agent is a beta2-adrenergic receptor agonist (e.g. albuterol).

Definitions and Technical Background:

The term beta2-adrenergic receptor agonist is used herein to define a class of drugs which act on the β2-adrenergic receptor, thereby causing smooth muscle relaxation resulting in dilation of bronchial passages, vasodilation in muscle and liver, relaxation of uterine muscle and release of insulin. A preferred beta2-adrenergic receptor agonist for use according to the invention is albuterol, an immunosuppressant drug that is widely used in inhalant form for asthmatics. Albuterol is thought to slow disease progression by suppressing the infiltration of macrophages and other immune cells that contribute to inflammatory tissue loss. Albuterol also appears to have some anabolic effects and promotes the growth of muscle tissue. Albuterol may also suppress protein degradation (possibly via calpain inhibition).

1.2 nNOS Stimulators

The loss of dystrophin leads to breaks in the membrane, and destabilizes neuronal nitric oxide synthase (nNOS), a protein which normally generates nitric oxide (NO). It is thought that at least part of the muscle degeneration observed in DMD patients may result from the reduced production of muscle membrane-associated neuronal nitric oxide synthase. This reduction may lead to impaired regulation of the vasoconstrictor response and eventual muscle damage.

1.3 Nuclear Factor Kappa-B Inhibitors

A preferred class of antiinflammatory agent suitable for use in the combinations of the invention are Nuclear Factor Kappa-B (NF-kB) inhibitors. NE-kB is a major transcription factor modulating the cellular immune, inflammatory and proliferative responses. NF-kB functions in activated macrophages to promote inflammation and muscle necrosis and in skeletal muscle fibers to limit regeneration through the inhibition of muscle progenitor cells. The activation of this factor in DMD contributes to diseases pathology. Thus, NF-kB plays an important role in the progression of muscular dystrophy and the IKK/NF-B signaling pathway is a potential therapeutic target for the treatment of DMD. Inhibitors of NF-kB (for example, IRFI 042, a vitamin E analogue) ameliorate muscle function, decrease serum CK level and muscle necrosis and enhance muscle regeneration. Furthermore, specific inhibition of NF-kB/IKK-mediated signalling has similar benefits.

1.4 TNF-α Antagonists

TNFα is one of the key cytokines that triggers and sustains the inflammation response. In one embodiment of the invention, the ancillary agent is a TNF-α antagonist (e.g. infliximab).

Preferences and Specific Embodiments:

Preferred TNF-α antagonists for use according to the invention include infliximab (Remicade™), a chimeric monoclonal antibody comprising murine VK and VH domains and human constant Fc domains. The drug blocks the action of TNFα by binding to it and preventing it from signaling the receptors for TNFα on the surface of cells. Another preferred TNF-α antagonists for use according to the invention is adalimumab (Humira™). Adalimumab is a fully human monoclonal antibody. Another preferred TNF-α antagonists for use according to the invention is etanercept (Enbrel™) Etanercept is a dimeric fusion protein comprising soluble human TNF receptor linked to an Fc portion of an IgG1. It is a large molecule that binds to and so blocks the action of TNFα. Etanercept mimics the inhibitory effects of naturally occurring soluble TNF receptors, but as a fusion protein it has a greatly extended half-life in the bloodstream and therefore a more profound and long-lasting inhibitory effect. Enbrel is marketed as a lyophylized powder in 25 mg vials which must be reconstituted with a diluent and then injected subcutaneously, typically by the patient at home.

Another preferred TNF-α antagonist for use according to the invention is pentoxifylline (Trental™), chemical name 1-(5-oxohexyl)-3,7-dimethylxanthine. The usual dosage in controlled-release tablet form is one tablet (400 mg) three times a day with meals.

Posology:

Remicade is administered by intravenous infusion, typically at 2-month intervals. The recommended dose is 3 mg/kg given as an intravenous infusion followed with additional similar doses at 2 and 6 weeks after the first infusion then every 8 weeks thereafter. For patients who have an incomplete response, consideration may be given to adjusting the dose up to 10 mg/kg or treating as often as every 4 weeks. Humira is marketed in both preloaded 0.8 ml syringes and also in preloaded pen devices, both injected subcutaneously, typically by the patient at home. Etanercept can be administered at a dose of 25 mg (twice weekly) or 50 mg (once weekly).

1.5 Ciclosporin

In one embodiment of the invention, the antinflammatory agent is ciclosporin. Ciclosporin A, the main form of the drug, is a cyclic nonribosomal peptide of 11 amino acids produced by the fungus *Tolypocladium inflatum*. Ciclosporin is thought to bind to the cytosolic protein cyclophilin (immunophilin) of immunocompetent lymphocytes (especially T-lymphocytes). This complex of ciclosporin and cyclophylin inhibits calcineurin, which under normal circumstances is responsible for activating the transcription of interleukin-2. It also inhibits lymphokine production and interleukin release and therefore leads to a reduced function of effector T-cells. It does not affect cytostatic activity. It has also an effect on mitochondria, preventing the mitochondrial PT pore from opening, thus inhibiting cytochrome c release (a potent apoptotic stimulation factor). Ciclosporin may be administered at a dose of 1-10 mg/kg/day.

2. Protease Inhibitors

Proteins in skeletal muscle are degraded by at least three different proteolytic pathways: (a) lysosomal proteases (e.g. the cathepsins); (b) non-lysosomal $Ca^{2+}$-dependent proteases (e.g. calpain); and (c) non-lysosomal ATP-ubiquitin-dependent proteases (e.g. the multicatalytic protease complex or proteasome). Several lines of evidence have suggested that enhanced activation of proteolytic degradation pathways underlies the pathogenesis of muscular dystrophy. Thus, protease inhibitors can be used in the treatment of muscular dystrophies, as discussed below.

Preferred protease inhibitors for use according to the invention may specifically target one of the three degradation pathways described above. Particularly preferred are protease inhibitors which target the non-lysosomal $Ca^{2+}$-dependent pathway (calpain inhibitors) or the non-lysosomal ATP-ubiquitin-dependent pathway (proteasome inhibitors), as described below:

2.1 Calpain Inhibitors

In one embodiment of the invention, the ancillary agent is a calpain inhibitor.

Definitions and Technical Background:

The term "calpain inhibitor" is used herein to define any agent capable of inhibiting the activity of calpain. Calpain is a ubiquitous calcium-dependent cysteine protease which cleaves many cytoskeletal and myelin proteins. Calpains belong to a family of $Ca^{2+}$ activated intracellular proteases whose activity is accelerated when abnormal amounts of $Ca^{2+}$ enter the cell by virtue of increased membrane permeability as a result of some traumatic or ischemic event and/or a genetic defect. Calpain is one of a relatively small family of cysteine proteases, which are active in promoting programmed cell death, or apoptosis. It has been implicated in the initiation of both necrotic and apoptotic cell death. When calpain is abnormally up regulated, the accelerated degradation process breaks down cells and tissues faster than they can be restored, resulting in several serious neuromuscular and neurodegenerative diseases. Calpain has been implicated in the accelerated tissue breakdown associated with muscular dystrophies (including DMD). The trigger which activates calpain is $Ca^+$ ions leaking into cells, where the levels are generally very low. The dystrophin gene is involved in maintaining membrane integrity, and when it is mutated, the membrane is more permeable to calcium ions. Thus, the inhibition of calpain activity in the muscles of DMD patients can preserve muscle integrity and prevent or slow muscle deterioration.

Preferences and Specific Embodiments:

Calpain inhibitors for use according to the invention preferably comprise a calpain inhibiting moiety linked to (or associated with) a carrier (which acts to facilitate targeting of the calpain inhibiting moiety to muscle tissue). The targeting moiety may be chemically linked to the calpain inhibiting moiety, or may be physically associated therewith (a liposome carrier). Preferred targeting moieties include carnitine or aminocarnitine. The calpain inhibiting moiety may be leupeptin. Particularly preferred may be Ceptor's Myodur™. Other such calpain inhibitors are described in WO2005124563 (the contents of which are incorporated herein by reference). Other suitable calpain inhibitors are the α-ketocarbonyl calpain inhibitors disclosed in WO 2004/078908 (the contents of which are incorporated herein by reference). Of the calpain inhibitors described in WO 2004/078908, preferred may be those which target both calpain and the proteasome.

The calpain inhibitors for use according to the invention may be chimaeric compounds or combinations in which the calpain inhibiting moiety is associated (e.g. combined with, co-administered with or covalently linked) to a ROS inhibitor. Such agents combine relief of oxidative stress with a reduction in calpain-mediated muscle tissue breakdown. Suitable dual action calpain/ROS inhibitors are described for example in WO01/32654, WO2007/045761, WO2005/056551 and WO 2002/40016 (the contents of which are incorporated herein by reference).

Other suitable calpain inhibitors can be identified using commercially available assay kits (e.g. the calpain activity kit based on a fluorogenic substrate from Oncogene Research Products, San Diego, Calif.). This assay measures the ability of calpain to digest the synthetic substrate Suc-LLVY-AMC: free AMC can be measured fluorometrically at an excitation of 360-380 nm and an emission of 440-460 nm.

2.2 Proteasome Inhibitors

Definitions and Technical Background:

Another class of adjunctive agents suitable for use in the combinations of the invention are proteasome inhibitors. Proteasomes control the half-life of many short-lived biological processes. At the plasma membrane of skeletal muscle fibers, dystrophin associates with a multimeric protein complex, termed the dystrophin-glycoprotein complex (DGC). Protein members of this complex are normally absent or greatly reduced in dystrophin-deficient skeletal muscle fibers and inhibition of the proteasomal degradation pathway rescues the expression and subcellular localization of dystrophin-associated proteins. Thus, proteasome inhibitors have recently been identified as potential therapeutics for the treatment of DMD (see Bonuccelli et al. (2003) Am J Pathol. October; 163(4): 1663-1675). The term "proteasome inhibitor" as used herein refers to compounds which directly or indirectly perturb, disrupt, block, modulate or inhibit the action of proteasomes (large protein complexes that are involved in the turnover of other cellular proteins). The term also embraces the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Preferences and Specific Embodiments:

There are several classes of proteasome Inhibitors suitable for us in the combinations of the invention, including peptide aldehydes (such as MG-132) and the dipeptidyl boronic acid bortezimib (Velcade™; formerly known as PS-341) which is a more specific inhibitor of the proteasome. Thus, preferred proteasome inhibitors for use in accordance with the invention include bortezimib ([(1R)-3-methyl-1-[[(2S)-1-oxo-3-phenyl-2-[(pyrazinylcarbonyl)amino]propyl]amino]butyl]-boronic acid). Bortezimib is commercially available for example from Millennium Pharmaceuticals Inc under the trade name Velcade, or may be prepared for example as described in PCT patent specification No. WO 96/13266, or by processes analogous thereto. Bortezimib specifically interacts with a key amino acid, namely threonine, within the catalytic site of the proteasome. Another preferred proteasome inhibitor for use in the combinations of the invention is the cell-permeable proteasomal inhibitor CBZ-leucyl-leucylleucinal (MG-132) (as described in Bonuccelli et al. (2003) Am J Pathol. October; 163(4): 1663-1675, the content of which relating to this compound is incorporated herein by reference). Other inhibitors include those structurally related to MG-132, including MG-115 (CBZ-leucyl-leucyl-norvalinal) and ALLN (N-acetyl-leucyl-leucyl-norleucinal) (as also described in Bonuccelli et al. (2003) Am J Pathol. October; 163(4): 1663-1675, the content of which relating to this compound is incorporated herein by reference).

Posology:

The proteasome inhibitor (such as bortezimib) can be administered in a dosage such as 100 to 200 mg/m$^2$. These dosages may be administered for example once, twice or more per course of treatment, which may be repeated for example every 7, 14, 21 or 28 days. MG-132 can be administered at a dose of 10 μg/kg/day.

3. Myostatin Antagonists

Definitions and Technical Background:

Another class of adjunctive agents suitable for use in the combinations of the invention are myostatin antagonists. Myostatin, also known as growth/differentiation factor 8 (GDF-8) is a transforming growth factor-β (TGF-β) family member involved in the regulation of skeletal muscle mass. Most members of the TGF-β-GDF family are widely expressed and are pleiotropic: however, myostatin is primarily expressed in skeletal muscle tissue where it negatively controls skeletal muscle growth. Myostatin is synthesized as an inactive preproprotein which is activated by proteolyic cleavage. The precurser protein is cleaved to produce an approximately 109 amino acid COOH-terminal protein which, in the form of a homodimer of about 25 kDa, is the mature, active form. The mature dimer appears to circulate in the blood as an inactive latent complex bound to the propeptide. As used herein the term "myostatin antagonist" defines a class of agents which inhibit or block at least one activity of myostatin, or alternatively, blocks or reduces the expression of myostatin or its receptor (for example, by interference with the binding of myostatin to its receptor and/or blocking signal transduction resulting from the binding of myostatin to its receptor). Such agents therefore include agents which bind to myostatin itself or to its receptor.

Preferences and Specific Embodiments:

Myostatin antagonists for use according to the invention include antibodies to GDF-8; antibodies to GDF-8 receptors; soluble GDF-8 receptors and fragments thereof (e.g. the ActRIIB fusion polypeptides as described in U.S. Ser. No. 10/689,677, including soluble ActRIIB receptors in which ActRIIB is joined to the Fc portion of an immunoglobulin); GDF-8 propeptide and modified forms thereof (e.g. as described in WO 02/068650 or U.S. Ser. No. 10/071,499, including forms in which GDF-8 propeptide is joined to the Fc portion of an immunoglobulin and/or form in which GDF-8 is mutated at an aspartate (asp) residue, e.g., asp-99 in murine GDF-8 propeptide and asp-100 in human GDF-8 propeptide); a small molecule inhibitor of GDF-8; follistatin (e.g. as described in U.S. Pat. No. 6,004,937) or follistatin-domain-containing proteins (e.g. GASP-1 or other proteins as described in U.S. Ser. No. 10/369,736 and U.S. Ser. No. 10/369,738); and modulators of metalloprotease activity that affect GDF-8 activation, as described in U.S. Ser. No. 10/662,438.

Preferred myostatin antagonists include myostatin antibodies which bind to and inhibit or neutralize myostatin (including the myostatin proprotein and/or mature protein, in monomeric or dimeric form). Myostatin antibodies are preferably mammalian or non-mammalian derived antibodies, for example an IgNAR antibody derived from sharks, or humanised antibodies (or comprise a functional fragment derived from antibodie. Such antibodies are described, for example, in US 2004/0142383, US 2003/1038422, WO 2005/094446 and WO 2006/116269 (the content of which is incorporated herein by reference). Myostatin antibodies also include those which bind to the myostatin proprotein and prevent cleavage into the mature active form. A particularly preferred myostatin antibody for use in the combinations of the invention is Wyeth's Stamulumab (MYO-029). MYO-029 is a recombinant human antibody which binds to and inhibits the activity of myostatin. Other preferred antibody antagonists include the antibodies described in U.S. Pat. No. 6,096,506 and U.S. Pat. No. 6,468,535 (incorporated herein by reference). In some embodiments, the GDF-8 inhibitor is a monoclonal antibody or a fragment thereof that blocks GDF-8 binding to its receptor. Other illustrative embodiments include murine monoclonal antibody JA-16 (as described in US2003/0138422 (ATCC Deposit No. PTA-4236); humanized derivatives thereof and fully human monoclonal anti-GDF-8 antibodies (e.g., Myo-29, Myo-28 and Myo-22, ATCC Deposit Nos. PTA-4741, PTA-4740, and PTA-4739, respectively, or derivatives thereof) as described in US2004/0142382 and incorporated herein by reference.

Other preferred myostatin antagonists include soluble receptors which bind to myostatin and inhibit at least one activity thereof. The term "soluble receptor" here includes truncated versions or fragments of the myostatin receptor which specifically bind myostatin thereby blocking or inhibiting myostatin signal transduction. Truncated versions of the myostatin receptor, for example, include the naturally-occurring soluble domains, as well as variations elaborated by proteolysis of the N- or C-termini. The soluble domain includes all or part of the extracellular domain of the receptor, either alone or attached to additional peptides or other moieties. Since myostatin binds activin receptors (including activin type IEB receptor (ActRHB) and activin type HA receptor (ActRHA), activin receptors can form the basis of soluble receptor antagonists. Soluble receptor fusion proteins can also be used, including soluble receptor Fc (see US2004/0223966 and WO2006/012627, both of which are incorporated herein by reference).

Other preferred myostatin antagonists based on the myostatin receptors are ALK-5 and/or ALK-7 inhibitors (see for example WO2006025988 and WO2005084699, the disclosure of which is incorporated herein by reference). As a TGF-β cytokine, myostatin signals through a family of single transmembrane serine/threonine kinase receptors. These receptors can be divided in two classes, the type I or activin like kinase (ALK) receptors and type II receptors. The ALK receptors are distinguished from the Type II receptors in that the ALK receptors (a) lack the serine/threonine rich intracellular tail, (b) possess serine/threonine kinase domains that are very homologous between Type I receptors, and (c) share a common sequence motif called the GS domain, consisting of a region rich in glycine and serine residues. The GS domain is at the amino terminal end of the intracellular kinase domain and is believed to be critical for activation by the Type II receptor. Several studies have shown that TGF-β signaling requires both the ALK (Type I) and Type II receptors. Specifically, the Type II receptor phosphorylates the GS domain of the Type 1 receptor for TGF-[beta] ALK5, in the presence of TGF-[beta]. The ALK5, in turn, phosphorylates the cytoplasmic proteins smad2 and smad3 at two carboxy terminal serines. Generally, it is believed that in many species, the Type II receptors regulate cell proliferation and the Type I receptors regulate matrix production. Various ALK5 receptor inhibitors have been described (see, for example, U.S. Pat.

No. 6,465,493, US2003/0149277, US2003/0166633, US20040063745, and US2004/0039198, the disclosure of which is incorporated herein by reference). Thus, the myostatin antagonists for use according to the invention may comprise the myostatin binding domain of an ALK5 and/or ALK7 receptor.

Other preferred myostatin antagonists include soluble ligand antagonists which compete with myostatin for binding to myostatin receptors. The term "soluble ligand antagonist" here refers to soluble peptides, polypeptides or peptidomimetics capable of non-productively binding the myostatin receptor(s) (e.g. the activin type IIB receptor (ActRIIA)) and thereby competitively blocking myostatin-receptor signal transduction. Soluble ligand antagonists include variants of myostatin, also referred to as "myostatin analogues" that have homology with but not the activity of myostatin. Such analogues include truncates (such an N- or C-terminal truncations, substitutions, deletions, and other alterations in the amino acid sequence, such as variants having non-amino acid substitutions).

Other preferred myostatin antagonists further include polynucleotide antagonists. These antagonists include antisense or sense oligonucleotides comprising a single-stranded polynucleotide sequence (either RNA or DNA) capable of binding to target mRNA (sense) or DNA (antisense) sequences. Antisense or sense oligonucleotides for use according to the invention comprise fragments of the targeted polynucleotide sequence encoding myostatin or its receptor, transcription factors, or other polynucleotides involved in the expression of myostatin or its receptor. Such a fragment generally comprises at least about 14 nucleotides, typically from about 14 to about 30 nucleotides. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L)-lysine and morpholinos. Further still, intercalating agents, such as ellipticine, and alkylating agents or metal complexes may be attached to sense or antisense oligonucleotides to modify binding specificities of the antisense or sense oligonucleotide for the target nucleotide sequence. Thus, RNA interference (RNAi) produced by the introduction of specific small interfering RNA (siRNA), may also be used to inhibit or eliminate the activity of myostatin.

Particularly preferred myostatin antagonists include but are not limited to follistatin, the myostatin prodomain, growth and differentiation factor 11 (GDF-11) prodomain, prodomain fusion proteins, antagonistic antibodies that bind to myostatin, antagonistic antibodies or antibody fragments that bind to the activin type IIB receptor, soluble activin type IIB receptor, soluble activin type IIB receptor fusion proteins, soluble myostatin analogs (soluble ligands), oligonucleotides, small molecules, peptidomimetics, and myostatin binding agents. disclose anti-myostatin antibodies. Other preferred antagonists include the peptide immunogens described in U.S. Pat. No. 6,369,201 and WO 01/05820 (incorporated herein by reference) and myostatin multimers and immunoconjugates capable of eliciting an immune response and thereby blocking myostatin activity. Other preferred antagonists include the protein inhibitors of myostatin described in WO02/085306 (and incorporated herein by reference), which include the truncated Activin type II receptor, the myostatin pro-domain, and follistatin. Other myostatin inhibitors include those released into culture from cells overexpressing myostatin (see WO00/43781), dominant negatives of myostatin (see WO 01/53350) including the Piedmontese allele, and mature myostatin peptides having a C-terminal truncation at a position either at or between amino acid positions 335 to 375. The small peptides described in US2004/0181033 (incorporated herein by reference) which comprise the amino acid sequence WMCPP, are also suitable for use in the combinations of the invention.

4. Cytokines and Mobilizing Agents

Definitions and Technical Background:

Another class of adjunctive agents suitable for use in the combinations of the invention are cytokines, and in particular anabolic cytokines and insulin-like growth factors (such as IGF-1 or IGF-2). The anabolic effect of IGF-1 on muscle is very well established. In muscular dystrophies, a progressive reduction in the proliferative capacity of satellite cells occurs and this loss of proliferative capacity may be ameliorated by treatment with IGF-1. Thus, IGF-1 (and other members of this class of cytokine) may help to slow the progress of the dystrophinopathies by enhancing activation of dormant satellite cells. Insulin-like growth factors (IGFs) are members of the highly diverse insulin gene family that includes insulin, IGF-I, IGF-II, relaxin, prothoraciotropic hormone (PTTH), and molluscan insulin-related peptide. The IGFs are circulating, mitogenic peptide hormones that have an important role in stimulating growth, differentiation, metabolism and regeneration both in vitro and in vivo.

Preferences and Specific Embodiments:

Preferred cytokines for use according to the invention include IGF-1 and IGF-2. Approximately 99% of IGF-1 in healthy individuals circulates in the blood stream bound to IGFBP-3 where it forms a large ternary 150 kD complex after association with acid-labile subunit protein (ALS). The ternary complex is restricted to the circulation by the capillary endothelium and thus serves as a circulatory reservoir of IGF-1. Thus, for therapeutic applications according to the invention IGF-1 is preferably administered in the form of a complex. For example, a preferred cytokine for use in the combinations of the invention is IPLEX™ (recombinant protein complex of insulin-like growth factor-I (IGF-1) and its most abundant binding protein, insulin-like growth factor binding protein-3 (IGFBP-3)). Another suitable cytokine is G-CSF (or other mobilizing agents as herein defined, e.g. GM-CSF), which can support muscle regeneration by mobilizing stem cells from the marrow. Other preferred cytokines include IGF-1 derivatives (IGF-1E peptides) as described in WO2006056885 (the content of which is incorporated herein by reference) which have the appropriate subsets of the function of the full-length IGF-1 and, in particular, its regenerative capacity. Thus, in a preferred embodiment the combinations of the invention comprise the IGF-I Ea peptide (i.e. the 35 amino acid C terminal peptide translated from part of exons 4 and 5 of the IGF-I gene as part of the IGF-I propeptide and which is cleaved off during post-translational processing) and/or the IGF-I Eb peptide (i.e. the 41 amino acid C terminal peptide translated from parts of exons 4, 5 and 6 of the IGF-I gene as part of the IGF-I propeptide and which is cleaved off during post-translational processing).

Posology:

IPLEX™ can be administered via subcutaneous injection at an initial dose of 0.5 mg/kg, to be increased into the therapeutic dose range of 1 to 2 mg/kg, given once daily. IPLEX™ can be given in the morning or in the evening but should be administered at approximately the same time every day. In order to establish tolerability to IPLEX™, glucose monitoring should be considered at treatment initiation or when a dose has been increased. If frequent symptoms of hypoglycemia or severe hypoglycemia occur, preprandial glucose monitoring should continue. Glucose monitoring is also advised for patients with recent occurrences of asymptomatic or symptomatic hypoglycemia. If evidence of hypoglycemia is present at the time of dosing, the dose should be withheld.

Dosage can be titrated up to a maximum of 2 mg/kg daily based on measurement of IGF-1 levels obtained 8-18 hours after the previous dose. Dosage should be adjusted downward in the event of adverse effects (including hypoglycemia) and/or IGF-1 levels that are greater than or equal to 3 standard deviations above the normal reference range for IGF-1.

5. Corticosteroids

In one embodiment of the invention, the ancillary agent is a corticosteroid.

Definition and Biological Activities:

The term "corticosteroid" as used herein refers to any of several steroid hormones secreted by the cortex of the adrenal glands and which are involved in one or more of the following physiological processes: stress response, immune response and regulation of inflammation, carbohydrate metabolism, protein catabolism and blood electrolyte levels. The term also includes synthetic analogues which share the aforementioned properties. Corticosteroids include glucocorticoids and mineralocorticoids. Glucocorticoids control carbohydrate, fat and protein metabolism and are anti-inflammatory. Mineralocorticoids control electrolyte and water levels, mainly by promoting sodium retention in the kidney. Some corticosteroids have dual glucocorticoid and mineralocorticoid activities. For example, prednisone (see below) and its derivatives have some mineralocorticoid action in addition to a glucocorticoid effect. The precise cellular mechanism(s) by which corticosteroids produce antidystrophic effects are not yet known. A multifactorial mechanism is likely and the effects of corticosteroids probably involve a reduction of inflammation, suppression of the immune system, improvement in calcium homeostasis, upregulation of the expression of compensatory proteins and an increase in myoblast proliferation.

Problems:

The use of corticosteroids is associated with side effects which vary from person to person and on the dosage of the regime used, but they can be severe. The most common side effects are weight gain and mood changes. Weight gain (and attendant changes in muscle activity and use) can abrogate some of the benefits of treatment. Long-term use may lead to growth suppression, cataracts, osteoporosis and muscle atrophy (affecting the same proximal muscles affected in DMD and BMD). These side effects may limit the long-term effectiveness of corticosteroid therapy. Other side effects include hypertension, diabetes, skin atrophy, poor wound healing and immunosuppression. Deflazacort was evaluated in the hope that it would have fewer side effects than prednisone.

Preferences and Specific Embodiments:

Preferred are glucocorticoids (or corticosteroids having dual glucocorticoid/minerlocorticoid activity). Synthetic corticosteroids are preferred. In one embodiment, the corticosteroid is prednisone (prodrug) or prednisolone (liver metabolite of prednisone and active drug). In another embodiment, the corticosteroid is deflazacort. Deflazacort is an oxazoline analogue of prednisone. Other synthetic corticosteroids suitable for use in the combinations of the invention include one or more corticosteroids selected from: alclometasone, amcinonide, beclomethasone (including beclomethasone dipropionate), betamethasone, budesonide, ciclesonide, clobetasol, clobetasone, clocortolone, cloprednol, cortivazol, deoxycorticosterone, desonide, desoximetasone, dexamethasone, diflorasone, diflucortolone, difluprednate, fluclorolone, fludrocortisone, fludroxycortide, flumetasone, flunisolide fluocinolone acetonide, fluocinonide, fluocortin, fluocortolone, fluorometholone, fluperolone, fluprednidene, fluticasone, formocortal, halcinonide, halometasone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednylidene, rimexolone, tixocortol, triamcinolone and ulobetasol (or combinations and/or derivatives (e.g. pharmaceutically acceptable salts) of one or more of the foregoing). Suitable endogenous corticosteroids for use in the combinations of the invention include include one or more corticosteroids selected from aldosterone, cortisone, hydrocortisone/cortisol and desoxycortone (or combinations and/or derivatives (e.g. pharmaceutically acceptable salts) of one or more of the foregoing).

Posology:

Prednisone may be administered daily in dosages ranging from 0.3 to 1.5 mg/kg (typically 0.7 mg/kg). Some patients respond better to ≧2.5 mg/kg every other day. Deflazacort has an estimated dosage equivalency of 1:1.3 compared with prednisone, though biological equivalence between deflazacort and prednisone also depends on the specific actions under examination. Corticosterods (including delazacort and prednisone) are usually taken orally but can be delivered by intramuscular injection.

6. Anabolic Steroids

In one embodiment of the invention, the ancillary agent is an anabolic steroid.

Definition and Biological Activities:

The term "anabolic steroid" as used herein refers to any of several steroid hormones related to the male hormone testosterone and synthetic analogues thereof. Such steroids are may also be referred to as "anabolic-androgenic steroids" or "AAS". Anabolic steroids increase protein synthesis within cells, promoting anabolism (especially in muscles). The precise cellular mechanism(s) by which anabolic steroids produce antidystrophic effects are not yet known, but it seems that their anabolic effects in muscles effectively compensates for muscle loss. Oxandrolone has been shown to have anabolic effects on DMD muscle as well as decreasing muscle degeneration and so easing the demands for muscle regeneration. By conserving regenerative capacity, anabolic steroids such as oxandrolone may prolong muscle function.

Problems:

The use of anabolic steroids is associated with severe side effects. The most common side effects are liver and kidney damage, sterility, stunting of growth and severe mood swings. Anabolic steroids also also tend to be androgenizing and can promote growth of beard and body hair, maturation of genitalia and development of acne. Withdrawal can lead to rapid and severe deterioration in muscle mass and function.

Preferences and Specific Embodiments:

Preferred are synthetic anabolic steroids such as oxandrolone (Anavar), norethandrolone and methandrostenolone (Dianabol). Oxandrolone (an oral synthetic analog of testosterone) may be particularly preferred because in addition to its anabolic properties it also blocks the binding of cortisol to glucocorticoid receptors on muscle, thus preventing muscle breakdown. Other anabolic steroids suitable for use in the combinations of the invention include one or more anabolic steroids selected from: DHEA, DHT, methenolone, oxymetholone, quinbolone, stanozolol, ethylestrenol, nandrolone (Deca Durabolin), oxabolone cipionate, boldenone undecylenate (Equipoise), stanozolol (Winstrol), oxymetholone (Anadrol-50), fluoxymesterone (Halotestin), trenbolone (Fina), methenolone enanthate (Primobolan), 4-chlordehydromethyltestosterone (Turinabol), mesterolone (Proviron), mibolerone (Cheque props), tetrahydrogestrinone and testosterone (or combinations and/or derivatives (e.g. pharmaceutically acceptable salts) of one or more of the foregoing).

Posology:

Anabolic steroids may be administered as orally in the form of pills, by injection or via skin patches. Oral administration is most convenient, but since the steroid must be chemically modified so that the liver cannot break it down before it reaches the blood stream these formulations can cause liver damage in high doses. Injectable steroids are typically administered intramuscularly. Transdermal patches can be sued to deliver a steady dose through the skin and into the bloodstream. Oxandrolone may be administered orally at a daily dosage of 0.1 mg/kg.

7. TGF-β Antagonists

Definitions and Technical Background:

Transforming growth factor beta (TGF-β) promotes fibrosis in response to muscle tissue damage associated with DMD that can contribute to disease pathology. In one embodiment of the invention, the ancillary agent is a TGF-β antagonist.

The term TGF-β antagonist is used herein to refer to compounds which directly or indirectly perturb, disrupt, block, modulate or inhibit the action of TGF-β. The term also embraces the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof).

Preferences and Specific Embodiments:

Preferred TGF-β antagonists for use according to the invention include anti-TGF-β antibodies, tamoxifen, losartan and pirfenidone. Pirfenodone is an orally active synthetic antifibrotic agent structurally similar to pyridine 2,4-dicarboxylate. Pirfenidone inhibits fibroblast, epidermal, platelet-derived, and TGF-β-1 growth factors and also inhibits DNA synthesis and the production of mRNA for collagen types I and III, resulting in a reduction in radiation-induced fibrosis. Losartan is an angiotensin II receptor antagonist drug used mainly to treat hypertension currently marketed by Merck & Co. under the trade name Cozaar™. However, losartan also downregulates the expression of (TGF-β types I and II receptors. Tamoxifen is an orally active selective estrogen receptor modulator (SERM) which is used in the treatment of breast cancer and is currently the world's largest selling drug for this indication. Tamoxifen is sold under the trade names Nolvadex™, Istubal™ and Valodex™. Tamoxifen may be administered at a dose of 10-100 mg per day (e.g. 20-40 mg/day).

8. Antioxidants and Mitochondrial Supporting Agents

In Duchenne Muscular Dystrophy (DMD), the cytoskeletal protein dystrophin is absent leading to numerous cellular dysfunctions that culminate in muscle cell necrosis. Subsequently, an inflammatory response develops in the necrotic muscle tissue, resulting in increased oxidative stress, responsible for further tissue damage. In the mdx dystrophic mouse, both inflammation and oxidative stress have been identified as aggravating factors for the course of the disease.

GTE and EGCG also display unexpected pro myogenic properties. Primary cultures of skeletal muscle cells were established from both normal and dystrophic mice and treated with GTE and EGCG for 1-7 days. As judged by in situ staining of myosin heavy chains (MyHC), we found that GTE and EGCG concentration-dependently stimulated the rate of formation of myotubes within the first 2-4 days of application. The amount of myotubes reached similar level with both agents compared to control thereafter. Western-blot analysis was performed on myotube cultures treated for 7 days. GTE and EGCG promoted the expression of several muscle-specific proteins, such as dystrophin (in control cultures), sarcomeric alpha actinin, and MyHC, while myogenin was unchanged. By contrast, the expression of desmin was downregulated and redistributed to Z discs. Our results suggest that green tea polyphenols display pro myogenic properties by acting directly on skeletal muscle cells. These findings suggest a beneficial action for muscle regeneration and strengthening in dystrophic condition.

Green tea polyphenols, such as epigallocatechin gallate (EGCG), are known to be powerful antioxidants. Because inflammation is involved in the degradation of muscle tissue in MD, oxidative stress is believed to play a role in this process. Thus, green tea and its active constituents (including EGCG and other polyphenols) may improve MD prognosis by reducing this oxidative stress. Feeding studies with mdx mice have shown a protective effect of EGCG against the first massive wave of necrosis. It also stimulated muscle adaptation toward a stronger and more resistant phenotype. The effective dosage corresponds to about seven cups of brewed green tea per day in humans Coenzyme Q10 (CoQ10; also called ubiquitin) is a powerful antioxidant and mitochondrial respiratory chain cofactor. It possesses membrane-stabilizing properties and is capable of penetrating cell membranes and mitochondria. Dosages of 100 mg CoQ10 daily for three months have been shown to be beneficial in human trials, though higher dosages are likely to yield better results.

Idebenone is a synthetic analog of Coenzyme Q10 and is thought to perform the same functions as CoQ10 without the risk of auto-oxidation. Like CoQ10, idebenone can therefore contribute to maintaining correct electron balance, which is necessary for the production of cellular energy. Since muscle cells are particularly energy-demanding, idebenone and CoQ10 can preserve mitochondrial function and protect cells from oxidative stress.

Glutamine is an important energy source and acute oral glutamine administration appears to have a protein-sparing effect. Arginine (and other pharmacological activators of the NO pathway) may enhance the production of utrophin in MDX mice. The increase is likely to be mediated by arginine-fueled production of nitric oxide (NO), which plays an important role in blood vessel function and is generally lower in people with MD. Studies with MDX mice have also shown that a combination of arginine and deflazacort may be more beneficial than deflazacort alone.

Other antioxidants suitable for use according to the invention are the chimaeric compounds or combinations in which the a ROS inhibitor is associated (e.g. combined with, co-administered with or covalently linked) to calpain inhibiting moiety. Such agents combine relief of oxidative stress with a reduction in calpain-mediated muscle tissue breakdown. Suitable dual action calpain/ROS inhibitors are described for example in WO01/32654, WO2007/045761, WO2005/056551 and WO 2002/40016 (the contents of which are incorporated herein by reference).

9. Dystrophin Expression Enhancing Agents 9.1 Read-Through Agents

A subset of DMD patients (around 15%) have a nonsense mutation that produces a premature stop signal in their RNA, resulting in abnormal truncation of protein translation. In one embodiment of the invention, the ancillary agent is an agent which promotes readthrough of premature stop codons ("read-through agent"), thereby bypassing the premature stop codon and restoring the expression of full-length, functional dystrophin.

Suitable read-through agents for use according to the invention are 1,2,4-oxadiazole compounds as described in U.S. Pat. No. 6,992,096 (which is incorporated herein by reference):

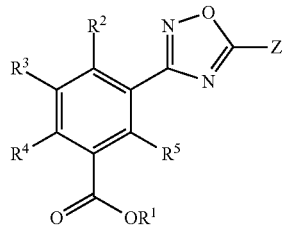

One such compound is 3-[5-(2-fluoro-phenyl)-[1,2,4]oxadiazol-3-yl]-benzoic acid. A preferred readthrough agent is PTC124. PTC124 is a 284-Dalton 1,2,4-oxadiazole that promotes ribosomal readthrough of premature stop codons in mRNA. Thus, the combinations of the invention may comprise 1,2,4-oxadiazole benzoic acid compounds (including 3-[5-(2-fluoro-phenyl)-[1,2,4]oxadiazol-3-yl]-benzoic acid) (see e.g. WO2006110483, the content of which is incorporated herein by reference).

PTC124, 3-[5-(2-fluoro-phenyl)-[1,2,4]oxadiazol-3-yl]-benzoic acid or a pharmaceutically acceptable salt, solvate or hydrate thereof can be administered in single or divided (e.g., three times daily) doses between 0.1 mg/kg and 500 mg/kg, 1 mg/kg and 250 mg/kg, 1 mg/kg and 150 mg/kg, 1 mg/kg and 100 mg/kg, 1 mg/kg and 50 mg/kg, 1 mg/kg and 25 mg/kg, 1 mg/kg and 10 mg/kg or 2 mg/kg and 10 mg/kg to a patent in need thereof. In a particular embodiment, the 3-[5-(2-fluoro-phenyl)-[1,2,4]oxadiazol-3-yl]-benzoic acid or a pharmaceutically acceptable salt, solvate or hydrate thereof is administered in a dose of about 4 mg/kg, about 7 mg/kg, about 8 mg/kg, about 10 mg/kg, about 14 mg/kg or about 20 mg/kg.

Other readthrough agents for use according to the invention include aminoglycoside antibiotics, including gentamicin. Particularly preferred may be aminoglycosides that contain a 6' hydroxyl group (e.g. paromomycin), which may be effective at lower doses and may display less toxicity than compounds such as gentamicin.

9.2 Exon Skipping

Most cases of Duchenne muscular dystrophy (DMD) are caused by dystrophin gene mutations that disrupt the mRNA reading frame. In some cases, forced exclusion (skipping) of a single exon can restore the reading frame, giving rise to a shorter, but still functional dystrophin protein (so called quasi-dystrophin). Antisense oligonucleotides (AONs) designed to cause exon skipping can target a broader range of mutations than can compounds that cause cells to ignore premature stop codons by induce cells to leave out sections of genetic instructions that contain mistakes and join together the surrounding, correct instructions. However, since AONs are not self-renewed, they cannot achieve long-term correction. To overcome this limitation, antisense sequences can be introduced into small nuclear RNAs (snRNA) and vectorized in AAV and lentiviral vectors.

10. Gene Replacement/Repair Agents

In one embodiment of the invention, the ancillary agent is a nucleic acid construct adapted to replace or repair non-functional endogenous genetic material. Gene therapy may be adeno-associated virus (AAV) vector-mediated gene therapy, preferably using the microdystrophin gene. Highly abbreviated microdystrophin cDNAs have been developed for adeno-associated virus (AAV)-mediated DMD gene therapy. Among these, a C-terminal-truncated ΔR4-R23/ΔC microgene (AR4/AC) is a very promising therapeutic candidate gene.

Targeted correction of mutations in the genome holds great promise for the repair/treatment of disease causing mutations either on their own applied directly to the affected tissue, or in combination with other techniques such as stem cell transplantation. Various DNA or RNA/DNA based Corrective Nucleic Acid (CNA) molecules such as chimeraplasts, single stranded oligonucleotides, triplex forming oligonucleotides and SFHR have been used to change specific mutant loci. MyoDys® is comprised of plasmid DNA encoding the full-length human dystrophin gene. Mirus' Pathway IV™ delivery technology is used to administer the pDNA to a patient's limb skeletal muscles.

11. Cell-Based Therapies

In one embodiment of the invention, the ancillary agent is a myogenic cell or tissue composition. Various types of myogenic cell have been shown to have potential in the treatment of DMD, including stem cells from umbilical cord, mesenchymal stem cells and muscle-derived stem cells.

12. Creatine

Definition and Biological Activities:

Creatine is an energy precursor that is naturally produced by the body. Creatine kinase (CK) phosphorylates creatine for later donation to contractile muscle filaments: phosphocreatine enters muscle cells and promotes protein synthesis while reducing protein breakdown. In healthy individuals, creatine has been shown to enhance endurance and increase energy levels by preventing depletion of adenosine triphosphate. Among MD patients, studies have suggested that supplemental creatine can improve muscle performance and strength, decrease fatigue, and slightly improve bone mineral density.

Problems:

High doses of creatine can cause kidney damage and requires cohydration. Behavioral changes have been recorded.

Posology:

Creatine can be administered as a powdered nutritional supplement. In recent trials with DMD patients, slight increases in muscle strength on administration of low levels (1 to 10 g/day) of creatine monohydrate have been recorded. Intermittent administration (involving a break of one to several weeks) may mitigate side effects whilst providing the same benefits as constant use. Dosages in the region of 100 mg/kg/day are well-tolerated and have been found to decrease bone degradation and increase strength and fat-free mass. Benefits have been reported for the co-administration of creatine with conjugated linoleic acid (alpha-lipoic acid), hydroxyl-beta-methylbutyrate and prednisolone.

13. Anti-Osteoporotic Agents

Combined therapy to inhibit bone resorption, prevent osteoporosis, reduce skeletal fracture, enhance the healing of bone fractures, stimulate bone formation and increase bone mineral density can be effectuated by combinations comprising various anti-osteoporotic agents. Preferred are bisphosphonates including alendronate, tiludronate, dimethyl-APD, risedronate, etidronate, YM-175, clodronate, pamidronate and BM-210995 (ibandronate). Others include oestrogen agonist/antagonists. The term oestrogen agonist/antagonists refers to compounds which bind with the estrogen receptor, inhibit bone turnover and prevent bone loss. In particular, oestrogen agonists are herein defined as chemical compounds capable of binding to the estrogen receptor sites in mammalian tissue, and mimicking the actions of estrogen in one or more tissue. Exemplary oestrogen agonist/antagonists include droloxifene and associated compounds (see U.S. Pat. No. 5,047,431), tamoxifen and associated compounds (see U.S. Pat. No. 4,536,516), 4-hydroxy tamoxifen (see U.S. Pat. No. 4,623,660), raloxifene and associated compounds (see U.S. Pat. No. 4,418,068 and idoxifene and associated compounds (see U.S. Pat. No. 4,839,155).

14. Auxiliary Utrophin Upregulating Agents

In addition to the compounds of formula (I) as defined herein, the combinations of the present invention may include one or more auxiliary utrophin upregulating agents. Such auxiliary utrophin upregulating agents are compounds that upregulate (i.e. increase the expression or activity of utrophin) and which do not conform to the structure of formula (I) as defined herein (or the ionic, salt, solvate, isomers, tautomers, N-oxides, ester, prodrugs, isotopes and protected forms thereof). The auxiliary utrophin upregulating agents for use in the combinations of the invention preferably upregulate utrophin via a mechanism that is different from that of the compounds of formula (I) described herein.

15. cGMP Signalling Modulators

It has recently been shown (Khairallah et al. (2008) PNAS 105(19): 7028-7033) that enhancement of cGMP signaling by administration of the phosphodiesterase 5 (PDE5) inhibitor sildenafil prevents deterioration of myocardial contractile performance in mdx hearts.

Thus, cGMP signaling enhancers, including in particular selective PDE5 inhibitors (including for example sildenafil, tadalafil, vardenafil, udenafil and avanafil) may be used in combination with the compounds of the invention to treat DMD or BMD. Such combinations find particular application in the treatment of dystrophic cardiopmyopathies and may be used to prevent or delay the onset of dystrophin-related cardiomyopathies as the clinical course of DMD/BMD progresses.

Thus, the invention contemplates combinations of the compounds of the invention with cGMP signaling enhancers, including in particular selective PDE5 inhibitors. Preferred combinations are comprise a compound of the invention and a PDE5 inhibitor selected from sildenafil, tadalafil, vardenafil, udenafil and avanafil. Particularly preferred is a combination comprising a compound of the invention and sildenafil. The compound of the invention for use in the aforementioned combinations is preferably compound number 390 of Table 1 being 5-(ethylsulfonyl)-2-(naphthalen-2-yl)benzo[d]oxazole.

Formulation and Posology

The compounds of formula I for use in the treatment of DMD will generally be administered in the form of a pharmaceutical composition.

Thus, according to a further aspect of the invention there is provided a pharmaceutical composition including preferably less than 80% w/w, more preferably less than 50% w/w, e.g. 0.1 to 20%, of a compound of formula I, or a pharmaceutically acceptable salt thereof, as defined above, in admixture with a pharmaceutically acceptable diluent or carrier.

We also provide a process for the production of such a pharmaceutical composition which comprises mixing the ingredients. Examples of pharmaceutical formulations which may be used, and suitable diluents or carriers, are as follows: for intravenous injection or infusion-purified water or saline solution; for inhalation compositions—coarse lactose; for tablets, capsules and dragees-microcrystalline cellulose, calcium phosphate, diatomaceous earth, a sugar such as lactose, dextrose or mannitol, talc, stearic acid, starch, sodium bicarbonate and/or gelatin; for suppositories—natural or hardened oils or waxes.

When the compound is to be used in aqueous solution, e.g. for infusion, it may be necessary to incorporate other excipients. In particular there may be mentioned chelating or sequestering agents, antioxidants, tonicity adjusting agents, pH-modifying agents and buffering agents.

Solutions containing a compound of formula I may, if desired, be evaporated, e.g. by freeze drying or spray drying, to give a solid composition, which may be reconstituted prior to use.

When not in solution, the compound of formula I preferably is in a form having a mass median diameter of from 0.01 to 10 µm. The compositions may also contain suitable preserving, stabilising and wetting agents, solubilisers, e.g. a water-soluble cellulose polymer such as hydroxypropyl methylcellulose, or a water-soluble glycol such as propylene glycol, sweetening and colouring agents and flavourings. Where appropriate, the compositions may be formulated in sustained release form.

The content of compound formula I in a pharmaceutical composition is generally about 0.01-about 99.9 wt %, preferably about 0.1-about 50 wt %, relative to the entire preparation.

The dose of the compound of formula I is determined in consideration of age, body weight, general health condition, diet, administration time, administration method, clearance rate, combination of drugs, the level of disease for which the patient is under treatment then, and other factors.

While the dose varies depending on the target disease, condition, subject of administration, administration method and the like, for oral administration as a therapeutic agent for the treatment of Duchenne muscular dystrophy in a patient suffering from such a disease is from 0.01 mg-10 g, preferably 0.1-100 mg, is preferably administered in a single dose or in 2 or 3 portions per day.

EXAMPLES

The potential activity of the compounds of formula I for use in the treatment of DMD may be demonstrated in the following predictive assay and screens.

1. Luciferase Reporter Assay (Murine H2K Cells)

The cell line used for the screen is an immortalized mdx mouse H2K cell line that has been stably transfected with a plasmid containing ∞5 kb fragment of the Utrophin A promoter including the first untranslated exon linked to a luciferase reporter gene. Under conditions of low temperature and interferon containing media, the cells remain as myoblasts. These are plated into 96 well plates and cultured in the presence of compound for three days. The level of luciferase is then determined by cell lysis and reading of the light output from the expressed luciferase gene utilising a plate luminometer. Example of pharmacological dose response of compounds in the assay is shown in FIG. 1.

2. mdx Mouse

Data obtained from the ADMET data was prioritised and the compounds with the best in vitro luciferase activity and reasonable ADMET data were prioritised for testing in the mdx proof of concept study where the outcome was to identify whether any of the compounds had the ability to increase the levels of utrophin protein in dystrophin deficient muscle when compared to vehicle only dosed control animals.

There were two animals injected with up to 50 mg/kg (e.g. 10 mg/kg) of compound administered ip daily for 28 days plus age matched controls. Muscle samples were taken and processed for sectioning (to identify increases in sarcolemmal staining of utrophin) and Western blotting (to identify overall increases in utrophin levels).

FIG. 2 shows an example of TA muscle sections stained with antibody specific for mouse utrophin. Comparison to the mdx muscle only injected with vehicle shows an increase in the amount of sarcolemmal bound utrophin. Muscles from the above treated mice were also excised and processed for Western blotting and stained with specific antibodies (see FIG. 3). Again using muscle dosed with CPD-A shows a significant increase in the overall levels of utrophin present in both the TA leg muscle and the diaphragm. Both mice exposed to CPD-A (V2 and V3) showed increased levels of utrophin expression compared to control. Positive upregulation data from the first 28 day study were then repeated in a further two mouse 28 day study. A total of three different compounds have shown in duplicate the ability to increase the level of utrophin expression in the mdx mouse when delivered daily by ip for 28 days. This data demonstrates the ability of the compound when delivered ip causes a significant increase in the levels of utrophin found in the mdx muscle and therefore gives us the confidence that this approach will ameliorate the disease as all the published data to date demonstrates that any increase of utrophin levels over three fold has significant functional effects on dystrophin deficient muscle.

H2K/mdx/Utro A reporter Cell Line Maintenance

The H2K/mdx/Utro A reporter cell line was passaged twice a week until 530% confluent. The cells were grown at 33° C. in the presence of 10% $CO_2$. To remove the myoblasts for platting, they were incubated with Trypsin EDTA until the monolayer started to detach.

Growth Medium
DMEM Gibco 41966
20% FCS
1% Pen/Strep
1% glutamine
10 mls Chick Embryo Extract
Interferon (1276 905 Roche) Add fresh 10 μl/50 mls medium Luciferase Assay for 96 Well Plates The H2K/mdx/Utro A reporter cell line cells were plated out into 96 well plates (Falcon 353296, white opaque) at a density of approximately 5000 cells/well in 190 μl normal growth medium. The plates were then incubated at 33° C. in the presence of 10% $CO_2$ for 24 hrs. Compounds were dosed by adding 10 μl of diluted compound to each well giving a final concentration of 10 μM. The plates were then incubated for a further 48 hrs. Cells were then lysed in situ following the manufacture's protocols (Promega Steady-Glo Luciferase Assay System (E2520). Then counted for 10 seconds using a plate luminometer (Victor1420).

Compound Storage

Compounds for screening were stored at −20° C. as 10 mM stocks in 100% DMSO until required.

Injection of mdx Mice with Compounds

Mdx from a breeding colony were selected for testing. Mice were injected daily with either vehicle or 10 mg/kg of compound using the intreperitoneal route (ip). Mice were weighed and compounds diluted in 5% DMSO, 0.1% tween in PBS.

Mice were sacrificed by cervical dislocation at desired time points, and muscles excised for analysis Muscle Analysis Immunohistochemistry Tissues for sectioning were dissected, immersed in OCT (Bright Cryo-M-Bed) and frozen on liquid nitrogen cooled isopentane. Unfixed 8 μM cryosections were cut on a Bright Cryostat, and stored at −80° C.

In readiness for staining, sections were blocked in 5% foetal calf serum in PBS for 30 mins. The primary antibodies were diluted in blocking reagent and incubated on sections for 1.5 hrs in a humid chamber then washed three times for 5 mins in PBS. Secondary antibodies also diluted in blocking reagent, were incubated for 1 hr in the dark in a humid chamber. Finally sections were washed three times 5 mins in PBS and coverslip Mounted with hydromount. Slides were analysed using a Leica fluorescent microscope.

Results

Biological activity as assessed using the luciferase reporter assay in murine H2K cells, and is classified as follows:
+ Up to 200% relative to control
++ Between 201% and 300% relative to control
+++ Between 301% and 400% relative to control
++++ Above 401% relative to control

TABLE 1

Compounds made by methods described herein

| Example | Chemical Name | Activity |
|---|---|---|
| 1 | N-(2-(4-(dimethylamino)phenyl)benzo[d]oxazol-5-yl)isonicotinamide | + |
| 2 | N-(2-(4-fluorophenyl)benzo[d]oxazol-5-yl)furan-2-carboxamide | + |
| 3 | 2-((4-chlorophenoxy)methyl)-1-methyl-1H-benzo[d]imidazole | +++ |
| 4 | 2-((4-methoxyphenoxy)methyl)-1H-benzo[d]imidazole | ++ |
| 5 | phenyl(2-phenyl-1H-benzo[d]imidazol-6-yl)methanone | + |
| 6 | N-(2-phenylbenzo[d]oxazol-5-yl)nicotinamide | + |
| 7 | 3-phenyl-N-(2-phenylbenzo[d]oxazol-5-yl)propanamide | + |
| 8 | N-(2-phenylbenzo[d]oxazol-5-yl)acetamide | ++ |
| 9 | N-(2-phenylbenzo[d]oxazol-5-yl)propionamide | ++ |
| 10 | N-(2-phenylbenzo[d]oxazol-5-yl)butyramide | +++ |
| 11 | N-(2-phenylbenzo[d]oxazol-5-yl)pentanamide | ++ |
| 12 | N-(2-phenylbenzo[d]oxazol-5-yl)isobutyramide | ++ |
| 13 | N-(2-phenylbenzo[d]oxazol-5-yl)furan-2-carboxamide | ++ |
| 14 | 2-phenylbenzo[d]oxazol-5-amine | +++ |
| 15 | 2-(4-(trifluoromethyl)phenyl)benzo[d]oxazol-5-amine | + |
| 16 | 2-(4-(diethylamino)phenyl)benzo[d]oxazol-5-amine | ++ |
| 17 | 2-(4-(diethylamino)phenyl)benzo[d]oxazol-5-amine | + |
| 18 | 2-p-tolylbenzo[d]oxazol-5-amine | + |
| 19 | 4-chloro-N-(2-p-tolylbenzo[d]oxazol-5-yl)benzamide | + |
| 20 | 4-methoxy-N-(2-p-tolylbenzo[d]oxazol-5-yl)benzamide | + |
| 21 | 2-(5-nitrobenzo[d]oxazol-2-yl)phenol | + |
| 22 | N-(2-phenylbenzo[d]oxazol-5-yl)isonicotinamide | + |
| 23 | 4-chloro-N-(2-phenylbenzo[d]oxazol-5-yl)benzamide | + |
| 24 | 4-methyl-N-(2-phenylbenzo[d]oxazol-5-yl)benzamide | + |
| 25 | 4-methoxy-N-(2-phenylbenzo[d]oxazol-5-yl)benzamide | + |
| 26 | 2-methoxy-N-(2-phenylbenzo[d]oxazol-5-yl)benzamide | + |
| 27 | 4-(dimethylamino)-N-(2-phenylbenzo[d]oxazol-5-yl)benzamide | + |
| 28 | 3,4-dichloro-N-(2-phenylbenzo[d]oxazol-5-yl)benzamide | + |
| 29 | N-(2-phenylbenzo[d]oxazol-5-yl)-4-(trifluoromethyl)benzamide | + |
| 30 | 3,5-dichloro-N-(2-phenylbenzo[d]oxazol-5-yl)benzamide | + |
| 31 | 4-fluoro-N-(2-phenylbenzo[d]oxazol-5-yl)benzamide | + |
| 32 | N-(2-phenylbenzo[d]oxazol-5-yl)biphenyl-4-carboxamide | + |
| 33 | 2-phenyl-N-(2-phenylbenzo[d]oxazol-5-yl)acetamide | + |
| 34 | N-(2-phenylbenzo[d]oxazol-5-yl)cinnamamide | + |
| 35 | N-(2-phenylbenzo[d]oxazol-5-yl)-1-naphthamide | + |

TABLE 1-continued

Compounds made by methods described herein

| Example | Chemical Name | Activity |
|---|---|---|
| 36 | N-(2-phenylbenzo[d]oxazol-5-yl)-2-naphthamide | + |
| 37 | N-(2-phenylbenzo[d]oxazol-5-yl)thiophene-2-carboxamide | ++ |
| 38 | 2-(5-aminobenzo[d]oxazol-2-yl)phenol | +++ |
| 39 | N-(2-(pyridin-3-yl)benzo[d]oxazol-5-yl)benzamide | + |
| 40 | 4-chloro-N-(2-(pyridin-3-yl)benzo[d]oxazol-5-yl)benzamide | + |
| 41 | 4-methyl-N-(2-(pyridin-3-yl)benzo[d]oxazol-5-yl)benzamide | + |
| 42 | 4-methoxy-N-(2-(pyridin-3-yl)benzo[d]oxazol-5-yl)benzamide | + |
| 43 | 2-methoxy-N-(2-(pyridin-3-yl)benzo[d]oxazol-5-yl)benzamide | + |
| 44 | 4-(dimethylamino)-N-(2-(pyridin-3-yl)benzo[d]oxazol-5-yl)benzamide | + |
| 45 | 3,4-dichloro-N-(2-(pyridin-3-yl)benzo[d]oxazol-5-yl)benzamide | + |
| 46 | N-(2-(pyridin-3-yl)benzo[d]oxazol-5-yl)-4-(trifluoromethyl)benzamide | + |
| 47 | 3,5-dichloro-N-(2-(pyridin-3-yl)benzo[d]oxazol-5-yl)benzamide | + |
| 48 | 4-fluoro-N-(2-(pyridin-3-yl)benzo[d]oxazol-5-yl)benzamide | + |
| 49 | N-(2-(pyridin-3-yl)benzo[d]oxazol-5-yl)biphenyl-4-carboxamide | + |
| 50 | 2-phenyl-N-(2-(pyridin-3-yl)benzo[d]oxazol-5-yl)acetamide | + |
| 51 | 3-phenyl-N-(2-(pyridin-3-yl)benzo[d]oxazol-5-yl)propanamide | + |
| 52 | N-(2-(pyridin-3-yl)benzo[d]oxazol-5-yl)cinnamamide | + |
| 53 | N-(2-(pyridin-3-yl)benzo[d]oxazol-5-yl)propionamide | + |
| 54 | N-(2-(pyridin-3-yl)benzo[d]oxazol-5-yl)butyramide | + |
| 55 | N-(2-(pyridin-3-yl)benzo[d]oxazol-5-yl)pentanamide | + |
| 56 | N-(2-(pyridin-3-yl)benzo[d]oxazol-5-yl)isobutyramide | ++ |
| 57 | N-(2-(pyridin-3-yl)benzo[d]oxazol-5-yl)furan-2-carboxamide | + |
| 58 | N-(2-(pyridin-3-yl)benzo[d]oxazol-5-yl)furan-2-carboxamide | + |
| 59 | N-(2-phenylbenzo[d]oxazol-5-yl)benzamide | ++ |
| 60 | N-(2-(4-(diethylamino)phenyl)benzo[d]oxazol-5-yl)nicotinamide | ++ |
| 61 | N-(2-(4-(diethylamino)phenyl)benzo[d]oxazol-5-yl)isonicotinamide | + |
| 62 | N-(2-(4-(diethylamino)phenyl)benzo[d]oxazol-5-yl)benzamide | + |
| 63 | 4-chloro-N-(2-(4-(diethylamino)phenyl)benzo[d]oxazol-5-yl)benzamide | + |
| 64 | N-(2-(4-(diethylamino)phenyl)benzo[d]oxazol-5-yl)-4-methylbenzamide | + |
| 65 | N-(2-(4-(diethylamino)phenyl)benzo[d]oxazol-5-yl)-4-methoxybenzamide | + |
| 66 | N-(2-(4-(diethylamino)phenyl)benzo[d]oxazol-5-yl)-2-methoxybenzamide | + |
| 67 | N-(2-(4-(diethylamino)phenyl)benzo[d]oxazol-5-yl)-4-(dimethylamino)benzamide | ++ |
| 68 | 3,4-dichloro-N-(2-(4-(diethylamino)phenyl)benzo[d]oxazol-5-yl)benzamide | + |
| 69 | N-(2-(4-(diethylamino)phenyl)benzo[d]oxazol-5-yl)-4-(trifluoromethyl)benzamide | + |
| 70 | 3,5-dichloro-N-(2-(4-(diethylamino)phenyl)benzo[d]oxazol-5-yl)benzamide | + |
| 71 | N-(2-(4-(diethylamino)phenyl)benzo[d]oxazol-5-yl)-4-fluorobenzamide | + |
| 72 | N-(2-(4-(diethylamino)phenyl)benzo[d]oxazol-5-yl)biphenyl-4-carboxamide | + |
| 73 | N-(2-(4-(diethylamino)phenyl)benzo[d]oxazol-5-yl)-2-phenylacetamide | ++ |
| 74 | N-(2-(4-(diethylamino)phenyl)benzo[d]oxazol-5-yl)-3-phenylpropanamide | + |
| 75 | N-(2-(4-(diethylamino)phenyl)benzo[d]oxazol-5-yl)propanamide | ++ |
| 76 | N-(2-(4-(diethylamino)phenyl)benzo[d]oxazol-5-yl)butyramide | + |
| 77 | N-(2-(4-(diethylamino)phenyl)benzo[d]oxazol-5-yl)pentanamide | ++ |
| 78 | N-(2-(4-(diethylamino)phenyl)benzo[d]oxazol-5-yl)isobutyramide | + |
| 79 | N-(2-(4-(diethylamino)phenyl)benzo[d]oxazol-5-yl)thiophene-2-carboxamide | + |
| 80 | 3-(5-propylbenzo[d]oxazol-2-yl)benzoic acid | + |
| 81 | N-(2-(pyridin-3-yl)benzo[d]oxazol-5-yl)nicotinamide | + |
| 82 | 5-amino-2-(5-aminobenzo[d]oxazol-2-yl)phenol | ++ |
| 83 | 4-methoxy-N-(2-(4-methoxyphenyl)benzo[d]oxazol-5-yl)benzamide | + |
| 84 | 5-(ethylsulfonyl)-2-phenylbenzo[d]oxazole | ++ |
| 85 | 2,5-diphenylbenzo[d]oxazole | +++ |
| 86 | 2-phenylnaphtho[1,2-d]oxazole | +++ |
| 87 | N-(2-(4-chlorophenyl)benzo[d]oxazol-5-yl)isonicotinamide | + |
| 88 | N-(2-(4-chlorophenyl)benzo[d]oxazol-5-yl)benzamide | + |
| 89 | 4-chloro-N-(2-(4-chlorophenyl)benzo[d]oxazol-5-yl)benzamide | + |
| 90 | N-(2-(4-chlorophenyl)benzo[d]oxazol-5-yl)-4-methylbenzamide | + |
| 91 | N-(2-(4-chlorophenyl)benzo[d]oxazol-5-yl)-4-methoxybenzamide | + |
| 92 | N-(2-(4-chlorophenyl)benzo[d]oxazol-5-yl)-2-methoxybenzamide | + |
| 93 | N-(2-(4-chlorophenyl)benzo[d]oxazol-5-yl)-4-(dimethylamino)benzamide | + |
| 94 | N-(2-(4-chlorophenyl)benzo[d]oxazol-5-yl)-4-(trifluoromethyl)benzamide | + |
| 95 | 3,5-dichloro-N-(2-(4-chlorophenyl)benzo[d]oxazol-5-yl)benzamide | + |
| 96 | N-(2-(4-chlorophenyl)benzo[d]oxazol-5-yl)-4-fluorobenzamide | + |
| 97 | N-(2-(4-chlorophenyl)benzo[d]oxazol-5-yl)-2-phenylacetamide | ++ |
| 98 | N-(2-(4-chlorophenyl)benzo[d]oxazol-5-yl)-3-phenylpropanamide | + |
| 99 | N-(2-(4-chlorophenyl)benzo[d]oxazol-5-yl)butyramide | ++++ |
| 100 | N-(2-(4-chlorophenyl)benzo[d]oxazol-5-yl)pentanamide | ++ |
| 101 | N-(2-(4-chlorophenyl)benzo[d]oxazol-5-yl)isobutyramide | ++++ |
| 102 | N-(2-(4-chlorophenyl)benzo[d]oxazol-5-yl)furan-2-carboxamide | + |
| 103 | N-(2-(4-chlorophenyl)benzo[d]oxazol-5-yl)thiophene-2-carboxamide | + |
| 104 | 5-amino-2-(5,6-dimethyl-1H-benzo[d]imidazol-2-yl)phenol | ++ |
| 105 | 2-(3-methyl-4-nitrophenyl)-1H-benzo[d]imidazole | ++++ |
| 106 | 2-(6-nitro-1H-benzo[d]imidazol-2-yl)phenol | + |
| 107 | 2-phenylbenzo[d]oxazole-5-carboxylic acid | +++ |
| 108 | 2-(4-propylphenyl)benzo[d]oxazole-5-carboxylic acid | + |
| 109 | 2-(4-propylphenyl)benzo[d]oxazole-6-carboxylic acid | + |
| 110 | 2'-(4-propylphenyl)-2,6'-bibenzo[d]oxazole-6-carboxylic acid | + |
| 111 | 5-chloro-2-phenylbenzo[d]oxazole | ++ |
| 112 | 6-chloro-2-phenylbenzo[d]oxazole | + |
| 113 | N-(2-p-tolylbenzo[d]oxazol-5-yl)nicotinamide | + |
| 114 | N-(2-p-tolylbenzo[d]oxazol-5-yl)isonicotinamide | + |
| 115 | N-(2-p-tolylbenzo[d]oxazol-5-yl)propionamide | ++++ |
| 116 | N-(2-p-tolylbenzo[d]oxazol-5-yl)butyramide | ++++ |
| 117 | N-(2-p-tolylbenzo[d]oxazol-5-yl)pentanamide | +++ |
| 118 | N-(2-p-tolylbenzo[d]oxazol-5-yl)isobutyramide | ++ |
| 119 | N-(2-p-tolylbenzo[d]oxazol-5-yl)furan-2-carboxamide | + |
| 120 | N-(2-p-tolylbenzo[d]oxazol-5-yl)thiophene-2-carboxamide | ++ |
| 121 | N-(2-(4-(trifluoromethyl)phenyl)benzo[d]oxazol-5-yl)nicotinamide | + |
| 122 | N-(2-(4-(trifluoromethyl)phenyl)benzo[d]oxazol-5-yl)isonicotinamide | + |
| 123 | N-(2-(4-(trifluoromethyl)phenyl)benzo[d]oxazol-5-yl)acetamide | ++ |

TABLE 1-continued

Compounds made by methods described herein

| Example | Chemical Name | Activity |
|---|---|---|
| 124 | N-(2-(4-(trifluoromethyl)phenyl)benzo[d]oxazol-5-yl)propionamide | + |
| 125 | N-(2-(4-(trifluoromethyl)phenyl)benzo[d]oxazol-5-yl)butyramide | + |
| 126 | N-(2-(4-(trifluoromethyl)phenyl)benzo[d]oxazol-5-yl)pentanamide | + |
| 127 | N-(2-(4-(trifluoromethyl)phenyl)benzo[d]oxazol-5-yl)isobutyramide | + |
| 128 | N-(2-(4-(trifluoromethyl)phenyl)benzo[d]oxazol-5-yl)furan-2-carboxamide | + |
| 129 | 5-tert-butyl-2-phenylbenzo[d]oxazole | ++++ |
| 130 | 6-nitro-2-phenylbenzo[d]oxazole | ++ |
| 131 | 4-(5-chlorobenzo[d]oxazol-2-yl)-N,N-diethylaniline | +++ |
| 132 | 4-(6-chlorobenzo[d]oxazol-2-yl)-N,N-diethylaniline | ++++ |
| 133 | 2-(5-amino-1H-benzo[d]imidazol-2-yl)phenol | + |
| 134 | N-(2-(4-methoxyphenyl)benzo[d]oxazol-5-yl)isonicotinamide | + |
| 135 | N-(2-(4-methoxyphenyl)benzo[d]oxazol-5-yl)acetamide | +++ |
| 136 | N-(2-(4-methoxyphenyl)benzo[d]oxazol-5-yl)propionamide | +++ |
| 137 | N-(2-(4-methoxyphenyl)benzo[d]oxazol-5-yl)butyramide | ++ |
| 138 | N-(2-(4-methoxyphenyl)benzo[d]oxazol-5-yl)pentanamide | + |
| 139 | N-(2-(4-methoxyphenyl)benzo[d]oxazol-5-yl)isobutyramide | ++ |
| 140 | N-(2-(4-methoxyphenyl)benzo[d]oxazol-5-yl)furan-2-carboxamide | + |
| 141 | N-(2-(4-methoxyphenyl)benzo[d]oxazol-5-yl)thiophene-2-carboxamide | + |
| 142 | 4-(5-tert-butylbenzo[d]oxazol-2-yl)-N,N-diethylaniline | ++ |
| 143 | 4-(benzo[d]oxazol-2-yl)-N,N-diethylaniline | ++ |
| 144 | N,N-diethyl-4-(5-(ethylsulfonyl)benzo[d]oxazol-2-yl)aniline | + |
| 145 | N,N-diethyl-4-(5-phenylbenzo[d]oxazol-2-yl)aniline | + |
| 146 | N,N-diethyl-4-(naphtho[1,2-d]oxazol-2-yl)aniline | ++ |
| 147 | 2-(pyridin-2-yl)benzo[d]oxazole | + |
| 148 | N-(2-(4-chlorophenyl)-2H-benzo[d][1,2,3]triazol-5-yl)propionamide | ++++ |
| 149 | 2-(4-(pyrrolidin-1-yl)phenyl)benzo[d]oxazol-5-amine | ++ |
| 150 | 2-(4-(piperidin-1-yl)phenyl)benzo[d]oxazol-5-amine | ++ |
| 151 | 2-(4-(4-methylpiperazin-1-yl)phenyl)benzo[d]oxazol-5-amine | ++ |
| 152 | 2-(4-(diethylamino)phenyl)benzo[d]oxazole-5-carboxylic acid | + |
| 153 | 6-nitro-2-phenyloxazolo[5,4-b]pyridine | + |
| 154 | 2-propylbenzo[d]oxazol-5-amine | + |
| 155 | 2-phenylbenzo[d]oxazol-6-amine | +++ |
| 156 | N-benzyl-2-phenylbenzo[d]oxazol-5-amine | +++ |
| 157 | 2-p-tolyloxazolo[5,4-b]pyridine | +++ |
| 158 | 2-p-tolyloxazolo[4,5-b]pyridine | + |
| 159 | 2-(4-morpholinophenyl)benzo[d]oxazol-5-amine | + |
| 160 | 3-methoxy-N-(2-p-tolylbenzo[d]oxazol-5-yl)propanamide | ++++ |
| 161 | 5-phenyl-2-p-tolylbenzo[d]oxazole | +++ |
| 162 | 2-(4-chlorophenyl)-5-phenylbenzo[d]oxazole | + |
| 163 | 2-cyclohexyl-5-nitrobenzo[d]oxazole | + |
| 164 | 2-(4-chlorophenyl)-6-nitro-1H-benzo[d]imidazole | ++ |
| 165 | N-(2-benzylbenzo[d]oxazol-5-yl)-2-phenylacetamide | + |
| 166 | N-(2-p-tolyl-1H-benzo[d]imidazol-5-yl)butyramide | + |
| 167 | N-butyl-2-phenylbenzo[d]oxazol-5-amine | ++++ |
| 168 | N-isobutyl-2-phenylbenzo[d]oxazol-5-amine | ++++ |
| 169 | 2-phenyloxazolo[5,4-b]pyridin-6-amine | + |
| 170 | N-(2-phenyloxazolo[5,4-b]pyridin-6-yl)butyramide | + |
| 171 | 5-nitro-2-(pyridin-2-yl)benzo[d]oxazole | + |
| 172 | 5-tert-butyl-2-p-tolylbenzo[d]oxazole | ++++ |
| 173 | 2-p-tolylbenzo[d]oxazole | +++ |
| 174 | 2-(3-(trifluoromethyl)phenyl)benzo[d]oxazol-5-amine | + |
| 175 | N-(2-p-tolyl-1H-benzo[d]imidazol-5-yl)isobutyramide | + |
| 176 | N-butyl-2-p-tolylbenzo[d]oxazole-5-carboxamide | ++ |
| 177 | N-propyl-2-p-tolylbenzo[d]oxazole-5-carboxamide | ++++ |
| 178 | N-(2-(4-chlorophenyl)-1H-benzo[d]imidazol-5-yl)butyramide | + |
| 179 | 5-(ethylsulfonyl)-2-p-tolylbenzo[d]oxazole | ++++ |
| 180 | 2-(4-chlorophenyl)-5-(ethylsulfonyl)benzo[d]oxazole | ++++ |
| 181 | N-isopropyl-2-p-tolylbenzo[d]oxazole-5-carboxamide | +++ |
| 182 | N-butyl-2-(4-chlorophenyl)benzo[d]oxazol-5-amine | +++ |
| 183 | 2-(4-chlorophenyl)-N-isobutylbenzo[d]oxazol-5-amine | +++ |
| 184 | N-benzyl-2-(4-chlorophenyl)benzo[d]oxazol-5-amine | + |
| 185 | N-butyl-2-p-tolylbenzo[d]oxazol-5-amine | +++ |
| 186 | N-isobutyl-2-p-tolylbenzo[d]oxazol-5-amine | +++ |
| 187 | N-benzyl-2-p-tolylbenzo[d]oxazol-5-amine | +++ |
| 188 | N-(2-phenyl-1H-benzo[d]imidazol-5-yl)isobutyramide | +++ |
| 189 | 4-nitro-2-p-tolylbenzo[d]oxazole | + |
| 190 | 6-nitro-2-p-tolylbenzo[d]oxazole | +++ |
| 191 | 2-(4-chlorophenyl)-6-nitrobenzo[d]oxazole | ++ |
| 192 | 2-p-tolyloxazolo[4,5-c]pyridine | + |
| 193 | N-(2-phenylbenzo[d]oxazol-5-yl)propane-1-sulfonamide | ++ |
| 194 | N-(2-phenyl-1H-benzo[d]imidazol-5-yl)butyramide | ++ |
| 195 | N-(2-(4-chlorophenyl)-1H-benzo[d]imidazol-5-yl)isobutyramide | ++ |
| 196 | 2-m-tolylbenzo[d]oxazol-5-amine | + |
| 197 | 2-(3-(dimethylamino)phenyl)benzo[d]oxazol-5-amine | + |
| 198 | 5-bromo-2-p-tolylbenzo[d]oxazole | +++ |
| 199 | 5-(4-methoxyphenyl)-2-p-tolylbenzo[d]oxazole | + |
| 200 | N-(2-m-tolylbenzo[d]oxazol-5-yl)butyramide | ++++ |
| 201 | N-(2-(3-(dimethylamino)phenyl)benzo[d]oxazol-5-yl)butyramide | + |
| 202 | N-(2-m-tolylbenzo[d]oxazol-5-yl)isobutyramide | ++++ |
| 203 | N-(2-(3-(trifluoromethyl)phenyl)benzo[d]oxazol-5-yl)isobutyramide | + |
| 204 | N-(2-(3-(dimethylamino)phenyl)benzo[d]oxazol-5-yl)isobutyramide | ++++ |
| 205 | 2-o-tolylbenzo[d]oxazol-5-amine | +++ |
| 206 | 2-(2-chlorophenyl)benzo[d]oxazol-5-amine | ++ |
| 207 | N-(2-(4-chlorophenyl)benzo[d]oxazol-5-yl)propionamide | ++++ |
| 208 | N-(2-p-tolylbenzo[d]oxazol-5-yl)pivalamide | ++ |
| 209 | 2,2,2-trifluoro-N-(2-p-tolylbenzo[d]oxazol-5-yl)acetamide | ++ |
| 210 | N-(2-(4-chlorophenyl)benzo[d]oxazol-5-yl)pivalamide | ++ |
| 211 | N-(2-(4-chlorophenyl)benzo[d]oxazol-5-yl)-2,2,2-trifluoroacetamide | ++ |
| 212 | 6-bromo-2-p-tolyloxazolo[5,4-b]pyridine | ++ |
| 213 | 2-p-tolylbenzo[d]thiazol-5-amine | + |
| 214 | 2-benzyl-5-nitrobenzo[d]oxazole | + |
| 215 | 5,6-dimethyl-2-p-tolylbenzo[d]oxazole | ++++ |
| 216 | N-(2-p-tolylbenzo[d]thiazol-5-yl)butyramide | ++++ |
| 217 | N-(2-p-tolylbenzo[d]thiazol-5-yl)isobutyramide | ++++ |
| 218 | 2-p-tolylbenzo[d]oxazole-5-carboxamide | ++++ |
| 219 | N-(2-(4-chlorophenyl)benzo[d]oxazol-5-yl)-N-methylpropionamide | +++ |
| 220 | N-(2-phenylbenzo[d]oxazol-5-yl)propane-2-sulfonamide | ++ |
| 221 | N-(2-phenylbenzo[d]oxazol-5-yl)benzenesulfonamide | + |
| 222 | 2-(4-chlorophenyl)-5,6-dimethylbenzo[d]oxazole | ++++ |
| 223 | 6-nitro-2-(pyridin-2-yl)benzo[d]oxazole | + |
| 224 | 2-(2,4-dichlorophenyl)-5,6-dimethylbenzo[d]oxazole | ++++ |
| 225 | N-(2-(3-(trifluoromethyl)phenyl)benzo[d]oxazol-5-yl)butyramide | + |
| 226 | N-(2-o-tolylbenzo[d]oxazol-5-yl)isobutyramide | ++++ |
| 227 | N-(2-benzylbenzo[d]oxazol-5-yl)butyramide | + |
| 228 | N-(2-benzylbenzo[d]oxazol-5-yl)isobutyramide | + |
| 229 | N-(2-(2-chlorophenyl)benzo[d]oxazol-5-yl)butyramide | +++ |
| 230 | N-(2-(2-chlorophenyl)benzo[d]oxazol-5-yl)isobutyramide | ++++ |
| 231 | N-(2-(3-chlorophenyl)benzo[d]oxazol-5-yl)isobutyramide | ++++ |
| 232 | 2-(3-fluorophenyl)benzo[d]oxazol-5-amine | ++++ |

TABLE 1-continued

Compounds made by methods described herein

| Example | Chemical Name | Activity |
|---|---|---|
| 233 | 4,4,4-trifluoro-N-(2-p-tolylbenzo[d]oxazol-5-yl)butanamide | + |
| 234 | 2-p-tolylbenzo[d]oxazol-4-amine | +++ |
| 235 | N-(2-p-tolylbenzo[d]oxazol-4-yl)butyramide | + |
| 236 | N-(2-p-tolylbenzo[d]oxazol-4-yl)isobutyramide | + |
| 237 | 2-p-tolylbenzo[d]oxazol-6-amine | ++++ |
| 238 | 2-(2,4-difluorobenzamido)-4,5-dimethylphenyl 2,4-difluorobenzoate | + |
| 239 | N-(2-(3-chlorophenyl)benzo[d]oxazol-5-yl)butyramide | + |
| 240 | 1-phenyl-3-(2-phenylbenzo[d]oxazol-5-yl)urea | +++ |
| 241 | 1-isopropyl-3-(2-phenylbenzo[d]oxazol-5-yl)urea | + |
| 242 | N-(2-(2-fluorophenyl)benzo[d]oxazol-5-yl)butyramide | + |
| 243 | N-(2-(2-fluorophenyl)benzo[d]oxazol-5-yl)isobutyramide | +++ |
| 244 | N-(2-(3-fluorophenyl)benzo[d]oxazol-5-yl)butyramide | ++++ |
| 245 | N-(2-(3-fluorophenyl)benzo[d]oxazol-5-yl)isobutyramide | +++ |
| 246 | tert-butyl 3-oxo-3-(2-phenylbenzo[d]oxazol-5-ylamino)propylcarbamate | + |
| 247 | 2-(2,4-difluorophenyl)-5,6-dimethylbenzo[d]oxazole | ++ |
| 248 | N-(2-cyclohexylbenzo[d]oxazol-5-yl)isobutyramide | ++++ |
| 249 | N-(2-cyclohexylbenzo[d]oxazol-5-yl)butyramide | + |
| 250 | 2-(5-butylpyridin-2-yl)-5-nitrobenzo[d]oxazole | + |
| 251 | 2-phenylbenzo[d]thiazol-5-amine | +++ |
| 252 | N-(4-(2-(4-chlorophenyl)benzo[d]oxazol-5-yl)phenyl)acetamide | +++ |
| 253 | N-(2-p-tolylbenzo[d]oxazol-5-yl)propane-1-sulfonamide | + |
| 254 | 3,3,3-trifluoro-N-(2-p-tolylbenzo[d]oxazol-5-yl)propanamide | ++ |
| 255 | N-(2-(4-chlorophenyl)benzo[d]oxazol-6-yl)isobutyramide | ++++ |
| 256 | N-(2-(4-chlorophenyl)benzo[d]oxazol-6-yl)butyramide | ++ |
| 257 | N-(2-(2,4-dichlorophenyl)benzo[d]oxazol-5-yl)isobutyramide | + |
| 258 | N-(2-(4-fluorophenyl)benzo[d]oxazol-5-yl)isobutyramide | +++ |
| 259 | N-(2-p-tolylbenzo[d]oxazol-5-yl)propane-2-sulfonamide | + |
| 260 | N-(2-(4-chlorophenyl)benzo[d]oxazol-5-yl)propane-1-sulfonamide | + |
| 261 | N-(2-(4-chlorophenyl)benzo[d]oxazol-5-yl)propane-2-sulfonamide | + |
| 262 | 2-(5-butylpyridin-2-yl)-6-nitrobenzo[d]oxazole | ++ |
| 263 | 2-(4-chlorophenyl)-N-isopropylbenzo[d]oxazole-5-carboxamide | +++ |
| 264 | 2-(4-chlorophenyl)benzo[d]oxazole-5-carboxamide | ++++ |
| 265 | N-(2-(4-chlorophenyl)benzo[d]oxazol-5-yl)cyclopropanecarboxamide | ++++ |
| 266 | N-(2-(4-chlorophenyl)benzo[d]oxazol-5-yl)cyclobutanecarboxamide | +++ |
| 267 | N-(2-phenylbenzo[d]thiazol-5-yl)isobutyramide | ++++ |
| 268 | N-(2-(3,4-dichlorophenyl)benzo[d]oxazol-5-yl)isobutyramide | ++++ |
| 269 | 2-(4-chlorophenyl)-5-(4-(ethylsulfonyl)phenyl)benzo[d]oxazole | + |
| 270 | N-(2-(5-chloropyridin-2-yl)benzo[d]oxazol-5-yl)isobutyramide | ++++ |
| 271 | N-(2-(3,5-dichlorophenyl)benzo[d]oxazol-5-yl)isobutyramide | ++ |
| 272 | (S)-2-amino-N-(2-(4-chlorophenyl)benzo[d]oxazol-5-yl)propanamide | +++ |
| 273 | N-(2-(2,3-dichlorophenyl)benzo[d]oxazol-5-yl)isobutyramide | ++++ |
| 274 | 2-(4-chlorophenyl)-N-isopropylbenzo[d]oxazole-5-carbothioamide | + |
| 275 | N-(2-(4-chlorophenyl)benzo[d]oxazol-5-yl)-2-methylpropanethioamide | ++ |
| 276 | 2-(4-chlorophenyl)benzo[d]thiazol-5-amine | ++++ |
| 277 | N-(2-(4-chlorophenyl)benzo[d]thiazol-5-yl)isobutyramide | +++ |
| 278 | 2-(4-chlorophenyl)-N-isopropyl-N-methylbenzo[d]oxazole-5-carboxamide | +++ |
| 279 | 2-(4-chlorophenyl)-N-methylbenzo[d]oxazole-5-carboxamide | +++ |
| 280 | 2-phenethylbenzo[d]oxazol-5-amine | ++++ |
| 281 | 2-(4-chlorophenyl)-5-(isopropylsulfonyl)benzo[d]oxazole | ++++ |
| 282 | 2-(2-chlorophenyl)benzo[d]thiazol-5-amine | ++++ |
| 283 | 2-(3-chlorophenyl)benzo[d]thiazol-5-amine | ++++ |
| 284 | 2-(3,4-dichlorophenyl)benzo[d]thiazol-5-amine | ++++ |
| 285 | 3-morpholino-N-(2-phenylbenzo[d]oxazol-5-yl)propanamide | + |
| 286 | 2-(benzo[d][1,3]dioxol-5-yl)-5-nitrobenzo[d]oxazole | +++ |
| 287 | methyl 4-(2-(4-chlorophenyl)benzo[d]oxazol-5-yl)benzoate | + |
| 288 | 5-bromo-2-(4-chlorophenyl)benzo[d]oxazole | ++++ |
| 289 | 4-(5-chlorobenzo[d]oxazol-2-yl)aniline | ++++ |
| 290 | 4-(6-chlorobenzo[d]oxazol-2-yl)aniline | +++ |
| 291 | 2-(4-chlorophenyl)-5-(4-morpholinophenyl)benzo[d]oxazole | ++ |
| 292 | 2-(4-chlorophenyl)-5-(3-(ethylthio)phenyl)benzo[d]oxazole | ++ |
| 293 | 2-(3-chlorophenyl)-5-(ethylsulfonyl)benzo[d]oxazole | ++++ |
| 294 | N-(2-(2-(4-chlorophenyl)benzo[d]oxazol-5-yl)phenyl)acetamide | + |
| 295 | N-(2-(2-chlorophenyl)benzo[d]thiazol-5-yl)isobutyramide | ++++ |
| 296 | N-(2-(3-chlorophenyl)benzo[d]thiazol-5-yl)isobutyramide | ++++ |
| 297 | N-(2-(3,4-dichlorophenyl)benzo[d]thiazol-5-yl)isobutyramide | ++++ |
| 298 | 2-(2-Chlorophenyl)-5-(ethylsulfonyl)benzo[d]oxazole | ++ |
| 299 | 2-(benzo[d][1,3]dioxol-5-yl)benzo[d]oxazol-5-amine | ++ |
| 300 | N-(2-(benzo[d][1,3]dioxol-5-yl)benzo[d]oxazol-5-yl)isobutyramide | +++ |
| 301 | 2-(3,4-diChlorophenyl)-5-(ethylsulfonyl)benzo[d]oxazole | ++ |
| 302 | N-(2-phenethylbenzo[d]oxazol-5-yl)isobutyramide | + |
| 303 | N-(2-(2,3-dichlorophenyl)benzo[d]thiazol-5-yl)isobutyramide | +++ |
| 304 | 2-(2,3-diChlorophenyl)-5-(ethylsulfonyl)benzo[d]oxazole | + |
| 305 | 2-(4-chlorophenyl)-5-(6-methoxypyridin-3-yl)benzo[d]oxazole | ++ |
| 306 | 2-(4-chlorophenyl)-5-(6-methoxypyridin-3-yl)benzo[d]oxazole | + |
| 307 | 2-(2,3-dichlorophenyl)benzo[d]thiazol-5-amine | +++ |
| 308 | 2-(1-phenylethyl)benzo[d]oxazol-5-amine | + |
| 309 | N-(2-(1-phenylethyl)benzo[d]oxazol-5-yl)isobutyramide | + |
| 310 | 2-(4-chlorophenyl)-5,6-methylenedioxybenzoxazole | +++ |
| 311 | N-(2-(2,5-dichlorophenyl)benzo[d]oxazol-5-yl)isobutyramide | + |
| 312 | 2-(4-chlorophenyl)benzo[d]oxazole-5-sulfonic acid | + |
| 313 | 3-(2-(4-chlorophenyl)benzo[d]oxazol-5-yl)benzoic acidd | + |
| 314 | 2-(4-chlorophenyl)-5-(6-chloropyridin-3-yl)benzo[d]oxazole | + |
| 315 | 2-(4-chlorophenyl)-5-(6-fluoropyridin-3-yl)benzo[d]oxazole | + |
| 316 | 2-(4-chlorophenyl)-5-(6-morpholinopyridin-3-yl)benzo[d]oxazole | + |
| 317 | N-(4-(5-chlorobenzo[d]oxazol-2-yl)phenyl)acetamide | +++ |
| 318 | N-(4-(5-chlorobenzo[d]oxazol-2-yl)phenyl)isobutyramide | ++ |
| 319 | N-(4-(5-chlorobenzo[d]oxazol-2-yl)phenyl)thiophene-2-carboxamide | + |
| 320 | N-(2-(4-chlorophenyl)benzo[d]oxazol-5-yl)-N-methylisobutyramide | ++ |
| 321 | 5-tert-butyl-2-(4-chlorophenyl)benzo[d]oxazole | ++++ |
| 322 | 2-(4-chlorophenyl)-N-isobutyl-N-methylbenzo[d]oxazol-5-amine | + |
| 323 | N-(2-(4-chlorophenyl)benzo[d]oxazol-5-yl)-3-methoxypropanamide | ++++ |
| 324 | 2-(3,4-dichlorophenyl)-6-nitrobenzo[d]oxazole | ++ |
| 325 | 2-(4-chlorophenyl)benzo[d]oxazole-5-sulfonamide | ++++ |

TABLE 1-continued

Compounds made by methods described herein

| Example | Chemical Name | Activity |
|---|---|---|
| 326 | 5-chloro-2-(4-chlorophenyl)-6-nitrobenzo[d]oxazole | +++ |
| 327 | 2-(4-chlorophenyl)-5-(6-methoxypyridin-2-yl)benzo[d]oxazole | + |
| 328 | 3-(2-(4-chlorophenyl)benzo[d]oxazol-5-yl)aniline | ++++ |
| 329 | 4-(2-(4-chlorophenyl)benzo[d]oxazol-5-yl)aniline | ++++ |
| 330 | 5-chloro-2-(pyridin-4-yl)benzo[d]oxazole | + |
| 331 | 6-chloro-2-(pyridin-4-yl)benzo[d]oxazole | + |
| 332 | N-(4-(6-chlorobenzo[d]oxazol-2-yl)phenyl)acetamide | +++ |
| 333 | N-(4-(6-chlorobenzo[d]oxazol-2-yl)phenyl)isobutyramide | ++ |
| 334 | N-(4-(6-chlorobenzo[d]oxazol-2-yl)phenyl)thiophene-2-carboxamide | + |
| 335 | 2-(4-chlorophenyl)-N,N-diisobutylbenzo[d]oxazol-5-amine | + |
| 336 | 4-(5-bromobenzo[d]oxazol-2-yl)aniline | ++++ |
| 337 | 4-amino-N-(4-(5-bromobenzo[d]oxazol-2-yl)phenyl)benzamide | + |
| 338 | 5-(2-(4-chlorophenyl)benzo[d]oxazol-5-yl)pyridin-2-amine | ++++ |
| 339 | 2-(4-chlorophenyl)-5-phenyl-1H-indole | + |
| 340 | N-(2-(2-chloro-4-fluorophenyl)benzo[d]oxazol-5-yl)isobutyramide | ++++ |
| 341 | N-(2-(2-chloro-6-fluorophenyl)benzo[d]oxazol-5-yl)isobutyramide | + |
| 342 | N-(2-(3-chloro-2-fluorophenyl)benzo[d]oxazol-5-yl)isobutyramide | ++++ |
| 343 | N-(2-(4-chloro-2-fluorophenyl)benzo[d]oxazol-5-yl)isobutyramide | ++++ |
| 344 | N-(2-(2-chloro-5-fluorophenyl)benzo[d]oxazol-5-yl)isobutyramide | + |
| 345 | N-(2-(4-chlorophenyl)benzo[d]oxazol-5-yl)-3,3,3-trifluoropropanamide | +++ |
| 346 | N-(2-(4-chlorophenyl)benzo[d]oxazol-5-yl)cyclopentanecarboxamide | + |
| 347 | N-(5-chloro-2-(4-chlorophenyl)benzo[d]oxazol-6-yl)isobutyramide | ++ |
| 348 | 5-nitro-2-(4-(trifluoromethoxy)phenyl)benzo[d]oxazole | ++ |
| 349 | N-(2-(tetrahydro-2H-pyran-4-yl)benzo[d]oxazol-5-yl)isobutyramide | + |
| 350 | 2-(4-(trifluoromethoxy)phenyl)benzo[d]oxazol-5-amine | ++ |
| 351 | N-(2-(3,4-dichlorophenyl)benzo[d]oxazol-5-yl)cyclopropanecarboxamide | ++++ |
| 352 | N-(2-(3,4-dichlorophenyl)benzo[d]oxazol-5-yl)-3,3,3-trifluoropropanamide | ++++ |
| 353 | N-(2-(4-chlorophenyl)benzo[d]oxazol-6-yl)cyclopropanecarboxamide | ++ |
| 354 | N-(2-(2,3-dichlorophenyl)benzo[d]oxazol-6-yl)isobutyramide | +++ |
| 355 | N-(2-(4-(trifluoromethoxy)phenyl)benzo[d]oxazol-5-yl)isobutyramide | + |
| 356 | 4-(5-(4-chlorophenyl)benzo[d]oxazol-2-yl)aniline | + |
| 357 | 2-morpholino-5-nitrobenzo[d]oxazole | + |
| 358 | N-(5-(2-(4-chlorophenyl)benzo[d]oxazol-5-yl)pyridin-2-yl)acetamide | + |
| 359 | N-(4-(5-bromobenzo[d]oxazol-2-yl)phenyl)acetamide | ++++ |
| 360 | 2-morpholinobenzo[d]oxazol-5-amine | + |
| 361 | 2-(3,4-chlorophenyl)-5,6-methylenedioxybenzoxazole | + |
| 362 | (S)-N-(2-(4-chlorophenyl)benzo[d]oxazol-5-yl)pyrrolidine-2-carboxamide | ++ |
| 363 | N-(2-(2,3-dichlorophenyl)benzo[d]oxazol-5-yl)-3,3,3-trifluoropropanamide | ++++ |
| 364 | N-(2-cyclopentylbenzo[d]oxazol-5-yl)isobutyramide | + |
| 365 | N-(4-(5-acetamidobenzo[d]oxazol-2-yl)phenyl)acetamide | + |
| 366 | 2-(furan-2-yl)-5-nitrobenzo[d]oxazole | + |
| 367 | N-(4-(2-(4-chlorophenyl)-1H-indol-5-yl)phenyl)acetamide | + |
| 368 | N-(2-(2-chloro-3-(trifluoromethyl)phenyl)benzo[d]oxazol-5-yl)isobutyramide | + |
| 369 | 2-(3,4-dichlorophenyl)benzo[d]oxazol-6-amine | ++++ |
| 370 | N-(2-(3,4-dichlorophenyl)benzo[d]oxazol-6-yl)isobutyramide | ++++ |
| 371 | 2-(benzo[d][1,3]dioxol-5-yl)-5-chloro-6-nitrobenzo[d]oxazole | +++ |
| 372 | N-(4-(5-(4-chlorophenyl)benzo[d]oxazol-2-yl)phenyl)acetamide | + |
| 373 | N-(2-(naphthalen-2-yl)benzo[d]oxazol-5-yl)acetamide | ++++ |
| 374 | N-(2-(4-acetamidophenyl)benzo[d]oxazol-5-yl)isobutyramide | + |
| 375 | N-(2-phenyl-1H-indol-6-yl)isobutyramide | + |
| 376 | 2,3-dichloro-N-(2-(2,3-dichlorophenyl)benzo[d]oxazol-5-yl)benzamide | + |
| 377 | (S)-N-(2-(4-chlorophenyl)benzo[d]oxazol-5-yl)-2-(methylamino)propanamide | +++ |
| 378 | N-(1-methyl-1H-indol-6-yl)isobutyramide | + |
| 379 | 2-(4-chlorobenzylthio)-5-nitrobenzo[d]oxazole | + |
| 380 | 2-(4-chlorobenzylthio)benzo[d]oxazol-5-amine | + |
| 381 | N2-(4-chlorobenzyl)benzo[d]oxazole-2,5-diamine | + |
| 382 | 2-(4-methylbenzylthio)-5-nitrobenzo[d]oxazole | + |
| 383 | N-(2-(4-chlorobenzylthio)benzo[d]oxazol-5-yl)isobutyramide | + |
| 384 | N-(2-(naphthalen-2-yl)benzo[d]oxazol-5-yl)isobutyramide | +++ |
| 385 | N-(2-(naphthalen-2-yl)benzo[d]oxazol-5-yl)thiophene-2-carboxamide | + |
| 386 | ethyl 2-(4-chlorophenyl)benzo[d]oxazol-5-ylcarbamate | + |
| 387 | N-(1-benzyl-1H-indol-6-yl)isobutyramide | + |
| 388 | 5-nitro-2-(thiophen-2-yl)benzo[d]oxazole | + |
| 389 | N-(1-methyl-2-phenyl-1H-indol-6-yl)isobutyramide | + |
| 390 | 5-(ethylsulfonyl)-2-(naphthalen-2-yl)benzo[d]oxazole | +++ |
| 391 | 2-(3-chloro-2-fluorophenyl)-5-(ethylsulfonyl)benzo[d]oxazole | ++ |
| 392 | 2-cyclohexyl-5-(ethylsulfonyl)benzo[d]oxazole | + |
| 393 | 2-(5-chloropyridin-2-yl)-5-(ethylsulfonyl)benzo[d]oxazole | ++ |
| 394 | 2-(benzo[d][1,3]dioxol-5-yl)-5-(ethylsulfonyl)benzo[d]oxazole | ++++ |
| 395 | 5-chloro-2-(4-(methylsulfonyl)phenyl)benzo[d]oxazole | ++ |
| 396 | N-(2-phenylbenzofuran-5-yl)isobutyramide | ++++ |
| 397 | 2-(benzo[d][1,3]dioxol-5-yl)-5-chlorobenzo[d]oxazol-6-amine | +++ |
| 398 | N-(2-(benzo[d][1,3]dioxol-5-yl)-5-chlorobenzo[d]oxazol-6-yl)isobutyramide | + |
| 399 | 2-(4-chlorophenyl)-6-(methylthio)benzo[d]thiazole | +++ |
| 400 | 2-(4-chlorophenyl)-6-(methylsulfonyl)benzo[d]oxazole | ++ |
| 401 | 2-(biphenyl-4-yl)benzo[d]oxazol-5-amine | +++ |
| 402 | 2-(quinolin-2-yl)benzo[d]oxazol-5-amine | +++ |
| 403 | 2-(quinolin-3-yl)benzo[d]oxazol-5-amine | +++ |
| 404 | 2-(6-methoxynaphthalen-2-yl)benzo[d]oxazol-5-amine | ++ |
| 405 | 2-(6-bromonaphthalen-2-yl)benzo[d]oxazol-5-amine | + |
| 406 | 2-(4-chlorophenyl)-6-(methylsulfonyl)benzo[d]thiazole | ++++ |
| 407 | S-2-(4-chlorophenyl)benzo[d]oxazol-5-yl ethanethioate | + |
| 408 | 2-phenyl-5-(3',3',3'-trifluoropropanamido)benzofuran | + |
| 409 | 2-(4-chlorophenyl)naphtho[1,2-d]oxazole | ++++ |
| 410 | N-(2-(naphthalen-1-yl)benzo[d]oxazol-5-yl)isobutyramide | + |
| 411 | N-(2-(biphenyl-4-yl)benzo[d]oxazol-5-yl)isobutyramide | + |
| 412 | N-(2-(6-methoxynaphthalen-2-yl)benzo[d]oxazol-5-yl)isobutyramide | + |
| 413 | N-(2-(6-bromonaphthalen-2-yl)benzo[d]oxazol-5-yl)isobutyramide | + |
| 414 | 2-(4'-chlorophenyl)-5-isobutyramido-benzofuran | + |
| 415 | N-(2-(quinolin-3-yl)benzo[d]oxazol-5-yl)isobutyramide | ++++ |
| 416 | N-(2-(quinolin-2-yl)benzo[d]oxazol-5-yl)isobutyramide | ++++ |
| 417 | 1-(2-(4-chlorophenyl)benzo[d]oxazol-5-yl)propan-1-one | ++++ |
| 418 | 5-(ethylsulfonyl)-2-(5-methylthiophen-2-yl)benzo[d]oxazole | ++++ |

TABLE 1-continued

Compounds made by methods described herein

| Example | Chemical Name | Activity |
|---|---|---|
| 419 | N-(2-(furan-2-yl)benzo[d]oxazol-5-yl)isobutyramide | ++++ |
| 420 | 1-(2-(4-chlorophenyl)benzo[d]oxazol-5-yl)ethanone | ++++ |
| 421 | 2-(4-cyclohexylphenyl)benzo[d]oxazol-5-amine | ++++ |
| 422 | 5-(ethylsulfonyl)-2-(quinolin-2-yl)benzo[d]oxazole | ++++ |
| 423 | 5-(ethylsulfonyl)-2-(quinolin-3-yl)benzo[d]oxazole | ++++ |
| 424 | 2-(6-bromonaphthalen-2-yl)-5-(ethylsulfonyl)benzo[d]oxazole | + |
| 425 | 2-(4-cyclohexylphenyl)-5-(ethylsulfonyl)benzo[d]oxazole | + |
| 426 | 2-(biphenyl-4-yl)-5-(ethylsulfonyl)benzo[d]oxazole | + |
| 427 | 5-(ethylsulfonyl)-2-(naphthalen-1-yl)benzo[d]oxazole | + |
| 428 | 5-amino-2-(5,6-dichlorobenzo[d]oxazol-2-yl)phenol | +++ |
| 429 | 5-(ethylsulfonyl)-2-(thiophen-2-yl)benzo[d]oxazole | ++ |
| 430 | N-(2-(4-cyclohexylphenyl)benzo[d]oxazol-5-yl)isobutyramide | + |
| 431 | 5-(ethylsulfonyl)-2-(6-fluoronaphthalen-2-yl)benzo[d]oxazole | + |
| 432 | 2-(benzo[b]thiophen-5-yl)-5-(ethylsulfonyl)benzo[d]oxazole | ++++ |
| 433 | N-(4-(5,6-dimethylbenzo[d]oxazol-2-yl)-3-hydroxyphenyl)acetamide | ++ |
| 434 | 2-(3,4-dichlorophenyl)-5-(isopropylsulfonyl)benzo[d]oxazole | +++ |
| 435 | N-(4-(5,6-dimethylbenzo[d]oxazol-2-yl)-3-hydroxyphenyl)acetamide | ++ |
| 436 | 5-(ethylsulfonyl)-2-(3-methylthiophen-2-yl)benzo[d]oxazole | ++ |
| 437 | 2-(5-(ethylsulfonyl)benzo[d]oxazol-2-yl)naphthalen-1-ol | ++++ |
| 438 | 2-(2,2-difluorobenzo[d][1,3]dioxol-5-yl)-5-(ethylsulfonyl)benzo[d]oxazole | + |
| 439 | 2-(4'-chlorophenyl)-5-(N,N-diethylsulfonamidyl)-benzoxazole | + |
| 440 | 4-(5,6-dichlorobenzo[d]oxazol-2-yl)aniline | ++++ |
| 441 | 5-(ethylsulfonyl)-2-(5-methylfuran-2-yl)benzo[d]oxazole | +++ |
| 442 | N-(4-(naphtho[1,2-d]oxazol-2-yl)phenyl)isobutyramide | +++ |
| 443 | 5-(ethylsulfonyl)-2-(4-methylthiophen-2-yl)benzo[d]oxazole | ++++ |
| 444 | 5-(ethylsulfonyl)-2-(5,6,7,8-tetrahydronaphthalen-2-yl)benzo[d]oxazole | +++ |
| 445 | 2-(benzofuran-5-yl)-5-(ethylsulfonyl)benzo[d]oxazole | ++++ |
| 446 | 2-(4'-chlorophenyl)-5-(1'-hydroxyethyl)-benzoxazole | ++++ |
| 447 | 5-Amino-2-(5-(ethylsulfonyl)benzo[d]oxazol-2-yl)phenol | ++ |
| 448 | 2-(Naphthalen-2-yl)-5-(trifluoromethoxy)benzo[d]oxazole | ++++ |
| 449 | 2-(Naphthalen-2-yl)benzo[d]oxazole-5-carboxylic acid | ++++ |
| 450 | 2-(Naphthalen-2-yl)benzo[d]oxazole | ++++ |
| 451 | 5-tert-Butyl-2-(naphthalen-2-yl)benzo[d]oxazole | + |
| 452 | 5,6-Difluoro-2-(naphthalen-2-yl)benzo[d]oxazole | ++++ |
| 453 | 1-(2'-(3''',4''-Dichlorophenyl)benzo[d]oxazol-5'-yl)ethanone | ++++ |
| 454 | N-(4-(Benzo[d]oxazol-2-yl)phenyl)isobutyramide | ++++ |
| 455 | Methyl 2-(4-chlorophenyl)benzo[d]oxazol-5-yl)ethyl)phosphinate | ++++ |
| 456 | 2-(3',4'-Dichlorophenyl)-5-(1'-hydroxyethyl)-benzoxazole | ++++ |
| 457 | 2-(4-Chlorophenyl)-6-methylbenzo[d]oxazole | ++++ |
| 458 | 5-Methyl-2-(naphthalen-2-yl)benzo[d]oxazole | ++++ |

TABLE 2

Compounds made by analogues methods to those described herein, or by literature methods known or adapted by the persons skilled in the art.

| 459 | Chemical Name | Activity |
|---|---|---|
| 460 | 2-(4-((4-chlorophenylthio)methyl)phenyl)-1H-benzo[d]imidazole | + |
| 461 | 2-((2,4-dichlorophenoxy)methyl)-1H-benzo[d]imidazole | +++ |
| 462 | 2,6-dichloro-N-(5-methylbenzo[d]thiazol-2-ylcarbamoyl)benzamide | + |
| 463 | 2-(thiophen-2-yl)-1H-benzo[d]imidazole | + |
| 464 | N-(3-(1H-benzo[d]imidazol-2-yl)phenyl)benzamide | + |
| 465 | 1-(2-chlorobenzyl)-2-((2,4-dichlorophenoxy)methyl)-1H-benzo[d]imidazole | + |
| 466 | 1-(2-methylbenzo[d]oxazol-6-yl)-3-phenylurea | + |
| 467 | 1-methyl-3-(2-methylbenzo[d]oxazol-6-yl)urea | + |
| 468 | 2-chloro-N-(2-methylbenzo[d]oxazol-6-ylcarbamoyl)benzamide | + |
| 469 | 2-(4-chlorophenyl)-5-(piperidin-1-ylmethyl)benzo[d]oxazole | + |
| 470 | 2-(4-methoxyphenyl)-1H-benzo[d]imidazole | ++ |
| 471 | 2-(phenoxymethyl)-1H-benzo[d]imidazole | ++ |
| 472 | 1-methyl-2-(4-nitrophenyl)-1H-benzo[d]imidazole | + |
| 473 | 2-((4-methoxyphenoxy)methyl)-1H-benzo[d]imidazole | ++ |
| 474 | 1-methyl-2-(phenoxymethyl)-1H-benzo[d]imidazole | + |
| 475 | 4-(1H-benzo[d]imidazol-2-yl)aniline | + |
| 476 | 2,2'-(1,4-phenylene)bis(1H-benzo[d]imidazol-6-amine) | + |
| 477 | 2-(4-nitrophenyl)benzo[d]oxazole | + |
| 478 | 4-(benzo[d]oxazol-2-yl)aniline | ++ |
| 479 | 5-(benzo[d]thiazol-2-yl)-2-methylaniline | ++ |
| 480 | 2-(3,4-dichlorophenyl)benzo[d]oxazol-5-amine | ++ |
| 481 | 2-(4-ethylphenyl)benzo[d]oxazol-5-amine | ++ |
| 482 | 2-(3,5-dimethylphenyl)benzo[d]oxazol-5-amine | + |
| 483 | 2-(benzo[d]thiazol-2-yl)phenol | + |
| 484 | 5-amino-2-(benzo[d]oxazol-2-yl)phenol | ++ |
| 485 | 4-(5,6-dimethylbenzo[d]oxazol-2-yl)aniline | ++ |
| 486 | 4-(benzo[d]oxazol-2-yl)-N,N-dimethylaniline | + |
| 487 | 2-(4-aminophenyl)-1H-benzo[d]imidazol-6-amine | + |
| 488 | 2-(4-chlorophenyl)benzo[d]oxazol-5-amine | ++ |
| 489 | 2-(3-chlorophenyl)benzo[d]oxazol-5-amine | ++ |
| 490 | 2-(4-aminophenyl)-1-methyl-1H-benzo[d]imidazol-5-amine | + |
| 491 | 2-(4-(dimethylamino)phenyl)benzo[d]oxazol-5-amine | ++ |
| 492 | 5-nitro-2-phenylbenzo[d]oxazole | ++ |
| 493 | N-(4-(1H-benzo[d]imidazol-2-yl)phenyl)-2-(thiophen-2-yl)acetamide | + |
| 494 | N-(4-(1H-benzo[d]imidazol-2-yl)phenyl)-3,4-dimethoxybenzamide | + |
| 495 | 2-((4-chlorophenoxy)methyl)-1H-benzo[d]imidazole | + |
| 496 | 4-(5-aminobenzo[d]oxazol-2-yl)phenol | ++ |
| 497 | N-(4-(1H-benzo[d]imidazol-2-yl)phenyl)benzamide | + |
| 498 | 4-(1H-benzo[d]imidazol-2-yl)-N,N-dimethylaniline | + |
| 499 | 2-(methoxymethyl)-1H-benzo[d]imidazole | + |
| 500 | N-(2-(1H-benzo[d]imidazol-2-yl)phenyl)-2,4-dichlorobenzamide | + |
| 501 | N-(4-(1H-benzo[d]imidazol-2-yl)phenyl)-2-phenylacetamide | + |
| 502 | 3-(5-ethylbenzo[d]oxazol-2-yl)aniline | ++ |
| 503 | N-(3-(1H-benzo[d]imidazol-2-yl)phenyl)acetamide | + |
| 504 | N-(3-(1H-benzo[d]imidazol-2-yl)phenyl)thiophene-2-carboxamide | + |
| 505 | 5-methyl-2-(4-nitrophenyl)benzo[d]oxazole | ++ |
| 506 | 4-(6-methylbenzo[d]oxazol-2-yl)aniline | + |
| 507 | 2-(2-fluorophenyl)-1H-benzo[d]imidazole | ++ |
| 508 | 2-(furan-2-yl)-5-nitro-1H-benzo[d]imidazole | + |
| 509 | N,N-dimethyl-4-(5-nitro-1H-benzo[d]imidazol-2-yl)aniline | ++ |
| 510 | 2-(furan-2-yl)-1H-benzo[d]imidazol-5-amine dihydrochloride | + |
| 511 | N-(2-(1H-benzo[d]imidazol-2-yl)phenyl)-4-(pyrrolidin-1-ylsulfonyl)benzamide | + |
| 512 | 2-(4-methoxyphenyl)benzo[d]oxazol-5-amine | + |
| 513 | N-(3-(benzo[d]thiazol-2-yl)phenyl)acetamide | + |
| 514 | 2-(3-chlorophenyl)-1H-benzo[d]imidazole | + |
| 515 | 2-(3,4-dimethoxyphenyl)benzo[d]oxazol-5-amine | ++ |
| 516 | 2-(4-(piperidin-1-ylsulfonyl)phenyl)benzo[d]thiazole | ++ |
| 517 | N-(2-(2,4-dichlorophenyl)benzo[d]oxazol-5-yl)acetamide | ++ |
| 518 | 4-(5,7-dichlorobenzo[d]oxazol-2-yl)aniline | ++ |
| 519 | N-(2-(3-chloro-4-methoxyphenyl)benzo[d]oxazol-5-yl)acetamide | ++ |
| 520 | 2-(3,4-dimethoxyphenyl)-5-nitro-1H-benzo[d]imidazole | + |
| 521 | 2-(3,4-dimethoxyphenyl)-1-methyl-1H-benzo[d]imidazole | + |

TABLE 2-continued

Compounds made by analogues methods to those described herein, or by literature methods known or adapted by the persons skilled in the art.

| 459 | Chemical Name | Activity |
|---|---|---|
| 522 | 2-(2-methoxyphenyl)benzo[d]thiazole | + |
| 523 | 2-(4-chloro-3-nitrophenyl)benzo[d]thiazole | + |
| 524 | 2-(2-chloro-5-nitrophenyl)benzo[d]thiazole | + |
| 525 | 2-(4-fluorophenyl)-5-benzo[d]oxazole | + |
| 526 | 2-(3-chloro-4-methylphenyl)benzo[d]oxazol-5-amine | ++ |
| 527 | 2-(2-chloro-4-methylphenyl)benzo[d]oxazol-5-amine | ++ |
| 528 | 2-((4-methoxyphenoxy)methyl)-1-methyl-1H-benzo[d]imidazole | ++ |
| 529 | N-(4-(5,7-dimethylbenzo[d]oxazol-2-yl)phenyl)acetamide | ++ |
| 530 | 2-(((1H-benzo[d]imidazol-2-yl)methylthio)-5-phenyl-1,3,4-oxadiazole | + |
| 531 | 2-(p-tolyloxymethyl)-1H-benzo[d]imidazole | ++ |
| 532 | 4-(5-methyl-1H-benzo[d]imidazol-2-yl)aniline | + |
| 533 | 5-nitro-2-m-tolylbenzo[d]oxazole | ++ |
| 534 | N-(2-(furan-2-yl)-1H-benzo[d]imidazol-5-yl)acetamide | + |
| 535 | 2-(4-methoxyphenyl)-1H-benzo[d]imidazol-5-amine | ++ |
| 536 | N-(2-(furan-2-yl)-1H-benzo[d]imidazol-5-yl)-4-methylbenzenesulfonamide | + |
| 537 | 2-(3,4-dimethoxyphenyl)-5-nitrobenzo[d]oxazole | + |
| 538 | N-(3-(6-methyl-1H-benzo[d]imidazol-2-yl)phenyl)furan-2-carboxamide | + |
| 539 | 5-chloro-2-(3-methyl-4-nitrophenyl)benzo[d]oxazole | + |
| 540 | N-(4-(1H-benzo[d]imidazol-2-yl)phenyl)benzo[d][1,3]dioxole-5-carboxamide | + |
| 541 | 2-(4-chlorophenyl)-1-methyl-1H-benzo[d]imidazole | ++ |
| 542 | N-(5-(benzo[d]thiazol-2-yl)-2-methoxyphenyl)acetamide | ++ |
| 543 | 2-(4-(methylthio)phenyl)-1H-benzo[d]imidazole | ++ |
| 544 | 2-(4-aminophenyl)benzo[d]oxazol-6-amine | ++ |
| 545 | 2-(4-(6-methylbenzo[d]thiazol-2-yl)phenylcarbamoyl)benzoic acid | + |
| 546 | (Z)-1-(benzo[d]thiazol-2-yl)-4-(1-(cyclopropylamino)ethylidene)-3-methyl-1H-pyrazol-5(4H)-one | + |
| 547 | (E)-2-styryl-1H-benzo[d]imidazole | +++ |
| 548 | 2-((2,5-dimethylphenoxy)methyl)-1H-benzo[d]imidazole | + |
| 549 | 2-(4-ethoxyphenyl)benzo[d]oxazol-5-amine | + |
| 550 | 4-amino-2-(5-aminobenzo[d]thiazol-2-yl)phenol | + |
| 551 | 4-amino-2-(5-ethylbenzo[d]oxazol-2-yl)phenol | + |
| 552 | 2-(2-phenylhydrazinyl)benzo[d]thiazole | + |
| 553 | 4-(5-ethylbenzo[d]oxazol-2-yl)aniline | ++++ |
| 554 | 2-(5-methyl-1H-benzo[d]imidazol-2-yl)aniline | +++ |
| 555 | N-(6-ethoxybenzo[d]thiazol-2-yl)benzamide | + |
| 556 | N-(4-(6-acetamido-5-chloro-1H-benzo[d]imidazol-2-yl)phenyl)acetamide | + |
| 557 | 4-(4-(1H-benzo[d]imidazol-2-yl)phenoxy)aniline | ++++ |
| 558 | 2-(biphenyl-4-yl)-1H-benzo[d]imidazole | + |
| 559 | 4-amino-2-(5,6-dimethylbenzo[d]oxazol-2-yl)phenol | +++ |
| 560 | 2-(4-chlorophenyl)-1H-benzo[d]imidazol-5-amine | +++ |
| 561 | 2-(thiophen-2-yl)-1H-naphtho[2,3-d]imidazole | +++ |
| 562 | N-(4-(1H-benzo[d]imidazol-2-yl)phenyl)furan-2-carboxamide | +++ |
| 563 | 2-(ethylthio)benzo[d]thiazol-6-amine | ++ |
| 564 | N-(4-(6-methylbenzo[d]oxazol-2-yl)phenyl)isobutyramide | + |
| 565 | 4-amino-2-(5-isopropylbenzo[d]oxazol-2-yl)phenol | +++ |
| 566 | 3-(5-chlorobenzo[d]oxazol-2-yl)-2-methylaniline | + |
| 567 | N-(benzo[d]thiazol-2-yl)-2-chloro-4-methylbenzamide | + |
| 568 | N-(5-(1H-benzo[d]imidazol-2-yl)-2-methylphenyl)-2,2,2-trifluoroacetamide | +++ |
| 569 | 2-(2-fluorophenyl)benzo[d]oxazol-5-amine | +++ |
| 570 | 2-butyl-5-(ethylsulfonyl)benzo[d]oxazole | + |
| 571 | 5-(ethylsulfonyl)-2-propylbenzo[d]oxazole | + |
| 572 | 2-ethyl-5-(ethylsulfonyl)benzo[d]oxazole | + |
| 573 | 5-(ethylsulfonyl)benzo[d]oxazole | + |
| 574 | 5-(ethylsulfonyl)benzo[d]oxazole-2-thiol | + |
| 575 | N-(3-(2-(4-chlorophenyl)benzo[d]oxazol-5-yl)phenyl)acetamide | ++++ |
| 576 | 1-(2-tert-butyl-1H-indol-5-yl)-3-ethylurea | + |
| 577 | 2-(naphthalen-1-yl)benzo[d]oxazol-5-amine | + |
| 578 | 2-(4-chlorophenyl)-5-(propylsulfonyl)benzo[d]oxazole | + |
| 579 | 2-(4-chlorophenyl)benzo[d]oxazol-6-ol | ++++ |
| 580 | N-(4-(5-Methyl-1H-benzo[d]imidazol-2-yl)phenyl)furan-2-carboxamide | +++ |
| 581 | Phenyl (2-phenyl-1H-benzo[d]imidazol-6-yl)methanone | + |
| 582 | 2-(4-Methoxyphenyl)benzo[d]thiazole | ++++ |
| 583 | 2-(4-Methoxyphenyl)benzo[d]oxazole | +++ |
| 584 | 2-(4-Methoxyphenyl)-6-nitrobenzo[d]oxazole | +++ |
| 585 | N-(4-(1H-Benzo[d]imidazol-2-yl)phenyl)thiophene-2-carboxamide | ++++ |
| 586 | 2-(4-Methoxyphenyl)-5-nitro-1H-benzo[d]imidazole | ++ |
| 587 | N-(4-(1H-Benzo[d]imidazol-2-yl)phenyl)tetrahydrofuran-2-carboxamide | +++ |
| 588 | 1-Methyl-2-p-tolyl-1H-benzo[d]imidazole | +++ |
| 589 | N-(4-(Benzo[d]oxazol-2-yl)phenyl)acetamide | +++ |
| 590 | 4-(4,6-Dimethylbenzo[d]oxazol-2-yl)aniline | ++++ |
| 591 | N-(4-(1H-Benzo[d]imidazol-2-yl)phenyl)acetamide | +++ |
| 592 | 5-(Benzo[d]thiazol-2-yl)-2-chloroaniline | ++++ |
| 593 | 4-(5-Tert-butylbenzo[d]oxazol-2-yl)aniline | +++ |
| 594 | 3-(Benzo[d]thiazol-2-yl)phenol | ++++ |
| 595 | 2-(2,4-Dichlorophenyl)benzo[d]thiazole | ++ |
| 596 | 5-(Benzo[d]thiazol-2-yl)-2-methoxyphenol | ++++ |
| 597 | 5-(Benzo[d]thiazol-2-yl)-2-methoxyaniline | +++ |
| 598 | 2-(3-Chlorophenyl)benzo[d]oxazol-6-amine | +++ |
| 599 | 2-(3-Methyl-4-nitrophenyl)benzo[d]thiazole | ++++ |
| 600 | 2-(3-Methoxyphenyl)-1H-benzo[d]imidazole | ++ |
| 601 | 4-(Benzo[d]thiazol-2-yl)aniline | +++ |
| 602 | 3-(Benzo[d]thiazol-2-yl)aniline | +++ |
| 603 | 2-(3,4-Dimethylphenyl)benzo[d]oxazol-5-amine | +++ |
| 604 | 6-Nitro-2-phenyl-1H-benzo[d]imidazole | +++ |
| 605 | 5-Methyl-2-(4-nitrophenyl)-1H-benzo[d]imidazole | +++ |
| 606 | 2-(3-Methoxyphenyl)benzo[d]thiazole | +++ |
| 607 | 2-(3-Methyl-4-nitrophenyl)benzo[d]oxazole | ++++ |
| 608 | 2-(Benzo[d][1,3]dioxol-5-yl)benzo[d]thiazole | ++++ |
| 609 | 4-(5-Sec-butylbenzo[d]oxazol-2-yl)aniline | +++ |
| 610 | 5-Amino-2-(5,6-dimethylbenzo[d]oxazol-2-yl)phenol | ++++ |
| 611 | 6-Methyl-2-(4-(trifluoromethyl)phenyl)benzo[d]oxazole | +++ |
| 612 | 5-Methyl-2-(thiophen-2-yl)benzo[d]oxazole | ++ |
| 613 | 2-p-Tolyl-1H-benzo[d]imidazole | +++ |
| 614 | 2-(Benzo[d][1,3]dioxol-5-yloxy)-N-(benzo[d]thiazol-2-yl)acetamide | + |
| 615 | 1-ethyl-2-methyl-N-phenyl-1H-benzo[d]imidazole-5-carboxamide | ++++ |
| 616 | N-(benzo[d]thiazol-2-yl)-2-bromobenzamide | ++++ |
| 617 | 2-(benzo[d]thiazol-2-ylthio)-1-(piperidin-1-yl)ethanone | ++++ |
| 618 | N-(benzo[d][1,3]dioxol-5-yl)-3-chlorobenzo[b]thiophene-2-carboxamide | ++++ |
| 619 | 5-(benzo[d]oxazol-2-yl)-2-methoxyaniline | ++++ |
| 620 | 5-(1H-benzo[d]imidazol-2-yl)-2-methylaniline | ++++ |
| 621 | 3-chloro-N-(2-fluorophenyl)benzo[b]thiophene-2-carboxamide | ++++ |
| 622 | 3-(5-chlorobenzo[d]oxazol-2-yl)aniline | ++++ |
| 623 | N-(3-(5,6-dimethylbenzo[d]oxazol-2-yl)phenyl)furan-2-carboxamide | ++++ |
| 624 | N-(4-(1H-benzo[d]imidazol-2-yl)phenyl)-3-methylbutanamide | ++++ |
| 625 | 5-(5-ethylbenzo[d]oxazol-2-yl)-2-methylaniline | ++++ |
| 626 | N-(benzo[d]thiazol-2-yl)benzofuran-2-carboxamide | ++++ |
| 627 | 2-chloro-5-(5,7-dimethylbenzo[d]oxazol-2-yl)aniline | ++++ |
| 628 | 3-amino-N-(4-fluorophenyl)-6,7-dihydro-5H-cyclopenta[e]thieno[2,3-b]pyridine-2-carboxamide | ++++ |
| 629 | 2-bromo-N-(6-fluorobenzo[d]thiazol-2-yl)benzamide | ++++ |
| 630 | 3-(5-methoxybenzo[d]oxazol-2-yl)aniline | ++++ |
| 631 | N-(4-(1H-benzo[d]imidazol-2-yl)phenyl)-2-methylbutanamide | ++++ |
| 632 | 6-methyl-2-(5-methyl-1H-benzo[d]imidazol-2-yl)thieno[2,3-b]pyridin-3-amine | ++++ |
| 633 | 2-(phenoxymethyl)benzo[d]thiazole | +++ |
| 634 | 1-ethyl-2-methyl-5-phenyl-1H-benzo[d]imidazole | +++ |
| 635 | 2-methyl-5-(6-methylbenzo[d]oxazol-2-yl)aniline | +++ |
| 636 | 2-chloro-5-(5-methylbenzo[d]oxazol-2-yl)aniline | +++ |
| 637 | 1-(benzo[d]thiazol-2-yl)-3-p-tolylurea | +++ |
| 638 | N-(4-(6-methylbenzo[d]thiazol-2-yl)phenyl)nicotinamide | +++ |
| 639 | 2-(quinolin-2-yl)benzo[d]thiazole | +++ |
| 640 | 2-(4-methoxybenzylthio)-1H-benzo[d]imidazole | +++ |
| 641 | 2-chloro-N-(4-(oxazolo[4,5-b]pyridin-2-yl)phenyl)benzamide | +++ |
| 642 | N-(3-(5-ethylbenzo[d]oxazol-2-yl)phenyl)acetamide | +++ |
| 643 | 4-(6-methylbenzo[d]thiazol-2-yl)phenol | +++ |
| 644 | N-(3-(5-methylbenzo[d]oxazol-2-yl)phenyl)propionamide | +++ |
| 645 | 2-(3-fluoro-4-methoxybenzylthio)-1-methyl-1H-benzo[d]imidazole | +++ |
| 646 | 4-chloro-3-(5,6-dimethylbenzo[d]oxazol-2-yl)aniline | +++ |

TABLE 2-continued

Compounds made by analogues methods to those described herein, or by literature methods known or adapted by the persons skilled in the art.

| 459 | Chemical Name | Activity |
|---|---|---|
| 647 | 3-(benzo[d]thiazol-2-yl)-N-(pyridin-4-ylmethyl)aniline | +++ |
| 648 | N-(1H-benzo[d]imidazol-2-yl)-2-methylbenzamide | +++ |
| 649 | 2-(4-bromo-3-methylphenyl)benzo[d]oxazol-5-amine | +++ |
| 650 | 3-amino-4,6-dimethyl-N-m-tolylthieno[2,3-b]pyridine-2-carboxamide | +++ |
| 651 | N-(4-(benzo[d]thiazol-2-yl)phenyl)isobutyramide | +++ |
| 652 | N-(6-methylbenzo[d]thiazol-2-yl)furan-2-carboxamide | +++ |
| 653 | 5-(1H-benzo[d]imidazol-2-yl)-2-chloroaniline | +++ |
| 654 | 2-(4H-1,2,4-triazol-3-ylthio)-N-(4-(6-methylbenzo[d]thiazol-2-yl)phenyl)acetamide | +++ |
| 655 | 4-(4-(1H-benzo[d]imidazol-2-yl)phenylcarbamoyl)phenyl acetate | +++ |
| 656 | 3,5,6-trimethyl-N-(pyridin-4-ylmethyl)benzofuran-2-carboxamide | +++ |
| 657 | 2-ethoxy-N-(4-(6-methylbenzo[d]thiazol-2-yl)phenyl)acetamide | +++ |
| 658 | N-(6-fluorobenzo[d]thiazol-2-yl)thiophene-2-carboxamide | +++ |
| 659 | 1-(1H-benzo[d]imidazol-2-yl)-3-methyl-4-phenyl-1H-pyrazol-5-amine | +++ |
| 660 | 3-ethoxy-N-(4-(6-methylbenzo[d]thiazol-2-yl)phenyl)propanamide | +++ |
| 661 | N-(4-(benzo[d]thiazol-2-yl)phenyl)cyclopropanecarboxamide | +++ |
| 662 | N-(4-(5-methylbenzo[d]oxazol-2-yl)phenyl)acetamide | +++ |
| 663 | N-(2-bromo-4-methylphenyl)-2-(1H-indol-3-yl)-2-oxoacetamide | +++ |
| 664 | 4-(6-methylbenzo[d]thiazol-2-yl)aniline | ++ |
| 665 | N-phenethylbenzofuran-2-carboxamide | ++ |
| 666 | 4-chloro-N-((1-methyl-1H-benzo[d]imidazol-2-yl)methyl)aniline | ++ |
| 667 | N-(4-(benzo[d]thiazol-2-yl)phenyl)propionamide | ++ |
| 668 | N-(2-m-tolylbenzo[d]oxazol-5-yl)propionamide | ++ |
| 669 | N-(1-methyl-1H-benzo[d]imidazol-2-yl)benzimidamide | ++ |
| 670 | 4-methyl-N-(1-methyl-1H-benzo[d]imidazol-5-yl)benzamide | ++ |
| 671 | N-(benzo[d]thiazol-2-yl)-5-bromo-2-chlorobenzamide | ++ |
| 672 | N-(4-(6-methylbenzo[d]oxazol-2-yl)phenyl)thiophene-2-carboxamide | ++ |
| 673 | 3-amino-N-(2-fluorophenyl)-6,7-dihydro-5H-cyclopenta[e]thieno[2,3-b]pyridine-2-carboxamide | ++ |
| 674 | (3-(benzofuran-2-yl)-1-phenyl-1H-pyrazol-4-yl)methanol | ++ |
| 675 | 2-(4-methoxyphenyl)-5-methylbenzo[d]oxazole | ++ |
| 676 | 4-ethoxy-N-((1-methyl-1H-benzo[d]imidazol-2-yl)methyl)aniline | ++ |
| 677 | N-(2-chloro-5-(5-methylbenzo[d]oxazol-2-yl)phenyl)furan-2-carboxamide | ++ |
| 678 | N-(4-methyl-6,7-dihydro-5H-cyclopenta[d]pyrimidin-2-yl)benzo[d]oxazol-2-amine | ++ |
| 679 | N-(1H-benzo[d]imidazol-2-yl)-3-chlorobenzamide | ++ |
| 680 | N-(4-(benzo[d]thiazol-2-yl)phenyl)tetrahydrofuran-2-carboxamide | ++ |
| 681 | 1-(2-(benzo[d]oxazol-2-ylamino)-4,6-dimethylpyrimidin-5-yl)ethanone | ++ |
| 682 | N-(4-methylpyrimidin-2-yl)benzo[d]oxazol-2-amine | ++ |
| 683 | N-(6-(N,N-dimethylsulfamoyl)benzo[d]thiazol-2-yl)thiophene-2-carboxamide | ++ |
| 684 | 5-bromo-N-(4-hydroxy-3-(5-methylbenzo[d]oxazol-2-yl)phenyl)nicotinamide | ++ |
| 685 | 2-(1H-1,2,4-triazol-3-ylthio)-N-(4-(benzo[d]thiazol-2-yl)phenyl)acetamide | ++ |
| 686 | 5-(5-methoxybenzo[d]oxazol-2-yl)-2-methylaniline | ++ |
| 687 | N-(6-(N-methylsulfamoyl)benzo[d]thiazol-2-yl)thiophene-2-carboxamide | ++ |
| 688 | 2-chloro-N-(4-(5-methylbenzo[d]thiazol-2-yl)phenyl)-5-(4H-1,2,4-triazol-4-yl)benzamide | ++ |
| 689 | N-(2-fluorophenyl)-2-(1H-indol-3-yl)-2-oxoacetamide | ++ |
| 670 | N-(2,3-dihydrobenzo[b][1,4]dioxin-6-yl)-2-(1H-indol-3-yl)-2-oxoacetamide | ++ |

Experimental

HPLC-UV-MS was performed on a Gilson 321 HPLC with detection performed by a Gilson 170 DAD and a Finnigan AQA mass spectrometer operating in electrospray ionisation mode. The HPLC column used is a Phenomenex Gemini C18 150×4.6 mm. Preparative HPLC was performed on a Gilson 321 with detection performed by a Gilson 170 DAD. Fractions were collected using a Gilson 215 fraction collector. The preparative HPLC column used is a Phenomenex Gemini C18 150×10 mm and the mobile phase is acetonitrile/water.

$^1$H NMR spectra were recorded on a Bruker instrument operating at 300 MHz. NMR spectra were obtained as CDCl$_3$ solutions (reported in ppm), using chloroform as the reference standard (7.25 ppm) or DMSO-D$_6$ (2.50 ppm). When peak multiplicities are reported, the following abbreviations are used s (singlet), d (doublet), t (triplet), m (multiplet), br (broadened), dd (doublet of doublets), dt (doublet of triplets), td (triplet of doublets). Coupling constants, when given, are reported in Hertz (Hz). Column chromatography was performed either by flash chromatography (40-65 µm silica gel) or using an automated purification system (SP1™ Purification System from Biotage®). Reactions in the microwave were done in an Initiator 8™ (Biotage). The abbreviations used are DMSO (dimethylsulfoxide), HATU (O-(7-azabenzotriazol-1-yl)-N,N,N',N'-tetramethyluronium hexafluorophosphate), HCl (hydrochloric acid), MgSO$_4$ (magnesium sulfate), NaOH (sodium hydroxide), Na$_2$CO$_3$ (sodium carbonate), NaHCO$_3$ (sodium bicarbonate), STAB (sodium triacetoxyborohydride), THF (tetrahydrofuran).

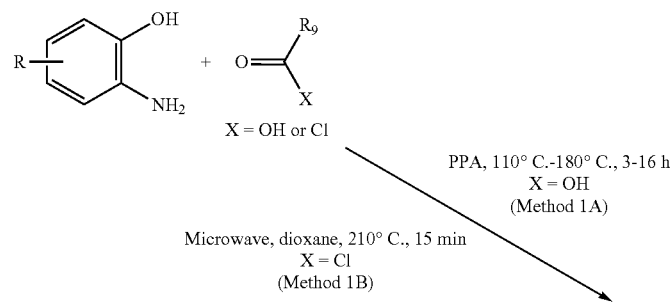

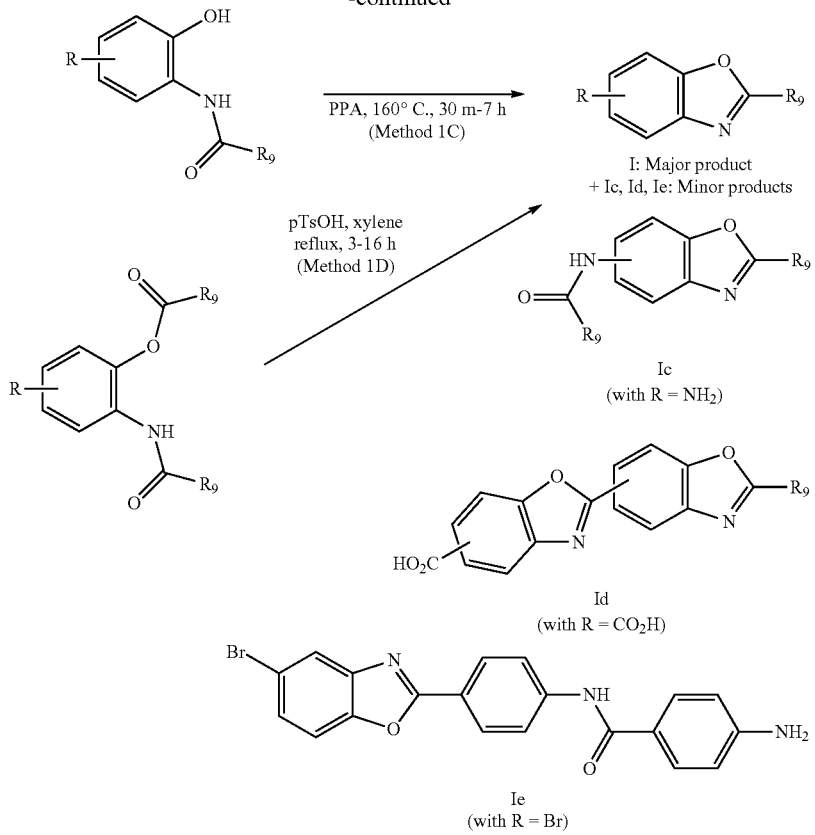

Method 1A (Compounds I)

2-Phenylbenzo[d]oxazol-5-amine

To polyphosphoric acid at 110° C. were added simultaneously 2,4-diaminophenol dihydrochloride (7.88 g, 40 mmol) and benzoic acid (4.88 g, 40 mmol). The resulting mixture was then heated to 180° C. for 3 h. The solution was then poured into water. The resulting precipitate was collected by filtration and washed with saturated sodium bicarbonate solution. The crude product was recrystallised from ethanol/water to afford 8.15 g (97%) of the title compound (LCMS RT=5.17 min, MH$^+$ 211.1)

$^1$H NMR (DMSO): 8.15-8.12 (2H, m), 7.60-7.56 (3H, m), 7.42 (1H, d, J 8.7 Hz), 6.89 (1H, d, J 2.1 Hz), 6.68 (1H, dd, J 8.6 2.2 Hz), 5.12 (2H, s)

All compounds below were prepared following the same general method and purified either by trituration, recrystallisation or column chromatography.

2-(4-(Trifluoromethyl)phenyl)benzo[d]oxazol-5-amine

LCMS RT=8.98 min, MH$^+$ 279.0; $^1$H NMR (DMSO): 8.26 (2H, d, J 8.2 Hz), 7.88 (2H, d, J 8.3 Hz), 7.40 (1H, d, J 8.7 Hz), 6.84 (1H, d, J 2.1 Hz), 6.66 (1H, dd, J 8.8 2.2 Hz), 5.13 (2H, s)

2-(4-(Diethylamino)phenyl)benzo[d]oxazol-5-amine

LCMS RT=8.98 min, MH$^+$ 282.2; $^1$H NMR (DMSO): 7.89 (2H, d, J 9.1 Hz), 7.30 (1H, d, J 8.5 Hz), 6.80-6.76 (3H, m), 6.54 (1H, dd, J 8.8 2.2 Hz), 4.99 (2H, s), 3.42 (2H, q, J 7.1 Hz), 1.14 (3H, q, J 7.1 Hz)

2-(Pyridin-3-yl)benzo[d]oxazol-5-amine

LCMS RT=6.42 min, MH$^+$ 212.2; NMR (DMSO): 9.29 (1H, d, J 1.9 Hz), 8.77 (1H, dd, J 4.8 1.4 Hz), 8.48-8.44 (1H, m), 7.62 (1H; dd, J 9.0 4.8 Hz), 7.46 (1H, d, J 8.8 Hz), 6.91 (1H, d, J 2.0 Hz), 6.71 (1H, dd, J 8.7 2.1 Hz), 5.18 (2H, s)

2-(5-Nitrobenzo[d]oxazol-2-yl)phenol

LCMS RT=6.94 min; $^1$H NMR (DMSO): 10.91 (1H, s), 8.74 (1H, d, J 2.3 Hz), 8.37 (1H, dd, J 9.0 2.4 Hz), 8.11-8.04 (2H, m), 7.60-7.55 (1H, m), 7.18-7.08 (2H, m)

2-(5-Aminobenzo[d]oxazol-2-yl)phenol

LCMS RT=6.08 min, MH$^+$ 227.2; $^1$H NMR (DMSO): 11.46 (1H, s), 8.02 (1H, dd, J 7.8 1.6 Hz), 7.58-7.53 (2H, m), 7.18-7.10 (2H, m), 6.96 (1H, d, J 2.1 Hz), 6.77 (1H, dd, J 8.7 2.2 Hz), 5.29 (2H, s)

3-(5-Propylbenzo[d]oxazol-2-yl)benzoic acid

LCMS RT=4.58 min, MH$^+$ 282.1; $^1$H NMR (DMSO): 13.44 (1H, s), 8.78 (1H, s), 8.47 (1H, d, J 8.0 Hz), 8.22 (1H, d, J 8.4 Hz), 7.84-7.74 (2H, m), 7.70 (1H, s), 7.35 (1H, d, J 9.0 Hz), 2.78-2.73 (2H, m), 1.71 (2H, q, J 7.6 Hz), 0.98 (3H, d, J 7.2 Hz)

5-Amino-2-(5-aminobenzo[d]oxazol-2-yl)phenol

LCMS RT=5.24 min, MH$^+$ 242.2; $^1$H NMR (DMSO): 11.40 (1H, s), 7.63 (1H, d, J 8.6 Hz), 7.40 (1H, d, J 8.7 Hz), 6.83 (1H, d, J 2.1 Hz), 6.63 (1H, dd, J 8.6 2.3 Hz), 6.31 (1H, d, J 8.4 2.2 Hz), 6.22 (1H, d, J 1.9 Hz), 6.05 (2H, s), 5.15 (2H, s)

5-(Ethylsulfonyl)-2-phenylbenzo[d]oxazole

LCMS RT=5.94 min, MH$^+$ 288.1; $^1$H NMR (DMSO): 8.32 (1H, d, J 1.3 Hz), 8.26 (2H, dd, J 6.4 1.6 Hz), 8.10 (1H, d, J 8.5 Hz), 7.97 (1H, dd, J 8.5 1.7 Hz), 7.72-7.64 (3H, m), 3.43-3.38 (2H, m), 1.14 (3H, t, J 7.4 Hz)

2,5-Diphenylbenzo[d]oxazole

LCMS RT=9.41 min, MH$^+$ 271.9; $^1$H NMR (DMSO): 8.26-8.23 (2H, m), 8.08 (1H, d, J 1.3 Hz), 7.89 (1H, d, J 8.5 Hz), 7.77-7.72 (3H, m), 7.68-7.61 (3H, m), 7.51 (2H, t, J 7.7 Hz), 7.43-7.38 (1H, m)

2-Phenylnaphtho[1,2-d]oxazole

LCMS RT=8.75 min, MH$^+$ 246.2; $^1$H NMR (DMSO): 8.48 (1H, d, J 8.1 Hz), 8.32-8.27 (2H, m), 8.14 (1H, d, J 8.1 Hz), 8.01 (2H, s), 7.78-7.72 (1H, m), 7.68-7.60 (4H, m)

2-Phenylbenzo[d]oxazole-5-carboxylic acid

LCMS RT=4.41 min, MH$^+$ 240.1; $^1$H NMR (DMSO): 13.00 (1H, br), 8.33 (1H, dd, J 1.6 0.5 Hz), 8.26-8.23 (2H, m), 8.06 (1H, dd, J 8.6 1.7 Hz), 7.91 (1H, dd, J 8.5 0.5 Hz), 7.72-7.62 (3H, m)

2-(4-Propylphenyl)benzo[d]oxazole-5-carboxylic acid $^1$H NMR (DMSO): 13.10 (1H, br), 8.30 (1H, dd, J 1.5 0.4 Hz), 8.15 (2H, d, J 8.3 Hz), 8.04 (1H, dd, J 8.6 1.7 Hz), 7.88 (1H, d, J 8.5 Hz), 7.47 (2H, d, J 8.4 Hz), 2.68 (2H, t, J 8.0 Hz), 1.70-1.62 (2H, m), 0.93 (3H, t, J 7.5 Hz)

2-(4-Propylphenyl)benzo[d]oxazole-6-carboxylic acid $^1$H NMR (DMSO): 13.10 (1H, br), 8.27 (1H, dd, J 1.5 0.5 Hz), 8.16 (2H, d, J 8.3 Hz), 8.02 (1H, dd, J 8.3 1.5 Hz), 7.88 (1H, dd, J 8.3 0.5 Hz), 7.48 (2H, d, J 8.4 Hz), 2.68 (2H, t, J 8.0 Hz), 1.72-1.58 (2H, m), 0.93 (3H, t, J 7.5 Hz)

5-Chloro-2-phenylbenzo[d]oxazole

LCMS RT=8.61 min, MH$^+$ 230.1; $^1$H NMR (DMSO): 8.21 (2H, dd, J 7.6 1.4 Hz), 7.94 (1H, d, J 2.1 Hz), 7.86 (1H, d, J 8.7 Hz), 7.72-7.60 (3H, m), 7.49 (1H, dd, J 8.7 2.1 Hz)

6-Chloro-2-phenylbenzo[d]oxazole

LCMS RT=9.00 min, MH$^+$ 230.1; $^1$H NMR (DMSO): 8.22-8.18 (2H, m), 8.02 (1H, d, J 1.9 Hz), 7.84 (1H, d, J 8.5 Hz), 7.70-7.60 (3H, m), 7.48 (1H, dd, J 8.5 2.0 Hz)

5-Tert-butyl-2-phenylbenzo[d]oxazole

LCMS RT=9.82 min, MH$^+$ 252.0; $^1$H NMR (DMSO): 7.72-7.70 (4H, m), 7.59 (2H, dt, J 7.6 1.0 Hz), 7.46-7.40 (2H, m), 1.38 (9H, s)

6-Nitro-2-phenyl benzo[d]oxazole

LCMS RT=7.30 min; NMR (DMSO): 8.77-8.76 (1H, m), 8.34 (1H, d, J 8.8 Hz), 8.27 (2H, d, J 7.7 Hz), 8.05 (1H, d, J 8.8 Hz), 7.80-7.65 (3H, m)

4-(5-Chlorobenzo[d]oxazol-2-yl)-N,N-diethylanaline

LCMS RT=10.17 min, MH$^+$ 301.1; $^1$H NMR (DMSO): 8.03 (2H, d, J 8.9 Hz), 7.82-7.76 (2H, m), 7.40 (1H, dd, J 8.6 2.0 Hz), 6.89 (2H, d, J 8.9 Hz)

4-(6-Chlorobenzo[d]oxazol-2-yl)-N,N-diethylaniline

LCMS RT=10.28 min, MH$^+$ 301.0; $^1$H NMR (DMSO): 7.95 (2H, d, J 9.1 Hz), 7.87 (1H, d, J 1.7 Hz), 7.67 (1H, d, J 8.4 Hz), 7.38 (1H, dd, J 8.4 2.1 Hz), 6.83 (2H, d, J 9.1 Hz), 3.45 (4H, q, J 7.2 Hz), 1.15 (6H, t, J 7.1 Hz)

4-(5-Tert-butylbenzo[d]oxazol-2-yl)-N,N-diethylaniline

LCMS RT=13.81 min, MH$^+$ 323.2; $^1$H NMR (DMSO): 7.94 (2H, d, J 9.3 Hz), 7.66 (1H, d, J 1.5 Hz), 7.58 (1H, d, J 8.6 Hz), 7.36 (1H, dd, J 8.6 1.9 Hz), 6.82 (2H, d, J 9.2 Hz), 3.44 (4H, q, J 7.0 Hz), 1.35 (9H, s), 1.15 (6H, t, J 7.1 Hz)

4-(Benzo[d]oxazol-2-yl)-N,N-diethylaniline

LCMS RT=10.50 min, MH$^+$ 267.0; $^1$H NMR (DMSO): 7.97 (2H, d, J 9.1 Hz), 7.71-7.64 (2H, m), 7.36-7.30 (2H, m), 6.82 (2H, d, J 9.2 Hz), 3.44 (4H, q, J 7.0 Hz), 1.15 (6H, t, J 7.1 Hz)

N,N-Diethyl-4-(5-(ethylsulfonyl)benzo[d]oxazol-2-yl)aniline

LCMS RT=7.45 min, MH$^+$ 358.9; $^1$H NMR (DMSO): 8.13 (1H, dd, J 1.3 0.4 Hz), 8.00 (2H, d, J 9.1 Hz), 7.95 (1H, dd, J 8.1 0.4 Hz), 7.83 (1H, dd, J 8.4 1.8 Hz), 6.85 (2H, d, J 9.2 Hz), 3.50-3.39 (6H, m), 1.23-1.04 (9H, m)

N,N-Diethyl-4-(5-phenylbenzo[d]oxazol-2-yl)aniline

LCMS RT=15.22 min, MH$^+$ 343.1; $^1$H NMR (DMSO): 7.99 (2H, d, J 8.9 Hz), 7.93 (1H, s), 7.77-7.71 (3H, m), 7.60 (1H, d, J 8.3 Hz), 7.52-7.46 (2H, m), 7.40-7.35 (1H, m), 6.84 (2H, d, J 9.0 Hz), 3.44 (4H, q, J 7.0 Hz), 1.15 (6H, t, J 7.1 Hz)

N,N-Diethyl-4-(naphthol-1,2-dioxazol-2-yl)aniline

LCMS RT=11.21 min, MH$^+$ 317.1; $^1$H NMR (DMSO): 8.41 (1H, d, J 8.3 Hz), 8.12-8.02 (3H, m), 7.94-7.86 (2H, m), 7.72-7.66 (1H, m), 7.60-7.55 (1H, m), 6.85 (2H, d, J 9.0 Hz), 3.44 (4H, q, J 7.0 Hz), 1.15 (6H, t, J 7.1 Hz)

2-(Pyridin-2-yl)benzo[d]oxazole

LCMS RT=5.68 min, MH$^+$ 197.0; $^1$H NMR (DMSO): 8.87 (1H, d, J 4.4 Hz), 8.41 (1H, d, J 8.0 Hz), 8.14 (1H, dt, J 7.8 1.5 Hz), 7.93 (2H, t, J 7.4 Hz), 7.73-7.69 (1H, m), 7.60-7.50 (2H, m)

2-(4-(Piperidin-1-yl)phenyl)benzo[d]oxazol-5-amine

LCMS RT=6.95 min, MH+ 206.1; ¹H NMR (DMSO): 7.92 (2H, d, J 9.0 Hz), 7.32 (1H, d, J 9.0 Hz), 7.05 (2H, d, J 9.0 Hz), 6.80 (1H, d, J 2.1 Hz), 6.58 (1H, dd, J 8.0 2.0 Hz), 5.01 (2H, s), 1.60 (6H, m)

2-(4-(4-Methylpiperazin-1-yl)phenyl)benzo[d]oxazol-5-amine

LCMS RT=5.34 min, MH+ 309.1; ¹H NMR (DMSO): 7.94 (2H, d, J 9.0 Hz), 7.33 (1H, d, J 9.0 Hz), 7.08 (2H, d, J 9.0 Hz), 6.80 (1H, d, J 2.1 Hz), 6.58 (1H, dd, J 8.0 2.0 Hz), 5.03 (2H, s), 2.60-2.57 (4H, m), 2.45-2.42 (4H, m), 2.23 (3H, s)

2-(4-(Diethylamino)phenyl)benzo[d]oxazole-5-carboxylic acid

¹H NMR (DMSO): 13.00 (1H, br), 8.17 (1H, d, J 1.5 Hz), 7.99 (2H, d, J 9.0 Hz), 7.94 (1H, dd, J 8.5 1.7 Hz), 7.77 (1H, d, J 8.4 Hz), 6.84 (2H, d, J 9.1 Hz), 3.45 (4H, q, J 7.0 Hz), 1.15 (6H, t, J 7.0 Hz)

2-Propylbenzo[d]oxazol-5-amine

LCMS RT=6.81 ruin, MH+ 177.2; ¹H NMR (DMSO): 7.26 (1H, d, J 8.6 Hz), 6.76 (1H, d, J 2.2 Hz), 6.57 (1H, dd, J 8.6 2.2 Hz), 4.98 (2H, s), 2.80 (2H, t, J 7.3 Hz), 1.81-1.70 (2H, m), 0.96 (3H, t, J 7.4 Hz)

2-p-Tolyloxazolo[5,4-b]pyridine

LCMS RT=6.72 min, MH+ 211.1; ¹H NMR (DMSO): 8.38 (1H, dd, J 5.0 1.5 Hz), 8.26 (1H, dd, J 7.9 1.6 Hz), 8.14 (2H, d, J 8.2 Hz), 7.53-7.45 (3H, m), 2.44 (3H, s)

2-p-Tolyloxazolo[4,5-b]pyridine

LCMS RT=6.12 min, MH+ 211.1; ¹H NMR (DMSO): 8.54 (1H, dd, J 4.9 1.4 Hz), 8.23 (1H, dd, J 8.2 1.4 Hz), 8.16 (2H, d, J 8.2 Hz), 7.59-7.44 (3H, m), 2.44 (3H, s)

2-(4-Morpholinophenyl)benzo[d]oxazol-5-amine

LCMS RT=5.52 min, MH+ 295.8; ¹H NMR (DMSO): 7.97 (2H, d, J 9.0 Hz), 7.33 (1H, d, J 9.0 Hz), 7.09 (2H, d, J 9.0 Hz), 6.81 (1H, d, J 2.1 Hz), 6.59 (1H, dd, J 8.0 2.0 Hz), 5.04 (2H, s), 3.77-3.74 (4H, m), 3.29-3.24 (4H, m)

5-Phenyl-2-p-tolylbenzo[d]oxazole

LCMS RT=10.00 min, MH+ 286.1; ¹H NMR (DMSO): 8.12 (2H, d, J 8.5 Hz), 8.06 (1H, d, J 1.8 Hz), 7.86 (1H, d, J 8.6 Hz), 7.77-7.70 (3H, m), 7.53-7.37 (5H, m), 2.43 (3H, s)

2-(4-Chlorophenyl)-5-phenylbenzo[d]oxazole

LCMS RT=10.54 min, MH+ 306.0; ¹H NMR (DMSO): 8.24 (2H, d, J 8.6 Hz), 8.09 (1H, d, J 1.8 Hz), 7.89 (1H, d, J 8.6 Hz), 7.77-7.70 (5H, m), 7.53-7.34 (3H, m)

2-Cyclohexyl-5-nitrobenzo[d]oxazole

LCMS RT=7.90 min, MH+ 247.3; ¹H NMR (CDCl₃): 8.62 (1H, d, J 2.2 Hz), 8.33 (1H, dd, J 8.9 2.3 Hz), 7.63 (1H, d, J 8.9 Hz), 3.11-3.01 (1H, m), 2.27-2.21 (2H, m), 1.98-1.92 (2H, m), 1.84-1.71 (3H, m), 1.57-1.37 (3H, m)

5-Tert-butyl-2-p-tolylbenzo[d]oxazole

LCMS RT=10.53 min, MH+ 266.1; ¹H NMR (DMSO): 8.08 (2H, d, J 8.2 Hz), 7.78 (1H, d, J 1.6 Hz), 7.68 (1H, d, J 8.6 Hz), 7.48 (1H, dd, J 8.7 2.0 Hz), 7.43 (2H, d, J 8.0 Hz), 2.42 (3H, s), 1.37 (9H, s)

2-p-Tolylbenzo[d]oxazole

LCMS RT=7.82 min, MH+ 210.1; ¹H NMR (DMSO): 8.11 (2H, d, J 8.2 Hz), 7.81-7.76 (2H, m), 7.46-7.40 (4H, m), 2.42 (3H, s)

2-(3-(Trifluoromethyl)phenyl)benzo[d]oxazol-5-amine

LCMS RT=6.39 min, MH+ 279.0; ¹H NMR (DMSO): 8.41 (1H, d, J 8.0 Hz), 8.37 (1H, s), 7.98 (1H, d, J 8.0 Hz), 7.84 (1H, t, J 8.0 Hz), 7.46 (1H, d, J 8.9 Hz), 6.91 (1H, d, J 1.9 Hz), 6.72 (1H, d, J 8.6 2.0 Hz), 5.18 (2H, s)

5-(Ethylsulfonyl)-2-p-tolylbenzo[d]oxazole

LCMS RT=6.46 min, MH+ 302.0; ¹H NMR (DMSO): 8.28 (1H, d, J 1.6 Hz), 8.14 (2H, d, J 8.2 Hz), 8.06 (1H, d, J 8.6 Hz), 7.94 (1H, dd, J 8.6 1.7 Hz), 7.47 (2H, d, J 8.1 Hz), 3.42-3.34 (2H, m), 2.44 (3H, s), 1.12 (3H, t, J 7.3 Hz)

2-(4-Chlorophenyl)-5-(ethylsulfonyl)benzo[d]oxazole

LCMS RT=6.63 min, MH+ 322.1; ¹H NMR (CDCl₃): 8.39 (1H, d, J 1.7 Hz), 8.27 (2H, d, J 8.7 Hz), 8.00 (1H, dd, J 8.5 1.8 Hz), 7.80 (1H, d, J 8.5 Hz), 7.60 (2H, d, J 8.6 Hz), 3.23 (2H, q, J 7.6 Hz), 1.36 (3H, t, J 7.4 Hz)

4-Nitro-2-p-tolylbenzo[d]oxazole

LCMS RT=6.97 min, MH+ 255.0; ¹H NMR (DMSO): 8.27 (1H, dd, J 8.1 0.8 Hz), 8.23 (1H, dd, J 8.2 0.8 Hz), 8.18 (2H, d, J 8.2 Hz), 7.65 (1H, t, J 8.2 Hz), 7.49 (2H, d, J 8.0 Hz), 2.45 (3H, s)

6-Nitro-2-p-tolylbenzo[d]oxazole

LCMS RT=7.83 min, MH+ 255.0; ¹H NMR (DMSO): 8.74 (1H, d, J 2.2 Hz), 8.33 (1H, dd, J 8.7 2.2 Hz), 8.17 (2H, d, J 8.2 Hz), 8.02 (1H, d, J 8.8 Hz), 7.49 (2H, d, J 7.9 Hz), 2.45 (3H, s)

2-(4-Chlorophenyl)-6-nitrobenzo[d]oxazole

LCMS RT=7.76 min; ¹H NMR (DMSO): 8.77 (1H, d, J 2.2 Hz), 8.35 (1H, dd, J 8.7 2.2 Hz), 8.27 (2H, d, J 8.2 Hz), 8.06 (1H, d, J 8.8 Hz), 7.76 (2H, d, J 7.9 Hz)

2-p-Tolyloxazolo[4,5-c]pyridine

LCMS RT=6.24 min, MH+ 211.0; ¹H NMR (DMSO): 9.11 (1H, d, J 0.9 Hz), 8.59 (1H, d, J 5.6 Hz), 8.14 (2H, d, J 8.2 Hz), 7.90 (1H, dd, J 5.6 1.0 Hz), 7.47 (2H, d, J 8.0 Hz), 2.44 (3H, s)

2-m-Tolylbenzo[d]oxazol-5-amine

LCMS RT=6.18 min, MH⁺ 225.0; ¹H NMR (DMSO): 7.97-7.91 (2H, m), 7.50-7.39 (3H, m), 6.87 (1H, d, J 2.0 Hz), 6.67 (1H, dd, J 8.7 2.2 Hz), 5.11 (2H, s), 2.42 (3H, s)

2-(3-(Dimethylamino)phenyl)benzo[d]oxazol-5-amine

LCMS RT=6.12 min, MH⁺ 254.0; ¹H NMR (DMSO): 7.48-7.31 (4H, m), 6.96-6.92 (1H, m), 6.87 (1H, d, J 2.2 Hz), 6.66 (1H, dd, J 8.6 2.2 Hz), 5.09 (2H, s), 3.00 (6H, s)

5-Bromo-2-p-tolylbenzo[d]oxazole

LCMS RT=9.41 min, MH⁺ 289.8; ¹H NMR (DMSO): 8.10 (2H, d, J 8.2 Hz), 8.04 (1H, d, J 1.9 Hz), 7.78 (1H, d, J 8.6 Hz), 7.58 (1H, dd, J 8.7 2.0 Hz), 7.45 (2H, d, J 8.0 Hz), 2.43 (3H, s)

2-o-Tolylbenzo[d]oxazol-5-amine

LCMS RT=6.16 min, MH⁺ 225.0; ¹H NMR (DMSO): 8.05 (1H, d, J 7.7 Hz), 7.53-7.37 (4H, m), 6.90 (1H, d, J 2.2 Hz), 6.68 (1H, dd, J 8.7 2.2 Hz), 5.10 (2H, s), 2.71 (3H, s)

2-(2-Chlorophenyl)benzo[d]oxazol-5-amine

LCMS RT=4.31 min, MH⁺ 245.0; ¹H NMR (DMSO): 8.10 (1H, d, J 7.3 Hz), 7.75-7.52 (3H, m), 7.45 (1H, d, J 8.6 Hz), 6.92 (1H, d, J 1.6 Hz), 6.73 (1H, dd, J 8.8 2.1 Hz), 5.16 (2H, s)

6-Bromo-2-p-tolyloxazolo[5,4-b]pyridine

LCMS RT=8.40 min, MH⁺ 288.8; ¹H NMR (DMSO): 8.59 (1H, d, J 2.1 Hz), 8.50 (1H, d, J 2.2 Hz), 8.13 (2H, d, J 8.2 Hz), 7.48 (2H, d, J 8.0 Hz)

5,6-Dimethyl-2-p-tolylbenzo[d]oxazole

LCMS RT=8.76 min, MH⁺ 238.0; ¹H NMR (DMSO): 8.06 (2H, d, J 8.2 Hz), 7.56 (2H, s), 7.41 (2H, d, J 8.2 Hz), 2.41 (3H, s), 2.35 (3H, s), 2.33 (3H, s)

2-(4-Chlorophenyl)-5,6-dimethylbenzo[d]oxazole

LCMS RT=9.07 min, MH⁺ 258.0; ¹H NMR (DMSO): 8.19 (2H, d, J 8.6 Hz), 7.69 (2H, d, J 8.6 Hz), 7.60 (2H, s), 2.38 (3H, s), 2.36 (3H, s)

2-(2,4-Dichlorophenyl)-5,6-dimethylbenzo[d]oxazole

LCMS RT=9.68 min, MH⁺ 291.9; ¹H NMR (DMSO): 8.16 (1H, d, J 8.5 Hz), 7.90 (1H, d, J 2.1 Hz), 7.69-7.61 (3H, m), 2.38 (3H, s), 2.36 (3H, s)

2-(3-Fluorophenyl)benzo[d]oxazol-5-amine

LCMS RT=9.45 min, MH⁺ 229.1; ¹H NMR (DMSO): 7.98 (1H, d, J 8.0 Hz), 7.89-7.84 (1H, m), 7.68-7.60 (1H, m), 7.48-7.42 (2H, m), 6.89 (1H, d, J 2.1 Hz), 6.71 (1H, dd, J 8.7 2.2 Hz), 5.15 (2H, s)

2-(5-Butylpyridin-2-yl)-6-nitrobenzo[d]oxazole

LCMS RT=7.34 min, MH⁺ 298.0; ¹H NMR (DMSO): 8.81 (1H, d, J 2.1 Hz), 8.71 (1H, d, J 1.5 Hz), 8.37-8.32 (2H, m), 8.08 (1H, d, J 8.8 Hz), 7.95 (1H, dd, J 8.1 2.1 Hz), 2.75 (2H, t, J 7.6 Hz), 1.70-1.59 (2H, m), 1.41-1.29 (2H, m), 0.93 (3H, t, J 7.3 Hz)

2-(4-Chlorophenyl)-5-(isopropylsulfonyl)benzo[d]oxazole

LCMS RT=6.98 min; ¹H NMR (DMSO): 8.29-8.24 (3H, m), 8.09 (1H, d, J 8.6 Hz), 7.94 (1H, dd, J 8.6 1.7 Hz), 7.74 (2H, d, J 8.6 Hz), 3.56-3.50 (1H, m), 1.19 (6H, d, J 6.8 Hz)

5-Bromo-2-(4-chlorophenyl)benzo[d]oxazole

LCMS RT=9.09 min, MH⁺ 307.9; ¹H NMR (DMSO): 8.21 (2H, d, J 8.7 Hz), 8.08 (1H, d, J 1.9 Hz), 7.80 (1H, d, J 8.7 Hz), 7.71 (2H, d, J 8.7 Hz), 7.62 (1H, dd, J 8.7 2.0 Hz)

4-(5-Chlorobenzo[d]oxazol-2-yl)aniline

LCMS RT=6.48 min, MH⁺ 244.9; ¹H NMR (DMSO): 7.86 (2H, d, J 8.5 Hz), 7.74 (1H, d, J 2.1 Hz), 7.70 (1H, d, J 8.6 Hz), 7.34 (1H, dd, J 8.8 2.1 Hz), 6.70 (2H, d, J 8.7 Hz), 6.06 (2H, s)

4-(6-Chlorobenzo[d]oxazol-2-yl)aniline

LCMS RT=6.57 min, MH⁺ 245.0; ¹H NMR (DMSO): 7.87-7.82 (3H, m), 7.66 (1H, d, J 8.5 Hz), 7.37 (1H, dd, J 8.7 2.0 Hz), 6.70 (2H, d, J 8.8 Hz), 6.04 (2H, s)

2-(3-Chlorophenyl)-5-(ethylsulfonyl)benzo[d]oxazole

LCMS RT=6.78 min; ¹H NMR (DMSO): 8.34 (1H, d, J 1.3 Hz), 8.23-8.20 (2H, m), 8.10 (1H, d, J 8.6 Hz), 7.99 (1H, dd, J 8.6 1.8 Hz), 7.80-7.76 (1H, m), 7.72-7.67 (1H, m), 3.40 (2H, q, J 7.3 Hz), 1.13 (3H, t, J 7.3 Hz)

2-(2-Chlorophenyl)-5-(ethylsulfonyl)benzo[d]oxazole

LCMS RT=6.37 min; ¹H NMR (DMSO): 8.39 (1H, d, J 1.6 Hz), 8.20 (1H, dd, J 7.6 1.7 Hz), 8.12 (1H, d, J 8.6 Hz), 8.01 (1H, dd, J 8.6 1.8 Hz), 7.78-7.60 (3H, m), 1.14 (3H, t, J 7.3 Hz)

2-(3,4-Dichlorophenyl)-5-(ethylsulfonyl)benzo[d]oxazole

LCMS RT=7.25 min; ¹H NMR (DMSO): 8.39 (1H, d, J 2.0 Hz), 8.35 (1H, d, J 1.4 Hz), 8.19 (1H, dd, J 8.4 2.0 Hz), 8.10 (1H, d, J 8.6 Hz), 7.99 (1H, dd, J 8.6 1.8 Hz), 7.94 (1H, d, J 8.4 Hz), 3.41 (2H, q, J 7.3 Hz), 1.13 (3H, t, J 7.3 Hz)

2-(2,3-Dichlorophenyl)-5-(ethylsulfonyl)benzo[d]oxazole

LCMS RT=6.80 min; ¹H NMR (DMSO): 8.42 (1H, d, J 1.8 0.6 Hz), 8.17-8.13 (2H, m), 8.05-7.96 (2H, m), 7.65 (1H, t, J 8.0 Hz), 3.41 (2H, q, J 7.3 Hz), 1.14 (3H, t, J 7.3 Hz)

2-(1-Phenylethyl)benzo[d]oxazol-5-amine

LCMS RT=5.80 min, MH⁺ 239.0; ¹H NMR (DMSO): 7.35-7.23 (6H, m), 6.80 (1H, d, J 2.1 Hz), 6.57 (1H, dd, J 8.6 2.2 Hz), 5.02 (2H, s), 4.42 (1H, q, J 7.1 Hz), 1.66 (3H, d, J 7.2 Hz)

2-(4-Chlorophenyl)benzo[d]oxazole-5-sulfonic acid

LCMS RT=4.44 min, MH+ 309.9; ¹H NMR (DMSO): 8.28 (2H, d, J 8.7 Hz), 8.03 (1H, s), 7.83-7.73 (4H, m)

5-Chloro-2-(pyridin-4-yl)benzo[d]oxazole

LCMS RT=6.51 min, MH+ 231.0; ¹H NMR (DMSO): 8.87 (2H, d, J 8.6 Hz), 8.11 (2H, d, J 6.1 Hz), 8.04 (1H, d, J 1.8 Hz), 7.92 (1H, d, J 8.8 Hz), 7.57 (1H, dd, J 8.7 2.1 Hz)

6-Chloro-2-(pyridin-4-yl)benzo[d]oxazole

LCMS RT=6.49 min, MH+ 231.0; ¹H NMR (DMSO): 8.87 (2H, d, J 6.1 Hz), 8.10-8.08 (3H, m), 7.93 (1H, d, J 8.6 Hz), 7.54 (1H, dd, J 8.6 2.0 Hz)

4-(5-Bromobenzo[d]oxazol-2-yl)aniline

LCMS RT=6.70 min, MH+ 289.2; ¹H NMR (DMSO): 7.88-7.83 (3H, m), 7.66 (1H, d, J 8.6 Hz), 7.46 (1H, dd, J 8.6 2.1 Hz), 6.69 (2H, d, J 8.8 Hz), 6.09 (2H, s)

2-(4-Chlorophenyl)-5-(methylsulfonyl)benzo[d]oxazole

LCMS RT=6.43 min, MH+ 308.2; ¹H NMR (CDCl₃): 8.43 (1H, dd, J 1.8 0.3 Hz), 8.28 (2H, d, J 8.7 Hz), 8.05 (1H, dd, J 8.6 1.9 Hz), 7.81 (1H, dd, J 8.5 0.4 Hz), 7.61 (2H, d, J 8.8 Hz), 3.18 (3H, s)

2-(4-Chlorophenyl)-5-(propylsulfonyl)benzo[d]oxazole

LCMS RT=7.09 min, MH+ 335.9; ¹H NMR (CDCl₃): 8.38 (1H, dd, J 1.7 0.4 Hz), 8.27 (2H, d, J 8.8 Hz), 8.00 (1H, dd, J 8.5 1.8 Hz), 7.80 (1H, dd, J 8.5 0.4 Hz), 7.60 (2H, d, J 8.8 Hz), 3.21-3.15 (2H, m), 1.89-1.76 (2H, m), 1.05 (3H, t, J 7.4 Hz)

2-(Naphthalen-1-yl)benzo[d]oxazol-5-amine

LCMS RT=6.59 min, MH+ 261.1; ¹H NMR (DMSO): 9.41 (1H, d, J 8.6 Hz), 8.38 (1H, dd, J 7.3 1.0 Hz), 8.19 (1H, d, J 8.2 Hz), 8.09 (1H, dd, J 7.8 0.9 Hz), 7.79-7.64 (3H, m), 7.49 (1H, d, J 8.7 Hz), 6.99 (1H, d, J 2.1 Hz), 6.74 (1H, d, J 8.7 2.2 Hz), 5.17 (2H, s)

2-(Biphenyl-4-yl)benzo[d]oxazol-5-amine

LCMS RT=6.92 min, MH+ 287.1; ¹H NMR (DMSO): 8.22 (2H, d, J 8.2 Hz), 7.90 (2H, d, J 8.3 Hz), 7.81-7.76 (2H, m), 7.53 (2H, t, J 7.8 Hz), 7.47-7.41 (2H, m), 6.90 (1H, d, J 2.2 Hz), 6.69 (1H, d, J 8.6 2.2 Hz), 5.14 (2H, s)

2-(Quinolin-2-yl)benzo[d]oxazol-5-amine

LCMS RT=5.78 min, MH+ 262.1; ¹H NMR (DMSO): 8.60 (1H, d, J 8.7 Hz), 8.39 (1H, d, J 8.6 Hz), 8.19 (1H, dd, J 8.3 0.5 Hz), 8.10 (1H, dd, J 8.4 0.8 Hz), 7.92-7.86 (1H, m), 7.76-7.70 (1H, m), 7.56 (1H, d, J 8.7 Hz), 6.97 (1H, d, J 2.1 Hz), 6.79 (1H, dd, J 8.7 2.2 Hz), 5.22 (2H, s)

2-(Quinolin-3-yl)benzo[d]oxazol-5-amine

LCMS RT=5.76 min, MH+ 262.1; ¹H NMR (DMSO): 9.58 (1H, d, J 2.1 Hz), 8.14 (1H, d, J 2.0 Hz), 8.24 (1H, dd, J 7.8 0.8 Hz), 8.13 (1H, d, J 8.3 Hz), 7.93-7.88 (1H, m), 7.74 (1H, td, J 8.0 0.9 Hz), 7.49 (1H, d, J 8.6 Hz), 6.95 (1H, d, J 2.1 Hz), 6.74 (1H, dd, J 8.7 2.2 Hz), 5.20 (2H, s)

2-(6-Methoxynaphthalen-2-yl)benzo[d]oxazol-5-amine

LCMS RT=6.56 min, MH+ 291.1; ¹H NMR (DMSO): 8.67 (1H, d, J 1.3 Hz), 8.16 (1H, dd, J 8.6 1.7 Hz), 8.07 (1H, d, J 9.1 Hz), 7.99 (1H, d, J 8.8 Hz), 7.45-7.42 (2H, m), 7.27 (1H, dd, J 8.7 2.5 Hz), 6.90 (1H, d, J 2.0 Hz), 6.68 (1H, dd, J 8.6 2.2 Hz), 5.12 (2H, s), 3.92 (3H, s)

2-(6-Bromonaphthalen-2-yl)benzo[d]oxazol-5-amine

LCMS RT=7.59 min, MH+ 339.3; ¹H NMR (DMSO): 8.78 (1H, s), 8.34 (1H, d, J 1.7 Hz), 8.26 (1H, d, J 8.6 1.6 Hz), 8.14 (1H, d, J 8.9 Hz), 8.09 (1H, d, J 8.7 Hz), 7.76 (1H, dd, J 8.9 2.0 Hz), 7.46 (1H, d, J 8.7 Hz), 6.92 (1H, d, J 2.2 Hz), 6.72 (1H, dd, J 8.6 2.2 Hz), 5.16 (2H, s)

2-(4-Chlorophenyl)naphtho[1,2-d]oxazole

LCMS RT=9.55 min, MH+ 280.1; ¹H NMR (DMSO): 8.47 (1H, dd, J 8.2 0.6 Hz), 8.29 (2H, d, J 8.7 Hz), 8.17-8.13 (1H, m), 8.02 (2H, s), 7.78-7.70 (3H, m), 7.67-7.61 (1H, m)

1-(2-(4-Chlorophenyl)benzo[d]oxazol-5-yl)propan-1-one

LCMS RT=7.92 min, MH+ 286.1; ¹H NMR (DMSO): 8.44 (1H, dd, J 1.7 0.4 Hz), 8.24 (2H, d, J 8.7 Hz), 8.09 (1H, dd, J 8.6 1.7 Hz), 7.93 (1H, dd, J 8.6 0.4 Hz), 7.73 (2H, d, J 8.8 Hz), 3.17 (2H, q, J 7.2 Hz), 1.13 (3H, t, 17.1 Hz)

1-(2-(4-Chlorophenyl)benzo[d]oxazol-5-yl)ethanone

LCMS RT=7.27 min, MH+ 271.7; ¹H NMR (DMSO): 8.44 (1H, dd, J 1.7 0.4 Hz), 8.24 (2H, d, J 8.8 Hz), 8.08 (1H, dd, J 8.6 1.7 Hz), 7.93 (1H, dd, J 8.5 0.5 Hz), 7.73 (2H, d, J 8.8 Hz), 2.69 (3H, s)

2-(4-Cyclohexylphenyl)benzo[d]oxazol-5-amine

LCMS RT=8.15 min, MH+ 293.1; ¹H NMR (DMSO): 8.05 (2H, d, J 8.4 Hz), 7.45-7.38 (3H, m), 6.86 (1H, d, J 2.0 Hz), 6.65 (1H, dd, J 8.8 2.2 Hz), 5.10 (2H, s), 2.64-2.56 (1H, m), 1.83-1.70 (5H, m), 1.51-1.23 (5H, m)

5-(Ethylsulfonyl)-2-(quinolin-2-yl)benzo[d]oxazole

LCMS RT=6.14 min, MH+ 339.1; ¹H NMR (DMSO): 8.69 (1H, dd, J 8.5 2.2 Hz), 8.52-8.43 (2H, m), 8.28-8.21 (2H, m), 8.16 (1H, d, J 8.1 Hz), 8.09-8.04 (1H, m), 7.97-7.90 (1H, m), 7.82-7.76 (1H, m), 3.48-3.38 (2H, m), 1.15 (3H, td, J 7.3 1.3 Hz)

5-(Ethylsulfonyl)-2-(quinolin-3-yl)benzo[d]oxazole

LCMS RT=6.05 min, MH+ 339.1; ¹H NMR (DMSO); 9.65 (1H, d, J 2.1 Hz), 9.31 (1H, d, J 2.1 Hz), 8.40 (1H, d, J 1.8 Hz), 8.31 (1H, d, J 8.1 Hz), 8.17 (2H, dd, J 8.3 2.2 Hz), 8.02 (1H, dd, J 8.7 1.8 Hz), 8.00-7.93 (1H, m), 7.82-7.76 (1H, m), 3.43 (2H, q, J 7.3 Hz), 1.15 (3H, t, J 7.5 Hz)

2-(6-Bromonaphthalen-2-yl)-5-(ethylsulfonyl)benzo[d]oxazole

LCMS RT=7.86 min, MH+ 418.0; ¹H NMR (DMSO): 8.95 (1H, m), 8.39-8.33 (3H, m), 8.21 (1H, d, J 9.0 Hz), 8.17 (1H, d, J 8.9 Hz), 8.13 (1H, dd, J 8.5 0.5 Hz), 7.99 (1H, dd, J 8.6 1.8 Hz), 7.81 (1H, dd, J 8.7 1.9 Hz), 3.41 (2H, q, J 7.3 Hz), 1.15 (3H, t, J 7.5 Hz)

2-(4-Cyclohexylphenyl)-5-(ethylsulfonyl)benzo[d]oxazole

LCMS RT=8.56 min; $^1$H NMR (DMSO): 8.29 (1H, dd, J 1.8 0.4 Hz), 8.17 (2H, d, J 8.3 Hz), 8.07 (1H, dd, J 8.6 0.5 Hz), 7.94 (1H, dd, J 8.5 1.8 Hz), 7.51 (2H, d, J 8.4 Hz), 3.39 (2H, q, J 7.3 Hz), 2.74-2.60 (1H, m), 1.84-1.71 (5H, m), 1.53-1.24 (5H, m), 1.13 (3H, t, J 7.5 Hz)

2-(Biphenyl-4-yl)-5-(ethylsulfonyl)benzo[d]oxazole

LCMS RT=7.31 min, MH$^+$ 364.1; $^1$H NMR (DMSO): 8.36-8.32 (3H, m), 8.11 (1H, dd, J 8.6 0.5 Hz), 8.00-7.95 (3H, m), 7.84-7.79 (2H, m), 7.57-7.43 (3H, m), 3.41 (2H, q, J 7.3 Hz), 1.14 (3H, t, J 7.5 Hz)

5-(Ethylsulfonyl)-2-(naphthalen-1-yl)benzo[d]oxazole

LCMS RT=7.03 min, MH$^+$ 338.1; $^1$H NMR (DMSO): 9.41 (1H, d, J 8.8 Hz), 8.52 (1H, dd, J 7.2 1.2 Hz), 8.44 (1H, d, J 1.7 Hz), 8.30 (1H, d, J 8.3 Hz), 8.17-8.12 (2H, m), 8.02 (1H, dd, J 8.6 1.8 Hz), 7.84-7.68 (3H, m), 3.43 (2H, q, J 7.3 Hz), 1.15 (3H, t, J 7.5 Hz)

5-(Ethylsulfonyl)-2-(6-fluoronaphthalen-2-yl)benzo[d]oxazole

LCMS RT=7.29 min, MH$^+$ 356.1; $^1$H NMR (DMSO): 8.97 (1H, m), 8.37-8.32 (3H, m), 8.17 (1H, d, J 8.9 Hz), 8.12 (1H, d, J 8.6 Hz), 7.99 (1H, dd, J 8.6 1.6 Hz), 7.89 (1H, dd, J 10.0 2.0 Hz), 7.61 (1H, td, J 8.7 2.0 Hz), 3.41 (2H, q, J 7.3 Hz), 1.14 (3H, t, J 7.5 Hz)

2-(Benzo[b]thiophen-5-yl)-5-(ethylsulfonyl)benzo[d]oxazole

LCMS RT=6.77 min, MH$^+$ 344.1; $^1$H NMR (CDCl$_3$): 8.70 (1H, d, J 1.2 Hz), 8.27 (1H, dd, J 1.8 0.4 Hz), 8.18 (1H, dd, J 8.5 1.5 Hz), 7.99 (1H, d, J 8.6 Hz), 7.88 (1H, dd, J 8.5 1.8 Hz), 7.70 (1H, dd, J 8.5 0.4 Hz), 7.52 (1H, d, J 5.5 Hz), 7.43 (1H, dd, J 5.5 0.6 Hz), 3.12 (2H, q, J 7.4 Hz), 1.25 (3H, t, J 7.4 Hz)

5-Amino-2-(5,6-dichlorobenzo[d]oxazol-2-yl)phenol

LCMS RT=7.83 min, MH$^+$ 295.1; $^1$H NMR (DMSO): 10.88 (1H, s), 8.19 (1H, s), 8.06 (1H, s), 7.69 (1H, d, J 8.7 Hz), 6.35 (1H, dd, J 8.7 2.1 Hz), 6.29 (2H, br), 6.24 (1H, d, J 2.1 Hz)

2-(3,4-Dichlorophenyl)-5-(isopropylsulfonyl)benzo[d]oxazole

LCMS RT=7.68 min; $^1$H NMR (DMSO): 8.41 (1H, d, J 2.0 Hz), 8.31 (1H, dd, J 1.8 0.4 Hz), 8.21 (1H, dd, J 8.4 2.0 Hz), 8.11 (1H, dd, J 8.6 0.5 Hz), 7.98-7.93 (2H, m), 3.59-3.50 (1H, m), 1.19 (6H, d, J 6.8 Hz)

N-(4-(5,6-Dimethylbenzo[d]oxazol-2-yl)-3-hydroxyphenyl)acetamide

LCMS RT=6.70 min, MH$^+$ 263.1; $^1$H NMR (DMSO): 10.83 (1H, s), 8.02 (1H, dd, J 9.9 6.9 Hz), 7.85 (1H, d, J 10.4 7.5 Hz), 7.62 (1H, d, J 8.6 Hz), 6.29 (1H, dd, J 8.7 2.1 Hz), 6.18 (1H, d, J 2.0 Hz), 6.15 (2H, br)

4-(5,6-Dichlorobenzo[d]oxazol-2-yl)aniline

LCMS RT=7.27 min, MH$^+$ 279.0; $^1$H NMR (DMSO): 8.10 (1H, s), 7.97 (1H, s), 7.85 (2H, d, J 8.7 Hz), 6.70 (2H, d, J 8.8 Hz), 6.14 (2H, s)

5-(Ethylsulfonyl)-2-(5,6,7,8-tetrahydronaphthalen-2-yl)benzo[d]oxazole

LCMS RT=7.71 min, MH$^+$ 342.2; $^1$H NMR (CDCl$_3$): 8.03 (1H, dd, J 1.8 0.5 Hz), 7.93-7.87 (2H, m), 7.85 (1H, dd, J 8.5 1.8 Hz), 7.65 (1H, dd, J 8.5 0.5 Hz), 7.23-7.15 (1H, m), 3.11 (2H, q, J 7.4 Hz), 2.85-2.76 (4H, m), 1.81-1.76 (4H, m), 1.24 (3H, t, J 7.3 Hz)

5-Amino-2-(5-(ethylsulfonyl)benzo[d]oxazol-2-yl)phenol

LCMS RT=5.99 min, MH$^+$ 319.2; $^1$H NMR (DMSO): 10.88 (1H, s), 8.16 (1H, dd, J 1.8 0.5 Hz), 7.97 (1H, dd, J 8.5 0.5 Hz), 7.84 (1H, dd, J 8.4 1.9 Hz), 7.69 (1H, d, J 8.6 Hz), 6.31 (1H, dd, J 8.7 2.1 Hz), 6.24 (2H, s), 6.20 (1H, d, J 2.1 Hz), 3.37 (2H, q, J 7.5 Hz), 1.12 (3H, t, J 7.3 Hz)

Method 1A (Compounds Ic)

N-(2-(Pyridin-3-yl)benzo[d]oxazol-5-yl)nicotinamide

LCMS RT=4.64 min, MH$^+$ 317.1; $^1$H NMR (DMSO): 10.67 (1H, s), 9.37 (1H, d, J 1.5 Hz), 9.16 (1H, d, J 1.6 Hz), 8.84-8.78 (2H, m), 8.56 (1H, dt, J 8.0 1.7 Hz), 8.36-8.32 (2H, m), 7.86 (1H, d, J 8.8 Hz), 7.80 (1H, dd, J 8.9 2.0 Hz), 7.70-7.58 (2H, m)

4-Methoxy-N-(2-(4-methoxyphenyl)benzo[d]oxazol-5-yl)benzamide $^1$H NMR (DMSO): 10.25 (1H, s), 8.23 (1H, s), 8.16 (2H, d, J 8.9 Hz), 8.00 (2H, d, J 8.9 Hz), 7.72 (2H, s), 7.17 (2H, d, J 9.0 Hz), 7.09 (2H, d, J 8.8 Hz), 3.88 (3H, s), 3.85 (3H, s)

N-(2-benzylbenzo[d]oxazol-5-yl)-2-phenylacetamide

LCMS RT=6.22 min, MH$^+$ 343.1; $^1$H NMR (CDCl$_3$): 7.70 (1H, s), 7.42 (1H, s), 7.30-7.15 (12H, m), 4.14 (2H, s), 3.63 (2H, s)

2,3-Dichloro-N-(2-(2,3-dichlorophenyl)benzo[d]oxazol-5-yl)benzamide

LCMS RT=8.09 min, MH$^+$ 450.9; $^1$H NMR (DMSO): 10.84 (1H, s), 8.32 (1H, d, J 1.7 Hz), 8.14 (1H, dd, J 8.9 1.5 Hz), 7.95 (1H, dd, J 8.1 1.6 Hz), 7.85 (1H, d, J 8.8 Hz), 7.81 (1H, dd, J 8.0 1.6 Hz), 7.73 (1H, dd, J 8.8 2.1 Hz), 7.65-7.50 (3H, m)

Method 1A (Compounds Id)

2'-(4-Propylphenyl)-2,6'-bibenzo[d]oxazole-6-carboxylic acid $^1$H NMR (DMSO): 13.20 (1H, br), 8.58 (1H, dd, J 1.5 0.4 Hz), 8.33-8.30 (2H, m), 8.19 (2H, d, J 8.2 Hz), 8.06-0.802 (2H, m), 7.93 (1H, d, J 8.3 Hz), 7.50 (2H, d, J 8.4 Hz), 2.69 (2H, t, J 7.8 Hz), 1.73-1.61 (2H, m), 0.94 (3H, t, J 7.4 Hz)

Method 1A (Compounds Ie)

4-Amino-N-(4-(5-bromobenzo[d]oxazol-2-yl)phenyl)benzamide

LCMS RT=6.87 min, MH+ 408.0; $^1$H NMR (DMSO): 10.14 (1H, s), 8.16 (2H, d, J 8.9 Hz), 8.07-8.01 (3H, m), 7.79-7.74 (3H, m), 7.57 (1H, dd, J 8.6 2.0 Hz), 6.62 (2H, d, J 8.7 Hz), 5.86 (2H, s)

Method 1B (Compounds I)

2-Benzyl-5-nitrobenzo[d]oxazole

To 2-amino-4-nitrophenol (300 mg, 1.95 mmol) in dioxane (2.5 mL) was added 2-phenylacetyl chloride (290 µL, 2.15 mmol) at room temperature. The reaction vessel was heated in the microwave at 210° C. for 15 min. After cooling, the mixture was slowly poured into 1M aqueous sodium hydroxide (50 mL), and the resulting precipitate filtered and washed with water. The resulting solid was purified by column chromatography eluting using a gradient (ethyl acetate/hexanes 1:7 v/v to ethyl acetate/hexanes 1:5 v/v) to afford 165 mg (33%) of the title compound (LCMS RT=6.47 min, MH+ 255.2)

$^1$H NMR (DMSO): 8.60 (1H, d, J 2.4 Hz), 8.30 (1H, dd, J 9.0 2.4 Hz), 7.95 (1H, d, J 9.0 Hz), 7.43-7.27 (5H, m), 4.44 (2H, s)

All compounds below were prepared following the same general method. The acid chloride used was either a commercially available compound or synthesized from the corresponding carboxylic acid using standard conditions.

2-(Benzo[d][1,3]dioxol-5-yl)-5-nitrobenzo[d]oxazole

LCMS RT=6.74 min, MH+ 284.9; $^1$H NMR (DMSO): 8.60 (1H, d, J 2.3 Hz), 8.31 (1H, dd, J 8.9 2.3 Hz), 7.99 (1H, d, J 9.0 Hz), 7.82 (1H, dd, J 8.2 1.7 Hz), 7.66 (1H, d, J 1.6 Hz), 7.18 (1H, d, J 8.4 Hz), 6.20 (2H, s)

2-(4-Chlorophenyl)-5,6-methylenedioxybenzoxazole

LCMS RT=7.54 min, MH+ 274.0; $^1$H NMR (DMSO): 8.11 (2H, d, J 8.8 Hz), 7.66 (2H, d, J 8.7 Hz), 7.49 (1H, s), 7.36 (1H, s), 6.13 (2H, s)

5-Tert-butyl-2-(4-chlorophenyl)benzo[d]oxazole

LCMS RT=10.20 min, MH+ 286.0; $^1$H NMR (DMSO): 8.20 (2H, d, J 8.6 Hz), 7.80 (1H, d, J 1.9 Hz), 7.72-7.68 (3H, m), 7.52 (1H, dd, J 8.7 2.0 Hz), 1.37 (9H, s)

2-(3,4-Dichlorophenyl)-6-nitrobenzo[d]oxazole

LCMS RT=8.40 min; $^1$H NMR (DMSO): 8.77 (1H, d, J 2.1 Hz), 8.40 (1H, d, J 2.0 Hz), 8.36 (1H, dd, J 8.8 2.2 Hz), 8.21 (1H, dd, J 8.5 2.1 Hz), 8.07 (1H, d, J 8.8 Hz), 7.96 (1H, d, J 8.4 Hz)

2-(4-Chlorophenyl)benzo[d]oxazole-5-sulfonamide

LCMS RT=6.04 min; $^1$H NMR (DMSO): 8.27-8.22 (3H, m) 8.02 (1H, d, J 8.6 Hz), 7.95-7.91 (1H, m), 7.74-7.71 (2H, m), 7.50 (2H, s)

5-Chloro-2-(4-chlorophenyl)-6-nitrobenzo[d]oxazole

LCMS RT=8.10 min; $^1$H NMR (DMSO): 8.73 (1H, s), 8.31 (1H, s), 8.24 (2H, d, J 8.7 Hz), 7.76 (2H, d, J 8.7 Hz)

5-Nitro-2-(4-(trifluoromethoxy)phenyl)benzo[d]oxazole

LCMS RT=7.66 min; $^1$H NMR (DMSO): 8.72 (1H, d, J 2.3 Hz), 8.38 (3H, m), 8.09 (1H, d, J 8.8 Hz), 7.66 (2H, d, J 8.2 Hz)

2-(3,4-Dichlorophenyl)benzo[d]oxazole[1,3]dioxole

LCMS RT=8.70 min, MH+ 307.9; $^1$H NMR (CDCl$_3$): 8.18 (1H, d, J 2.0 Hz), 7.91 (1H, dd, J 8.4 2.0 Hz), 7.50 (1H, d, J 8.4 Hz), 7.09 (1H, s), 6.99 (1H, s), 5.99 (2H, s)

2-(Furan-2-yl)-5-nitrobenzo[d]oxazole

LCMS RT=6.24 min; $^1$H NMR (DMSO): 8.66 (1H, d, J 2.3 Hz), 8.35 (1H, dd, J 9.0 2.4 Hz), 8.18 (1H, d, J 1.0 Hz), 8.05 (1H, d, J 9.0 Hz), 7.62 (1H, d, J 3.5 Hz), 6.90-6.88 (1H, m)

2-(Benzo[d][1,3]dioxol-5-yl)-5-chloro-6-nitrobenzo[d]oxazole

LCMS RT=7.21 min; $^1$H NMR (DMSO): 8.68 (1H, s), 8.23 (1H, s), 7.83 (1H, dd, J 8.2 1.6 Hz), 7.66 (1H, d, J 1.7 Hz), 7.20 (1H, d, J 8.4 Hz), 6.22 (2H, s)

5-(Ethylsulfonyl)-2-(naphthalen-2-yl)benzo[d]oxazole

LCMS RT=6.94 min, MH+ 338.1; $^1$H NMR (DMSO): 8.90 (1H, br), 8.34 (1H, d, J 1.4 Hz), 8.30 (1H, dd, J 8.6 1.7 Hz), 8.24-8.05 (4H, m), 7.99 (1H, dd, J 8.5 1.8 Hz), 7.73-7.64 (2H, m), 3.41 (2H, q, J 7.3 Hz), 1.15 (3H, t, J 7.3 Hz)

2-(3-Chloro-2-fluorophenyl)-5-(ethylsulfonyl)benzo[d]oxazole

LCMS RT=6.48 min, MH+ 338.8; $^1$H NMR (DMSO): 8.40 (1H, dd, J 1.7 0.5 Hz), 8.27-8.21 (1H, m), 8.14 (1H, dd, J 8.6 0.4 Hz), 8.01 (1H, dd, J 8.6 1.8 Hz), 7.97-7.92 (1H, m), 7.51 (1H, td, J 8.0 1.0 Hz), 3.41 (2H, q, J 7.3 Hz), 1.13 (3H, t, J 7.3 Hz)

2-Cyclohexyl-5-(ethylsulfonyl)benzo[d]oxazole

LCMS RT=6.57 min, MH+ 293.9; $^1$H NMR (DMSO): 8.20 (1H, d, J 1.5 Hz), 7.97 (1H, dd, J 8.5 Hz), 7.88 (1H, dd, J 8.6 1.8 Hz), 3.35 (2H, q, J 7.4 Hz), 3.13-3.04 (1H, m), 2.14-2.09 (2H, m), 1.82-1.58 (5H, m), 1.50-1.18 (3H, m), 1.10 (3H, t, J 7.4 Hz)

2-(5-Chloropyridin-2-yl)-5-(ethylsulfonyl)benzo[d]oxazole

LCMS RT=5.92 min, MH+ 323.1; $^1$H NMR (DMSO): 8.91 (1H, d, J 2.4 Hz), 8.42-8.39 (2H, m), 8.25 (1H, dd, J 8.5 2.4 Hz), 8.16 (1H, d, J 8.6 Hz), 8.03 (1H, dd, J 8.6 1.8 Hz), 3.41 (2H, q, J 7.2 Hz), 1.13 (3H, t, J 7.3 Hz)

2-(Benzo[d][1,3]dioxol-5-yl)-5-(ethylsulfonyl)benzo[d]oxazole

LCMS RT=6.09 min, MH+ 332.0; $^1$H NMR (DMSO): 8.26 (1H, dd, J 1.8 0.5 Hz), 8.03 (1H, dd, J 8.5 0.5 Hz), 7.92 (1H, dd, J 8.5 1.8 Hz), 7.83 (1H, dd, J 8.2 1.7 Hz), 7.68 (1H, d, J 1.6 Hz), 7.19 (1H, d, J 8.2 Hz), 6.20 (2H, s), 3.39 (2H, g, J 7.3 Hz), 1.12 (3H, t, J 7.3 Hz)

5-Chloro-2-(4-(methylsulfonyl)phenyl)benzo[d]oxazole

LCMS RT=6.43 min; $^1$H NMR (DMSO): 8.45 (2H, d, J 8.4 Hz), 8.18 (2H, d, J 8.5 Hz), 8.02 (1H, d, J 1.9 Hz), 7.92 (1H, d, J 8.7 Hz), 7.56 (1H, dd, J 8.7 2.1 Hz)

2-(2,2-Difluorobenzo[d][1,3]dioxol-5-yl)-5-(ethylsulfonyl)benzo[d]oxazole

LCMS RT=6.70 min; $^1$H NMR (DMSO): 8.32 (1H, dd, J 1.8 0.5 Hz), 8.24 (1H, d, J 1.6 Hz), 8.16 (1H, dd, J 8.5 1.7 Hz), 8.09 (1H, dd, J 8.6 0.5 Hz), 7.97 (1H, dd, J 8.5 1.8 Hz), 7.71 (1H, d, J 8.5 Hz), 3.40 (2H, q, J 7.3 Hz), 1.13 (3H, t, J 7.4 Hz)

2-(4-Chlorophenyl)benzo[d]oxazol-6-01

LCMS RT=6.42 min, MH$^+$ 246.0; $^1$H NMR (DMSO): 9.94 (1H, s), 8.13 (2H, d, J 8.6 Hz), 7.66 (2H, d, J 8.6 Hz), 7.60 (1H, d, J 8.6 Hz), 7.10 (1H, d, J 2.2 Hz), 6.87 (1H, dd, J 8.7 2.3 Hz)

2-(5-(Ethylsulfonyl)benzo[d]oxazol-2-yl)naphthalen-1-ol

LCMS RT=7.77 min, MH$^+$ 353.9; $^1$H NMR (DMSO): 12.24 (1H, s), 8.44-8.39 (2H, m), 8.19-7.98 (4H, m), 7.77-7.63 (3H, m), 3.42 (2H, q, J 7.3 Hz), 1.15 (3H, t, J 7.3 Hz)

2-(Benzofuran-5-yl)-5-(ethylsulfonyl)benzo[d]oxazole

LCMS RT=6.47 min, MH$^+$ 328.2; $^1$H NMR (DMSO): 8.61 (1H, d, J 1.7 Hz), 8.31 (1H, d, J 1.7 Hz), 8.22 (1H, dd, J 8.5 1.7 Hz), 8.19 (1H, d, J 2.2 Hz), 8.09 (1H, d, J 8.5 Hz), 7.95 (1H, dd, J 8.5 1.9 Hz), 7.88 (1H, d, J 8.7 Hz), 7.19-7.17 (1H, m), 3.40 (2H, q, J 7.4 Hz), 1.15 (3H, t, J 7.3 Hz)

2-(4-Chlorophenyl)-N,N-diethylbenzo[d]oxazole-5-sulfonamide

LCMS RT=7.75 min, MH$^+$ 364.9; $^1$H NMR (DMSO): 8.26-8.21 (3H, m), 8.03 (1H, d, J 8.6 Hz), 7.89 (1H, dd, J 8.6 1.8 Hz), 7.74 (2H, d, J 8.6 Hz), 3.22 (4H, q, J 7.2 Hz), 1.06 (6H, t, J 7.2 Hz)

2-(Naphthalen-2-yl)-5-(trifluoromethoxy)benzo[d]oxazole

LCMS RT=9.10 min, MH$^+$ 330.1; $^1$H NMR (DMSO): 8.88 (1H, br), 8.27 (1H, dd, J 8.5 1.7 Hz), 8.23-8.19 (1H, m), 8.16 (1H, d, J 8.7 Hz), 8.08-8.04 (1H, m), 7.97 (1H, d, J 8.9 Hz), 7.95-7.93 (1H, m), 7.73-7.64 (2H, m), 7.52-7.47 (1H, m)

2-(Naphthalen-2-yl)benzo[d]oxazole-5-carboxylic acid

LCMS RT=4.83 min, MH$^+$ 289.0; $^1$H NMR (DMSO): 13.20 (1H, br), 8.89 (1H, br), 8.36 (1H, dd, J 1.6 0.5 Hz), 8.30 (1H, dd, J 8.6 1.8 Hz), 8.24-8.20 (1H, m), 8.17 (1H, d, J 8.8 Hz), 8.10-8.04 (2H, m), 7.94 (1H, dd, J 8.5 0.5 Hz), 7.73-7.63 (2H, m)

2-(Naphthalen-2-yl)benzo[d]oxazole

LCMS RT=8.19 min, MH$^+$ 246.1; $^1$H NMR (DMSO): 8.86 (1H, br), 8.29 (1H, dd, J 8.6 1.8 Hz), 8.22-8.18 (1H, m), 8.15 (1H, d, J 8.7 Hz), 8.07-8.03 (1H, m), 7.88-7.83 (2H, m), 7.71-7.62 (2H, m), 7.51-7.42 (2H, m)

5-tert-Butyl-2-(naphthalen-2-yl)benzo[d]oxazole

LCMS RT=10.50 min, MH$^+$ 302.2; $^1$H NMR (CDCl$_3$): 8.70 (1H, s), 8.25 (1H, dd, J 8.6 1.5 Hz), 7.94-7.89 (2H, m), 7.85-7.81 (1H, m), 7.77 (1H, d, J 1.6 Hz), 7.54-7.45 (3H, m), 7.37 (1H, dd, J 8.5 1.8 Hz), 1.35 (9H, s)

5,6-Difluoro-2-(naphthalen-2-yl)benzo[d]oxazole

LCMS RT=8.57 min, MH$^+$ 282.1; $^1$H NMR (DMSO): 8.82 (1H, br), 8.24 (1H, dd, J 8.6 1.8 Hz), 8.21-8.12 (3H, m), 8.07-8.00 (2H, m), 7.72-7.63 (2H, m)

1-(2'-(3",4"-Dichlorophenyl)benzo[d]oxazol-5'-yl)ethanone

LCMS RT=8.19 min, MH$^+$ 305.9; $^1$H NMR (DMSO): 8.45 (1H, dd, J 1.7 0.5 Hz), 8.38 (1H, d, J 2.0 Hz), 8.18 (1H, dd, J 8.5 2.1 Hz), 8.09 (1H, dd, J 8.6 1.8 Hz), 7.96-7.91 (2H, m), 2.69 (3H, s)

2-(4-Chloro phenyl)-6-methyl benzo[d]oxazole

LCMS RT=8.41 min, MH$^+$ 244.1; $^1$H NMR (DMSO): 8.18 (2H, d, J 8.7 Hz), 7.72-7.61 (4H, m), 7.27-7.23 (1H, m), 2.48 (3H, s)

5-Methyl-2-(naphthalen-2-yl)benzo[d]oxazole

LCMS RT=8.82 min, MH$^+$ 260.2; $^1$H NMR (DMSO): 8.83 (1H, d, J 1.1 Hz), 8.26 (1H, dd, J 8.6 1.7 Hz), 8.21-8.16 (1H, m), 8.13 (1H, d, J 8.7 Hz), 8.06-8.02 (1H, m), 7.72-7.64 (4H, m), 7.30-7.26 (1H, m), 2.47 (3H, s)

Method 1C (Compounds I)

6-Nitro-2-phenyloxazolo[5,4-b]pyridine

To polyphosphoric acid at 165° C. was added N-(5-nitro-2-oxo-1,2-dihydropyridin-3-yl)benzamide (300 mg, 1.16 mmol). The resulting mixture was then heated to 165° C. for 30 min. The solution was then poured into water. The resulting precipitate was collected by filtration, dissolved in diethyl ether, filtered through alumina and evaporated to afford 9 mg (3%) of the title compound.

$^1$H NMR (DMSO): 9.31 (1H, d, J 2.5 Hz), 9.12 (1H, d, J 2.5 Hz), 8.32-8.27 (2H, m), 7.79-7.67 (3H, m)

All compounds below were prepared following the same general method.

5-Nitro-2-(pyridin-2-yl)benzo[d]oxazole

LCMS RT=5.83 min, MH$^+$ 241.9; $^1$H NMR (DMSO): 8.87-8.84 (1H, m), 8.78 (1H, d, J 2.3 Hz), 8.44-8.40 (2H, m), 8.16-8.10 (2H, m), 7.74-7.69 (1H, m)

6-Nitro-2-(pyridin-2-yl)benzo[d]oxazole

LCMS RT=5.84 min, MH$^+$ 242.0; $^1$H NMR (DMSO): 8.79-8.76 (2H, m), 8.34 (1H, dt, J 7.9 1.0 Hz), 8.29 (1H, dd, J 8.8 2.0 Hz), 8.07-8.02 (2H, m), 7.64 (1H, ddd, J 7.7 4.8 1.2 Hz)

2-(5-Butylpyridin-2-yl)-5-nitrobenzo[d]oxazole

LCMS RT=7.32 min, MH$^+$ 298.1; $^1$H NMR (DMSO): 8.68 (1H, dd, J 2.3 0.3 Hz), 8.64 (1H, dd, J 2.1 0.5 Hz), 8.33 (1H, dd, J 9.0 2.4 Hz), 8.26 (1H, dd, J 8.0 0.6 Hz), 8.05 (1H, dd, J 9.0 0.3 Hz), 7.88 (1H, dd, J 8.1 2.1 Hz), 2.70-2.66 (2H, m), 1.62-1.52 (2H, m), 1.34-1.22 (2H, m), 0.86 (3H, t, J 7.4 Hz)

Method 1D (Compounds I)

2-(2,4-Difluorophenyl)-5,6-dimethylbenzo[d]oxazole

A suspension of 2-(2,4-difluorobenzamido)-4,5-dimethylphenyl 2,4-difluorobenzoate (90 mg, 0.22 mmol) and 4-methylbenzenesulfonic acid (82 mg, 0.43 mmol) in xylene (2 mL) was heated at reflux for 16 h. After cooling, the solution was diluted with ethyl acetate and washed with aqueous sodium bicarbonate solution followed by brine. The combined organic layers were dried over anhydrous $MgSO_4$ and evaporated. The resulting solid was purified by column chromatography eluting with ethyl acetate/hexanes 1:15 v/v to afford 36 mg (64%) of the title compound (LCMS RT=7.81 min, $MH^+$ 260.0)

$^1H$ NMR (DMSO): 8.30-8.22 (1H, m), 7.63-7.52 (3H, m), 7.39-7.30 (1H, m), 2.37 (3H, s), 2.35 (3H, s)

Method 2A (Compounds Ib)

2-p-Tolylbenzo[d]oxazol-5-amine

To 5-nitro-2-p-tolylbenzo[d]oxazole (4.8 g, 18.90 mmol) in ethyl acetate/acetic acid (250 ml/1 mL) was added palladium on carbon (480 mg). The reaction vessel was purged three times with nitrogen, followed by hydrogen three times, and then left stirring under hydrogen for 16 h. The reaction vessel was finally purged three times with nitrogen, before filtration on a pad of Celite®, which was washed with ethyl acetate. The organic solution was washed with saturated aqueous $Na_2CO_3$, followed by brine. The combined organic layers were dried over anhydrous $MgSO_4$ and evaporated to afford 2.5 g (60%) of the title compound.

$^1H$ NMR (DMSO): 8.02 (2H, d, J 8.2 Hz), 7.39 (3H, d, J 8.5 Hz), 6.86 (1H, d, J 2.0 Hz), 6.65 (1H, dd, J 8.7 2.2 Hz), 5.09 (2H, s), 2.40 (3H, s)

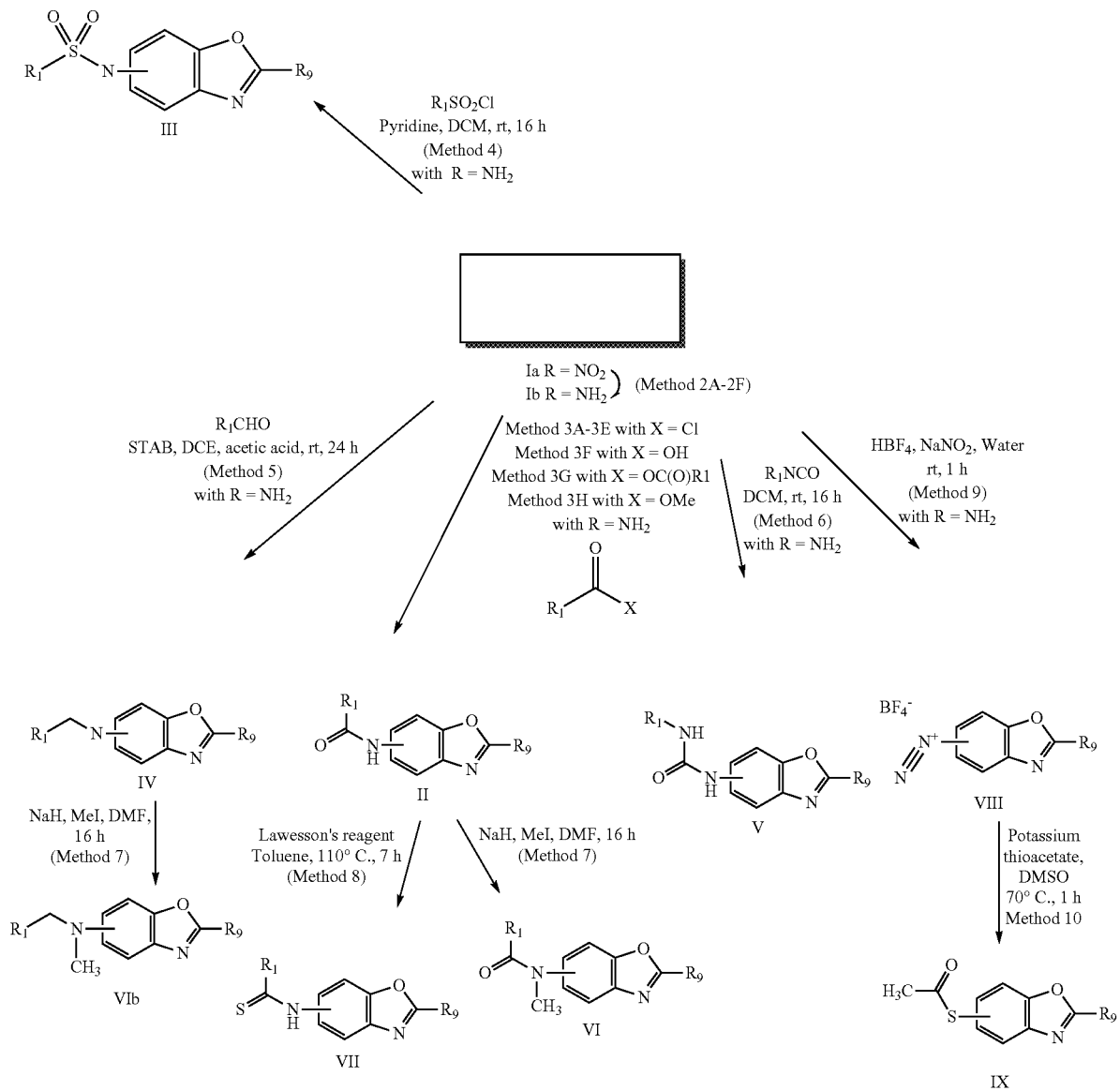

Method 2B (Compounds Ib)

As Method 2A, except ethanol was used instead of ethyl acetate/acetic acid. After evaporation of the solvents, the material was taken up in 2M HCl, the resulting precipitate was discarded, and the solution was basified with 2N NaOH to afford the title compound as a precipitate.

2-Phenylbenzo[d]oxazol-6-amine

LCMS RT=5.93 min, MH$^+$ 211.1; $^1$H NMR (DMSO): 8.10-8.07 (2H, m), 7.58-7.54 (3H, m), 7.42 (1H, d, J 8.4 Hz), 6.83 (1H, d, J 1.9 Hz), 6.65 (1H, dd, J 8.5 2.0 Hz), 5.46 (2H, s)

Method 2C (Compounds Ib)

2-(4-(Trifluoromethoxy)phenyl)benzo[d]oxazol-5-amine

To 5-nitro-2-(4-(trifluoromethoxy)phenyl)benzo[d]oxazole (850 mg, 2.62 mmol) in ethanol (20 mL) was added ammonium formate (827 mg, 13.1 mmol) and palladium on carbon (85 mg). The mixture was stirred at room temperature for 20 min, then filtrated through a pad of Celite®, and washed with ethyl acetate. The organic solution was washed with water, followed by brine. The combined organic layers were dried over anhydrous MgSO$_4$ and evaporated to afford 434 mg (56%) of the title compound (LCMS RT=6.51 min, MH$^+$ 294.9)

$^1$H NMR (DMSO): 8.25 (2H, d, J 8.9 Hz), 7.62-7.56 (2H, m), 7.44 (1H, d, J 8.7 Hz), 6.89 (1H, d, J 2.0 Hz), 6.70 (1H, dd, J 8.7 2.3 Hz), 5.16 (2H, s)

Method 2D (Compounds Ib)

2-p-Tolylbenzo[d]oxazol-4-amine

To 4-nitro-2-p-tolylbenzo[d]oxazole (330 mg, 1.30 mmol) in ethanol (20 mL) was added tin (II) chloride (1.23 g, 6.5 mmol). The suspension was stirred at 70° C. for 16 h. After cooling, the solution was poured into ice/water and neutralize with saturated aqueous NaHCO$_3$. The aqueous layer was then extracted twice with ethyl acetate (500 mL). The combined organic layers were dried over anhydrous MgSO$_4$ and evaporated to afford 188 mg (65%) of the title compound (LCMS RT=6.76 min, MH$^+$ 225.1)

$^1$H NMR (DMSO): 8.04 (2H, d, J 8.2 Hz), 7.41 (2H, d, J 8.0 Hz), 7.07 (1H, t, J 8.0 Hz), 6.85 (1H, dd, J 8.0 0.8 Hz), 6.55 (1H, dd, J 8.0 0.8 Hz), 5.67 (2H, s), 2.41 (3H, s)

The compound below was prepared following the same general method.

2-Phenyloxazolo[5,4-b]pyridin-6-amine

LCMS RT=5.41 min, MH$^+$ 212.1; $^1$H NMR (DMSO): 8.19-8.15 (2H, m), 7.73 (1H, d, J 2.4 Hz), 7.63-7.58 (3H, m), 7.32 (1H, d, J 2.4 Hz), 5.38 (2H, s)

Method 2E (Compounds Ib)

2-p-Tolylbenzo[d]oxazol-6-amine

To 6-nitro-2-p-tolylbenzo[d]oxazole (2.1 g, 8.27 mmol) in ethanol:water 2:1 v/v (60 mL) at 70° C. was added iron powder (2.14 g, 38.3 mmol) and ammonium chloride (819 mg, 15.3 mmol). The suspension was stirred at reflux for 16 h. After cooling, the solution was filtered through a pad of Celite® and washed with ethanol. After evaporation of the solvent, the aqueous layer was extracted twice with ethyl acetate. The combined organic layers were dried over anhydrous MgSO$_4$ and evaporated. The resulting solid was purified by column chromatography eluting with ethyl acetate: hexanes 1:3 v/v to afford 70 mg (4%) of the title compound (LCMS RT=6.12 min, MH$^+$ 223.1)

$^1$H NMR (DMSO): 7.97 (2H, d, J 8.1 Hz), 7.40-7.36 (3H, m), 6.82 (1H, d, J 1.9 Hz), 6.64 (1H, dd, J 8.5 2.0 Hz), 5.41 (2H, s), 2.39 (3H, s)

All compounds below were prepared following the same general method.

2-Phenethylbenzo[d]oxazol-5-amine

LCMS RT=5.82 min, MH$^+$ 238.9; $^1$H NMR (DMSO): 7.29-7.16 (6H, m), 6.76 (1H, d, J 1.9 Hz), 6.57 (1H, dd, J 8.6 2.2 Hz), 4.98 (2H, s), 3.19-3.06 (4H, m)

2-(Benzo[d][1,3]dioxol-5-yl)benzo[d]oxazol-5-amine

LCMS RT=5.77 min, MH$^+$ 254.9; $^1$H NMR (DMSO): 7.69 (1H, dd, J 8.2 1.7 Hz), 7.58 (1H, d, J 1.7 Hz), 7.37 (1H, d, J 8.6 Hz), 7.11 (1H, d, J 8.2 Hz), 6.84 (1H, d, J 2.0 Hz), 6.64 (1H, dd, J 8.8 2.2 Hz), 6.16 (2H, s), 5.07 (2H, s)

2-(benzo[d][1,3]dioxol-5-yl)-5-chlorobenzo[d]oxazol-6-amine

LCMS RT=6.52 min, MH$^+$ 289.1; 41 NMR (DMSO): 7.72 (1H, dd, J 8.2 1.8 Hz), 7.69 (1H, s), 7.61 (1H, d, J 1.6 Hz), 7.17 (1H, d, J 8.2 Hz), 7.13 (1H, s), 6.21 (2H, s), 5.66 (2H, s)

Method 2F (Compounds Ib)

As Method 2E, except THF:water (2:1 v/v) was used instead of ethanol:water (2:1 v/v).

2-(3,4-Dichlorophenyl)benzo[d]oxazol-6-amine

LCMS RT=7.12 min, MH$^+$ 278.1; $^1$H NMR (DMSO): 8.22 (1H, d, J 1.8 Hz), 8.03 (1H, dd, J 8.4 2.0 Hz), 7.83 (1H, d, J 8.4 Hz), 7.44 (1H, d, J 8.4 Hz), 6.82 (1H, d, J 2.0 Hz), 6.68 (1H, dd, J 8.6 2.0 Hz), 5.57 (2H, s)

Method 3A (Compounds II)

3-Phenyl-N-(2-phenylbenzo[d]oxazol-5-yl)propanamide

To a solution of 2-phenylbenzo[d]oxazol-5-amine (50 mg, 0.24 mmol) in dichloromethane (2 mL) at room temperature was added 3-phenylpropanoyl chloride (44.1 mg, 0.26 mmol) followed immediately by diisopropylethylamine (82 μL, 0.48 mmol). The resulting mixture was stirred at room temperature for 16 h. Dichloromethane was added and the organic layer was washed with saturated aqueous Na$_2$CO$_3$. The combined organic layers were dried over anhydrous MgSO$_4$ and evaporated. The resulting solid was dissolved in methanol, passed through an acidic scavenger column (silica-based quaternary amine SPE-AX from Biotage®) and then evaporated to afford 61.1 mg (75%) of the title compound (LCMS RT=6.45 min, MH$^+$ 343.2)

$^1$H NMR (DMSO): 10.11 (1H, s), 8.22-8.15 (3H, m), 7.71 (1H, d, J 8.8 Hz), 7.66-7.59 (3H, m), 7.51 (1H, dd, J 8.9 2.1 Hz), 7.33-7.17 (5H, m), 2.96 (2H, t, J 7.2 Hz), 2.67 (2H, t, J 7.1 Hz)

All compounds below were prepared following the same general method.

N-(2-Phenylbenzo[d]oxazol-5-yl)acetamide

LCMS RT=5.16 min, MH⁺ 253.1; ¹H NMR (DMSO): 10.14 (1H, s), 8.21-8.14 (3H, m), 7.71 (1H, d, J 8.8 Hz), 7.65-7.60 (3H, m), 7.51 (1H, dd, J 9.0 2.1 Hz), 2.09 (3H, s)

N-(2-Phenylbenzo[d]oxazol-5-yl)propionamide

LCMS RT=5.49 min, MH⁺ 267.1; ¹H NMR (DMSO): 10.09 (1H, s), 8.21-8.16 (3H, m), 7.71 (1H, d, J 8.8 Hz), 7.66-7.61 (3H, m), 7.54 (1H, dd, J 9.0 2.1 Hz), 2.37 (2H, q, J 7.6 Hz), 1.12 (3H, t, J 7.6 Hz)

N-(2-Phenylbenzo[d]oxazol-5-yl)butyramide

LCMS RT=5.78 min, MH⁺ 281.1; ¹H NMR (DMSO): 10.09 (1H, s), 8.21-8.16 (3H, m), 7.71 (1H, d, J 8.8 Hz), 7.64-7.60 (3H, m), 7.54 (1H, dd, J 9.0 2.1 Hz), 2.33 (2H, q, J 7.6 Hz), 1.69-1.61 (2H, m), 0.94 (3H, t, J 7.6 Hz)

N-(2-Phenylbenzo[d]oxazol-5-yl)pentanamide

LCMS RT=6.21 min, MH⁺ 295.1; ¹H NMR (DMSO): 10.09 (1H, s), 8.21-8.16 (3H, m), 7.71 (1H, d, J 8.8 Hz), 7.65-7.60 (3H, m), 7.54 (1H, dd, J 9.0 2.1 Hz), 2.35 (2H, q, J 7.6 Hz), 1.66-1.58 (2H, m), 1.39-1.31 (2H, m), 0.92 (3H, t, J 7.6 Hz)

N-(2-Phenylbenzo[d]oxazol-5-yl)isobutyramide

LCMS RT=5.79 min, MH⁺ 281.1; ¹H NMR (DMSO): 10.02 (1H, s), 8.22-8.18 (3H, m), 7.71 (1H, d, J 8.8 Hz), 7.66-7.60 (3H, m), 7.55 (1H, dd, J 9.0 2.1 Hz), 2.67-2.58 (1H, m), 1.14 (6H, s)

N-(2-Phenylbenzo[d]oxazol-5-yl)furan-2-carboxamide

LCMS RT=5.82 min, MH⁺ 305.1; ¹H NMR (DMSO): 10.42 (1H, s), 8.26-8.20 (3H, m), 7.97 (1H, dd, J 1.7 0.8 Hz), 7.77 (2H, d, J 1.3 Hz), 7.66-7.62 (3H, m), 7.38 (1H, d, J 3.4 Hz), 6.73 (1H, dd, J 3.4 1.7 Hz)

4-Chloro-N-(2-p-tolylbenzo[d]oxazol-5-yl)benzamide

LCMS RT=7.23 min, MH⁺ 363.1; ¹H NMR (DMSO): 10.55 (1H, s), 8.32-8.31 (1H, m), 8.17 (2H, d, J 8.1 Hz), 8.08 (2H, d, J 8.6 Hz), 7.84-7.77 (2H, m), 7.70 (2H, d, J 8.6 Hz), 7.50 (2H, d, J 8.1 Hz), 2.49 (3H, s)

4-Methoxy-N-(2-p-tolylbenzo[d]oxazol-5-yl)benzamide

LCMS RT=6.41 min, MH⁺ 359.1; ¹H NMR (DMSO): 10.35 (1H, s), 8.33 (1H, s), 8.17 (2H, d, J 8.1 Hz), 8.07 (2H, d, J 8.7 Hz), 7.81 (2H, s), 7.51 (2H, d, J 8.3 Hz), 7.16 (2H, d, J 8.8 Hz), 3.17 (3H, s), 2.49 (3H, s)

Method 3B (Compounds II)

As Method 3A, except instead of diisopropylamine, triethylamine was used as a base.

N-(2-Phenylbenzo[d]oxazol-5-yl)nicotinamide

LCMS RT=5.48 min, MH⁺ 316.1; ¹H NMR (DMSO): 10.70 (1H, s), 9.21 (1H, d, J 2.1 Hz), 8.85 (1H, dd, J 4.8 1.6 Hz), 8.40 (1H, dt, J 8.0 2.0 Hz), 8.37 (1H, d, J 1.8 Hz), 8.30-8.27 (2H, m), 7.89-7.80 (2H, m), 7.72-7.64 (4H, m)

N-(2-Phenylbenzo[d]oxazol-5-yl)isonicotinamide

LCMS RT=5.46 min, MH⁺ 316.1; ¹H NMR (DMSO): 10.76 (1H, s), 8.88 (2H, d, J 5.9 Hz), 8.36 (1H, d, J 1.7 Hz), 8.31-8.27 (2H, m), 7.97 (2H, d, J 6.1 Hz), 7.90-7.80 (2H, m), 7.73-7.68 (3H, m)

4-Chloro-N-(2-phenylbenzo[d]oxazol-5-yl)benzamide

LCMS RT=7.07 min, MH⁺ 349.1; ¹H NMR (DMSO): 10.57 (1H, s), 8.35-8.34 (1H, m), 8.30-8.27 (2H, m), 8.09 (2H, d, J 8.6 Hz), 7.88-7.80 (2H, m), 7.72-7.67 (5H, m)

4-Methyl-N-(2-phenylbenzo[d]oxazol-5-yl)benzamide

LCMS RT=6.80 min, MH⁺ 329.2; ¹H NMR (DMSO): 10.41 (1H, s), 8.37-8.35 (1H, m), 8.30-8.26 (2H, m), 7.98 (2H, d, J 8.1 Hz), 7.84 (2H, s), 7.72-7.67 (3H, m), 7.43 (2H, d, J 8.0 Hz), 2.47 (3H, s)

4-Methoxy-N-(2-phenylbenzo[d]oxazol-5-1/1)benzamide

LCMS RT=6.37 min, MH⁺ 345.1; ¹H NMR (DMSO): 10.33 (1H, s), 8.35 (1H, s), 8.30-8.26 (2H, m), 8.06 (2H, d, J 8.7 Hz), 7.83 (2H, s), 7.71-7.67 (3H, m), 7.14 (2H, d, J 8.8 Hz), 3.92 (3H, s)

2-Methoxy-N-(2-phenylbenzo[d]oxazol-5-yl)benzamide

LCMS RT=7.06 min, MH⁺ 345.1; ¹H NMR (DMSO): 10.37 (1H, s), 8.38-8.36 (1H, m), 8.30-8.26 (2H, m), 7.84-7.56 (7H, m), 7.27 (1H, d, J 8.4 Hz), 7.14 (1H, 1, J 7.3 Hz), 3.99 (3H, s)

4-(Dimethylamino)-N-(2-phenylbenzo[d]oxazol-5-yl)benzamide

LCMS RT=6.63 min, MH⁺ 358.2; ¹H NMR (DMSO): 10.10 (1H, s), 8.35-8.34 (1H, m), 8.30-8.26 (2H, m), 7.96 (2H, d, J 8.9 Hz), 7.82-7.80 (2H, m), 7.71-7.68 (3H, m), 6.84 (2H, d, J 8.9 Hz), 3.08 (6H, s)

3,4-Dichloro-N-(2-phenylbenzo[d]oxazol-5-yl)benzamide

LCMS RT=7.95 min, MH⁺ 382.8; ¹H NMR (DMSO): 10.63 (1H, s), 8.37-8.26 (4H, m), 8.04 (1H, dd, J 8.4 2.1 Hz), 7.92-7.78 (3H, m), 7.73-7.65 (3H, m)

N-(2-Phenylbenzo[d]oxazol-5-yl)-4-(trifluoromethyl)benzamide

LCMS RT=7.19 min, MH⁺ 383.1; ¹H NMR (DMSO): 10.72 (1H, s), 8.37-8.24 (5H, m), 8.00 (2H, d, J 8.4 Hz), 7.89-7.82 (2H, m), 7.74-7.67 (3H, m)

3,5-Dichloro-N-(2-phenylbenzo[d]oxazol-5-yl)benzamide

LCMS RT=8.30 min, MH⁺ 382.9; ¹H NMR (DMSO): 10.67 (1H, s), 8.33-8.26 (3H, m), 8.09 (2H, d, J 2.1 Hz), 7.96 (1H, t, J 2.0 Hz), 7.89-7.78 (2H, m), 7.72-7.67 (3H, m)

4-Fluoro-N-(2-phenylbenzo[d]oxazol-5-yl)benzamide

LCMS RT=6.53 min, MH⁺ 333.2; ¹H NMR (DMSO): 10.50 (1H, s), 8.34-8.33 (1H, m), 8.39-8.26 (2H, m), 8.16-8.11 (2H, m), 7.86-7.79 (2H, m), 7.71-7.65 (3H, m), 7.45 (2H, J 8.8 Hz)

N-(2-Phenylbenzo[d]oxazol-5-yl)biphenyl-4-carboxamide

LCMS RT=7.74 min, MH⁺ 391.1; ¹H NMR (DMSO): 10.55 (1H, s), 8.39-8.38 (1H, m), 8.31-8.27 (2H, m), 8.17 (2H, d, J 8.5 Hz), 7.93 (2H, d, J 8.4 Hz), 7.86-7.83 (4H, m), 7.72-7.69 (3H, m), 7.62-7.50 (3H, m)

2-Phenyl-N-(2-phenylbenzo[d]oxazol-5-yl)acetamide

LCMS RT=6.32 min, MH⁺ 329.2; ¹H NMR (DMSO): 10.42 (1H, s), 8.27-8.21 (3H, m), 7.78 (1H, d, J 8.9 Hz), 7.71-7.65 (3H, m), 7.61 (1H, dd, J 8.9 2.1 Hz), 7.45-7.30 (5H, m), 3.75 (2H, s)

N-(2-Phenylbenzo[d]oxazol-5-yl)cinnamamide

LCMS RT=6.86 min, MH⁺ 341.1; ¹H NMR (DMSO): 10.48 (1H, s), 8.37 (1H, d, J 1.9 Hz), 8.29-8.26 (2H, m), 7.83 (1H, d, J 8.9 Hz), 7.73-7.67 (7H, m), 7.56-7.48 (3H, m), 6.93 (1H, d, J 15.6 Hz)

N-(2-Phenylbenzo[d]oxazol-5-yl)-1-naphthamide

LCMS RT=7.07 min, MH⁺ 365.0; ¹H NMR (DMSO): 10.82 (1H, s), 8.44 (1H, s), 8.31-8.28 (3H, m), 8.18-8.10 (2H, m), 7.88-7.83 (3H, m), 7.73-7.65 (6H, m)

N-(2-Phenylbenzo[d]oxazol-5-yl)-2-naphthamide

LCMS RT=7.37 min, MH⁺ 365.1; ¹H NMR (DMSO): 10.69 (1H, s), 8.69 (1H, s), 8.42 (1H, s), 8.31-8.28 (2H, m), 8.20-8.08 (4H, m), 7.90-7.88 (2H, m), 7.75-7.68 (5H, m)

N-(2-Phenylbenzo[d]oxazol-5-yl)thiophene-2-carboxamide

LCMS RT=6.31 min, MH⁺ 321.1; ¹H NMR (DMSO): 10.47 (1H, s), 8.30-8.26 (3H, m), 8.12 (1H, dd, J 3.8 1.1 Hz), 7.94 (1H, dd, J 5.0 1.1 Hz), 7.85 (1H, d, J 8.8 Hz), 7.77 (1H, dd, J 8.9 2.0 Hz), 7.73-7.65 (3H, m), 7.33-7.30 (1H, m)

N-(2-(Pyridin-3-yl)benzo[d]oxazol-5-yl)benzamide

LCMS RT=5.63 min, MH⁺ 315.8; ¹H NMR (DMSO): 10.53 (1H, s), 9.45-9.42 (1H, m), 8.88 (1H, dd, J 4.9 1.6 Hz), 8.62 (1H, dt, J 8.0 1.8 Hz), 8.42-8.40 (1H, m), 8.06 (2H, dd, J 6.6 1.2 Hz), 7.88 (2H, s), 7.75-7.59 (4H, m)

4-Chloro-N-(2-(pyridin-3-yl)benzo[d]oxazol-5-yl)benzamide

LCMS RT=6.12 min, MH⁺ 349.9; ¹H NMR (DMSO): 10.58 (1H, s), 9.43-9.42 (1H, m), 8.89-8.87 (1H, m), 8.64-8.59 (1H, m), 8.40-8.38 (1H, m), 8.09 (2H, d, J 8.5 Hz), 7.91-7.83 (2H, m), 7.76-7.69 (3H, m)

4-Methyl-N-(2-(pyridin-3-yl)benzo[d]oxazol-5-yl)benzamide

LCMS RT=5.91 min, MH⁺ 330.2; ¹H NMR (DMSO): 10.43 (1H, s), 9.43 (1H, dd, J 2.1 0.9 Hz), 8.88 (1H, dd, J 4.8 1.6 Hz), 8.61 (1H, dt, J 8.0 1.9 Hz), 8.40 (1H, t, J 1.2 Hz), 7.98 (2H, d, J 8.2 Hz), 7.87 (2H, d, J 1.2 Hz), 7.75-7.70 (1H, m), 7.43 (2H, d, J 8.0 Hz), 2.47 (3H, s)

4-Methoxy-N-(2-(pyridin-3-yl)benzo[d]oxazol-5-yl)benzamide

LCMS RT=5.64 min, MH⁺ 345.9; ¹H NMR (DMSO): 10.37 (1H, s), 9.45 (1H, dd, J 1.6 0.8 Hz), 8.90 (1H, dd, J 4.9 1.7 Hz), 8.63 (1H, dt, J 8.0 1.9 Hz), 8.41 (1H, t, J 1.2 Hz), 8.08 (2H, d, J 8.5 Hz), 7.88 (2H, d, J 1.2 Hz), 7.77-7.72 (1H, m), 7.17 (2H, d, J 8.7 Hz), 3.94 (3H, s)

2-Methoxy-N-(2-(pyridin-3-yl)benzo[d]oxazol-5-yl)benzamide

LCMS RT=6.02 min, MH⁺ 345.9; ¹H NMR (DMSO): 10.33 (1H, s), 9.38-9.36 (1H, m), 8.82 (1H, dd, J 4.9 1.7 Hz), 8.55 (1H, dt, J 8.0 1.8 Hz), 8.36-8.34 (1H, m), 7.82-7.73 (2H, m), 7.69-7.65 (2H, m), 7.57-7.50 (1H, m), 7.21 (1H, d, J 8.4 Hz), 7.09 (1H, t, J 7.6 Hz), 3.93 (3H, s)

4-(Dimethylamino)-N-(2-(pyridin-3-yl)benzo[d]oxazol-5-yl)benzamide

LCMS RT=5.82 min, MH⁺ 358.9; ¹H NMR (DMSO): 10.13 (1H, s), 9.45 (1H, dd, J 2.3 0.9 Hz), 8.88 (1H, dd, J 4.8 1.6 Hz), 8.64-8.59 (1H, m), 8.40-8.39 (1H, m), 7.97 (2H, d, J 9.1 Hz), 7.86-7.85 (2H, m), 7.75-7.70 (1H, m), 6.86 (2H, d, J 9.1 Hz), 3.08 (6H, s)

3,4-Dichloro-N-(2-(pyridin-3-yl)benzo[d]oxazol-5-yl)benzamide

LCMS RT=6.78 min, MH⁺ 383.5; ¹H NMR (DMSO): 10.66 (1H, s), 9.43 (1H, d, J 2.1 0.6 Hz), 8.88 (1H, dd, J 4.8 1.6 Hz), 8.61 (1H, dt, J 8.0 2.0 Hz), 8.37 (1H, d, J 2.0 Hz), 8.32 (1H, d, J 2.1 Hz), 8.04 (1H, dd, J 8.4 2.1 Hz), 7.92-7.82 (3H, m), 7.75-7.71 (1H, m)

N-(2-(Pyridin-3-yl)benzo[d]oxazol-5-yl)-4-(trifluoromethyl)benzamide

LCMS RT=6.32 min, MH⁺ 383.6; ¹H NMR (DMSO): 10.68 (1H, s), 9.37 (1H, d, J 2.1 Hz), 8.82 (1H, dd, J 4.9 1.5 Hz), 8.56 (1H, dt, J 8.0 2.0 Hz), 8.34 (1H, d, J 1.7 Hz), 8.20 (2H, d, J 8.1 Hz), 7.95 (2H, d, J 8.4 Hz), 7.88-7.79 (2H, m), 7.69-7.65 (1H, m)

3,5-Dichloro-N-(2-(pyridin-3-yl)benzo[d]oxazol-5-yl)benzamide

LCMS RT=7.06 min, MH⁺ 383.7; ¹H NMR (DMSO): 10.69 (1H, s), 9.43-9.41 (1H, m), 8.88 (1H, dd, J 4.9 1.7 Hz), 8.61 (1H, dt, J 8.0 2.0 Hz), 8.37 (1H, d, J 1.9 Hz), 8.09 (2H, d, J 1.9 Hz), 7.96-7.82 (3H, m), 7.75-7.71 (1H, m)

4-Fluoro-N-(2-(pyridin-3-yl)benzo[d]oxazol-5-yl)benzamide

LCMS RT=5.70 min, MH⁺ 334.0; ¹H NMR (DMSO): 10.47 (1H, s), 9.38-9.36 (1H, m), 8.82 (1H, dd, J 4.9 1.7 Hz), 8.56 (1H, dt, J 8.0 2.0 Hz), 8.33-8.32 (1H, m), 8.11-8.06 (2H, m), 7.85-7.80 (2H, m), 7.69-7.65 (1H, m), 7.40 (2H, t, J 8.9 Hz)

N-(2-(Pyridin-3-yl)benzo[d]oxazol-5-yl)biphenyl-4-carboxamide

LCMS RT=6.78 min, MH+ 391.6;

2-Phenyl-N-(2-(pyridin-3-yl)benzo[d]oxazol-5-yl)acetamide

LCMS RT=5.63 min, MH+ 329.7; $^1$H NMR (DMSO): 10.46 (1H, s), 9.41-9.39 (1H, m), 8.87 (1H, dd, J 4.9 1.7 Hz), 8.59 (1H, dt, J 8.0 2.0 Hz), 8.26 (1H, d, J 2.0 Hz), 7.82 (1H, d, J 8.8 Hz), 7.73-7.69 (1H, m), 7.64 (1H, dd, J 8.8 2.0 Hz), 7.44-7.30 (5H, m), 3.75 (2H, s)

3-Phenyl-N-(2-(pyridin-3-yl)benzo[d]oxazol-5-yl)propanamide

LCMS RT=5.84 min, MH+ 343.8; $^1$H NMR (DMSO): 10.14 (1H, s), 9.35-9.34 (1H, m), 8.81 (1H, dd, J 4.9 1.7 Hz), 8.53 (1H, dt, J 8.0 2.0 Hz), 8.19 (1H, d, J 2.0 Hz), 7.76 (1H, d, J 8.8 Hz), 7.69-7.63 (1H, m), 7.54 (1H, dd, J 8.8 2.0 Hz), 7.33-7.17 (5H, m), 2.95 (2H, t, J 7.6 Hz), 2.67 (2H, t, J 8.0 Hz)

N-(2-(Pyridin-3-yl)benzo[d]oxazol-5-yl)cinnamamide

LCMS RT=6.03 min, MH+ 342.0; $^1$H NMR (DMSO): 10.46 (1H, s), 9.37-9.35 (1H, m), 8.82 (1H, dd, J 4.9 1.7 Hz), 8.55 (1H, dt, J 8.0 2.0 Hz), 8.35 (1H, d, J 1.9 Hz), 7.82 (1H, d, J 8.9 Hz), 7.69-7.63 (5H, m), 7.49-7.41 (3H, m), 6.87 (1H, d, J 15.8 Hz)

N-(2-(Pyridin-3-yl)benzo[d]oxazol-5-yl)propionamide

LCMS RT=4.97 min, MH+ 267.9; $^1$H NMR (DMSO): 10.08 (1H, s), 9.34 (1H, dd, J 2.2 0.7 Hz), 8.81 (1H, dd, J 4.9 1.7 Hz), 8.53 (1H, dt, J 8.0 2.0 Hz), 8.21 (1H, d, J 2.0 Hz), 7.76 (1H, d, J 8.9 Hz), 7.68-7.63 (1H, m), 7.57 (1H, dd, J 9.0 2.1 Hz), 2.37 (2H, q, J 7.6 Hz), 1.12 (3H, t, J 7.6 Hz)

N-(2-(Pyridin-3-yl)benzo[d]oxazol-5-yl)butyramide

LCMS RT=5.26 min, MH+ 281.9; $^1$H NMR (DMSO): 10.17 (1H, s), 9.43 (1H, dd, J 2.2 0.7 Hz), 8.89 (1H, dd, J 4.9 1.7 Hz), 8.62 (1H, dt, J 8.0 2.0 Hz), 8.29 (1H, d, J 2.0 Hz), 7.84 (1H, d, J 8.9 Hz), 7.76-7.72 (1H, m), 7.65 (1H, dd, J 9.0 2.1 Hz), 2.42 (2H, q, J 7.6 Hz), 1.80-1.67 (2H, m), 1.03 (3H, t, J 7.6 Hz)

N-(2-(Pyridin-3-yl)benzo[d]oxazol-5-yl)pentanamide

LCMS RT=5.60 min, MH+ 296.0; $^1$H NMR (DMSO): 10.09 (1H, s), 9.36-9.33 (1H, m), 8.81 (1H, dd, J 4.9 1.7 Hz), 8.53 (1H, dt, J 8.0 2.0 Hz), 8.20 (1H, d, J 2.0 Hz), 7.75 (1H, d, J 8.9 Hz), 7.648-7.64 (1H, m), 7.57 (1H, dd, J 9.0 2.1 Hz), 2.35 (2H, q, J 7.6 Hz), 1.66-1.56 (2H, m), 1.42-1.29 (2H, m), 0.92 (3H, t, J 7.6 Hz)

N-(2-(Pyridin-3-yl)benzo[d]oxazol-5-yl)isobutyramide

LCMS RT=5.22 min, MH+ 282.0; $^1$H NMR (DMSO): 10.11 (1H, s), 9.41 (1H, dd, J 2.2 0.7 Hz), 8.87 (1H, dd, J 4.9 1.7 Hz), 8.60 (1H, dt, J 8.0 2.0 Hz), 8.29 (1H, d, J 2.0 Hz), 7.83 (1H, d, J 8.9 Hz), 7.74-7.69 (1H, m), 7.65 (1H, dd, J 9.0 2.1 Hz), 2.70 (1H, t, J 6.8 Hz), 1.20 (6H, d, J 6.8 Hz)

N-(2-(Pyridin-3-yl)benzo[d]oxazol-5-yl)furan-2-carboxamide

LCMS RT=5.23 min, MH+ 305.7; $^1$H NMR (DMSO); 10.41 (1H, s), 9.37 (1H, dd, J 2.2 0.8 Hz), 8.82 (1H, dd, J 4.9 1.7 Hz), 8.55 (1H, dt, J 8.0 2.0 Hz), 8.30 (1H, t, J 1.3 Hz), 7.97 (1H, dd, J 1.7 0.8 Hz), 7.82-7.81 (2H, m), 7.69-7.64 (1H, m), 7.37 (1H, dd, J 3.5 0.8 Hz), 6.74 (1H, dd, J 3.5 1.7 Hz)

N-(2-(Pyridin-3-yl)benzo[d]oxazol-5-yl)thiophene-2-carboxamide

LCMS RT=5.55 min, MH+ 322.0; $^1$H NMR (DMSO): 10.44 (1H, s), 9.37 (1H, dd, J 2.2 0.8 Hz), 8.82 (1H, dd, J 4.9 1.7 Hz), 8.56 (1H, dt, J 8.0 2.0 Hz), 8.28 (1H, t, J 1.3 Hz), 8.06 (1H, dd, J 1.7 0.8 Hz), 7.89 (1H, dd, J 5.0 1.0 Hz), 7.83 (1H, d, J 9.0 Hz), 7.77-7.73 (1H, m), 7.70-7.65 (1H, m), 7.26 (1H, dd, J 5.0 1.2 Hz)

N-(2-Phenylbenzo[d]oxazol-5-yl)benzamide

LCMS RT=6.82 min, MH+ 314.9; $^1$H NMR (DMSO): 10.43 (1H, s), 8.31-8.30 (1H, m), 8.25-8.20 (2H, m), 8.02-7.98 (2H, m), 7.79 (2H, d, J 1.2 Hz), 7.65-7.53 (6H, m)

N-(2-(4-(Diethylamino)phenyl)benzo[d]oxazol-5-yl)nicotinamide

LCMS RT=6.55 min, MH+ 386.8; $^1$H NMR (DMSO): 10.57 (1H, s), 9.14 (1H, d, J 2.1 Hz), 8.78 (1H, dd, J 4.8 1.6 Hz), 8.33 (1H, dt, J 8.0 2.0 Hz), 8.14 (1H, d, J 1.8 Hz), 7.96 (2H, d, J 9.0 Hz), 7.70-7.52 (3H, m), 6.82 (2H, d, J 9.1 Hz), 3.50-3.41 (4H, m), 1.15 (6H, t, J 7.0 Hz)

N-(2-(4-(Diethylamino)phenyl)benzo[d]oxazol-5-yl)isonicotinamide

LCMS RT=6.63 min, MH+ 386.8; $^1$H NMR (DMSO): 10.69 (1H, s), 8.87 (2H, d, J 6.1 Hz), 8.20 (1H, d, J 1.5 Hz), 8.04 (2H, d, J 9.1 Hz), 7.96 (2H, d, J 6.0 Hz), 7.77-7.69 (2H, m), 6.89 (2H, d, J 9.1 Hz), 3.50-3.46 (4H, m), 1.21 (6H, t, J 7.0 Hz)

N-(2-(4-(Diethylamino)phenyl)benzo[d]oxazol-5-yl)benzamide

LCMS RT=7.84 min, MH+ 386.1; $^1$H NMR (DMSO); 10.43 (1H, s), 8.22-8.20 (1H, m), 8.06-8.01 (4H, m), 7.72 (2H, d, J 1.2 Hz), 7.68-7.58 (3H, m), 6.89 (2H, d, J 9.1 Hz), 3.51 (4H, q, J 7.0 Hz), 1.21 (6H, t, J 7.0 Hz)

4-Chloro-N-(2-(4-(diethylamino)phenyl)benzo[d]oxazol-5-yl)benzamide

LCMS RT=8.60 min, MH+ 419.9; $^1$H NMR (DMSO): 10.44 (1H, s), 8.13 (1H, s), 8.00-7.95 (4H, m), 7.66-7.62 (4H, m), 6.82 (2H, d, J 9.1 Hz), 3.45 (4H, q, J 7.0 Hz), 1.15 (6H, t, J 7.0 Hz)

N-(2-(4-(Diethylamino)phenyl)benzo[d]oxazol-5-yl)-4-methylbenzamide

LCMS RT=8.28 min, MH+ 400.2; $^1$H NMR (DMSO): 10.28 (1H, s), 8.14 (1H, s), 7.97 (2H, d, J 8.9 Hz), 8.03 (2H, d, J 8.1 Hz), 7.65 (2H, d, J 1.2 Hz), 7.36 (2H, d, J 8.1 Hz), 6.82 (2H, d, J 9.1 Hz), 3.44 (4H, q, J 7.0 Hz), 2.40 (3H, s), 1.15 (6H, t, J 7.0 Hz)

N-(2-(4-(Diethylamino)phenyl)benzo[d]oxazol-5-yl)-4-methoxybenzamide

LCMS RT=7.86 min, MH+ 416.2; ¹H NMR (DMSO): 10.20 (1H, s), 8.13-8.12 (1H, m), 8.00-7.95 (4H, m), 7.64 (2H, d, J 1.3 Hz), 7.07 (2H, d, J 8.9 Hz), 6.82 (2H, d, J 9.1 Hz), 3.85 (3H, s), 3.44 (4H, q, J 7.0 Hz), 1.15 (6H, t, J 7.0 Hz)

N-(2-(4-(Diethylamino)phenyl)benzo[d]oxazol-5-yl)-2-methoxybenzamide

LCMS RT=8.69 min, MH+ 416.0; ¹H NMR (DMSO): 10.24 (1H, s), 8.15 (1H, d, J 1.5 Hz), 7.96 (2H, d, J 8.9 Hz), 7.68-7.49 (4H, m), 7.19 (1H, d, J 8.4 Hz), 7.08 (1H, t, J 7.5 Hz), 6.83 (2H, d, J 9.1 Hz), 3.92 (3H, s), 3.44 (4H, q, J 7.0 Hz), 1.15 (6H, t, J 7.0 Hz)

N-(2-(4-(Diethylamino)phenyl)benzo[d]oxazol-5-yl)-4-(dimethylamino)benzamide LCMS RT=8.08 min, MH+ 429.0; ¹H NMR (DMSO): 9.98 (1H, s), 8.13 (1H, s), 7.96 (2H, d, J 8.9 Hz), 7.90 (2H, d, J 8.9 Hz), 7.64-7.61 (2H, m), 6.84-6.76 (4H, m), 3.44 (4H, g, J 7.0 Hz), 3.01 (6H, s), 1.15 (6H, t, J 7.0 Hz)

3,4-Dichloro-N-(2-(4-(diethylamino)phenyl)benzo[d]oxazol-5-yl)benzamide

LCMS RT=9.66 min, MH+ 453.9; ¹H NMR (DMSO): 10.52 (1H, s), 8.25 (1H, d, J 2.0 Hz), 8.12 (1H, d, J 1.8 Hz), 7.98-7.94 (3H, m), 7.85 (1H, d, J 8.4 Hz), 7.70-7.60 (2H, m), 6.82 (2H, d, J 9.2 Hz), 3.45 (4H, q, J 7.0 Hz), 1.15 (6H, t, J 7.0 Hz)

N-(2-(4-(Diethylamino)phenyl)benzo[d]oxazol-5-yl)-4-(trifluoromethyl)benzamide LCMS RT=8.87 min, MH+ 454.4; ¹H NMR (DMSO): 10.60 (1H, s), 8.20-8.15 (3H, m), 7.99-7.93 (4H, m), 7.70-7.63 (2H, m), 6.83 (2H, d, J 9.2 Hz), 3.45 (4H, q, J 7.0 Hz), 1.15 (6H, t, J 7.0 Hz)

3,5-Dichloro-N-(2-(4-(diethylamino)phenyl)benzo[d]oxazol-5-yl)benzamide

LCMS RT=10.25 min, MH+ 453.8; ¹H NMR (DMSO): 10.63 (1H, s), 8.21-8.19 (1H, m), 8.09 (2H, d, J 1.9 Hz), 8.05 (2H, d, J 9.1 Hz), 7.97 (1H, t, J 1.9 Hz), 7.78-7.69 (2H, m), 6.91 (2H, d, J 9.1 Hz), 3.50 (4H, q, J 7.0 Hz), 1.23 (6H, t, J 7.0 Hz)

N-(2-(4-(Diethylamino)phenyl)benzo[d]oxazol-5-yl)-4-fluorobenzamide

LCMS RT=7.95 min, MH+ 404.1; ¹H NMR (DMSO): 10.38 (1H, s), 8.13-8.12 (1H, m), 8.09-8.04 (2H, m), 7.96 (2H, d, J 9.1 Hz), 7.68-7.61 (2H, m), 7.39 (2H, t, J 8.9 Hz), 6.82 (2H, d, J 9.2 Hz), 3.45 (4H, q, J 7.0 Hz), 1.15 (6H, t, J 7.0 Hz)

N-(2-(4-(Diethylamino)phenyl)benzo[d]oxazol-5-yl) biphenyl-4-carboxamide

LCMS RT=9.67 min, MH+ 461.9; ¹H NMR (DMSO): 10.42 (1H, s), 8.18-8.17 (1H, m), 8.09 (2H, d, J 8.5 Hz), 7.98 (2H, d, J 9.0 Hz), 7.87 (2H, d, J 8.6 Hz), 7.78 (2H, d, J 7.1 Hz), 7.71-7.65 (2H, m), 7.45-7.41 (3H, m), 6.82 (2H, d, J 9.2 Hz), 3.45 (4H, q, J 7.0 Hz), 1.15 (6H, t, J 7.0 Hz)

N-(2-(4-(Diethylamino)phenyl)benzo[d]oxazol-5-yl)-2-phenylacetamide

LCMS RT=7.70 min, MH+ 400.1; ¹H NMR (DMSO): 10.29 (1H, s), 8.00 (1H, d, J 1.8 Hz), 7.94 (2H, d, J 9.1 Hz), 7.59 (1H, d, J 8.7 Hz), 7.45-7.23 (6H, m), 6.81 (2H, d, J 9.2 Hz), 3.67 (2H, s), 3.43 (4H, q, J 7.0 Hz), 1.14 (6H, t, J 7.0 Hz)

N-(2-(4-(Diethylamino)phenyl)benzo[d]oxazol-5-yl)-3-phenylpropanamide

LCMS RT=8.10 min, MH+ 413.9; ¹H NMR (DMSO): 10.03 (1H, s), 7.99 (1H, d, J 1.9 Hz), 7.94 (2H, d, J 9.1 Hz), 7.58 (1H, d, J 8.7 Hz), 7.40 (1H, dd, J 8.7 2.0 Hz), 7.36-7.17 (5H, m), 6.82 (2H, d, J 9.2 Hz), 3.44 (4H, g, J 7.0 Hz), 2.94 (2H, d, J 8.1 Hz), 2.65 (1H, d, J 8.3 Hz), 1.15 (6H, t, J 7.0 Hz)

N-(2-(4-(Diethylamino)phenyl)benzo[d]oxazol-5-yl) propionamide

LCMS RT=6.79 min, MH+ 338.2; ¹H NMR (DMSO): 10.11 (1H, s), 8.07 (1H, d, J 1.9 Hz), 7.99 (2H, d, J 9.0 Hz), 7.65 (1H, d, J 8.7 Hz), 7.48 (1H, dd, J 8.8 2.0 Hz), 6.87 (2H, d, J 9.1 Hz), 3.49 (4H, q, J 7.0 Hz), 2.41 (2H, q, J 7.5 Hz), 1.24-1.14 (9H, m)

N-(2-(4-(Diethylamino)phenyl)benzo[d]oxazol-5-yl) butyramide

LCMS RT=7.24 min, MH+ 352.2; ¹H NMR (DMSO): 9.97 (1H, s), 8.00 (1H, d, J 1.9 Hz), 7.95 (2H, d, J 9.0 Hz), 7.58 (1H, d, J 8.7 Hz), 7.43 (1H, dd, J 8.8 2.0 Hz), 6.81 (2H, d, J 9.1 Hz), 3.44 (4H, q, J 7.0 Hz), 2.31 (2H, t, J 7.4 Hz), 1.68-1.58 (2H, m), 1.15 (6H, t, J 7.0 Hz), 0.94 (3H, t, J 7.4 Hz)

N-(2-(4-(Diethylamino)phenyl)benzo[d]oxazol-5-yl) pentanamide

LCMS RT=7.84 min, MH+ 366.0; ¹H NMR (DMSO): 9.98 (1H, s), 8.00 (1H, d, J 1.9 Hz), 7.95 (2H, d, J 9.0 Hz), 7.58 (1H, d, J 8.7 Hz), 7.42 (1H, dd, J 8.8 2.0 Hz), 6.81 (2H, d, J 9.1 Hz), 3.44 (4H, q, J 7.0 Hz), 2.33 (2H, t, J 7.5 Hz), 1.65-1.55 (2H, m), 1.41-1.28 (2H, m), 1.15 (6H, t, J 7.0 Hz), 0.91 (3H, t, J 7.4 Hz)

N-(2-(4-(Diethylamino)phenyl)benzo[d]oxazol-5-yl) isobutyramide

LCMS RT=7.25 min, MH+ 352.2; ¹H NMR (DMSO): 9.99 (1H, s), 8.08 (1H, d, J 1.9 Hz), 8.01 (2H, d, J 9.0 Hz), 7.65 (1H, d, J 8.7 Hz), 7.51 (1H, dd, J 8.8 2.0 Hz), 6.88 (2H, d, J 9.1 Hz), 3.50 (4H, q, J 7.0 Hz), 2.70-2.64 (1H, m), 1.24-1.17 (12H, m)

N-(2-(4-(Diethylamino)phenyl)benzo[d]oxazol-5-yl) thiophene-2-carboxamide

LCMS RT=7.77 min, MH+ 392.1; ¹H NMR (DMSO): 10.41 (1H, s), 8.14 (1H, d, J 1.8 Hz), 8.12 (1H, dd, J 3.8 1.0 Hz), 8.04 (2H, d, J 9.1 Hz), 7.95 (1H, dd, J 4.9 1.0 Hz), 7.73 (1H, d, J 8.6 Hz), 7.66 (1H, dd, J 8.7 1.9 Hz), 7.34-7.30 (1H, m), 6.90 (2H, d, J 9.2 Hz), 3.51 (4H, q, J 7.0 Hz), 1.22 (6H, t, J 7.0 Hz)

N-(2-(4-Chlorophenyl)benzo[d]oxazol-5-yl)isonicotinamide

LCMS RT=6.36 min, MH$^+$ 350.0; $^1$H NMR (DMSO): 10.71 (1H, s), 8.82 (2H, d, J 9.0 Hz), 8.32-8.30 (1H, m), 8.22 (2H, d, J 8.6 Hz), 7.90 (2H, d, J 6.0 Hz), 7.85-7.79 (2H, m), 7.71 (2H, d, J 8.6 Hz)

N-(2-(4-Chlorophenyl)benzo[d]oxazol-5-yl)benzamide

LCMS RT=7.67 min, MH$^+$ 349.0; $^1$H NMR (DMSO): 10.46 (1H, s), 8.32 (1H, s), 8.22 (2H, d, J 8.5 Hz), 8.01-7.98 (2H, m), 7.79 (2H, d, J 1.1 Hz), 7.71 (2H, d, J 8.6 Hz), 7.65-7.50 (3H, m)

4-Chloro-N-(2-(4-chlorophenyl)benzo[d]oxazol-5-yl)benzamide

LCMS RT=8.51 min, MH$^+$ 383.2; $^1$H NMR (DMSO): 10.52 (1H, s), 8.30 (1H, s), 8.22 (2H, d, J 8.8 Hz), 8.03 (2H, d, J 8.8 Hz), 7.82-7.77 (2H, m), 7.71 (2H, d, J 8.4 Hz), 7.64 (2H, d, J 8.4 Hz)

N-(2-(4-Chlorophenyl)benzo[d]oxazol-5-yl)-4-methylbenzamide

LCMS RT=8.21 min, MH$^+$ 362.8; $^1$H NMR (DMSO): 10.36 (1H, s), 8.31 (1H, s), 8.22 (2H, d, J 8.7 Hz), 7.92 (2H, d, J 8.2 Hz), 7.78 (2H, d, J 1.3 Hz), 7.71 (2H, d, J 8.7 Hz), 7.37 (2H, d, J 8.0 Hz), 2.41 (3H, s)

N-(2-(4-Chlorophenyl)benzo[d]oxazol-5-yl)-4-methoxybenzamide

LCMS RT=7.62 min, MH$^+$ 378.7; $^1$H NMR (DMSO): 10.28 (1H, s), 8.30 (1H, s), 8.22 (2H, d, J 8.9 Hz), 7.99 (2H, d, J 8.9 Hz), 7.77 (2H, s), 7.70 (2H, d, J 8.3 Hz), 7.08 (2H, d, J 8.9 Hz), 3.86 (3H, s)

N-(2-(4-Chlorophenyl)benzo[d]oxazol-5-yl)-2-methoxybenzamide

LCMS RT=8.55 min, MH$^+$ 379.0; $^1$H NMR (DMSO): 10.29 (1H, s), 8.29 (1H, d, J 1.5 Hz), 8.18 (2H, d, J 8.6 Hz), 7.77-7.62 (5H, m), 7.52-7.46 (1H, m), 7.17 (1H, d, J 8.3 Hz), 7.05 (1H, t, J 7.5 Hz), 3.89 (3H, s)

N-(2-(4-Chlorophenyl)benzo[d]oxazol-5-yl)-4-(dimethylamino)benzamide

LCMS RT=7.96 min, MH$^+$ 392.3; $^1$H NMR (DMSO): 10.12 (1H, s), 8.36 (1H, s), 8.27 (2H, d, J 8.6 Hz), 7.96 (2H, d, J 8.8 Hz), 7.83-7.81 (2H, m), 7.76 (2H, d, J 8.5 Hz), 6.84 (2H, d, J 9.0 Hz), 3.07 (6H, s)

N-(2-(4-Chlorophenyl)benzo[d]oxazol-5-yl)-4-(trifluoromethyl)benzamide

LCMS RT=8.65 min, MH$^+$ 416.7; $^1$H NMR (DMSO): 10.67 (1H, s), 8.32 (1H, s), 8.24-8.18 (4H, m), 7.95 (2H, d, J 8.6 Hz), 7.84-7.77 (2H, m), 7.71 (2H, d, J 8.6 Hz)

3,5-Dichloro-N-(2-(4-chlorophenyl)benzo[d]oxazol-5-yl)benzamide

LCMS RT=10.09 min, MH$^+$ 417.1; $^1$H NMR (DMSO): 10.68 (1H, s), 8.34 (1H, d, J 1.8 Hz), 8.28 (2H, d, J 8.6 Hz), 8.08 (2H, d, J 1.9 Hz), 7.96 (1H, t, J 1.9 Hz), 7.89-7.78 (2H, m), 7.76 (2H, d, J 8.7 Hz)

N-(2-(4-Chlorophenyl)benzo[d]oxazol-5-yl)-4-fluorobenzamide

LCMS RT=7.78 min, MH$^+$ 367.3; $^1$H NMR (DMSO): 10.58 (1H, s), 8.35 (1H, s), 8.28 (2H, d, J 8.9 Hz), 8.16-8.11 (2H, m), 7.90-7.82 (2H, m), 7.77 (2H, d, J 8.4 Hz), 7.52-7.42 (2H, m)

N-(2-(4-Chlorophenyl)benzo[d]oxazol-5-yl)-2-phenylacetamide

LCMS RT=7.48 min, MH$^+$ 362.8; $^1$H NMR (DMSO): 10.38 (1H, s), 8.22-8.17 (3H, m), 7.75-7.65 (3H, m), 7.55 (1H, dd, J 9.0 2.1 Hz), 7.38-7.24 (5H, m), 3.69 (2H, s)

N-(2-(4-Chlorophenyl)benzo[d]oxazol-5-yl)-3-phenylpropanamide

LCMS RT=7.92 min, MH$^+$ 377.3; $^1$H NMR (DMSO): 10.12 (1H, s), 8.19 (2H, d, J 8.8 Hz), 8.16 (1H, d, J 1.8 Hz), 7.74-7.68 (3H, m), 7.51 (1H, dd, J 8.8 2.0 Hz), 7.33-7.17 (5H, m), 2.95 (2H, t, J 7.3 Hz), 2.67 (2H, t, J 7.3 Hz),

N-(2-(4-Chlorophenyl)benzo[d]oxazol-5-yl)butyramide

LCMS RT=7.04 min, MH$^+$ 315.1; $^1$H NMR (DMSO): 10.07 (1H, s), 8.21-8.18 (3H, m), 7.73-7.67 (3H, m), 7.54 (1H, dd, J 8.8 1.9 Hz), 2.32 (2H, t, J 7.4 Hz), 1.72-1.58 (2H, m), 0.94 (3H, t, J 7.4 Hz)

N-(2-(4-Chlorophenyl)benzo[d]oxazol-5-yl)pentanamide

LCMS RT=7.66 min, MH$^+$ 329.1; $^1$H NMR (DMSO): 10.07 (1H, s), 8.22-8.16 (3H, m), 7.73-7.68 (3H, m), 7.56-7.51 (1H, m), 2.34 (2H, t, J 7.5 Hz), 1.66-1.56 (2H, m), 1.42-1.30 (2H, m), 0.92 (3H, t, J 7.2 Hz)

N-(2-(4-Chlorophenyl)benzo[d]oxazol-5-yl)isobutyramide

LCMS RT=7.04 min, MH$^+$ 315.1; $^1$H NMR (DMSO): 10.03 (1H, s), 8.22-8.18 (3H, m), 7.74-7.67 (3H, m), 7.56 (1H, dd, J 8.9 2.1 Hz), 2.67-2.59 (1H, m), 1.14 (6H, d, J 6.8 Hz)

N-(2-(4-Chlorophenyl)benzo[d]oxazol-5-yl)furan-2-carboxamide

LCMS RT=7.01 min, MH$^+$ 338.9; $^1$H NMR (DMSO): 10.40 (1H, s), 8.27 (1H, d, J 1.1 Hz), 8.22 (2H, d, J 8.5 Hz), 7.97 (1H, s), 7.78 (2H, s), 7.70 (2H, d, J 8.5 Hz), 7.36 (1H, d, J 3.4 Hz), 6.74-6.73 (1H, m)

N-(2-(4-Chlorophenyl)benzo[d]oxazol-5-yl)thiophene-2-carboxamide

LCMS RT=7.54 min, MH$^+$ 355.0; $^1$H NMR (DMSO): 10.42 (1H, s), 8.25-8.21 (3H, m), 8.06 (1H, dd, J 3.9 1.2 Hz), 7.89 (1H, dd, J 5.0 1.0 Hz), 7.80 (1H, d, J 8.8 Hz), 7.74-7.69 (3H, m), 7.26 (1H, dd, J 5.0 3.8 Hz)

N-(2-p-Tolylbenzo[d]oxazol-5-yl)nicotinamide

LCMS RT=6.12 min, MH$^+$ 330.1; $^1$H NMR (DMSO): 10.62 (1H, s), 9.15 (1H, dd, J 2.1 0.7 Hz), 8.79 (1H, dd, J 4.8

1.7 Hz), 8.34 (1H, dt, J 7.9 1.8 Hz), 8.27 (1H, d, J 1.6 Hz), 8.11 (2H, d, J 8.2 Hz), 7.82-7.72 (2H, m), 7.63-7.58 (1H, m), 7.44 (2H, d, J 8.0 Hz), 2.43 (3H, s)

N-(2-p-Tolylbenzo[d]oxazol-5-yl)isonicotinamide

LCMS RT=6.17 min, MH+ 330.1; $^1$H NMR (DMSO): 10.68 (1H, s), 8.82 (2H, d, J 6.0 Hz), 8.27 (1H, d, J 1.5 Hz), 8.22 (2H, d, J 8.2 Hz), 7.90 (2H, d, J 6.0 Hz), 7.81-7.72 (2H, m), 7.45 (2H, d, J 8.0 Hz), 2.43 (3H, s)

N-(2-p-Tolylbenzo[d]oxazol-5-yl)propionamide

LCMS RT=6.34 min, MH+ 281.0; $^1$H NMR (DMSO): 10.03 (1H, s), 8.14 (1H, d, J 1.8 Hz), 8.08 (2H, d, J 8.2 Hz), 7.69 (1H, d, J 8.8 Hz), 7.51 (1H, dd, J 8.8 2.0 Hz), 7.44 (2H, d, J 8.0 Hz), 2.42 (3H, s), 2.36 (2H, q, J 7.5 Hz), 1.12 (3H, t, J 7.6 Hz)

N-(2-p-Tolylbenzo[d]oxazol-5-yl)butyramide

LCMS RT=6.73 min, MH+ 295.1; $^1$H NMR (DMSO): 10.04 (1H, s), 8.13 (1H, d, J 1.8 Hz), 8.08 (2H, d, J 8.2 Hz), 7.69 (1H, d, J 8.8 Hz), 7.51 (1H, dd, J 8.8 2.0 Hz), 7.43 (2H, d, J 8.0 Hz), 2.42 (3H, s), 2.32 (2H, t, J 7.4 Hz), 1.71-1.58 (2H, m), 0.94 (3H, t, J 7.4 Hz)

N-(2-p-Tolylbenzo[d]oxazol-5-yl)pentanamide

LCMS RT=7.20 min, MH+ 309.1; $^1$H NMR (DMSO): 10.04 (1H, s), 8.13 (1H, d, J 1.8 Hz), 8.08 (2H, d, J 8.2 Hz), 7.68 (1H, d, J 8.8 Hz), 7.51 (1H, dd, J 8.8 2.0 Hz), 7.43 (2H, d, J 8.0 Hz), 2.42 (3H, s), 2.34 (2H, t, J 7.4 Hz), 1.67-1.56 (2H, m), 1.41-1.29 (2H, m), 0.92 (3H, t, J 7.4 Hz)

N-(2-p-Tolylbenzo[d]oxazol-5-yl)isobutyramide

LCMS RT=6.74 min, MH+ 295.1; $^1$H NMR (DMSO): 10.00 (1H, s), 8.15 (1H, d, J 1.8 Hz), 8.09 (2H, d, J 8.2 Hz), 7.69 (1H, d, J 8.8 Hz), 7.53 (1H, dd, J 8.8 2.0 Hz), 7.43 (2H, d, J 8.0 Hz), 2.66-2.60 (1H, m), 2.42 (3H, s), 1.13 (6H, d, J 6.8 Hz)

N-(2-p-Tolylbenzo[d]oxazol-5-yl)furan-2-carboxamide

LCMS RT=6.71 min, MH+ 319.0; $^1$H NMR (DMSO): 10.37 (1H, s), 8.23 (1H, s), 8.10 (2H, d, J 8.2 Hz), 7.98-7.96 (1H, m), 7.75 (2H, d, J 1.0 Hz), 7.44 (2H, d, J 8.0 Hz), 7.36 (1H, d, J 3.6 Hz), 6.74-6.72 (1H, m), 2.43 (3H, s)

N-(2-p-Tolylbenzo[d]oxazol-5-yl)thiophene-2-carboxamide

LCMS RT=7.15 min, MH+ 335.0; $^1$H NMR (DMSO): 10.40 (1H, s), 8.21 (1H, d, J 1.7 Hz), 8.11 (2H, d, J 8.2 Hz), 8.05 (1H, dd, J 3.8 1.0 Hz), 7.89 (1H, d, J 4.9 1.0 Hz), 7.76 (1H, d, J 8.8 Hz), 7.69 (1H, dd, J 8.9 2.0 Hz), 7.44 (2H, d, J 8.0 Hz), 7.26 (1H, dd, J 5.0 3.8 Hz), 2.43 (3H, s)

N-(2-(4-(Trifluoromethyl)phenyl)benzo[d]oxazol-5-yl)nicotinamide

LCMS RT=6.49 min, MH+ 383.9; $^1$H NMR (DMSO): 10.70 (1H, s), 9.20-9.18 (1H, m), 8.82 (1H, dd, J 4.6 1.5 Hz), 8.46 (2H, d, J 8.1 Hz), 8.40-8.36 (2H, m), 8.04 (2H, d, J 8.0 Hz), 7.92-7.82 (2H, m), 7.66-7.61 (1H, m)

N-(2-(4-(Trifluoromethyl)phenyl)benzo[d]oxazol-5-yl)isonicotinamide

LCMS RT=6.52 min; $^1$H NMR (DMSO): 10.80 (1H, s), 8.90 (2H, d, J 6.0 Hz), 8.51 (2H, d, J 8.2 Hz), 8.44 (1H, d, J 1.6 Hz), 8.09 (2H, d, J 8.2 Hz), 8.01-7.93 (3H, m), 7.89 (1H, dd, J 8.9 1.9 Hz)

N-(2-(4-(Trifluoromethyl)phenyl)benzo[d]oxazol-5-yl)acetamide

LCMS RT=6.30 min, MH+ 320.7; $^1$H NMR (DMSO): 10.17 (1H, s), 8.40 (2H, d, J 8.7 Hz), 8.22-8.19 (1H, m), 7.99 (2H, d, J 8.5 Hz), 7.77 (1H, d, J 8.7 Hz), 7.58-7.53 (1H, m), 2.09 (3H, s)

N-(2-(4-(Trifluoromethyl)phenyl)benzo[d]oxazol-5-yl)propionamide

LCMS RT=6.73 min, MH+ 335.0; $^1$H NMR (DMSO): 10.09 (1H, s), 8.40 (2H, d, J 7.8 Hz), 8.23 (1H, d, J 1.9 Hz), 7.99 (2H, d, J 8.2 Hz), 7.77 (1H, d, J 8.7 Hz), 7.57 (1H, dd, J 8.8 2.0 Hz), 2.37 (2H, q, J 7.5 Hz), 1.12 (3H, t, J 7.5 Hz)

N-(2-(4-(Trifluoromethyl)phenyl)benzo[d]oxazol-5-yl)butyramide

LCMS RT=7.18 min, MH+ 348.9; $^1$H NMR (DMSO): 10.10 (1H, s), 8.40 (2H, d, J 7.8 Hz), 8.23 (1H, d, J 1.9 Hz), 7.99 (2H, d, J 8.2 Hz), 7.77 (1H, d, J 8.7 Hz), 7.58 (1H, dd, J 8.8 2.0 Hz), 2.33 (2H, t, J 7.3 Hz), 1.69-1.59 (2H, m), 0.94 (3H, t, J 7.6 Hz)

N-(2-(4-(Trifluoromethyl)phenyl)benzo[d]oxazol-5-yl)pentanamide

LCMS RT=7.74 min, MH+ 363.1; $^1$H NMR (DMSO): 10.10 (1H, s), 8.40 (2H, d, J 7.8 Hz), 8.22 (1H, d, J 1.9 Hz), 7.99 (2H, d, J 8.2 Hz), 7.77 (1H, d, J 8.7 Hz), 7.57 (1H, dd, J 8.8 2.0 Hz), 2.36 (2H, t, J 7.3 Hz), 1.66-1.58 (2H, m), 1.42-1.29 (2H, m), 0.92 (3H, t, J 7.6 Hz)

N-(2-(4-(Trifluoromethyl)phenyl)benzo[d]oxazol-5-yl)isobutyramide

LCMS RT=7.15 min, MH+ 349.1; $^1$H NMR (DMSO): 10.09 (1H, s), 8.43 (2H, d, J 7.8 Hz), 8.27 (1H, d, J 1.9 Hz), 8.02 (2H, d, J 8.2 Hz), 7.80 (1H, d, J 8.7 Hz), 7.63 (1H, dd, J 8.8 2.0 Hz), 2.72-2.63 (1H, m), 1.18 (6H, d, J 6.8 Hz)

N-(2-(4-(Trifluoromethyl)phenyl)benzo[d]oxazol-5-yl)furan-2-carboxamide

LCMS RT=7.15 min, MH+ 373.0; $^1$H NMR (DMSO): 10.28 (1H, s), 8.27 (2H, d, J 8.0 Hz), 8.18-8.16 (1H, m), 7.86 (2H, d, J 8.2 Hz), 7.84-7.82 (1H, m), 7.69-7.67 (2H, m), 7.23 (1H, dd, J 3.5 0.8 Hz), 6.59 (1H, dd, J 3.5 1.7 Hz)

N-(2-(4-Methoxyphenyl)benzo[d]oxazol-5-yl)isonicotinamide

LCMS RT=5.76 min, MH+ 346.0; $^1$H NMR (DMSO): 10.66 (1H, s), 8.81 (2H, d, J 6.1 Hz), 8.24 (1H, d, J 1.7 Hz), 8.16 (2H, d, J 9.0 Hz), 7.90 (2H, d, J 6.1 Hz), 7.77 (1H, d, J 8.8 Hz), 7.72 (1H, dd, J 8.8 1.9 Hz), 7.18 (2H, d, J 8.9 Hz), 3.88 (3H, s)

N-(2-(4-Methoxyphenyl)benzo[d]oxazol-5-yl)acetamide

LCMS RT=5.59 min, MH⁺ 283.0; ¹H NMR (DMSO): 10.09 (1H, s), 8.13 (2H, d, J 8.9 Hz), 8.08 (1H, d, J 1.8 Hz), 7.67 (1H, d, J 8.9 Hz), 7.47 (1H, dd, J 8.8 2.0 Hz), 7.16 (2H, d, J 9.0 Hz), 3.87 (3H, s), 2.08 (3H, s)

N-(2-(4-Methoxyphenyl)benzo[d]oxazol-5-yl)propionamide

LCMS RT=5.89 min, MH⁺ 297.1; ¹H NMR (DMSO): 10.02 (1H, s), 8.15-8.10 (3H, m), 7.67 (1H, d, J 8.7 Hz), 7.49 (1H, dd, J 8.8 1.8 Hz), 7.16 (2H, d, J 8.8 Hz), 3.88 (3H, s), 2.36 (2H, q, J 7.7 Hz), 1.11 (3H, t, J 7.5 Hz)

N-(2-(4-Methoxyphenyl)benzo[d]oxazol-5-yl)butyramide

LCMS 6.19 min, MH⁺311.1; ¹H NMR (DMSO): 10.02 (1H, s), 8.13 (2H, d, J 9.0 Hz), 8.10 (1H, d, J 1.9 Hz), 7.66 (1H, d, J 8.9 Hz), 7.49 (1H, dd, J 8.8 1.8 Hz), 7.16 (2H, d, J 9.0 Hz), 3.87 (3H, s), 2.32 (2H, t, J 7.3 Hz), 1.70-1.58 (2H, m), 0.94 (3H, t, J 7.5 Hz)

N-(2-(4-Methoxyphenyl)benzo[d]oxazol-5-yl)pentanamide

LCMS RT=6.59 min, MH⁺ 325.1; ¹H NMR (DMSO): 10.02 (1H, s), 8.13 (2H, d, J 9.0 Hz), 8.10 (1H, d, J 1.9 Hz), 7.66 (1H, d, J 8.9 Hz), 7.49 (1H, dd, J 8.8 1.8 Hz), 7.16 (2H, d, J 9.0 Hz), 3.87 (3H, s), 2.34 (2H, t, J 7.3 Hz), 1.66-1.56 (2H, m), 1.41-1.29 (2H, m), 0.92 (3H, t, J 7.5 Hz)

N-(2-(4-Methoxyphenyl)benzo[d]oxazol-5-yl)isobutyramide

LCMS RT=6.19 min, MH⁺ 311.1; ¹H NMR (DMSO): 9.98 (1H, s), 8.15-8.11 (3H, m), 7.66 (1H, d, J 8.9 Hz), 7.51 (1H, dd, J 8.8 1.8 Hz), 7.16 (2H, d, J 9.0 Hz), 3.88 (3H, s), 1.13 (6H, d, J 6.9 Hz)

N-(2-(4-Methoxyphenyl)benzo[d]oxazol-5-yl)furan-2-carboxamide

LCMS RT=6.16 min, MH⁺ 335.1; ¹H NMR (DMSO): 10.36 (1H, s), 8.20-8.13 (3H, m), 7.96 (1H, dd, J 1.8 0.8 Hz), 7.72 (2H, d, J 1.2 Hz), 7.36 (1H, dd, J 3.5 0.8 Hz), 7.17 (2H, d, J 9.0 Hz), 6.73 (1H, dd, J 3.5 1.7 Hz), 3.88 (3H, s)

N-(2-(4-Methoxyphenyl)benzo[d]oxazol-5-yl)thiophene-2-carboxamide

LCMS RT=6.54 min, MH⁺" 351.0; ¹H NMR (DMSO): 10.38 (1H, s), 8.19-8.14 (3H, m), 8.05 (1H, dd, J 3.7 1.0 Hz), 7.88 (1H, dd, J 4.1 1.0 Hz), 7.74 (1H, d, J 8.8 Hz), 7.67 (1H, dd, J 8.8 2.0 Hz), 7.27-7.23 (1H, m), 7.17 (2H, d, J 8.9 Hz), 3.88 (3H, s)

N-(2-m-Tolylbenzo[d]oxazol-5-yl)butyramide

LCMS RT=6.67 min, MH⁺ 295.0;

N-(2-(3-(Dimethylamino)phenyl)benzo[d]oxazol-5-yl)butyramide

LCMS RT=6.62 min, MH⁺ 324.1; ¹H NMR (DMSO): 10.06 (1H, s), 8.13 (1H, d, J 1.8 Hz), 7.70 (1H, d, J 8.8 Hz), 7.53 (1H, dd, J 8.8 2.0 Hz), 7.49-7.37 (3H, m), 7.00-6.96 (1H, m), 3.00 (6H, s), 2.32 (2H, t, J 7.6 Hz), 1.71-1.55 (2H, m), 0.94 (3H, t, J 7.4 Hz)

N-(2-m-Tolylbenzo[d]oxazol-5-yl)isobutyramide

LCMS RT=6.64 min, MH⁺ 295.0; ¹H NMR (DMSO): 10.02 (1H, s), 8.17 (1H, d, J 1.9 Hz), 8.03-7.98 (2H, m), 7.71 (1H, d, J 8.8 Hz), 7.56-7.44 (3H, m), 2.60-2.58 (1H, m), 2.44 (3H, s), 1.14 (6H, d, J 6.8 Hz)

N-(2-(3-(Trifluoromethyl)phenyl)benzo[d]oxazol-5-yl)isobutyramide

LCMS RT=6.88 min, MH⁺ 349.0; ¹H NMR (DMSO): 10.06 (1H, s), 8.51-8.43 (2H, m), 8.23 (1H, s), 8.03 (1H, d, J 7.4 Hz), 7.91-7.85 (1H, m), 7.77 (1H, d, J 8.5 Hz), 7.62-7.57 (1H, m), 2.63 (1H, t, J 6.8 Hz), 1.14 (6H, d, J 6.8 Hz)

N-(2-(3-(Dimethylamino)phenyl)benzo[d]oxazol-5-yl)isobutyramide

LCMS RT=6.59 min, MH⁺ 324.1; ¹H NMR (DMSO): 10.01 (1H, s), 8.15 (1H, d, J 1.8 Hz), 7.70 (1H, d, J 8.8 Hz), 7.55 (1H, dd, J 8.8 2.0 Hz), 7.49-7.37 (3H, m), 7.00-6.96 (1H, m), 3.01 (6H, s), 2.65-2.58 (1H, m), 1.13 (6H, d, J 7.0 Hz)

N-(2-(3-(Trifluoromethyl)phenyl)benzo[d]oxazol-5-yl)butyramide

LCMS RT=6.85 min, MH⁺ 349.0; ¹H NMR (DMSO): 10.08 (1H, s), 8.48 (1H, d, J 7.8 Hz), 8.43 (1H, s), 8.21 (1H, d, J 1.9 Hz), 8.02 (1H, d, J 8.0 Hz), 7.88 (1H, d, J 7.7 Hz), 7.76 (1H, d, J 8.8 Hz), 7.58 (1H, dd, J 8.8 2.0 Hz), 2.33 (2H, t, J 7.4 Hz), 1.71-1.59 (2H, m), 0.95 (3H, t, J 7.4 Hz)

N-(2-o-Tolylbenzo[d]oxazol-5-yl)isobutyramide

LCMS RT=6.62 min, MH⁺ 295.1; ¹H NMR (DMSO): 10.00 (1H, s), 8.19 (1H, d, J 1.9 Hz), 8.12 (1H, dd, J 7.4 1.5 Hz), 7.71 (1H, d, J 8.8 Hz), 7.57-7.40 (4H, m), 2.75 (3H, s), 2.65-2.59 (1H, m), 1.14 (6H, d, J 6.7 Hz)

N-(2-(2-Chlorophenyl)benzo[d]oxazol-5-yl)butyramide

LCMS RT=6.42 min, MH⁺ 315.0; ¹H NMR (DMSO): 10.08 (1H, s), 8.22 (1H, d, J 1.8 Hz), 8.15 (1H, dd, J 7.6 1.8 Hz), 7.76-7.55 (5H, m), 2.34 (2H, t, J 7.4 Hz), 1.71-1.59 (2H, m), 0.95 (3H, t, J 7.4 Hz)

N-(2-(2-Chlorophenyl)benzo[d]oxazol-5-yl)isobutyramide

LCMS RT=6.41 min, MH⁺ 315.0; ¹H NMR (DMSO): 10.03 (1H, s), 8.23 (1H, d, J 1.8 Hz), 8.15 (1H, dd, J 7.6 1.7 Hz), 7.71-7.55 (5H, m), 2.68-2.58 (1H, m), 1.14 (6H, d, J 6.7 Hz)

N-(2-(3-Chlorophenyl)benzo[d]oxazol-5-yl)isobutyramide

LCMS RT=6.89 min, MH⁺ 315.0; ¹H NMR (DMSO): 10.05 (1H, s), 8.21-8.15 (3H, m), 7.75-7.63 (3H, m), 7.57 (1H, d, J 8.8 2.0 Hz), 2.62-2.58 (1H, m), 1.14 (6H, d, J 6.8 Hz)

N-(2-(3-chlorophenyl)benzo[d]oxazol-5-yl)butyramide

LCMS RT=6.89 min, MH⁺ 315.1; ¹H NMR (DMSO): 10.07 (1H, s), 8.19-8.11 (3H, m), 7.75-7.63 (3H, m), 7.56 (1H, d, J 8.8 2.0 Hz), 2.33 (2H, t, J 7.4 Hz), 1.71-1.59 (2H, m), 0.94 (3H, t, J 7.4 Hz)

Method 3C (Compounds II)

As Method 3A, except instead of diisopropylamine in dichloromethane, pyridine was used both as solvent and base.

N-(2-Phenyloxazolo[5,4-b]pyridin-6-yl)butyramide

LCMS RT=5.95 min, MH⁺ 282.0; ¹H NMR (DMSO): 10.31 (1H, s), 8.54 (1H, d, J 2.3 Hz), 8.48 (1H, d, J 2.3 Hz), 8.24-8.21 (2H, m), 7.72-7.62 (3H, m), 2.37 (2H, t, J 7.3 Hz), 1.72-1.60 (2H, m), 0.95 (3H, t, J 7.5 Hz)

N-(2-(4-Chlorophenyl)benzo[d]oxazol-5-yl)propionamide

LCMS RT=6.54 min, MH⁺ 301.0; ¹H NMR (DMSO): 10.07 (1H, s), 8.21-8.18 (3H, m), 7.73-7.67 (3H, m), 7.53 (1H, dd, J 8.8 2.0 Hz), 2.36 (2H, q, J 7.6 Hz), 1.12 (3H, t, J 7.5 Hz)

N-(2-p-Tolylbenzo[d]oxazol-5-yl)pivalamide

LCMS RT=6.94 min, MH⁺ 309.1; ¹H NMR (DMSO): 9.36 (1H, s), 8.13 (1H, d, J 1.8 Hz), 8.09 (2H, d, J 8.2 Hz), 7.69 (1H, d, J 8.8 Hz), 7.61 (1H, dd, J 8.8 2.0 Hz), 7.43 (2H, d, J 8.0 Hz), 2.42 (3H, s), 1.26 (9H, s)

N-(2-(4-Chlorophenyl)benzo[d]oxazol-5-yl)pivalamide

LCMS RT=7.28 min, MH⁺ 329.1; ¹H NMR (DMSO): 9.39 (1H, s), 8.20 (2H, d, J 8.6 Hz), 8.17 (1H, d, J 1.7 Hz), 7.74-7.62 (4H, m), 1.26 (9H, s)

N-(2-Benzylbenzo[d]oxazol-5-yl)butyramide

LCMS RT=5.98 min, MH⁺ 295.1; ¹H NMR (DMSO): 9.97 (1H, s), 8.03 (1H, d, J 1.8 Hz), 7.56 (1H, d, J 8.7 Hz), 7.44 (1H, dd, J 8.9 2.1 Hz), 7.38-7.35 (4H, m), 7.33-7.25 (1H, m), 4.31 (2H, s), 2.28 (2H, t, J 7.3 Hz), 1.69-1.53 (2H, m), 0.92 (3H, t, J 7.5 Hz)

N-(2-Benzylbenzo[d]oxazol-5-yl)isobutyramide

LCMS RT=5.96 min, MH⁺ 295.1; ¹H NMR (DMSO): 9.93 (1H, s), 8.04 (1H, d, J 2.1 Hz), 7.56 (1H, d, J 8.9 Hz), 7.47 (1H, dd, J 9.0 2.0 Hz), 7.38-7.35 (4H, m), 7.33-7.28 (1H, m), 4.31 (2H, s), 2.60-2.58 (1H, m), 1.11 (6H, d, J 6.8 Hz)

N-(2-p-Tolylbenzo[d]oxazol-4-yl)butyramide

LCMS RT=7.54 min, MH⁺ 295.1; ¹H NMR (DMSO): 10.03 (1H, s), 8.13 (2H, d, J 8.2 Hz), 8.03 (1H, d, J 8.2 Hz), 7.48-7.44 (3H, m), 7.34 (1H, t, J 8.2 Hz), 2.43 (3H, s), 1.72-1.60 (2H, m), 1.09 (3H, t, J 6.9 Hz)

N-(2-p-Tolylbenzo[d]oxazol-4-yl)isobutyramide

LCMS RT=7.51 min, MH⁺ 295.1; ¹H NMR (DMSO): 9.78 (1H, s), 7.93 (2H, d, J 8.4 Hz), 7.83 (1H, d, J 8.2 Hz), 7.28-7.23 (3H, m), 7.14 (1H, t, J 8.4 Hz), 2.22 (3H, s), 0.94 (6H, d, J 6.8 Hz)

N-(2-Cyclohexylbenzo[d]oxazol-5-yl)isobutyramide

LCMS RT=6.48 min, MH⁺ 287.1; ¹H NMR (CDCl₃): 7.82 (1H, d, J 1.7 Hz), 7.66-7.56 (1H, m), 7.46 (1H, d, J 8.8 Hz), 7.30-7.25 (1H, m), 3.07-2.97 (1H, m), 2.65-2.53 (1H, m), 2.26-2.16 (2H, m), 1.97-1.72 (5H, m), 1.56-1.37 (3H, m), 1.33 (6H, t, J 6.8 Hz)

N-(2-Cyclohexylbenzo[d]oxazol-5-yl)butyramide

LCMS RT=6.51 min, MH⁺ 287.2; ¹H NMR (CDCl₃): 7.69 (1H, s), 7.45 (1H, d, J 8.8 Hz), 7.33 (1H, d, J 8.8 Hz), 7.16 (1H, s), 2.93-2.83 (1H, m), 2.29 (2H, t, J 7.6 Hz), 2.11-2.06 (2H, m), 1.83-1.57 (6H, m), 1.43-1.18 (4H, m), 0.95 (3H, t, J 7.5 Hz)

N-(2-(2,4-Dichlorophenyl)benzo[d]oxazol-5-yl)isobutyramide

LCMS RT=7.17 min, MH⁺ 348.9; ¹H NMR (DMSO): 10.11 (1H, s), 8.23 (1H, d, J 1.7 Hz), 8.19 (1H, d, J 8.8 Hz), 7.92 (1H, d, J 2.1 Hz), 7.75 (1H, d, J 9.0 Hz), 7.68 (1H, dd, J 8.5 2.1 Hz), 7.60 (1H, dd, J 8.7 2.0 Hz), 2.64 (1H, t, J 6.8 Hz), 1.14 (6H, d, J 6.8 Hz)

N-(2-(4-Fluorophenyl)benzo[d]oxazol-5-yl)isobutyramide

LCMS RT=6.39 min, MH⁺ 299.0; ¹H NMR (DMSO): 10.00 (1H, s), 8.27-8.23 (2H, m), 8.18-8.17 (1H, m), 7.70 (1H, d, J 8.6 Hz), 7.55 (1H, dd, J 8.7 2.0 Hz), 7.46 (2H, t, J 8.7 Hz), 2.64-2.59 (1H, m), 1.14 (6H, d, J 6.8 Hz)

N-(2-(3,4-Dichlorophenyl)benzo[d]oxazol-5-yl)isobutyramide

LCMS RT=7.55 min, MH⁺ 349.5; ¹H NMR (DMSO): 10.03 (1H, s), 8.35 (1H, d, J 1.9 Hz), 8.21 (1H, d, J 1.9 Hz), 8.15 (1H, d, J 8.4 2.0 Hz), 7.89 (1H, d, J 8.4 Hz), 7.74 (1H, d, J 8.9 Hz), 7.58 (1H, dd, J 8.9 2.0 Hz), 2.67-2.60 (1H, m), 1.14 (6H, d, J 6.8 Hz)

N-(2-(5-Chloropyridin-2-yl)benzo[d]oxazol-5-yl)isobutyramide

LCMS RT=5.95 min, MH⁺ 316.0; ¹H NMR (DMSO): 10.05 (1H, s), 8.86 (1H, d, J 2.1 Hz), 8.35 (1H, d, J 8.5 Hz), 8.25 (1H, d, J 1.7 Hz), 8.19 (1H, dd, J 8.5 2.4 Hz), 7.77 (1H, d, J 8.8 Hz), 7.60 (1H, dd, J 8.8 2.0 Hz), 2.65-2.61 (1H, m), 1.14 (6H, d, J 6.7 Hz)

N-(2-(3,5-Dichlorophenyl)benzo[d]oxazol-5-yl)isobutyramide

LCMS RT=7.83 min, MH⁺ 348.7; ¹H NMR (DMSO): 10.05 (1H, s), 8.23 (1H, d, J 1.9 Hz), 8.15 (2H, d, J 2.0 Hz), 7.92 (1H, t, J 2.0 Hz), 7.75 (1H, d, J 8.8 Hz), 7.60 (1H, dd, J 8.9 2.0 Hz), 2.68-2.60 (1H, m), 1.14 (6H, d, J 6.8 Hz)

N-(2-(2,3-Dichlorophenyl)benzo[d]oxazol-5-yl) isobutyramide

LCMS RT=6.80 min, MH+ 348.9; $^1$H NMR (DMSO): 10.04 (1H, s), 8.24 (1H, d, J 1.8 Hz), 8.11 (1H, dd, J 7.9 1.6 Hz), 7.93 (1H, dd, J 8.1 1.6 Hz), 7.76 (1H, d, J 8.8 Hz), 7.63-7.59 (2H, m), 2.70-2.58 (1H, m), 1.14 (6H, d, J 6.8 Hz)

N-(2-Phenethylbenzo[d]oxazol-5-yl)isobutyramide

LCMS RT=6.22 min, MH+ 309.1; $^1$H NMR (DMSO): 9.92 (1H, s), 8.03 (1H, d, J 1.8 Hz), 7.57 (1H, d, J 8.8 Hz), 7.46 (1H, dd, J 8.7 2.0 Hz), 7.29-7.27 (4H, m), 7.23-7.16 (1H, m), 3.21-3.10 (4H, m), 1.12 (6H, d, J 6.7 Hz)

N-(2-(1-Phenylethyl)benzo[d]oxazol-5-yl)isobutyramide

LCMS RT=6.23 min, MH+ 309.1; $^1$H NMR (DMSO): 9.93 (1H, s), 8.06 (1H, d, J 1.9 Hz), 7.54 (1H, d, J 8.8 Hz), 7.47 (1H, dd, J 8.8 2.1 Hz), 7.36-7.32 (4H, m), 7.30-7.24 (1H, m), 4.51 (1H, q, J 7.1 Hz), 2.65-2.57 (1H, m), 1.71 (3H, d, J 7.2 Hz), 1.12 (6H, d, J 6.8 Hz)

N-(2-(2,5-Dichlorophenyl)benzo[d]oxazol-5-yl) isobutyramide

LCMS RT=7.10 min, MH+ 349.0; $^1$H NMR (DMSO): 10.11 (1H, s), 8.31 (1H, d, J 1.8 Hz), 8.25 (1H, dd, J 2.4 0.5 Hz), 7.83 (2H, d, J 8.7 Hz), 7.80 (1H, dd, J 8.7 2.5 Hz), 7.67 (1H, dd, J 8.9 2.0 Hz), 2.74-2.64 (1H, m), 1.20 (6H, d, J 6.8 Hz)

N-(2-(2-Chloro-4-fluorophenyl)benzo[d]oxazol-5-yl) Isobutyramide

LCMS RT=6.59 min, MH+ 333.0; $^1$H NMR (DMSO): 10.05 (1H, s), 8.30-8.20 (2H, m), 7.77-7.73 (2H, m), 7.59 (1H, dd, J 8.8 2.0 Hz), 7.51-7.45 (1H, m), 2.68-2.57 (1H, m), 1.14 (6H, d, J 6.8 Hz)

N-(2-(2-Chloro-6-fluorophenyl)benzo[d]oxazol-5-yl) isobutyramide

LCMS RT=6.29 min, MH+ 333.1; $^1$H NMR (DMSO): 10.08 (1H, s), 8.26 (1H, d, J 1.9 Hz), 7.80-7.71 (2H, m), 7.64-7.60 (2H, m), 7.57-7.50 (1H, m), 2.68-2.58 (1H, m), 1.14 (6H, d, J 6.9 Hz)

N-(2-(3-Chloro-2-fluorophenyl)benzo[d]oxazol-5-yl) isobutyramide

LCMS RT=6.65 min, MH+ 333.1; $^1$H NMR (DMSO): 10.06 (1H, s), 8.31-8.16 (2H, m), 7.88 (1H, dt, J 8.4 1.7 Hz), 7.77 (1H, d, J 8.8 Hz), 7.60 (1H, dd, J 8.9 2.0 Hz), 7.47 (1H, dt, J 8.0 1.0 Hz), 2.66-2.60 (1H, m), 1.14 (6H, d, J 6.7 Hz)

N-(2-(4-Chloro-2-fluorophenyl)benzo[d]oxazol-5-yl) isobutyramide

LCMS RT=6.69 min, MH+ 333.1; $^1$H NMR (DMSO): 10.05 (1H, s), 8.28-8.21 (2H, m), 7.79-7.73 (2H, m), 7.60-7.53 (2H, m), 2.67-2.58 (1H, m), 1.14 (6H, d, J 6.7 Hz)

N-(2-(2-Chloro-5-fluorophenyl)benzo[d]oxazol-5-yl) isobutyramide

LCMS RT=6.54 min, MH+ 333.1; $^1$H NMR (DMSO): 10.07 (1H, s), 8.25 (1H, d, J 1.9 Hz), 7.99 (1H, dd, J 9.2 3.2 Hz), 7.80-7.75 (2H, m), 7.63-7.52 (2H, m), 2.68-2.59 (1H, m), 1.14 (6H, d, J 6.7 Hz)

N-(2-(4-Chlorophenyl)benzo[d]oxazol-5-yl)cyclopentanecarboxamide

LCMS RT=7.52 min, MH+ 341.0; $^1$H NMR (DMSO): 10.08 (1H, s), 8.20-8.16 (3H, m), 7.73-7.66 (3H, m), 7.55 (1H, dd, J 8.8 2.0 Hz), 2.85-2.75 (1H, m), 1.93-1.57 (8H, m)

N-(5-Chloro-2-(4-chlorophenyl)benzo[d]oxazol-6-yl)isobutyramide

LCMS RT=8.10 min; $^1$H NMR (DMSO): 9.59 (1H, s), 8.20 (2H, d, J 8.8 Hz), 8.12 (1H, s), 8.02 (1H, s), 7.71 (2H, d, J 8.6 Hz), 2.84-2.73 (1H, m), 1.16 (6H, d, J 6.8 Hz)

N-(2-(Tetrahydro-2H-pyran-4-yl)benzo[d]oxazol-5-yl)isobutyramide

LCMS RT=5.38 min, MH+ 289.0; $^1$H NMR (DMSO): 9.95 (1H, s), 8.04 (1H, d, J 1.9 Hz), 7.59 (1H, d, J 8.8 Hz), 7.48 (1H, dd, J 8.8 2.0 Hz), 3.95-3.88 (2H, m), 3.47-3.43 (3H, m), 2.64-2.55 (1H, m), 2.06-1.99 (2H, m), 1.89-1.75 (2H, m), 1.12 (6H, d, J 6.8 Hz)

N-(2-(3,4-Dichlorophenyl)benzo[d]oxazol-5-yl)cyclopropanecarboxamide

LCMS RT=6.99 min, MH+ 348.8; $^1$H NMR (DMSO): 10.45 (1H, s), 8.30 (1H, dd, J 2.0 Hz), 8.15 (1H, d, J 1.9 Hz), 8.10 (1H, dd, J 8.4 2.0 Hz), 7.86 (1H, d, J 8.4 Hz), 7.71 (1H, d, J 8.9 Hz), 7.53 (1H, dd, J 8.9 2.0 Hz), 1.81-1.74 (1H, m), 0.82-0.76 (4H, m)

N-(2-(4-Chlorophenyl)benzo[d]oxazol-6-yl)cyclopropanecarboxamide

LCMS RT=6.93 min, MH+ 312.9; $^1$H NMR (DMSO): 10.53 (1H, s), 8.27 (1H, dd, J 1.7 Hz), 8.18 (2H, d, J 8.7 Hz), 7.74 (1H, d, J 8.7 Hz), 7.68 (2H, d, J 8.7 Hz), 7.44 (1H, dd, J 8.7 1.9 Hz), 1.86-1.78 (1H, m), 0.85-0.80 (4H, m)

N-(2-(2,3-Dichlorophenyl)benzo[d]oxazol-6-yl) isobutyramide

LCMS RT=7.05 min; $^1$H NMR (DMSO): 10.21 (1H, s), 8.34 (1H, d, J 1.8 Hz), 8.11 (1H, dd, J 7.9 1.6 Hz), 7.92 (1H, dd, J 8.1 1.5 Hz), 7.81 (1H, d, J 8.7 Hz), 7.60 (1H, t, J 8.0 Hz), 7.48 (1H, dd, J 8.7 1.9 Hz), 2.67-2.61 (1H, m), 1.14 (6H, d, J 6.8 Hz)

N-(2-(4-(Trifluoromethoxy)phenyl)benzo[d]oxazol-5-yl)isobutyramide

LCMS RT=7.04 min; $^1$H NMR (DMSO): 10.05 (1H, s), 8.32 (2H, d, J 9.0 Hz), 8.20 (1H, d, J 1.9 Hz), 7.74 (1H, d, J 8.9 Hz), 7.63-7.55 (3H, m), 2.68-2.57 (1H, m), 1.14 (6H, d, J 6.8 Hz)

N-(2-Cyclopentylbenzo[d]oxazol-5-yl)isobutyramide

LCMS RT=5.23 min, MH+ 273.0; $^1$H NMR (DMSO): 9.93 (1H, s), 8.01 (1H, d, J 1.8 Hz), 7.57 (1H, d, J 8.7 Hz), 7.46 (1H, dd, J 8.8 1.8 Hz), 3.42-3.39 (1H, m), 2.61-2.57 (1H, m), 2.15-2.04 (2H, m), 1.95-1.87 (2H, m), 1.78-1.62 (4H, m), 1.12 (6H, d, J 6.8 Hz)

N-(4-(5-Acetamidobenzo[d]oxazol-2-yl)phenyl)acetamide

LCMS RT=5.08 min, MH+ 309.9; $^1$H NMR (DMSO): 10.31 (1H, s), 10.11 (1H, s), 8.13-8.08 (3H, m), 7.82 (2H, d, J 8.7 Hz), 7.68 (1H, d, J 8.7 Hz), 7.48 (1H, dd, J 8.8 2.0 Hz), 2.11 (3H, s), 2.08 (3H, s)

N-(2-(2-Chloro-3-(trifluoromethyl)phenyl)benzo[d]oxazol-5-yl)isobutyramide

LCMS RT=6.78 min, MH+ 383.0; $^1$H NMR (DMSO): 10.07 (1H, s), 8.40 (1H, dd, J 8.1 1.3 Hz), 8.27 (1H, d, J 1.8 Hz), 8.14 (1H, dd, J 7.9 1.3 Hz), 7.82-7.77 (2H, m), 7.62 (1H, dd, J 8.8 2.1 Hz), 2.66-2.61 (1H, m), 1.14 (6H, d, J 6.8 Hz)

N-(2-(3,4-Dichlorophenyl)benzo[d]oxazol-6-yl)isobutyramide

LCMS RT=7.82 min, MH+ 349.1; $^1$H NMR (DMSO): 10.20 (1H, s), 8.33 (1H, d, J 2.0 Hz), 8.31 (1H, J 1.7 Hz), 8.14 (1H, dd, J 8.4 2.0 Hz), 7.88 (1H, d, J 8.5 Hz), 7.75 (1H, d, J 8.8 Hz), 7.48 (1H, dd, J 3.7 1.9 Hz), 2.68-2.60 (1H, m), 1.14 (6H, d, J 6.8 Hz)

N-(2-(Naphthalen-2-yl)benzo[d]oxazol-5-yl)acetamide

LCMS RT=6.45 min, MH+ 303.1; $^1$H NMR (DMSO): 10.15 (1H, s), 8.84 (1H, s), 8.27 (1H, dd, J 8.6 1.7 Hz), 8.20-8.13 (3H, m), 8.06-8.03 (1H, m), 7.76 (1H, d, J 8.6 Hz), 7.71-7.63 (2H, m), 7.54 (1H, dd, J 8.8 2.1 Hz), 2.17 (3H, s)

N-(2-(4-Acetamidophenyl)benzo[d]oxazol-5-yl)isobutyramide

LCMS RT=5.52 min, MH+ 338.0; $^1$H NMR (DMSO): 10.46 (1H, s), 10.31 (1H, s), 8.15-8.11 (3H, m), 7.82 (2H, d, J 8.7 Hz), 7.67 (1H, d, J 8.7 Hz), 7.52 (1H, dd, J 8.8 1.9 Hz), 2.67-2.58 (1H, m), 2.11 (3H, s), 1.13 (6H, d, J 6.9 Hz)

N-(2-(Naphthalen-2-yl)benzo[d]oxazol-5-yl)isobutyramide

LCMS RT=7.10 min, MH+ 331.1; $^1$H NMR (DMSO): 10.04 (1H, s), 8.84 (1H, s), 8.28-8.12 (4H, m), 8.07-8.03 (1H, m), 7.76 (1H, d, J 8.9 Hz), 7.77-7.62 (2H, m), 7.58 (1H, dd, J 8.8 2.1 Hz), 2.64 (1H, t, J 7.4 Hz), 1.15 (6H, d, J 6.9 Hz)

N-(2-(Naphthalen-2-yl)benzo[d]oxazol-5-yl)thiophene-2-carboxamide

LCMS RT=7.47 min, MH+ 370.8; $^1$H NMR (DMSO): 10.44 (1H, s), 8.86 (1H, s), 8.30-8.14 (4H, m), 8.08-8.04 (2H, m), 7.89 (1H, dd, J 5.0 1.0 Hz), 7.83 (1H, d, J 8.8 Hz), 7.76-7.64 (3H, m), 7.28-7.25 (1H, m)

N-(2-(Naphthalen-1-yl)benzo[d]oxazol-5-yl)isobutyramide

LCMS RT=7.25 min, MH+ 331.2; $^1$H NMR (DMSO): 10.07 (1H, s), 9.42 (1H, dd, J 8.2 0.7 Hz), 8.45 (1H, dd, J 7.4 1.2 Hz), 8.29 (1H, d, J 1.9 Hz), 8.26-8.21 (1H, m), 8.13-8.09 (1H, m), 7.81-7.66 (4H, m), 7.61 (1H, dd, J 8.8 2.1 Hz), 2.70-2.61 (1H, m), 1.16 (6H, d, J 6.8 Hz)

N-(2-(Biphenyl-4-yl)benzo[d]oxazol-5-yl)isobutyramide

LCMS RT=7.56 min, MH+ 357.3; $^1$H NMR (DMSO): 10.03 (1H, s), 8.28 (2H, d, J 8.5 Hz), 8.20 (1H, d, J 2.0 Hz), 7.94 (2H, d, J 8.6 Hz), 7.82-7.78 (2H, m), 7.74 (1H, d, J 8.8 Hz), 7.58-7.41 (4H, m), 2.68-2.59 (1H, m), 1.15 (6H, d, J 6.8 Hz)

N-(2-(6-Methoxynaphthalen-2-yl)benzo[d]oxazol-5-yl)isobutyramide

LCMS RT=7.02 min, MH+ 361.2; $^1$H NMR (DMSO): 10.03 (1H, s), 8.75 (1H, d, J 0.8 Hz), 8.21 (2H, dd, J 8.9 1.6 Hz), 8.10 (1H, d, J 9.0 Hz), 8.02 (1H, d, J 8.7 Hz), 7.73 (1H, d, J 8.7 Hz), 7.56 (1H, dd, J 8.8 2.0 Hz), 7.46 (1H, d, J 2.3 Hz), 7.29 (1H, dd, J 8.8 2.5 Hz), 3.93 (3H, s), 2.68-2.58 (1H, m), 1.15 (6H, d, J 6.8 Hz)

N-(2-(6-Bromonaphthalen-2-yl)benzo[d]oxazol-5-yl)isobutyramide

LCMS RT=8.13 min, MH+ 411.1; $^1$H NMR (DMSO): 10.06 (1H, s), 8.86 (1H, s), 8.36 (1H, d, J 1.7 Hz), 8.31 (1H, d, J 8.7 1.7 Hz), 8.23 (1H, d, J 1.9 Hz), 8.18 (1H, d, J 8.9 Hz), 8.13 (1H, d, J 8.7 Hz), 7.80-7.74 (2H, m), 7.58 (1H, dd, J 8.9 2.2 Hz), 2.68-2.59 (1H, m), 1.15 (6H, d, J 6.8 Hz)

N-(2-(Quinolin-3-yl)benzo[d]oxazol-5-yl)isobutyramide

LCMS RT=6.24 min, MH+ 332.2; $^1$H NMR (DMSO): 10.08 (1H, s), 9.62 (1H, d, J 2.1 Hz), 9.22 (1H, d, J 1.9 Hz), 8.29-8.24 (2H, m), 8.15 (1H, d, J 8.6 Hz), 7.95-7.90 (1H, m), 7.80-7.73 (2H, m), 7.61 (1H, dd, J 8.8 2.2 Hz), 2.69-2.60 (1H, m), 1.15 (6H, d, J 6.9 Hz)

N-(2-(Quinolin-2-yl)benzo[d]oxazol-5-yl)isobutyramide

LCMS RT=6.28 min, MH+ 332.2; $^1$H NMR (DMSO): 10.09 (1H, s), 8.64 (1H, d, J 8.4 Hz), 8.45 (1H, d, J 8.5 Hz), 8.32 (1H, d, J 1.8 Hz), 8.22 (1H, d, J 8.7 Hz), 8.13 (1H, dd, J 8.5 0.9 Hz), 7.94-7.84 (2H, m), 7.78-7.73 (1H, m), 7.63 (1H, dd, J 8.8 2.0 Hz), 2.69-2.60 (1H, m), 1.15 (6H, d, J 6.8 Hz)

N-(2-(4-Cyclohexylphenyl)benzo[d]oxazol-5-yl)isobutyramide

LCMS RT=8.87 min, MH+ 363.3; $^1$H NMR (DMSO): 10.00 (1H, s), 8.15 (1H, d, J 1.9 Hz), 8.11 (2H, d, J 8.4 Hz), 7.69 (1H, d, J 8.7 Hz), 7.53 (1H, dd, J 8.8 2.1 Hz), 7.47 (2H, d, J 8.3 Hz), 2.67-2.58 (2H, m), 1.84-1.71 (5H, m), 1.52-1.23 (5H, m), 1.13 (6H, d, J 6.8 Hz)

N-(2-(Benzo[d][1,3]dioxol-5-yl)-5-chlorobenzo[d]oxazol-6-yl)isobutyramide $^1$H NMR (DMSO): 9.56 (1H, s), 8.05 (1H, s), 7.94 (1H, s), 7.77 (1H, dd, J 8.1 1.7 Hz), 7.64 (1H, d, J 1.6 Hz), 7.16 (1H, d, J 8.2 Hz), 6.19 (2H, s), 2.83-2.72 (1H, m), 1.15 (6H, d, J 6.8 Hz)

N-(2-(Furan-2-yl)benzo[d]oxazol-5-yl)isobutyramide

LCMS RT=5.75 min, MH+ 271.1; NMR (DMSO): 9.95 (1H, s), 8.08 (1H, d, J 1.8 Hz), 8.01 (1H, dd, J 1.7 0.7 Hz), 7.62

(1H, d, J 8.9 Hz), 7.47 (1H, dd, J 8.9 2.0 Hz), 7.39 (1H, dd, J 3.5 0.7 Hz), 6.75 (1H, dd, J 3.5 1.8 Hz), 2.60-2.50 (1H, m), 1.07 (6H, d, J 6.8 Hz)

N-(4-(Naphtho[1,2-d]oxazol-2-yl)phenyl)isobutyramide

LCMS RT=7.49 min, MH+ 331.1; $^1$H NMR (DMSO): 10.22 (1H, s), 8.45 (1H, d, J 8.1 Hz), 8.22 (2H, d, J 8.7 Hz), 8.13 (1H, d, J 8.5 Hz), 7.98 (2H, s), 7.89 (2H, d, J 8.9 Hz), 7.77-7.70 (1H, m), 7.65-7.59 (1H, m), 2.69-2.60 (1H, m), 1.14 (6H, d, J 6.7 Hz)

N-(4-(Benzo[d]oxazol-2-yl)phenyl)isobutyramide

LCMS RT=6.48 min, MH+ 281.1; NMR (DMSO): 10.23 (1H, s), 8.14 (2H, d, J 8.9 Hz), 7.86 (2H, d, J 8.8 Hz), 7.79-7.75 (2H, m), 7.42-7.38 (2H, m), 2.70-2.60 (1H, m), 1.13 (6H, d, J 6.8 Hz)

Method 3D (Compounds II)

As Method 3A, except instead of diisopropylethylamine in dichloromethane, pyridine in dichloromethane was used.

N-(2-(2-Fluorophenyl)benzo[d]oxazol-5-yl)butyramide

LCMS RT=6.10 min, MH+ 299.0; $^1$H NMR (DMSO): 10.07 (1H, s), 8.25-8.19 (2H, m), 7.75 (1H, d, J 8.8 Hz), 7.72-7.66 (1H, m), 7.58-7.42 (3H, m), 2.33 (2H, t, J 7.5 Hz), 1.71-1.59 (2H, m), 0.94 (3H, t, J 7.4 Hz)

N-(2-(2-Fluorophenyl)benzo[d]oxazol-5-yl)isobutyramide

LCMS RT=6.09 min, MH+ 299.0; $^1$H NMR (DMSO): 10.09 (1H, s), 8.31-8.25 (2H, m), 7.81 (1H, d, J 8.8 Hz), 7.78-7.72 (1H, m), 7.64 (1H, d, J 8.7 1.8 Hz), 7.58-7.48 (2H, m), 2.74-2.65 (1H, m), 1.20 (6H, d, J 6.8 Hz)

N-(2-(3-Fluorophenyl)benzo[d]oxazol-5-yl)butyramide

LCMS RT=6.39 min, MH+ 299.0; $^1$H NMR (DMSO): 10.12 (1H, s), 8.24 (1H, d, J 1.9 Hz), 8.12-8.08 (1H, m), 8.02-7.97 (1H, m), 7.79 (1H, d, J 8.8 Hz), 7.75-7.70 (1H, m), 7.63-7.53 (2H, m), 2.38 (2H, t, J 7.4 Hz), 1.77-1.64 (2H, m), 1.00 (3H, t, J 7.4 Hz)

N-(2-(3-Fluorophenyl)benzo[d]oxazol-5-yl)isobutyramide

LCMS RT=6.37 min, MH+ 299.0; $^1$H NMR (DMSO): 10.08 (1H, s), 8.26 (1H, d, J 1.9 Hz), 8.12-8.08 (1H, m), 8.02-7.97 (1H, m), 7.79 (1H, d, J 9.0 Hz), 7.75-7.69 (1H, m), 7.63 (1H, dd, J 8.8 1.9 Hz), 7.59-7.52 (1H, m), 2.73-2.66 (1H, m), 1.19 (6H, d, J 6.9 Hz)

N-(2-(Benzo[d][1,3]dioxol-5-yl)benzo[d]oxazol-5-yl)isobutyramide

LCMS RT=6.14 min, MH+ 324.9; $^1$H NMR (DMSO): 10.04 (1H, s), 8.18 (1H, d, J 1.8 Hz), 7.82 (1H, dd, J 8.2 1.8 Hz), 7.73-7.69 (2H, m), 7.58 (1H, dd, J 8.7 2.0 Hz), 7.20 (1H, d, J 8.2 Hz), 6.24 (2H, s), 2.72-2.65 (1H, m), 1.19 (6H, d, J 6.9 Hz)

Ethyl 2-(4-chlorophenyl)benzo[d]oxazol-5-ylcarbamate

LCMS RT=7.14 min, MH+ 317.1; $^1$H NMR (DMSO): 9.80 (1H, s), 8.18 (2H, d, J 8.6 Hz), 7.96 (1H, d, J 1.7 Hz), 7.71-7.67 (3H, m), 7.45 (1H, dd, J 8.8 2.0 Hz), 4.16 (2H, q, J 7.2 Hz), 1.27 (3H, t, J 7.1 Hz)

Method 3E (Compounds II)

As Method 3C, except a flake of DMAP is added to the reaction

N-(2-(4-Chlorophenyl)benzo[d]oxazol-6-yl)isobutyramide

LCMS RT=7.07 min, MH+ 314.9; $^1$H NMR (DMSO): 10.15 (1H, s), 8.29 (1H, d, J 1.7 Hz), 8.18 (2H, d, J 8.8 Hz), 7.73 (1H, d, J 8.7 Hz), 7.68 (2H, d, J 8.7 Hz), 7.49 (1H, dd, J 8.7 1.9 Hz), 2.64 (1H, t, J 6.8 Hz), 1.14 (6H, d, J 6.8 Hz)

N-(2-(4-Chlorophenyl)benzo[d]oxazol-6-yl)butyramide

LCMS RT=7.07 min, MH+ 314.9; $^1$H NMR (DMSO): 10.20 (1H, s), 8.29 (1H, d, J 1.7 Hz), 8.18 (2H, d, J 8.8 Hz), 7.73 (1H, d, J 8.7 Hz), 7.68 (2H, d, J 8.7 Hz), 7.43 (1H, dd, J 8.7 1.9 Hz), 2.34 (2H, t, J 7.3 Hz), 1.71-1.59 m), 0.94 (3H, t, J 7.4 Hz)

N-(2-(4-Chlorophenyl)benzo[d]oxazol-5-yl)cyclopropanecarboxamide

LCMS RT=6.69 min, MH+ 313.1; $^1$H NMR (DMSO): 10.39 (1H, s), 8.20-8.15 (3H, m), 7.74-7.68 (3H, m), 7.54 (1H, d, J 8.9 2.1 Hz), 1.84-1.76 (1H, m), 0.81-0.78 (4H, m)

N-(2-(4-Chlorophenyl)benzo[d]oxazol-5-yl)cyclobutanecarboxamide

LCMS RT=7.07 min, MH+ 327.0; $^1$H NMR (DMSO): 9.91 (1H, s), 8.21-8.17 (3H, m), 7.73-7.67 (3H, m), 7.55 (1H, d, J 8.9 2.1 Hz), 2.33-1.81 (7H, m)

Method 3F (Compounds II)

4,4,4-Trifluoro-N-(2-p-tolylbenzo[d]oxazol-5-yl)butanamide

To 4,4,4-trifluorobutanoic acid (128 mg, 0.90 mmol) in dry dimethylformamide (5 mL) was added HATU (397 mg, 1.05 mmol) and diisopropylethylamine (494 μL, 2.85 mmol). The mixture was then stirred at room temperature for 10 min. 2-p-Tolylbenzo[d]oxazol-5-amine (200 mg, 0.95 mmol) was then added and the resulting mixture was stirred at room temperature for 16 h. Ethyl acetate was added and the organic layer was washed once with saturated aqueous $Na_2CO_3$, followed by another wash with brine. The combined organic layers were dried over anhydrous $MgSO_4$ and evaporated. The resulting solid was purified by column chromatography eluting with ethyl acetate/hexanes 40:60 v/v to afford 26.7 mg (8%) of the title compound (LCMS RT=6.77 min, MH+ 348.9)

$^1$H NMR (DMSO): 10.28 (1H, s), 8.12 (1H, d, J 1.9 Hz), 8.08 (2H, d, J 8.2 Hz), 7.72 (1H, d, J 8.8 Hz), 7.50 (1H, dd, J 8.8 2.1 Hz), 7.43 (2H, d, J 8.1 Hz), 2.67-2.56 (4H, m), 2.42 (3H, s)

All compounds below were prepared following the same general method.

3-Methoxy-N-(2-p-tolylbenzo[d]oxazol-5-yl)propanamide

LCMS RT=6.03 min, MH+ 311.0; $^1$H NMR (DMSO): 10.13 (1H, s), 8.14 (1H, d, J 2.2 Hz), 8.08 (2H, d, J 8.4 Hz), 7.70 (1H, d, J 8.9 Hz), 7.52 (1H, dd, J 8.9 2.0 Hz), 7.43 (2H, d, J 8.3 Hz), 3.65 (2H, t, J 6.2 Hz), 3.26 (3H, s), 2.61-2.56 (2H, m), 2.42 (3H, s)

Tert-butyl-3-oxo-3-(2-phenylbenzo[d]oxazol-5-ylamino)propylcarbamate

LCMS RT=6.22 min, MH+ 382.0; $^1$H NMR (CDCl$_3$): 8.19-8.14 (2H, m), 7.89 (2H, s), 7.50-7.42 (5H, m), 5.15-5.05 (1H, br), 3.49-3.43 (2H, m), 2.59 (2H, t, J 7.6 Hz), 1.38 (9H, s)

3,3,3-Trifluoro-N-(2-p-tolylbenzo[d]oxazol-5-yl)propanamide

LCMS RT=14.01 min, MH+ 335.0; $^1$H NMR (DMSO): 10.48 (1H, s), 8.11-8.08 (3H, m), 7.75 (1H, d, J 9.0 Hz), 7.49 (1H, dd, J 8.7 2.1 Hz), 7.44 (2H, d, J 8.0 Hz), 3.55 (2H, q, J 10.9 Hz)

N-(2-(4-Chlorophenyl)benzo[d]oxazol-5-yl)-3-methoxypropanamide

LCMS RT=6.32 min, MH+ 331.1; $^1$H NMR (DMSO): 10.17 (1H, s), 8.22-8.17 (3H, m), 7.74-7.68 (3H, m), 7.54 (1H, dd, J 8.9 2.1 Hz), 3.65 (2H, t, J 6.1 Hz), 3.26 (3H, s), 2.59 (2H, t, J 6.1 Hz)

N-(2-(4-Chlorophenyl)benzo[d]oxazol-5-yl)-3,3,3-trifluoropropanamide

LCMS RT=6.72 min, MH+ 354.7; $^1$H NMR (DMSO): 10.52 (1H, s), 8.21 (2H, d, J 8.7 Hz), 8.14 (1H, d, J 2.0 Hz), 7.78 (1H, d, J 8.7 Hz), 7.70 (2H, d, J 8.7 Hz), 7.52 (1H, dd, J 8.8 2.1 Hz), 3.56 (2H, q, J 11.1 Hz)

N-(2-(3,4-Dichlorophenyl)benzo[d]oxazol-5-yl)-3,3,3-trifluoropropanamide

LCMS RT=7.41 min, MH+ 388.8; $^1$H NMR (DMSO): 10.54 (1H, s), 8.36 (1H, d, J 2.0 Hz), 8.17-8.14 (2H, m), 7.90 (1H, d, J 8.4 Hz), 7.80 (1H, d, J 8.8 Hz), 7.54 (1H, dd, J 8.9 2.1 Hz), 3.56 (2H, q, J 11.1 Hz)

N-(2-(2,3-Dichlorophenyl)benzo[d]oxazol-5-yl)-3,3,3-trifluoropropanamide

LCMS RT=6.76 min, MH+ 388.9; $^1$H NMR (DMSO): 10.55 (1H, s), 8.20 (1H, d, J 1.9 Hz), 8.12 (1H, dd, J 7.9 1.6 Hz), 7.94 (1H, dd, J 8.1 1.6 Hz), 7.83 (1H, d, J 8.8 Hz), 7.64-7.55 (2H, m), 3.58 (2H, q, J 11.1 Hz)

The compounds below were obtained by Method 3F, using the appropriate Boc-amino acid. Coupling was followed by deprotection of Boc group using 4M HCl in dioxane for 20 min at room temperature.

(S)-N-(2-(4-Chlorophenyl)benzo[d]oxazol-5-yl)pyrrolidine-2-carboxamide

LCMS RT=4.54 min, MH+ 342.0; $^1$H NMR (DMSO): 10.15 (1H, s), 8.23 (1H, d, J 1.7 Hz), 8.19 (2H, d, J 8.7 Hz), 7.74-7.63 (4H, m), 3.75-3.69 (1H, m), 2.91 (2H, t, J 6.5 Hz), 2.12-2.00 (1H, m), 1.90-1.60 (3H, m)

(S)-N-(2-(4-Chlorophenyl)benzo[d]oxazol-5-yl)-2-(methylamino)propanamide

LCMS RT=4.46 min, MH+ 330.1; $^1$H NMR (DMSO): 8.20-8.10 (3H, m), 7.67 (2H, d, J 8.8 Hz), 7.58-7.47 (2H, m), 3.00 (1H, q, J 6.8 Hz), 2.24 (3H, s), 1.16 (3H, d, J 6.8 Hz)

The compound below was obtained by Method 3F, using the appropriate Fmoc-amino acid. Coupling was followed by deprotection of the Fmoc group using piperidine/DMF 20:80 v/v.

(S)-2-Amino-N-(2-(4-chlorophenyl)benzo[d]oxazol-5-yl)propanamide

LCMS RT=4.46 min, MH+ 316.1; $^1$H NMR (CDCl$_3$): 9.56 (1H, s), 8.11 (2H, d, J 8.7 Hz), 7.98 (1H, d, J 1.9 Hz), 7.55 (1H, dd, J 8.8 2.1 Hz), 7.46-7.41 (3H, m), 3.60 (1H, q, J 7.0 Hz), 1.41 (3H, d, J 7.0 Hz)

Method 3G (Compounds II)

As Method 3C, except instead of the acid chloride, the corresponding anhydride was used

2,2,2-Trifluoro-N-(2-p-tolylbenzo[d]oxazol-5-yl)acetamide

LCMS RT=6.93 min, MH+ 321.0; $^1$H NMR (DMSO): 11.46 (1H, br), 8.22 (2H, d, J 8.6 Hz), 8.15 (1H, d, J 1.9 Hz), 7.85 (1H, d, J 8.8 Hz), 7.73-7.68 (3H, m)

N-(2-(4-Chlorophenyl)benzo[d]oxazol-5-yl)-2,2,2-trifluoroacetamide

LCMS RT=7.12 min, MH+340.8; $^1$H NMR (DMSO): 11.43 (1H, br), 8.12-8.09 (3H, m), 7.82 (1H, d, J 8.8 Hz), 7.67 (1H, dd, J 8.9 2.1 Hz), 7.45 (2H, d, J 8.0 Hz)

Method 3H (Compounds II)

3-Morpholino-N-(2-phenylbenzo[d]oxazol-5-yl)propanamide

To 2-phenylbenzo[d]oxazol-5-amine (75 mg, 0.36 mmol) and methyl 3-morpholinopropanoate (63 μL, 0.39 mmol) in toluene (2.5 mL) was added a 2M solution of trimethylaluminum in toluene (0.22 mL, 0.43 mmol). The resulting solution was heated twice for 5 min at 160° C. in the microwave. After cooling, sodium bicarbonate solution was added and the aqueous layer was extracted with ethyl acetate. The organic layer was then washed with brine and the combined organic layers were dried over anhydrous MgSO$_4$. After evaporation, the impurities were removed by filtering through on a plug of silica eluting with ethyl acetate/hexanes 50:50 v/v and the desired product was obtained by elution with methanol to afford 17.5 mg (14%) of the title compound (LCMS RT=5.54 min, MH+ 352.0)

$^1$H NMR (DMSO): 10.25 (1H, s), 8.22-8.15 (3H, m), 7.73 (1H, d, J 8.8 Hz), 7.65-7.59 (3H, m), 7.52 (1H, dd, J 8.8 2.0 Hz), 3.60-3.57 (4H, m), 2.68-2.64 (2H, m), 2.44-2.41 (4H, m)

Method 4 (Compounds III)

N-(2-Phenylbenzo[d]oxazol-5-yl)propane-1-sulfonamide

To a solution of 2-phenylbenzo[d]oxazol-5-amine (100 mg, 0.48 mmol) in dichloromethane (2 mL) at room temperature was added pyridine (83 µL, 0.95 mmol) followed by propane-1-sulfonyl chloride (61 µL, 0.52 mmol). The resulting solution was then stirred at room temperature for 16 h. Dichloromethane was added and the organic layer was washed with saturated aqueous copper sulfate solution. The combined organic layers were dried over anhydrous $MgSO_4$ and evaporated. The resulting insoluble solid was washed with saturated aqueous $NaHCO_3$ to afford 37.2 mg (25%) of the title compound (LCMS RT=6.25 min, $MH^+$ 317.0)

$^1$H NMR (DMSO): 9.89 (1H, br), 8.21-8.18 (2H, m), 7.77 (1H, d, J 8.8 Hz), 7.66-7.59 (4H, m), 7.28 (1H, dd, J 8.8 2.1 Hz), 3.10-3.04 (2H, m), 1.77-1.64 (2H, m), 0.94 (3H, t, J 7.5 Hz)

The compounds below were prepared following the same general method, and purified by column chromatography eluting with ethyl acetate:hexanes 30:70 v/v.

N-(2-Phenylbenzo[d]oxazol-5-yl)propane-2-sulfonamide

LCMS RT=6.16 min, $MH^+$ 317.0; $^1$H NMR (DMSO): 9.89 (1H, br), 8.21-8.18 (2H, m), 7.76 (1H, d, J 8.8 Hz), 7.69-7.59 (4H, m), 7.30 (1H, dd, J 8.8 2.2 Hz), 1.26 (6H, d, J 6.9 Hz)

N-(2-Phenylbenzo[d]oxazol-5-yl)benzenesulfonamide

LCMS RT=6.43 min, $MH^+$ 350.8; $^1$H NMR (DMSO): 10.40 (1H, br), 8.15 (2H, dd, J 7.2 1.6 Hz), 7.77-7.74 (2H, m), 7.68-7.51 (7H, m), 7.46 (1H, d, J 2.1 Hz), 7.12 (1H, dd, J 8.8 2.1 Hz)

N-(2-p-Tolylbenzo[d]oxazol-5-yl)propane-1-sulfonamide

LCMS RT=6.53 min, $MH^+$ 331.0; $^1$H NMR (DMSO): 9.85 (1H, br), 8.80 (2H, d, J 7.8 Hz), 7.74 (1H, d, J 9.0 Hz), 7.60 (1H, d, J 2.0 Hz), 7.44 (2H, d, J 8.1 Hz), 7.26 (1H, dd, J 8.7 2.2 Hz), 3.09-3.04 (2H, m), 2.42 (3H, s), 1.74-1.64 (2H, m), 0.94 (3H, t, J 7.6 Hz)

N-(2-p-Tolylbenzo[d]oxazol-5-yl)propane-2-sulfonamide

LCMS RT=6.58 min, $MH^+$ 330.9; $^1$H NMR (DMSO); 9.85 (1H, br), 8.08 (2H, d, J 8.2 Hz), 7.72 (1H, d, J 8.6 Hz), 7.62 (1H, d, J 1.8 Hz), 7.43 (2H, d, J 8.2 Hz), 7.28 (1H, dd, J 8.8 2.2 Hz), 2.60-2.57 (1H, m), 2.42 (3H, s), 1.26 (6H, d, J 6.8 Hz)

N-(2-(4-Chlorophenyl)benzo[d]oxazol-5-yl)propane-1-sulfonamide

LCMS RT=6.81 min, $MH^+$ 350.9; $^1$H NMR (DMSO): 9.73 (1H, br), 8.20 (2H, d, J 8.7 Hz), 7.77 (1H, d, J 8.6 Hz), 7.71 (2H, d, J 8.7 Hz), 7.63 (1H, d, J 1.9 Hz), 7.29 (1H, dd, J 8.8 2.2 Hz), 3.10-3.05 (2H, m), 1.77-1.65 (2H, m), 0.94 (3H, t, J 7.6 Hz)

N-(2-(4-Chlorophenyl)benzo[d]oxazol-5-yl)propane-2-sulfonamide

LCMS RT=6.68 min, $MH^+$ 351.0; $^1$H NMR (DMSO): 9.88 (1H, br), 8.19 (2H, d, J 8.7 Hz), 7.76 (1H, d, J 8.8 Hz), 7.70 (2H, d, J 8.7 Hz), 7.65 (1H, d, J 2.0 Hz), 7.32 (1H, dd, J 8.8 2.2 Hz), 3.24 (1H, t, J 6.7 Hz), 1.26 (6H, d, J 6.7 Hz)
Method 5 (Compounds IV)

N-(Pyridin-4-ylmethyl)-2-p-tolylbenzo[d]oxazol-5-amine

To 2-p-tolylbenzo[d]oxazol-5-amine (500 mg, 2.32 mmol) in 1,2-dichloroethane (20 mL) at room temperature was added acetic acid (142 µL, 2.32 mmol) and isonicotinaldehyde (222.5 µL, 2.29 mmol) and the mixture was stirred for 1 h. Sodium triacetoxyborohydride (707 mg, 3.35 mmol) was then added and the mixture was stirred at room temperature for 24 h. The mixture was then diluted with dichloromethane and the organic layer was washed with saturated aqueous $NaHCO_3$. The combined organic layers were dried over anhydrous $MgSO_4$ and evaporated. The resulting solid was purified by column chromatography eluting with ethyl acetate: hexanes 20:80 to afford 328 mg (47%) of the title compound (LCMS RT=6.27 min, $MH^+$ 316.1)

$^1$H NMR (DMSO): 8.50 (2H, d, J 6.0 Hz), 8.00 (2H, d, J 8.1 Hz), 7.48-7.37 (5H, m), 6.76-6.72 (2H, m), 6.51 (1H, t, J 6.2 Hz), 4.38 (2H, d, J 6.1 Hz), 2.39 (3H, s)

All compounds below were prepared following the same general method.

N-Benzyl-2-phenylbenzo[d]oxazol-5-amine

LCMS RT=7.90 min, $MH^+$ 301.0; $^1$H NMR (DMSO); 9.14-8.10 (2H, m), 7.61-7.56 (3H, m), 7.48-7.21 (6H, m), 6.79-6.75 (2H, m), 6.39 (1H, t, J 6.0 Hz), 4.32 (2H, d, J 6.1 Hz)

N-Butyl-2-phenylbenzo[d]oxazol-5-amine

LCMS RT=8.25 min, $MH^+$ 267.0; $^1$H NMR (DMSO): 8.16-8.12 (2H, m), 7.61-7.58 (3H, m), 7.47 (1H, d, J 8.7 Hz), 6.81 (1H, d, J 2.1 Hz), 6.72 (1H, dd, J 8.8 2.3 Hz), 6.64 (1H, t, J 5.5 Hz), 3.08-3.00 (2H, m), 1.64-1.51 (2H, m), 1.49-1.35 (2H, m), 0.94 (3H, t, J 7.2 Hz)

N-Isobutyl-2-phenylbenzo[d]oxazol-5-amine

LCMS RT=8.26 min, $MH^+$ 267.0; $^1$H NMR (DMSO): 8.15-8.12 (2H, m), 7.62-7.51 (3H, m), 7.46 (1H, d, J 8.8 Hz), 6.81 (1H, d, J 2.1 Hz), 6.74 (1H, dd, J 8.8 2.3 Hz), 5.73 (1H, t, J 5.6 Hz), 2.87 (2H, t, J 6.1 Hz), 1.95-1.82 (1H, m), 0.97 (6H, d, J 6.6 Hz)

N-Butyl-2-(4-chlorophenyl)benzo[d]oxazol-5-amine

LCMS RT=9.58 min, $MH^+$ 301.1; $^1$H NMR (DMSO): 8.14 (2H, d, J 8.7 Hz), 7.66 (2H, d, J 8.7 Hz), 7.47 (1H, d, J 8.7 Hz), 6.81 (1H, d, J 2.1 Hz), 6.73 (1H, dd, J 8.8 2.2 Hz), 6.67 (1H, t, J 5.7 Hz), 3.07-3.00 (2H, m), 1.62-1.53 (2H, m), 1.48-1.36 (2H, m), 0.94 (3H, t, J 7.2 Hz)

2-(4-Chlorophenyl)-N-isobutylbenzo[d]oxazol-5-amine

LCMS RT=8.85 min, $MH^+$ 301.0; $^1$H NMR (DMSO): 8.14 (2H, d, J 8.7 Hz), 7.66 (2H, d, J 8.7 Hz), 7.47 (1H, d, J 8.8 Hz), 6.80 (1H, d, J 2.0 Hz), 6.75 (1H, dd, J 8.8 2.2 Hz), 5.75 (1H, t, J 5.7 Hz), 2.87 (2H, d, J 6.2 Hz), 1.93-1.82 (1H, m), 0.97 (6H, d, J 6.7 Hz)

N-Benzyl-2-(4-chlorophenyl)benzo[d]oxazol-5-amine

LCMS RT=8.39 min, $MH^+$ 335.0; $^1$H NMR (DMSO): 8.11 (2H, d, J 8.8 Hz), 7.65 (2H, d, J 8.7 Hz), 7.47 (1H, d, J 9.4 Hz), 7.42-7.21 (5H, m), 6.81-6.78 (2H, m), 6.42 (1H, t, J 5.8 Hz), 4.32 (2H, d, J 6.8 Hz)

N-Butyl-2-p-tolylbenzo[d]oxazol-5-amine

LCMS RT=8.44 min, MH⁺ 281.0; ¹H NMR (DMSO): 8.02 (2H, d, J 8.2 Hz), 7.46-7.38 (3H, m), 6.79 (1H, d, J 2.0 Hz), 6.69 (1H, dd, J 8.8 2.4 Hz), 5.62 (1H, t, J 5.7 Hz), 3.06-3.00 (2H, m), 2.40 (3H, s), 1.62-1.53 (2H, m), 1.48-1.36 (2H, m), 0.94 (3H, t, J 7.2 Hz)

N-Isobutyl-2-p-tolylbenzo[d]oxazol-5-amine

LCMS RT=8.48 min, MH⁺ 281.0; ¹H NMR (DMSO): 8.03 (2H, d, J 8.1 Hz), 7.45-7.38 (3H, m), 6.79 (1H, d, J 2.1 Hz), 6.71 (1H, dd, J 8.8 2.3 Hz), 5.70 (1H, t, J 5.7 Hz), 2.86 (2H, t, J 6.3 Hz), 2.40 (3H, s), 1.95-1.81 (1H, m), 0.97 (6H, d, J 6.7 Hz)

N-Benzyl-2-p-tolylbenzo[d]oxazol-5-amine

LCMS RT=7.95 min, MH⁺ 315.1; ¹H NMR (DMSO): 8.00 (2H, d, J 8.1 Hz), 7.46-7.21 (8H, m), 6.77-6.73 (2H, m), 6.37 (1H, t, J 6.4 Hz), 4.32 (2H, d, J 6.0 Hz), 2.40 (3H, s)

2-(4-Chlorophenyl)-N,N-diisobutylbenzo[d]oxazol-5-amine

LCMS RT=17.03 min, MH⁺ 357.1; ¹H NMR (DMSO): 8.26 (2H, d, J 8.5 Hz), 7.80 (2H, d, J 8.6 Hz), 7.67 (1H, d, J 9.0 Hz), 7.09 (1H, d, J 2.3 Hz), 6.96 (1H, dd, J 9.1 2.4 Hz), 3.32 (4H, d, J 7.2 Hz), 2.20-2.10 (2H, m), 1.02 (12H, d, J 6.6 Hz)

Method 6 (Compounds V)

1-Phenyl-3-(2-phenylbenzo[d]oxazol-5-yl)urea

To 2-phenylbenzo[d]oxazol-5-amine (75 mg, 0.36 mmol) in dichloromethane (2 mL) at room temperature was added phenyl isocyanate (43 μL, 0.39 mmol). The solution was stirred at room temperature for 16 h. The resulting precipitate was filtered off and washed with dichloromethane to afford 99.9 mg (85%) of the title compound (LCMS RT=6.45 min, MH⁺ 330.1)

¹H NMR (DMSO): 8.85 (1H, s), 8.71 (1H, s), 8.22-8.19 (2H, m), 8.00 (1H, d, J 2.0 Hz), 7.71 (1H, d, J 8.9 Hz), 7.65-7.60 (3H, m), 7.50-7.47 (2H, m), 7.40 (1H, dd, J 8.8 2.1 Hz), 7.30 (2H, t, J 8.4 Hz), 7.02-6.95 (1H, m)

The compound below was prepared following the same general method.

1-Isopropyl-3-(2-phenylbenzo[d]oxazol-5-yl)urea

LCMS RT=5.94 min, MH⁺ 296.0; ¹H NMR (DMSO): 8.47 (1H, s), 8.20-8.16 (2H, m), 7.93 (1H, d, J 1.9 Hz), 7.64-7.59 (4H, m), 7.30 (1H, dd, J 8.8 2.1 Hz), 6.03 (1H, d, J 7.5 Hz), 3.85-3.74 (1H, m), 1.12 (6H, d, J 6.5 Hz)

Method 7 (Compounds VI)

N-(2-(4-Chlorophenyl)benzo[d]oxazol-5-yl)-N-methylpropionamide

To sodium hydride (15 mg, 0.37 mmol) under nitrogen at 0° C. was slowly added a solution of N-(2-(4-chlorophenyl)benzo[d]oxazol-5-yl)propionamide (100 mg, 0.33 mmol) in dimethylformamide (10 mL). After 10 min at 0° C., methyl iodide (56 μL, 0.37 mmol) was added, and the solution was left warming up to room temperature for 16 h. The mixture was then diluted with ethyl acetate, and then washed three times with water. The combined organic layers were dried over anhydrous MgSO₄ and evaporated. The resulting solid was purified by column chromatography eluting with ethyl acetate/hexanes 50:50 v/v to afford 36.4 mg (35%) of the title compound (LCMS RT=7.00 min, MH⁺ 315.0)

¹H NMR (CDCl₃): 8.13 (2H, d, J 8.6 Hz), 7.55-7.52 (2H, m), 7.46 (2H, d, J 8.6 Hz), 7.13 (1H, dd, J 8.3 2.0 Hz), 3.26 (3H, s), 2.04 (2H, q, J 7.6 Hz), 1.00 (3H, t, J 7.6 Hz)

Method 7 (Compounds VIb)

N-(2-(4-Chlorophenyl)benzo[d]oxazol-5-yl)-N-methylisobutyramide

LCMS RT=7.44 min, MH⁺ 329.1; ¹H NMR (DMSO): 8.22 (2H, d, J 8.7 Hz), 7.91-7.87 (2H, m), 7.72 (2H, d, J 8.6 Hz), 7.43 (1H, d, J 8.3 Hz), 3.20 (3H, s), 2.46-2.42 (1H, m), 0.93 (6H, d, J 6.6 Hz)

2-(4-Chlorophenyl)-N-isobutyl-N-methylbenzo[d]oxazol-5-amine

LCMS RT=10.59 min, MH⁺ 315.1; ¹H NMR (DMSO): 8.15 (2H, d, J 8.6 Hz), 7.67 (2H, d, J 8.6 Hz), 7.56 (1H, d, J 9.0 Hz), 6.96 (1H, d, J 2.5 Hz), 6.84 (1H, dd, J 9.1 2.5 Hz), 3.17 (2H, d, J 7.3 Hz), 2.97 (3H, s), 2.13-1.97 (1H, m), 0.90 (6H, d, J 6.7 Hz)

Method 8 (Compounds VII)

N-(2-(4-Chlorophenyl)benzo[d]oxazol-5-yl)-2-methylpropanethioamide

To N-(2-(4-chlorophenyl)benzo[d]oxazol-5-yl)isobutyramide (50 mg, 0.16 mmol) in toluene (2 mL) at 110° C. was added Lawesson's reagent (35 mg, 0.09 mmol). The resulting solution was heated at 110° C. for 7 h. After cooling, the solution was diluted with water and extracted with ethyl acetate. The combined organic layers were washed with brine, then dried over anhydrous MgSO₄ and evaporated. The resulting solid was purified by column chromatography eluting with ethyl acetate/hexanes 20:80 v/v to afford 13.8 mg (26%) of the title compound (LCMS RT=7.36 min, MH⁺331.2)

¹H NMR (DMSO): 11.59 (1H, s), 8.37 (1H, d, J 2.0 Hz), 8.22 (2H, d, J 8.8 Hz), 7.83 (1H, d, J 8.7 Hz), 7.73-7.65 (3H, m), 3.18-3.09 (1H, m), 1.25 (6H, d, J 6.7 Hz)

Method 9 (Compound VIII)

2-(4-Chlorophenyl)benzo[d]oxazole-5-diazonium tetrafluoroboric acid salt

To a solution of 2-(4-chlorophenyl)benzo[d]oxazol-5-amine (500 mg, 2.04 mmol) in water (3 mL) and tetrafluoroboric acid (50% in water, 2 mL) at 0° C. was added a solution of sodium nitrite (140 mg, 2.04 mmol) in water (2 mL), dropwise over 5 min. The resulting mixture was stirred at 0° C. for 15 min, and then at room temperature for 1 h. The solid was then filtered off, washed with dilute aqueous tetrafluoroboric acid solution and methanol to afford 370 mg (53%) of the title compound, which was used directly without characterization.

Method 10 (Compound IX)

S-2-(4-Chlorophenyl)benzo[d]oxazol-5-yl ethanethioate

To a stirred solution of potassium thioacetate (130 mg, 1.13 mmol) in DMSO (2.8 mL) at room temperature was added dropwise a solution of 2-(4-chlorophenyl)benzo[d]oxazole-5-diazonium tetrafluoroboric acid salt (370 mg, 1.08 mmol) in DMSO (1.4 mL). After 15 min, the mixture was heated at 70° C. for 1 h. After cooling, the mixture was diluted with water, and then extracted several times with ethyl acetate. The combined organic layers were washed with brine, dried over anhydrous MgSO₄ and evaporated. The resulting solid was purified by column chromatography eluting using a gradient (ethyl acetate/hexanes 5:95 v/v to ethyl acetate/hexanes 15:85 v/v) and triturated with diethyl ether/hexanes to afford 11.3 mg (3%) of the title compound (LCMS RT=7.89 min, MH+ 304.2)

$^1$H NMR (CDCl$_3$): 8.24 (2H, d, J 8.7 Hz), 7.88 (1H, dd, J 1.7 0.4 Hz), 7.67 (1H, dd, J 8.7 0.4 Hz), 7.57 (2H, d, J 8.8 Hz), 7.46 (1H, dd, J 8.4 1.7 Hz), 2.51 (3H, s)

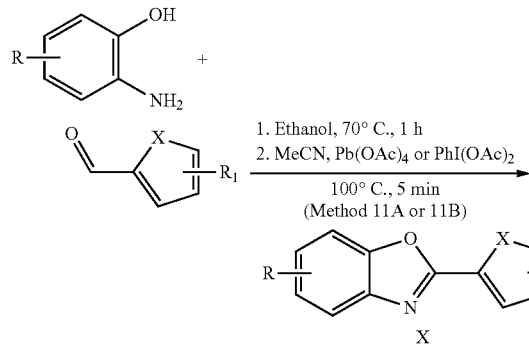

Method 11A (Compound X)

5-(Ethylsulfonyl)-2-(5-methylthiophen-2-yl)benzo[d]oxazole

To a stirred solution of 2-amino-4-(ethylsulfonyl)phenol (452.7 mg, 2.25 mmol) in ethanol (17 mL) was added 5-methyl-2-thiophenecarboxaldehyde (242 μL, 2.25 mmol). The mixture was heated at 70° C. for 70 min. After cooling, a small amount of precipitate was formed. After filtration and evaporation of the filtrate, the resulting product was dissolved in acetonitrile (9.8 mL) and lead tetraacetate (887 mg, 2 mmol) was added. The resulting mixture was heated at 100° C. for 5 min. After cooling, the reaction mixture was filtered off, and the filtrate evaporated in vacuo. The resulting mixture was purified by column chromatography eluting with ethyl acetate/hexanes 20:80 v/v, and then purified by reverse phase HPLC to afford 2.2 mg (0.3%) of the title product (LCMS RT=6.41 min, MH+ 308.1)

$^1$H NMR (DMSO): 8.22 (1H, dd, J 1.8 0.5 Hz), 8.02 (1H, dd, J 8.6 0.5 Hz), 7.92-7.88 (2H, m), 7.08 (1H, dd, J 3.7 1.0 Hz), 3.37 (2H, q, J 7.3 Hz), 2.60 (3H, d, J 0.6 Hz), 1.12 (3H, t, J 7.4 Hz)

Method 11B (Compounds X)

As for Method 11A, but iodosobenzene diacetate was used instead of lead tetraacetate 5-(Ethylsulfonyl)-2-(thiophen-2-yl)benzo[d]oxazole LCMS RT=6.08 min, MH+ 294.1; $^1$H NMR (DMSO): 8.26 (1H, d, J 1.7 Hz), 8.08-8.04 (3H, m), 7.93 (1H, dd, J 8.5 1.8 Hz), 7.36 (1H, dd, J 4.9 3.8 Hz), 3.38 (2H, q, J 7.3 Hz), 1.13 (3H, t, J 7.4 Hz)

5-(Ethylsulfonyl)-2-(3-methylthiophen-2-yl)benzo[d]oxazole

LCMS RT=6.45 min, MH+ 308.1; $^1$H NMR (DMSO): 8.02 (1H, d, J 1.8 0.5 Hz), 7.81 (1H, dd, J 8.5 0.5 Hz), 7.69-7.66 (2H, m), 6.98 (1H, dd, J 5.0 0.4 Hz), 3.15 (2H, q, J 7.3 Hz), 2.47 (3H, s), 0.88 (3H, t, J 7.4 Hz)

5-(Ethylsulfonyl)-2-(5-methylfuran-2-yl)benzo[d]oxazole

LCMS RT=5.53 min, MH+ 292.1; $^1$H NMR (DMSO): 8.00 (1H, d, J 1.8 0.6 Hz), 7.81 (1H, d, J 6.6 Hz), 7.69 (1H, dd, J 8.6 1.9 Hz), 7.26 (1H, d, J 3.7 Hz), 6.31-6.27 (1H, m), 3.18-3.14 (2H, m), 2.24 (3H, s), 0.90 (3H, t, J 7.4 Hz)

5-(Ethylsulfonyl)-2-(4-methylthiophen-2-yl)benzo[d]oxazole

LCMS RT=6.40 min, MH+ 616.9; $^1$H NMR (DMSO): 8.24 (1H, d, J 1.8 0.5 Hz), 8.03 (1H, dd, J 8.6 0.5 Hz), 7.94-7.89 (2H, m), 7.65 (1H, t, J 1.2 Hz), 3.42-3.36 (2H, m), 2.32 (3H, d, J 0.6 Hz), 1.12 (3H, t, J 7.5 Hz)

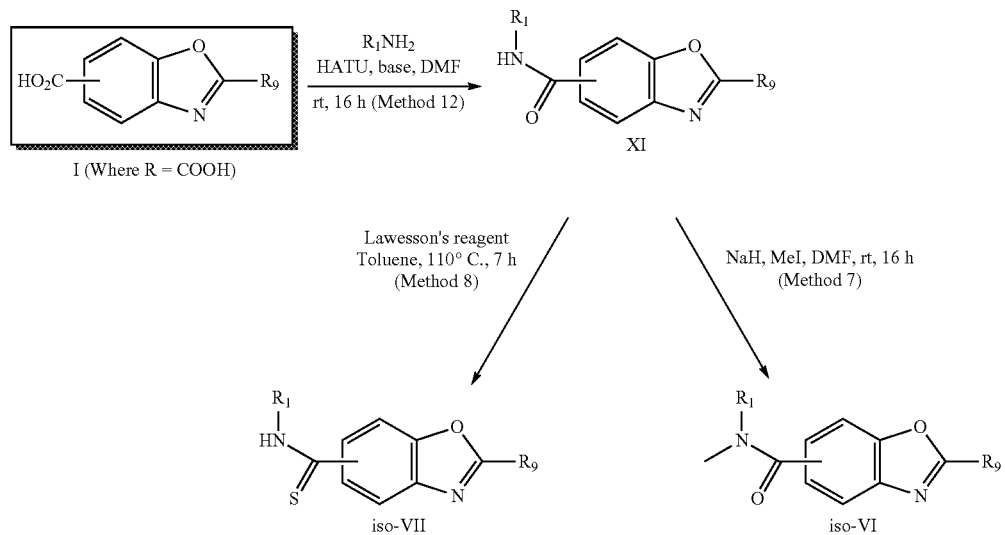

Method 12 (Compounds XI)

N-Butyl-2-p-tolylbenzo[d]oxazole-5-carboxamide

To 2-p-tolylbenzo[d]oxazole-5-carboxylic acid (100 mg, 0.39 mmol) in dry dimethylformamide (10 mL) was added HATU (165 mg, 0.44 mmol) and diisopropylethylamine (206 μL, 1.18 mmol). The mixture was then stirred at room temperature for 10 min. Butan-1-amine (43 μL, 0.44 mmol) was then added and the resulting mixture was stirred at room temperature for 16 h. Ethyl acetate was added and the organic layer was washed three times with water. The combined organic layers were dried over anhydrous $MgSO_4$ and evaporated. The resulting solid was purified by column chromatography eluting with ethyl acetate/hexanes 40:60 v/v to afford 26 mg (11%) of the title compound (LCMS RT=6.81 min, $MH^+$ 309.1)

$^1H$ NMR ($CDCl_3$): 8.22-8.15 (3H, m), 7.89 (1H, dd, J 8.1 1.1 Hz), 7.67 (1H, d, J 8.3 Hz), 7.40 (2H, d, J 7.5 Hz), 6.17 (1H, br), 3.59-3.52 (2H, m), 2.51 (3H, s), 1.72-1.64 (2H, m), 1.54-1.46 (2H, m), 1.03 (3H, t, J 7.3 Hz)

All compounds below were prepared following the same general method.

N-Propyl-2-p-tolylbenzo[d]oxazole-5-carboxamide

LCMS RT-=6.42 min, $MH^+$ 295.1; $^1H$ NMR ($CDCl_3$): 8.08 (2H, d, J 8.2 Hz), 8.04 (1H, d, J 1.4 Hz), 7.77 (1H, dd, J 8.5 1.7 Hz), 7.54 (1H, d, J 8.6 Hz), 7.28 (2H, d, J 7.9 Hz), 6.07 (1H, br), 3.44-3.37 (2H, m), 2.39 (3H, s), 1.65-1.55 (2H, m), 0.95 (3H, t, J 7.5 Hz)

N-Isopropyl-2-p-tolylbenzo[d]oxazole-5-carboxamide

LCMS RT=6.38 min, $MH^+$ 295.1; $^1H$ NMR ($CDCl_3$): 8.20 (2H, d, J 8.2 Hz), 8.15 (1H, d, J 1.4 Hz), 7.87 (1H, dd, J 8.5 1.8 Hz), 7.65 (1H, d, J 8.5 Hz), 7.40 (2H, d, J 8.0 Hz), 6.00 (1H, br), 4.43-4.31 (1H, m), 2.51 (3H, s), 1.35 (6H, d, J 6.6 Hz)

2-p-Tolylbenzo[d]oxazole-5-carboxamide

LCMS RT=5.61 min, $MH^+$ 253.0; $^1H$ NMR (DMSO): 8.30 (1H, d, J 1.2 Hz), 8.12 (2H, d, J 8.2 Hz), 7.98 (1H, dd, J 8.5 1.7 Hz), 7.81 (1H, d, J 8.5 Hz), 7.45 (2H, d, J 8.0 Hz), 2.44 (3H, s)

2-(4-Chlorophenyl)-N-isopropylbenzo[d]oxazole-5-carboxamide

LCMS RT=6.68 min, $MH^+$ 315.5; $^1H$ NMR (DMSO): 8.36-8.31 (2H, m), 8.23 (2H, d, J 8.7 Hz), 7.98 (1H, dd, J 8.5 1.7 Hz), 7.87 (1H, d, J 8.5 Hz), 7.72 (2H, d, J 8.7 Hz), 4.19-4.08 (1H, m), 1.21 (6H, d, J 6.6 Hz)

2-(4-Chlorophenyl)benzo[d]oxazole-5-carboxamide

LCMS RT=5.81 min, $MH^+$ 273.2; $^1H$ NMR (DMSO): 8.11 (1H, s), 8.01 (2H, d, J 8.3 Hz), 7.89 (1H, br), 7.78 (1H, d, J 8.6 Hz), 7.64 (1H, d, J 8.6 Hz), 7.49 (2H, d, J 8.3 Hz), 7.25 (1H, br)

Method 8 (Compounds iso-VI)

2-(4-Chlorophenyl)-N-methylbenzo[d]oxazole-5-carboxamide

LCMS RT=6.09 min, $MH^+$286.9; $^1H$ NMR (DMSO): 8.57 (1H, br), 8.28 (1H, d, J 1.2 Hz), 8.23 (2H, d, J 8.7 Hz), 7.96 (1H, dd, J 8.6 1.7 Hz), 7.87 (1H, d, J 8.6 Hz), 7.72 (2H, d, J 8.6 Hz), 2.83 (3H, d, J 4.5 Hz)

2-(4-Chlorophenyl)-N-isopropyl-N-methylbenzo[d]oxazole-5-carboxamide

LCMS RT=6.90 min, $MH^+$ 329.0; $^1H$ NMR (DMSO): 8.23 (2H, d, J 8.6 Hz), 7.88-7.81 (2H, m), 7.72 (2H, d, J 8.7 Hz), 7.44 (1H, d, J 8.2 Hz), 2.88-2.78 (3H, m), 1.18-1.12 (6H, m)

Method 7 (Compounds iso-VII)

2-(4-Chlorophenyl)-N-isopropylbenzo[d]oxazole-5-carbothioamide

LCMS RT=7.37 min, $MH^+$ 331.0; $^1H$ NMR (DMSO): 10.18 (1H, d, J 7.3 Hz), 8.23 (2H, d, J 8.8 Hz), 8.11 (1H, dd, J 1.7 0.5 Hz), 7.88 (1H, dd, J 8.6 1.8 Hz), 7.83 (1H, dd, J 8.8

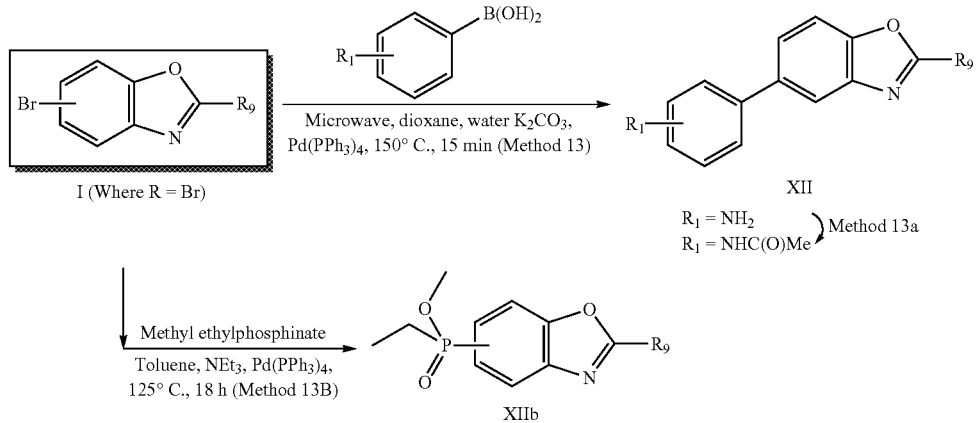

Method 13 (Compounds XII)

5-(4-Methoxyphenyl)-2-p-tolylbenzo[d]oxazole

To a solution of 5-bromo-2-p-tolylbenzo[d]oxazole (146.1 mg, 0.50 mmol) in dioxane (1.5 mL) was added water (0.5 mL), 4-methoxyphenylboronic acid (114 mg, 0.75 mmol), potassium carbonate (138 mg, 1.00 mmol) and tetrakis(triphenylphosphine)palladium(0) (3 mg). The resulting suspension was heated in the microwave at 150° C. for 15 min. After cooling, the reaction was diluted with water and extracted with ethyl acetate. The combined organic layers were dried over anhydrous $MgSO_4$ and evaporated. The resulting solid was purified by column chromatography eluting with ethyl acetate/hexanes 1:99 v/v to afford 60 mg (38%) of the title compound (LCMS RT=9.18 min, $MH^+$ 316.1)

$^1H$NMR (DMSO): 8.12 (2H, d, J 8.2 Hz), 7.99 (1H, d, J 1.5 Hz), 7.82 (1H, d, J 8.5 Hz), 7.71-7.64 (3H, m), 7.45 (2H, d, J 8.0 Hz), 7.06 (2H, d, J 8.8 Hz), 3.82 (3H, s), 2.43 (3H, s)

All compounds below were prepared following the same general method.

N-(4-(2-(4-Chlorophenyl)benzo[d]oxazol-5-yl)phenyl)acetamide

LCMS RT=7.51 min, MH+ 362.8; $^1$H NMR (DMSO): 10.04 (1H, s), 8.23 (2H, d, J 8.5 Hz), 8.05 (1H, d, J 1.6 Hz), 7.86 (1H, d, J 8.5 Hz), 7.73-7.69 (7H, m), 2.09 (3H, s)

2-(4-Chlorophenyl)-5-(4-(ethylsulfonyl)phenyl)benzo[d]oxazole

LCMS RT=8.31 min, MH+ 397.8; $^1$H NMR (DMSO): 8.27-8.23 (3H, m), 8.09-7.94 (5H, m), 7.85 (1H, dd, J 8.6 1.8 Hz), 7.73 (2H, d, J 8.7 Hz), 3.39-3.34 (2H, m), 1.16 (3H, t, J 7.5 Hz)

Methyl 4-(2-(4-chlorophenyl)benzo[d]oxazol-5-yl)benzoate

LCMS RT=9.34 min, MH+ 363.9; $^1$H NMR (DMSO): 8.25 (2H, d, J 8.7 Hz), 8.20 (1H, d, J 1.3 Hz), 8.08 (2H, d, J 8.6 Hz), 7.95-7.91 (3H, m), 7.83 (1H, dd, J 8.6 1.8 Hz), 7.73 (2H, d, J 8.7 Hz), 3.90 (3H, s)

N-(3-(2-(4-Chlorophenyl)benzo[d]oxazol-5-yl)phenyl)acetamide

LCMS RT=7.40 min, MH+ 363.0; $^1$H NMR (DMSO): 10.05 (1H, s), 8.25 (2H, d, J 8.7 Hz), 8.00 (1H, d, J 1.4 Hz), 7.98-7.95 (1H, m), 7.90 (1H, d, J 8.5 Hz), 7.72 (2H, d, J 8.8 Hz), 7.67 (1H, dd, J 8.5 1.8 Hz), 7.60-7.57 (1H, m), 7.42-7.40 (2H, m), 2.09 (3H, s)

2-(4-Chlorophenyl)-5-(4-morpholinophenyl)benzo[d]oxazole

LCMS RT=17.49 min, MH+ 391.0; $^1$H NMR (DMSO): 8.23 (2H, d, J 8.9 Hz), 8.00 (1H, d, J 1.4 Hz), 7.83 (1H, d, J 8.6 Hz), 7.74-7.67 (3H, m), 7.64 (2H, d, J 8.9 Hz), 7.06 (2H, d, J 8.9 Hz), 3.79-3.75 (4H, m), 3.19-3.15 (4H, m)

2-(4-Chlorophenyl)-5-(3-(ethylthio)phenyl)benzo[d]oxazole

LCMS RT=10.82 min, MH+ 365.7; $^1$H NMR (DMSO): 8.25 (2H, d, J 8.7 Hz), 8.11 (1H, d, J 1.4 Hz), 7.89 (1H, d, J 8.6 Hz), 7.77-7.70 (3H, m), 7.62 (1H, t, J 1.7 Hz), 7.55 (1H, dt, J 7.6 1.2 Hz), 7.44 (1H, t, J 7.6 Hz), 7.35-7.32 (1H, m), 3.09 (2H, q, J 7.3 Hz), 1.29 (3H, t, J 7.4 Hz)

N-(2-(2-(4-Chlorophenyl)benzo[d]oxazol-5-yl)phenyl)acetamide

LCMS RT=6.84 min, MH+ 363.0; $^1$H NMR (DMSO): 9.29 (1H, s), 8.24 (2H, d, J 8.6 Hz), 7.86 (1H, d, J 8.4 Hz), 7.78-7.76 (1H, m), 7.72 (2H, d, J 8.5 Hz), 7.53-7.29 (5H, m), 1.87 (3H, s)

2-(4-Chlorophenyl)-5-(4-methoxypyridin-3-yl)benzo[d]oxazole

LCMS RT=7.46 min, MH+ 337.0; $^1$H NMR (DMSO): 8.49 (1H, d, J 5.8 Hz), 8.45 (1H, s), 8.24 (2H, d, J 8.9 Hz), 7.95 (1H, d, J 1.7 0.5 Hz), 7.87 (1H, dd, J 8.5 0.6 Hz), 7.72 (2H, d, J 8.8 Hz), 7.58 (1H, dd, J 8.5 1.7 Hz), 7.21 (1H, d, J 5.8 Hz), 3.89 (3H, s)

2-(4-Chlorophenyl)-5-(6-methoxypyridin-3-yl)benzo[d]oxazole

LCMS RT=8.83 min, MH+ 337.0; $^1$H NMR (DMSO): 8.57 (1H, dd, J 2.6 0.6 Hz), 8.24 (2H, d, J 8.8 Hz), 8.13-8.10 (2H, m), 7.89 (1H, dd, J 8.6 0.5 Hz), 7.75-7.70 (3H, m), 6.95 (1H, dd, J 8.6 0.6 Hz), 3.92 (3H, s)

3-(2-(4-Chlorophenyl)benzo[d]oxazol-5-yl)benzoic acid

LCMS RT=4.62 min, MH+ 350.1; $^1$H NMR (DMSO): 8.27-8.23 (3H, m), 8.12 (1H, d, J 1.4 Hz), 8.03-7.95 (2H, m), 7.91 (1H, d, J 8.7 Hz), 7.78 (1H, dd, J 8.5 1.8 Hz), 7.72 (2H, d, J 8.8 Hz), 7.64 (1H, t, J 7.7 Hz)

2-(4-Chlorophenyl)-5-(6-chloropyridin-3-yl)benzo[d]oxazole

LCMS RT=8.59 min, MH+ 340.9; $^1$H NMR (DMSO): 8.33 (1H, d, J 2.2 Hz), 8.28-8.23 (4H, m), 7.95 (1H, d, J 8.6 Hz), 7.83 (1H, dd, J 8.5 1.8 Hz), 7.73 (2H, d, J 8.7 Hz), 7.65 (1H, d, J 8.4 Hz)

2-(4-Chlorophenyl)-5-(6-fluoropyridin-3-yl)benzo[d]oxazole

LCMS RT=8.05 min, MH+ 325.0; $^1$H NMR (DMSO): 8.65 (1H, d, J 2.7 Hz), 8.39 (1H, td, J 8.2 2.7 Hz), 8.25 (2H, d, J 8.7 Hz), 8.20 (1H, dd, J 1.8 0.5 Hz), 7.94 (1H, dd, J 8.6 0.6 Hz), 7.80 (1H, dd, J 8.6 1.9 Hz), 7.73 (2H, d, J 8.7 Hz), 7.33 (1H, dd, J 8.6 3.0 Hz)

2-(4-Chlorophenyl)-5-(6-morpholinopyridin-3-yl)benzo[d]oxazole

LCMS RT=8.46 min, MH+ 391.8; $^1$H NMR (DMSO): 8.55 (1H, d, J 2.4 Hz), 8.23 (2H, d, J 8.7 Hz), 8.06 (1H, d, J 1.4 Hz), 7.98 (1H, dd, J 8.9 2.6 Hz), 7.86 (1H, d, J 8.8 Hz), 7.73-7.69 (3H, m), 6.96 (1H, d, J 8.9 Hz), 3.75-3.71 (4H, m), 3.53-3.49 (4H, m)

2-(4-Chlorophenyl)-5-(6-methoxypyridin-2-yl)benzo[d]oxazole

LCMS RT=9.84 min, MH+ 337.1; $^1$H NMR (DMSO): 8.54 (1H, d, J 1.6 Hz), 8.26-8.23 (3H, m), 7.91 (1H, d, J 8.7 Hz), 7.82 (1H, t, J 7.9 Hz), 7.74-7.68 (3H, m), 6.81 (1H, d, J 8.1 Hz), 4.00 (3H, s)

3-(2-(4-Chlorophenyl)benzo[d]oxazol-5-yl)aniline

LCMS RT=7.78 min, MH+ 321.1; $^1$H NMR (DMSO): 8.24 (2H, d, J 8.7 Hz), 7.73 (1H, dd, J 1.8 0.4 Hz), 7.85 (1H, d, J 8.5 Hz), 7.72 (2H, d, J 8.8 Hz), 7.63 (1H, dd, J 8.6 1.8 Hz), 7.13 (1H, t, J 7.8 Hz), 6.90 (1H, t, J 1.9 Hz), 6.87-6.82 (1H, m), 6.62-6.57 (1H, m), 5.19 (2H, s)

4-(2-(4-Chlorophenyl)benzo[d]oxazol-5-yl)aniline

LCMS RT=7.77 min, MH+ 321.1; $^1$H NMR (DMSO): 8.22 (2H, d, J 8.7 Hz), 7.91 (1H, d, J 1.5 Hz), 7.78 (1H, d, J 8.6 Hz), 7.71 (2H, d, J 8.6 Hz), 7.61 (1H, dd, J 8.6 1.8 Hz), 7.43 (2H, d, J 8.6 Hz), 6.67 (2H, d, J 8.6 Hz), 5.26 (2H, s)

5-(2-(4-Chlorophenyl)benzo[d]oxazol-5-yl)pyridin-2-amine

LCMS RT=7.12 min, MH+ 322.1; $^1$H NMR (DMSO): 8.32 (1H, d, J 2.2 Hz), 8.23 (2H, d, J 8.7 Hz), 7.98 (1H, d, J 1.4 Hz), 7.84-7.77 (2H, m), 7.72 (2H, d, J 8.7 Hz), 7.64 (1H, dd, J 8.5 1.8 Hz), 6.56 (1H, d, J 8.6 Hz), 6.09 (2H, s)

4-(5-(4-Chlorophenyl)benzo[d]oxazol-2-yl)aniline

LCMS RT=7.73 min, MH+ 320.9; $^1$H NMR (DMSO): 7.94 (1H, d, J 1.5 Hz), 7.89 (2H, d, J 8.6 Hz), 7.78-7.74 (3H, m), 7.60 (1H, dd, J 8.6 1.8 Hz), 7.53 (2H, d, J 8.6 Hz), 6.71 (2H, d, J 8.7 Hz), 6.04 (2H, s)

Method 13a (Compound XIIa)

N-(5-(2-(4-Chlorophenyl)benzo[d]oxazol-5-yl)pyridin-2-yl)acetamide

To 5-(2-(4-chlorophenyl)benzo[d]oxazol-5-yl)pyridin-2-amine (96.5 mg, 0.30 mmol) in dry pyridine (3 mL) at room temperature was added acetyl chloride (26 μL, 0.36 mmol), and stirred at 80° C. for 40 h. After cooling, the mixture was poured into water to give a precipitate, which was filtered off. The resulting solid was purified by column chromatography eluting with ethyl acetate/hexanes 20:80 v/v to afford 45 mg (41%) of the title compound.

$^1$H NMR (DMSO): 10.61 (1H, s), 8.73-8.71 (1H, m), 8.24 (2H, d, J 8.6 Hz), 8.18-8.16 (3H, m), 7.91 (1H, d, J 8.5 Hz), 7.79 (1H, dd, J 8.6 1.8 Hz), 7.73 (2H, d, J 8.6 Hz), 2.13 (3H, s)

Method 13b (Compound XIIb)

Methyl Ethylphosphinate

In accordance with well known procedures (see Xu, Y. et al., Synthesis, 1984, 778-780), a solution of methanol (2.70 mL, 66.75 mmol) and triethylamine (4.23 mL, 30.35 mmol) in diethyl ether (15 mL) was added dropwise at 0° C. to a solution of ethyl dichlorophosphine (3.15 mL, 30.35 mmol) in diethyl ether (30 mL). After the addition was complete, the resulting slurry was refluxed for 1 h. After cooling at 0° C., the precipitated solid was filtered off and washed with diethyl ether. The filtrate was then concentrated to afford a colourless oil, which was used without any purification in the next step.

Methyl 2-(4-chlorophenyl)benzo[d]oxazol-5-yl(ethyl)phosphinate

To 5-bromo-2-p-tolylbenzo[d]oxazole (519.7 mg, 1.68 mmol) and methyl ethylphosphinate (276.9 mg, 2.02 mmol) in anhydrous toluene (10 mL) was added tetrakis(triphenylphosphine)palladium(0) (101.6 mg) and triethylamine (7.5 mL, 5.4 mmol). The resulting suspension was refluxed under nitrogen for 18 h. After cooling, ethyl acetate was added, and the organic layer was washed with water. The combined organic layers were dried over anhydrous MgSO$_4$ and evaporated. The resulting solid was purified by column chromatography eluting using a gradient (starting with hexanes to ethyl acetate and then methanol/ethyl acetate 5:95 v/v) and then purified by reverse phase HPLC to afford 10.4 mg (2%) of the title product (LCMS RT=6.32 min, MH+ 336.1)

$^1$H NMR (DMSO): 8.24 (2H, d, J 8.7 Hz), 8.18-8.13 (1H, m), 8.00 (1H, ddd, J 8.5 2.4 0.6 Hz), 7.81 (1H, ddd, J 10.9 8.2 1.4 Hz), 7.73 (2H, d, J 8.7 Hz), 3.54 (3H, d, J 10.9 Hz), 2.09-1.94 (2H, m), 1.04-0.91 (3H, m)

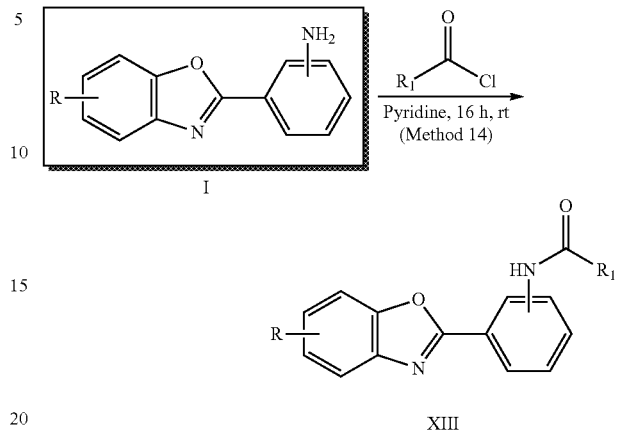

Method 14 (Compounds XIII)

N-(4-(5-Chlorobenzo[d]oxazol-2-yl)phenyl)acetamide

To a solution of 4-(5-chlorobenzo[d]oxazol-2-yl)aniline (122.3 mg, 0.50 mmol) in pyridine (3 mL) at room temperature was added acetyl chloride (39 μL, 0.55 mmol). The resulting mixture was stirred at room temperature for 16 h. The solution was then poured into water, and the resulting precipitate collected by filtration. The solid was washed with diluted hydrochloric acid solution, followed by diluted sodium hydroxide solution, and then by water to afford 120 mg (84%) of the title compound (LCMS RT=6.38 min, MH+ 287.0)

$^1$H NMR (DMSO): 10.33 (1H, s), 8.14 (2H, d, J 8.7 Hz), 7.88-7.80 (4H, m), 7.45 (1H, dd, J 8.7 2.1 Hz), 2.11 (3H, s)

All compounds below were prepared following the same general method.

N-(4-(5-Chlorobenzo[d]oxazol-2-yl)phenyl)isobutyramide

LCMS RT=7.03 min, MH+ 315.1; $^1$H NMR (DMSO): 10.22 (1H, s), 8.14 (2H, d, J 8.7 Hz), 7.88-7.79 (4H, m), 7.45 (1H, dd, J 8.7 2.1 Hz), 2.70-2.61 (1H, m), 1.13 (6H, d, J 6.8 Hz)

N-(4-(5-Chlorobenzo[d]oxazol-2-yl)phenyl)thiophene-2-carboxamide

LCMS RT=7.44 min, MH+ 355.0; $^1$H NMR (DMSO): 10.57 (1H, s), 8.21 (2H, d, J 8.9 Hz), 8.09 (1H, dd, J 3.8 1.1 Hz), 8.02 (2H, d, J 8.9 Hz), 7.93-7.90 (2H, m), 7.82 (1H, d, J 8.6 Hz), 7.46 (1H, dd, J 8.6 2.1 Hz), 7.27 (1H, dd, J 4.9 3.8 Hz)

N-(4-(6-Chlorobenzo[d]oxazol-2-yl)phenyl)acetamide

LCMS RT=6.37 min, MH+ 287.0; $^1$H NMR (DMSO): 10.32 (1H, s), 8.13 (2H, d, J 8.8 Hz), 7.96 (1H, d, J 1.8 Hz), 7.84-7.77 (3H, m), 7.45 (1H, dd, J 8.4 1.9 Hz), 2.11 (3H, s)

N-(4-(6-Chlorobenzo[d]oxazol-2-yl)phenyl)isobutyramide

LCMS RT=7.18 min, MH+ 315.1; $^1$H NMR (DMSO): 10.22 (1H, s), 8.12 (2H, d, J 8.8 Hz), 7.96 (1H, d, J 1.8 Hz), 7.86 (2H, d, J 8.9 Hz), 7.79 (1H, d, J 8.5 Hz), 7.45 (1H, dd, J 8.5 2.0 Hz), 2.70-2.61 (1H, m), 1.13 (6H, d, J 6.9 Hz)

N-(4-(6-Chlorobenzo[d]oxazol-2-yl)phenyl)thiophene-2-carboxamide

LCMS RT=7.61 min, MH⁺ 354.9; ¹H NMR (DMSO): 10.57 (1H, s), 8.19 (2H, d, J 8.9 Hz), 8.09 (1H, dd, J 3.7 1.0 Hz), 8.01 (2H, d, J 8.9 Hz), 7.98 (1H, d, J 1.8 Hz), 7.92 (1H, dd, J 5.0 1.0 Hz), 7.81 (1H, d, J 8.5 Hz), 7.46 (1H, dd, J 8.5 2.0 Hz), 7.26 (1H, dd, J 5.0 3.8 Hz)

N-(4-(5-Bromobenzo[d]oxazol-2-yl)phenyl)acetamide

¹H NMR (DMSO): 10.35 (1H, s), 8.14 (2H, d, J 8.8 Hz), 8.01 (1H, d, J 1.8 Hz), 7.83 (2H, d, J 8.7 Hz), 7.76 (1H, d, J 8.6 Hz), 7.57 (1H, dd, J 8.6 2.0 Hz), 2.11 (3H, s)

N-(4-(5-(4-Chlorophenyl)benzo[d]oxazol-2-yl)phenyl)acetamide

LCMS RT=7.53 min, MH⁺ 363.0; ¹H NMR (DMSO): 10.34 (1H, s), 8.17 (2H, d, J 8.7 Hz), 8.06-8.04 (1H, m), 7.87-7.82 (3H, m), 7.78 (2H, d, J 8.5 Hz), 7.72-7.67 (1H, m), 7.55 (2H, d, J 8.6 Hz), 2.12 (3H, s)

N-(4-(5,6-Dimethylbenzo[d]oxazol-2-yl)-3-hydroxyphenyl)acetamide

LCMS RT=7.22 min, MH⁺ 297.2; ¹H NMR (DMSO): 11.24 (1H, br), 10.24 (1H, s), 7.91 (1H, d, J 8.6 Hz), 7.59 (2H, d, J 6.4 Hz), 7.51 (1H, d, J 1.9 Hz), 7.22 (1H, dd, J 8.7 2.0 Hz), 2.37 (3H, s), 2.34 (3H, s), 2.09 (3H, s)

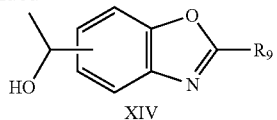

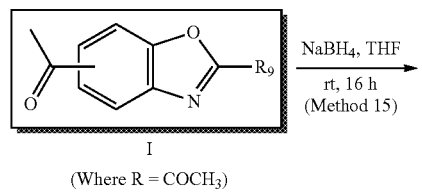

I
(Where R = COCH₃)

Method 15 (Compounds XIV)

1-(2-(4-Chlorophenyl)benzo[d]oxazol-5-yl)ethanol

To a solution of 1-(2-(4-chlorophenyl)benzo[d]oxazol-5-yl)ethanone (150 mg, 0.55 mmol) in tetrahydrofuran at 0° C. was added sodium borohydride (52 mg, 1.38 mmol). The resulting mixture was stirred at room temperature for 16 h. The reaction was then quenched at 0° C. with 1M hydrochloric acid solution and extracted three times with ethyl acetate. The combined organic layers were dried over anhydrous MgSO₄ and evaporated. The resulting solid was purified by column chromatography eluting using a gradient (ethyl acetate/hexanes 1:3 v/v to ethyl acetate/hexanes 1:2 v/v) to afford 81.7 mg (54%) of the title compound. (LCMS RT=6.47 min, MH⁺ 274.0)

¹H NMR (DMSO): 8.20 (2H, d, J 8.7 Hz), 7.76-7.68 (4H, m), 7.44 (1H, dd, J 8.6 1.6 Hz), 5.31 (1H, d, J 4.3 Hz), 4.92-4.83 (1H, m), 1.38 (3H, d, J 6.4 Hz)

2-(3',4'-Dichlorophenyl)-5-(1'-hydroxyethyl)-benzoxazole

LCMS RT=7.18 min, MH⁺ 308.1; ¹H NMR (DMSO): 8.36 (1H, d, J 2.0 Hz), 8.16 (1H, dd, J 8.5 2.0 Hz), 7.90 (1H, d, J 8.4 Hz), 7.78-7.77 (1H, m), 7.74 (1H, d, J 8.4 Hz), 7.47 (1H, dd, J 8.6 1.7 Hz), 5.32 (1H, d, J 4.3 Hz), 4.93-4.84 (1H, m), 1.39 (3H, d, J 6.4 Hz)

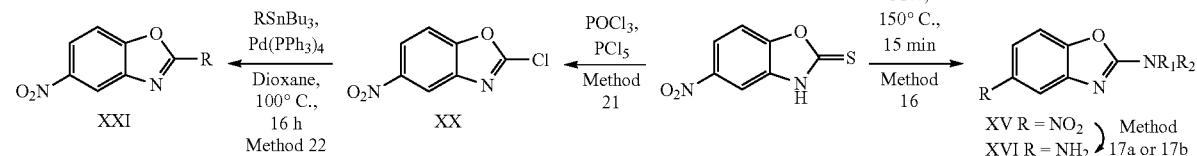

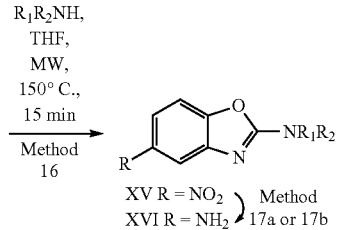

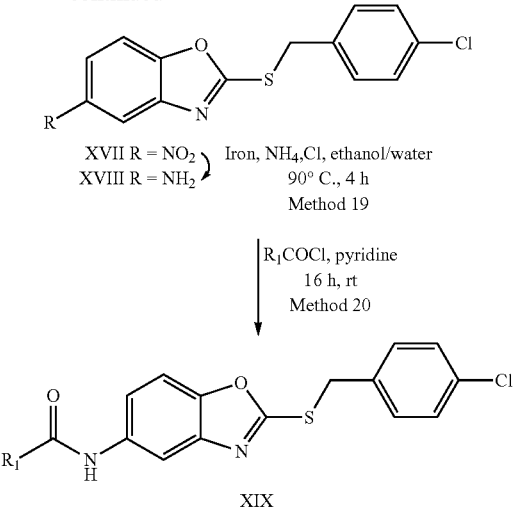

5-Nitrobenzo[d]oxazole-2(3H)-thione

In accordance with well known procedures, (see Batista-Parra, A et at Heterocycles, 2003, 60, 1367), a suspension of 2-amino-4-nitrophenol (1.54 g, 10 mmol) and potassium O-ethyl carbonodithioate (1.68 g, 10.5 mmol) in dry pyridine (10 mL) was stirred at 120° C. for 6 h, and then at room temperature for 16 h. The solution was poured into water and aqueous hydrochloric acid was added. The resulting precipitate was collected by filtration, washed with dilute aqueous hydrochloric acid, followed by water and then dried in the vacuum oven to afford 3.3 g (84%) of the title compound.
$^1$H NMR (DMSO): 8.18 (1H, dd, J 8.9 2.4 Hz), 7.94 (1H, dd, J 2.4 0.4 Hz), 7.73 (1H, dd, J 8.9 0.4 Hz)
Method 16 (Compound XV)

2-Morpholino-5-nitrobenzo[d]oxazole 5-nitrobenzo[d]oxazole-2(3H)-thione (98.1 mg, 0.5 mmol) and morpholine (66 μL, 0.75 mmol) in tetrahydrofuran (3 mL) were heated at 150° C. for 15 min in the microwave. After cooling, the mixture was poured into water and extracted with ethyl acetate. The organic layer was washed with brine, dried over anhydrous MgSO$_4$ and absorbed on silica. Purification by column chromatography, eluting with ethyl acetate/hexanes 25:75 v/v affords 115 mg (92%) of the title compound.
$^1$H NMR (DMSO): 8.10 (1H, d, J 2.3 Hz), 8.00 (1H, dd, J 8.8 2.4 Hz), 7.66 (1H, d, J 8.8 Hz), 3.76-3.72 (4H, m), 3.67-3.64 (4H, m)
Method 17a (Compound XVI)

2-Morpholinobenzo[d]oxazol-5-amine

A solution of 2-morpholino-5-nitrobenzo[d]oxazole (130 mg, 0.52 mmol) in ethanol/water 1:1 v/v (10 mL) was treated with sodium dithionite (182 mg, 1.04 mmol) at room temperature and then refluxed for 16 h. After cooling, the mixture was diluted with water and extracted with ethyl acetate. The organic layer was dried over anhydrous MgSO$_4$ and evaporated to afford 35 mg (30%) of the title compound.
$^1$H NMR (DMSO): 7.03 (1H, d, J 8.5 Hz), 6.50 (1H, d, J 2.1 Hz), 6.25 (1H, dd, J 8.4 2.2 Hz), 4.80 (2H, s), 3.71-3.68 (4H, m), 3.53-3.50 (4H, m)

Method 17b (Compound XVI)

N-2-(4-Chlorobenzyl)benzo[d]oxazole-2,5-diamine

To a suspension of N-(4-chlorobenzyl)-5-nitrobenzo[d]oxazol-2-amine (150 mg, 0.50 mmol) in ethanol/water 1:1 v/v (10 mL) at 90° C. was added ammonium chloride (53 mg, 1.0 mmol), followed by iron powder (140 mg, 2.5 mmol). The resulting mixture was stirred for 4 h at 90° C. After cooling, ethyl acetate was added and the solution was passed through a pad of Celite®. The organic layer was then washed with brine, dried over anhydrous MgSO$_4$ and evaporated. The resulting solid was purified by column chromatography eluting with ethyl acetate/hexanes 50:50 v/v to afford 60 mg (44%) of the title compound (LCMS RT=5.60 min, MH$^+$ 274.0)
$^1$H NMR (DMSO): 8.20 (1H, t, J 6.2 Hz), 7.42-7.36 (4H, m), 6.97 (1H, d, J 8.4 Hz), 6.45 (1H, d, J 2.1 Hz), 6.20 (1H, dd, J 8.4 2.2 Hz), 4.72 (2H, s), 4.46 (2H, d, J 6.2 Hz)
Method 18 (Compound XVII)

2-(4-Chlorobenzylthio)-5-nitrobenzo[d]oxazole

To a suspension of 5-nitrobenzo[d]oxazole-2(3H)-thione (196.2 mg, 1.0 mmol) in chloroform (10 mL) was added triethylamine (278 μL, 2 mmol) followed by 1-(bromomethyl)-4-chlorobenzene (226 mg, 1.1 mmol). The reaction was stirred at 60° C. for 2 h. After cooling, the reaction was diluted with ethyl acetate, washed with dilute aqueous hydrochloric solution and brine. The combined organic layers were dried over anhydrous MgSO$_4$ and evaporated. The resulting solid was purified by column chromatography eluting with ethyl acetate/hexanes 1:10 v/v to afford 250 mg (78%) of the title compound (LCMS RT=7.64 min)
$^1$H NMR (DMSO): 8.52 (1H, d, J 2.3 Hz), 8.27 (1H, dd, J 8.9 2.3 Hz), 7.92 (1H, d, J 9.0 Hz), 7.58 (2H, d, J 8.5 Hz), 7.42 (2H, d, J 8.5 Hz), 4.67 (2H, s)
Method 19 (Compound XVIII)

2-(4-Chlorobenzylthio)benzo[d]oxazol-5-amine

To a suspension of 2-(4-chlorobenzylthio)-5-nitrobenzo[d]oxazole (220 mg, 0.70 mmol) in ethanol/water (5 mL/5 mL) at 90° C. was added ammonium chloride (75 mg, 1.4 mmol), followed by iron powder (192 mg, 3.44 mmol). The resulting mixture was stirred for 4 h at 90° C. After cooling, ethyl acetate was added and the solution was passed through a pad of Celite®. The organic layer was then washed with brine, dried over anhydrous MgSO$_4$ and evaporated to afford 190 mg (94%) of the title compound (LCMS RT=6.54 min, MH$^+$ 290.9)

$^1$H NMR (DMSO): 7.52 (2H, d, J 8.7 Hz), 7.40 (2H, d, J 8.5 Hz), 7.26 (1H, d, J 8.7 Hz), 6.74 (1H, d, J 1.9 Hz), 6.54 (1H, dd, J 8.7 2.2 Hz), 5.06 (2H, s), 4.55 (2H, s)

Method 20 (Compounds XIX)

N-(2-(4-Chlorobenzylthio)benzo[d]oxazol-5-yl)acetamide

To a solution of 2-(4-chlorobenzylthio)benzo[d]oxazol-5-amine (87 mg, 0.30 mmol) in dry pyridine (3 mL) at room temperature was added acetyl chloride (21 μL, 0.30 mmol). The resulting solution was stirred at room temperature for 16 h. Water was then added, the precipitate was collected by filtration, washed with diluted aqueous hydrochloric acid and then with water. Trituration with diethyl ether afforded 40 mg (40%) of the title compound (LCMS RT=6.40 min, MH$^+$ 333.1)

$^1$H NMR (DMSO): 10.08 (1H, s), 8.01 (1H, d, J 1.8 Hz), 7.58-7.52 (3H, m), 7.43-7.35 (3H, m), 4.60 (2H, s), 2.06 (3H, s)

The compound below was prepared following the same general method.

N-(2-(4-Chlorobenzylthio)benzo[d]oxazol-5-yl)isobutyramide

LCMS RT=7.00 min, MH$^+$ 361.1; $^1$H NMR (DMSO): 9.96 (1H, s), 8.04 (1H, d, J 1.8 Hz), 7.58-7.52 (3H, m), 7.43-7.39 (3H, m), 4.60 (2H, s), 2.65-2.60 (1H, m), 1.12 (6H, d, J 6.8 Hz)

Method 21 (Compound XX)

2-Chloro-5-nitrobenzo[d]oxazole

To a solution of 5-nitrobenzo[d]oxazole-2(3H)-thione (2.52 g, 12.86 mmol) in phosphorous oxychloride (21 mL) was added phosphorous pentachloride (2.68 g, 12.86 mmol) in one portion. The mixture was then heated to 100° C. for 2.5 h. After cooling, the excess of phosphorous oxychloride was removed in vacuo and the resulting mixture was used crude without characterisation.

Method 22 (Compound XXI)

5-Nitro-2-(thiophen-2-yl)benzo[d]oxazole

A mixture of 2-chloro-5-nitrobenzo[d]oxazole (404 mg, 2.04 mmol), 2-(tributylstannyl)-thiophene (648 μL, 2.04 mmol) and tetrakis(triphenylphosphine)palladium (0) (40.8 mg) in dioxane (12.2 mL) was heated at 100° C. for 16 h under nitrogen. Ethyl acetate was added, the organic layer was washed with water, dried over anhydrous MgSO$_4$ and evaporated. The resulting solid was purified by column chromatography eluting with ethyl acetate/hexanes 10:90 v/v, and then purified by reverse phase HPLC to afford 3 mg (2%) of the title product (LCMS RT=6.95 min)

$^1$H NMR (DMSO): 8.54 (1H, d, J 2.2 Hz), 8.27 (1H, dd, J 9.0 2.3 Hz), 8.04 (1H, dd, J 5.4 1.2 Hz), 7.93 (1H, d, J 9.0 Hz), 7.69 (1H, dd, J 3.7 1.2 Hz), 7.29 (1H, dd, J 5.4 3.7 Hz)

Method 23 (Compounds XXII)

5-Amino-2-(5,6-dimethyl-1H-benzo[d]imidazol-2-yl)phenol

To polyphosphoric acid at 130° C. were added 4,5-dimethylbenzene-1,2-diamine (500 mg, 3.67 mmol) and 4-amino-2-hydroxybenzoic acid (562 mg, 3.67 mmol), and the resulting mixture was then heated to 130° C. for 16 h. The solution was then poured into water and the resulting precipitate was dissolved in ethyl acetate and washed with Na$_2$CO$_3$. The aqueous layer was separated and extracted twice with ethyl acetate. The combined organic layers were dried over anhydrous MgSO$_4$ and evaporated. The resulting solid was purified by column chromatography eluting with ethyl acetate/hexanes 50:50 v/v to afford 260 mg (28%) of the title compound (LCMS RT=6.14 min, MH$^+$254.1)

$^1$H NMR (DMSO): 13.07 (1H, s), 12.40 (1H, s), 7.61 (1H, d, J 8.3 Hz), 7.35 (1H, s), 7.24 (1H, s), 6.19 (1H, dd, J 8.5 2.2 Hz), 6.12 (1H, d, J 2.1 Hz), 5.59 (2H, s), 2.32 (3H, s), 2.30 (3H, s)

All compounds below were prepared following the same general method.

2-(3-Methyl-4-nitrophenyl)-1H-benzo[d]imidazole

LCMS RT=5.87 min, MH$^+$ 254.1; $^1$H NMR (DMSO): 13.20 (1H, br), 9.31 (1H, s), 8.21-8.19 (2H, m), 7.67-7.64 (2H, m), 7.28-7.25 (2H, m), 2.65 (3H, s)

2-(6-Nitro-1H-benzo[d]imidazol-2-yl)phenol

LCMS RT=6.48 min, MH$^+$ 256.0; $^1$H NMR (DMSO): 13.50 (1H, br), 12.40 (1H, br), 8.56 (1H, s), 8.20-8.14 (2H, m), 7.84 (1H, d, J 8.8 Hz), 7.48-7.43 (1H, m), 7.12-7.04 (2H, m)

2-(4-Chlorophenyl)-6-nitro-1H-benzo[d]imidazole

LCMS RT=6.24 min, MH$^+$ 273.9; $^1$H NMR (DMSO): 13.80 (1H, br), 8.54 (1H, d, J 2.1 Hz), 8.29 (2H, d, J 8.6 Hz), 8.21 (1H, dd, J 8.9 2.2 Hz), 7.84 (1H, d, J 8.9 Hz), 7.75 (2H, d, J 8.5 Hz)

Method 24 (Compound XXIIb)

2-(5-Amino-1H-benzo[d]imidazol-2-yl)phenol

To 2-(5-nitro-1H-benzo[d]imidazol-2-yl)phenol (90 mg, 0.35 mmol) in ethyl acetate/water/acetic acid 1:1:0.01 v/v/v (10 mL) was added palladium on carbon (15 mg). The reaction vessel was purged three times with nitrogen, followed by three times with hydrogen, and then left stirring under hydrogen for 2 h. The reaction vessel was finally purged three times with nitrogen, before filtration on a pad of Celite®, which was washed with ethyl acetate. The organic layer was washed with saturated aqueous $NaHCO_3$. The combined organic layers were dried over anhydrous $MgSO_4$ and evaporated. The resulting solid was purified by column chromatography eluting with ethyl acetate/hexanes 2:1 v/v to afford 60 mg (76%) of the title compound (LCMS RT=5.39 min, $MH^+$ 226.1)

$^1$H NMR (DMSO): 13.28 (1H, br), 12.63 (1H, br), 7.72 (1H, d, J 8.4 Hz), 7.33-7.28 (2H, m), 6.99-6.94 (2H, m), 6.71-6.58 (2H, m), 5.12 (2H, s)

Method 25 (Compounds XXIII)

N-(2-p-Tolyl-1H-benzo[d]imidazol-5-yl)butyramide

To a solution of 2-p-tolyl-1H-benzo[d]imidazol-5-amine (150 mg, 0.67 mmol) in pyridine (10 mL) at room temperature was added butyryl chloride (77 µL, 0.74 mmol). The resulting mixture was stirred at room temperature for 16 h. Ethyl acetate was added and the organic layer was washed twice with saturated aqueous copper sulfate, followed by sodium bicarbonate and brine. The combined organic layers were dried over anhydrous $MgSO_4$ and evaporated. The resulting solid was purified by column chromatography eluting with ethyl acetate/hexanes 50:50 v/v to afford 56 mg (28%) of the title compound (LCMS RT=6.96 min, $MH^+$ 294.0)

$^1$H NMR (DMSO): 12.68 (1H, br), 9.87 (1H, s), 8.08-8.00 (3H, m), 7.52-7.20 (4H, m), 2.38 (3H, s), 2.31 (2H, t, J 7.3 Hz), 1.70-1.58 (2H, m), 0.94 (3H, t, J 7.4 Hz)

All compounds below were prepared following the same general method.

N-(2-p-Tolyl-1H-benzo[d]imidazol-5-yl)isobutyramide

LCMS RT=5.43 min, $MH^+$ 294.1; $^1$H NMR (DMSO): 12.67 (1H, br), 9.91 (1H, s), 8.08-8.01 (3H, m), 7.50-7.28 (4H, m), 4.03 (1H, q, J 7.2 Hz), 2.38 (3H, s), 1.13 (6H, d, J 6.8 Hz)

N-(2-(4-Chlorophenyl)-1H-benzo[d]imidazol-5-yl)butyramide

LCMS RT=5.54 min, $MH^+$ 314.0; $^1$H NMR (DMSO): 12.85 (1H, br), 9.90 (1H, s), 8.14 (3H, d, J 8.6 Hz), 7.62 (2H, d, J 8.7 Hz), 7.53 (1H, br), 7.25 (1H, br), 2.32 (2H, t, J 7.1 Hz), 1.71-1.58 (2H, m), 0.94 (3H, t, J 7.5 Hz)

N-(2-Phenyl-1H-benzo[d]imidazol-5-yl)isobutyramide

LCMS RT=5.32 min, $MH^+$ 280.0; $^1$H NMR (DMSO): 12.80 (1H, br), 9.85 (1H, s), 8.16-8.09 (3H, m), 7.58-7.47 (4H, m), 7.28 (1H, d, J 8.1 Hz), 2.68-2.60 (1H, m), 1.13 (6H, d, J 6.9 Hz)

N-(2-Phenyl-1H-benzo[d]imidazol-5-yl)butyramide

LCMS RT=5.32 min, $MH^+$ 280.0; $^1$H NMR (DMSO): 12.77 (1H, br), 9.90 (1H, s), 8.15-8.12 (3H, m), 7.58-7.45 (4H, m), 7.26 (1H, br), 2.31 (2H, t, J 7.1 Hz), 1.71-1.58 (2H, m), 0.94 (3H, t, J 7.5 Hz)

N-(2-(4-Chlorophenyl)-1H-benzo[d]imidazol-5-yl)isobutyramide

LCMS RT=5.71 min, $MH^+$ 314.0; $^1$H NMR (DMSO): 12.89 (1H, br), 9.86 (1H, s), 8.18-8.10 (3H, m), 7.62 (2H, d, J 8.8 Hz), 7.52 (1H, d, J 8.8 Hz), 7.29 (1H, d, J 8.3 Hz), 2.66-2.60 (1H, m), 1.13 (6H, d, J 6.9 Hz)

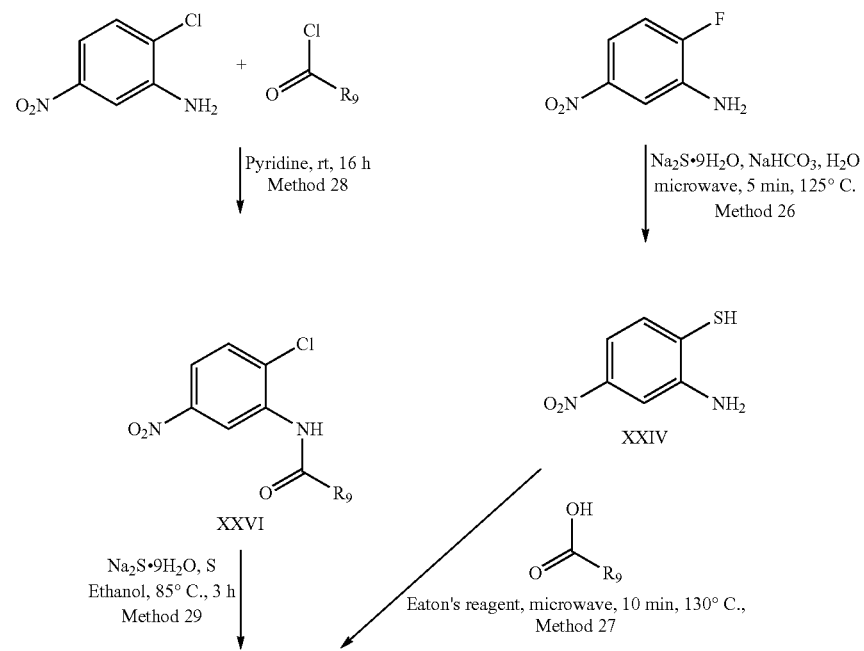

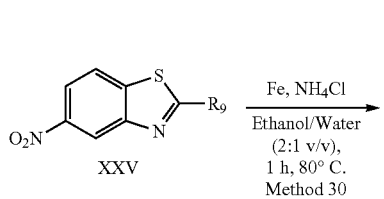 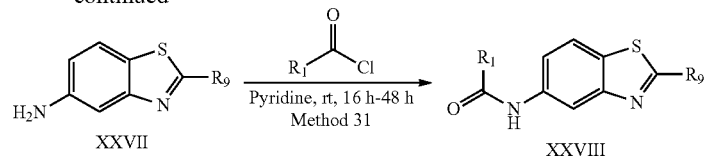

Method 26 (Compound XXIV)

2-Amino-4-nitrobenzenethiol

2-Fluoro-5-nitroaniline (1 g, 6.41 mmol), sodium sulfide nonahydrate (1.7 g, 7.05 mmol), sodium bicarbonate (600 mg, 7.05 mmol) and water (15 mL) were combined and heated in the microwave at 125° C. for 5 min. After cooling, dichloromethane was added, and the organic layer was washed with 2M aqueous hydrochloric acid and then brine. The combined organic layers were dried over anhydrous $MgSO_4$ and evaporated to afford 1.1 g (33%) of the title compound.

$^1$H NMR (DMSO): 7.61-7.55 (2H, m), 7.47 (1H, d, J 8.2 Hz), 7.31 (3H, s)

Method 27 (Compound XXV)

2-(2-Chlorophenyl)-5-nitrobenzo[d]thiazole

2-Amino-4-nitrobenzenethiol (315 mg, 1.85 mmol), 2-chlorobenzoic acid (290 mg, 1.85 mmol) and Eaton's reagent (5 mL) were combined and heated in the microwave at 130° C. for 10 min. After cooling, the mixture was poured into water and basified with 5M aqueous sodium hydroxide to give a precipitate, which was filtered off and dried to afford 530 mg (98%) of the title compound.

$^1$H NMR (DMSO): 8.93 (1H, d, J 2.2 Hz), 8.53 (1H, d, J 8.9 Hz), 8.37 (1H, dd, J 8.9 2.2 Hz), 8.29 (1H, dd, J 7.4 1.9 Hz), 7.78-7.75 (1H, m), 7.70-7.60 (2H, m)

Method 28 (Compound XXVI)

N-(2-Chloro-5-nitrophenyl)-4-methylbenzamide

To 2-chloro-5-nitroaniline (2 g, 11.59 mmol) in pyridine (5 mL) at room temperature was added 4-methylbenzoyl chloride (1.6 mL, 12.17 mmol), followed by pyridine (5 mL). The mixture was then stirred at room temperature for 16 h. Ethyl acetate was then added to the solution to give a precipitate, which was filtered off and washed twice with ethyl acetate, and then hexanes. The resulting solid was then washed with aqueous sodium bicarbonate, 1M aqueous sodium hydroxide, water and hexanes to afford (1.4 g, 42%) of the title compound.

$^1$H NMR (DMSO): 10.26 (1H, s), 8.58 (1H, d, J 2.8 Hz), 8.11 (1H, dd, J 8.9 2.8 Hz), 7.93 (2H, d, J 8.2 Hz), 7.87 (1H, d, J 8.9 Hz), 7.38 (2H, d, J 8.0 Hz), 2.41 (3H, s)

Method 29 (Compound XXV)

5-Nitro-2-p-tolylbenzo[d]thiazole

Sodium sulfide nonahydrate (875 mg, 3.78 mmol) and sulfur (120 mg, 3.78 mmol) were heated until molten. The water was driven off with nitrogen to give a solid. The obtained solid was added in portions to N-(2-chloro-5-nitrophenyl)-4-methylbenzamide (1 g, 3.44 mmol) in ethanol (20 mL) at 85° C. The solution was stirred at 85° C. for 3 h. After cooling, 2M aqueous HCl was added, and the solution was extracted three times with ethyl acetate. The combined organic layers were dried over anhydrous $MgSO_4$ and evaporated. The resulting solid was purified by column chromatography eluting with ethyl acetate/hexanes 10:90 v/v to afford 400 mg (43%) of the title compound.

$^1$H NMR (DMSO): 8.81 (1H, d, J 2.2 Hz), 8.45 (1H, d, J 8.8 Hz), 8.29 (1H, dd, J 8.8 2.3 Hz), 8.06 (2H, d, J 8.2 Hz), 7.44 (2H, d, J 8.0 Hz), 2.42 (3H, s)

Method 30 (Compounds XXVII)

2-p-Tolylbenzo[d]thiazol-5-amine

5-Nitro-2-p-tolylbenzo[d]thiazole (400 mg, 1.48 mmol) was suspended in ethanol/water (8 mL/4 mL) and heated at 80° C. Ammonium chloride (160 mg, 2.96 mmol) and iron powder (414 mg, 7.40 mmol) were added to the suspension, and the mixture was left stirring at 80° C. for 75 min. After cooling, the solution was filtrated through a pad of Celite® and the pad washed with ethanol. Water was added to the filtrate, ethanol was evaporated and the remaining aqueous layer was extracted with ethyl acetate. The combined organic layers were dried over anhydrous $MgSO_4$ and evaporated to afford 220 mg (62%) of the title compound (LCMS RT=6.51 min, $MH^+$ 241.0)

$^1$H NMR (DMSO): 7.91 (2H, d, J 8.1 Hz), 7.68 (1H, d, J 8.6 Hz), 7.35 (2H, d, J 8.0 Hz), 7.15 (1H, d, J 2.0 Hz), 6.77 (1H, dd, J 8.6 2.0 Hz), 5.32 (2H, s), 2.39 (3H, s)

All compounds below were prepared following the same general method.

2-Phenylbenzo[d]thiazol-5-amine

LCMS RT=6.11 min, $MH^+$ 227.1; $^1$H NMR (DMSO): 8.04-8.01 (2H, m), 7.71 (1H, d, J 8.5 Hz), 7.56-7.53 (3H, m), 7.18 (1H, d, J 2.1 Hz), 6.79 (1H, dd, J 8.6 2.3 Hz), 5.33 (2H, s)

2-(4-Chlorophenyl)benzo[d]thiazol-5-amine

LCMS RT=6.72 min, $MH^+$ 260.7; $^1$H NMR (DMSO): 8.04 (2H, d, J 8.7 Hz), 7.72 (1H, d, J 8.6 Hz), 7.61 (2H, d, J 8.7 Hz), 7.17 (1H, d, J 2.0 Hz), 6.80 (1H, dd, J 8.6 2.2 Hz), 5.35 (2H, s)

2-(2-Chlorophenyl)benzo[d]thiazol-5-amine

LCMS RT=6.49 min, $MH^+$ 260.8; $^1$H NMR (DMSO): 8.19-8.16 (1H, m), 7.76 (1H, d, J 8.6 Hz), 7.69-7.66 (1H, m), 7.56-7.52 (2H, m), 7.22 (1H, d, J 2.0 Hz), 6.85 (1H, dd, J 8.6 2.1 Hz), 5.37 (2H, s)

2-(3-Chlorophenyl)benzo[d]thiazol-5-amine

LCMS RT=6.79 min, $MH^+$ 260.8; $^1$H NMR (DMSO): 8.05-8.04 (1H, m), 7.96 (1H, dt, J 7.0 1.7 Hz), 7.74 (1H, d, J 8.6 Hz), 7.64-7.55 (2H, m), 7.19 (1H, d, J 1.7 Hz), 6.82 (1H, dd, J 8.6 2.2 Hz), 5.37 (2H, s)

2-(3,4-Dichlorophenyl)benzo[d]thiazol-5-amine

LCMS RT=7.49 min, MH+ 294.9; $^1$H NMR (DMSO): 8.24 (1H, d, J 2.1 Hz), 8.00 (1H, dd, J 8.4 2.1 Hz), 7.82 (1H, d, J 8.4 Hz), 7.76 (1H, d, J 8.6 Hz), 7.20 (1H, d, J 1.9 Hz), 6.84 (1H, dd, J 8.6 2.2 Hz), 5.41 (2H, s)

2-(2,3-Dichlorophenyl)benzo[d]thiazol-5-amine

LCMS RT=7.00 min, MH+ 294.9; $^1$H NMR (DMSO): 8.08 (1H, dd, J 7.9 1.6 Hz), 7.84 (1H, dd, J 8.0 1.6 Hz), 7.78 (1H, d, J 8.6 Hz), 7.55 (1H, t, J 8.0 Hz), 7.22 (1H, d, J 2.0 Hz), 6.87 (1H, dd, J 8.6 2.2 Hz), 5.38 (2H, s)
Method 31 (Compounds XXVIII)

N-(2-p-Tolylbenzo[d]thiazol-5-yl)butyramide

To a solution of 2-p-tolylbenzo[d]thiazol-5-amine (110 mg, 0.46 mmol) in pyridine (3 mL) at room temperature was added butyryl chloride (53 μL, 0.50 mmol). The resulting mixture was stirred at room temperature for 2 days. Ethyl acetate was added and the organic layer was washed with saturated aqueous copper sulfate, followed by aqueous sodium bicarbonate and finally with brine. The combined organic layers were dried over anhydrous MgSO$_4$ and evaporated. The resulting solid was purified by column chromatography eluting with ethyl acetate/hexanes 50:50 v/v to afford 25 mg (18%) of the title compound (LCMS RT=7.10 min, MH+ 311.0)

$^1$H NMR (DMSO): 10.12 (1H, s), 8.43 (1H, d, J 1.8 Hz), 8.02-7.96 (3H, m), 7.58 (1H, dd, J 8.6 2.0 Hz), 7.38 (2H, d, J 8.0 Hz), 2.40 (3H, s), 2.35 (2H, t, J 7.5 Hz), 1.72-1.60 (2H, m), 0.95 (3H, t, J 7.4 Hz)

All compounds below were prepared following the same general method.

N-(2-p-Tolylbenzo[d]thiazol-5-yl)isobutyramide

LCMS RT=7.06 min, MH+311.0; $^1$H NMR (DMSO): 10.08 (1H, s), 8.44 (1H, d, J 1.3 Hz), 8.03-7.96 (3H, m), 7.60 (1H, dd, J 8.7 1.6 Hz), 7.38 (2H, d, J 8.0 Hz), 2.69-2.60 (1H, m), 2.40 (3H, s), 1.15 (6H, d, J 6.8 Hz)

N-(2-Phenylbenzo[d]thiazol-5-yl)isobutyramide

LCMS RT=6.56 min, MH+ 297.0; $^1$H NMR (DMSO): 10.07 (1H, s), 8.47 (1H, d, J 1.8 Hz), 8.11-8.07 (2H, m), 8.04 (1H, d, J 8.6 Hz), 7.64-7.56 (4H, m), 2.70-2.61 (1H, m), 1.15 (6H, d, J 6.8 Hz)

N-(2-(4-Chlorophenyl)benzo[d]thiazol-5-yl)isobutyramide

LCMS RT=7.42 min, MH+ 331.0; $^1$H NMR (DMSO): 10.08 (1H, s), 8.47 (1H, d, J 1.9 Hz), 8.10 (2H, d, J 8.6 Hz), 8.05 (1H, d, J 8.7 Hz), 7.67-7.61 (3H, m), 2.70-2.60 (1H, m), 1.15 (6H, d, J 6.8 Hz)

N-(2-(2-Chlorophenyl)benzo[d]thiazol-5-yl)isobutyramide

LCMS RT=6.99 min, MH+ 330.9; $^1$H NMR (DMSO): 10.12 (1H, s), 8.55 (1H, d, J 1.9 Hz), 8.25-8.22 (1H, m), 8.10 (1H, d, J 8.8 Hz), 7.74-7.55 (4H, m), 2.72-2.63 (1H, m), 1.17 (6H, d, J 6.8 Hz)

N-(2-(3-Chlorophenyl)benzo[d]thiazol-5-yl)isobutyramide

LCMS RT=7.34 min, MH+ 330.9; $^1$H NMR (DMSO): 10.11 (1H, s), 8.50 (1H, d, J 1.7 Hz), 8.13-8.03 (3H, m), 7.69-7.60 (3H, m), 2.71-2.62 (1H, m), 1.17 (6H, d, J 6.8 Hz)

N-(2-(3,4-Dichlorophenyl)benzo[d]thiazol-5-yl)isobutyramide

LCMS RT=8.21 min, MH+ 364.7; $^1$H NMR (DMSO): 10.11 (1H, s), 8.52-8.50 (1H, m), 8.30 (1H, d, J 2.1 Hz), 8.10-8.04 (2H, m), 7.85 (1H, d, J 8.4 Hz), 7.69-7.64 (1H, m), 2.71-2.64 (1H, m), 1.17 (6H, d, J 6.8 Hz)

N-(2-(2,3-Dichlorophenyl)benzo[d]thiazol-5-yl)isobutyramide

LCMS RT=7.62 min, MH+ 364.9; $^1$H NMR (DMSO): 10.12 (1H, s), 8.55 (1H, d, J 1.7 Hz), 8.14-8.10 (2H, m), 7.88 (1H, dd, J 8.0 1.4 Hz), 7.67 (1H, dd, J 8.8 2.0 Hz), 7.58 (1H, t, J 8.0 Hz), 2.70-2.61 (1H, m), 1.15 (6H, d, J 6.8 Hz)

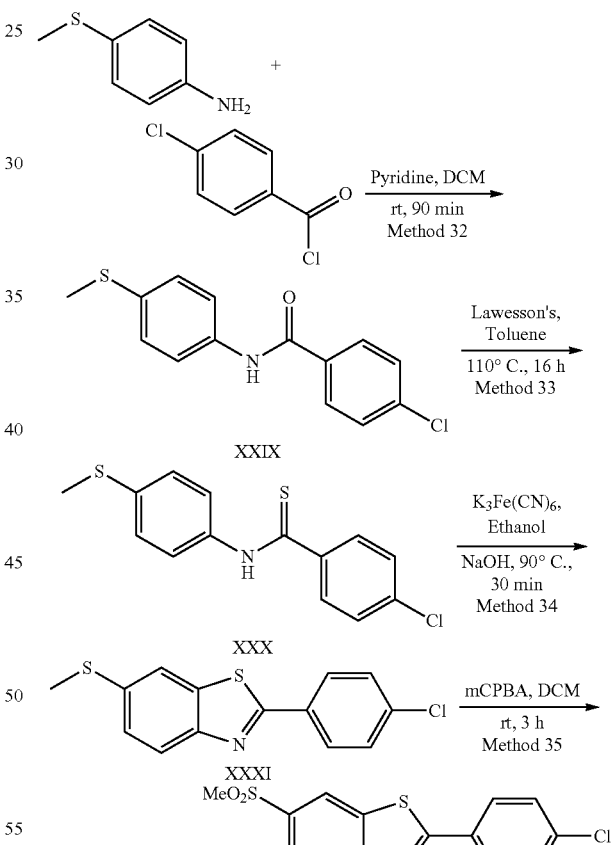

Method 32 (Compound XXIX)

4-Chloro-N-(4-(methylthio)phenyl)benzamide

To 4-(methylthio)aniline (1 mL, 8.19 mmol) in dichloromethane (20 mL) was added pyridine (2 mL, 24.6 mmol). The resulting solution was cooled to 10-15° C. and 4-chlorobenzoyl chloride (1.14 mL, 9.00 mmol) was added over 5 min. The mixture was stirred at room temperature for 90 min. The precipitate was filtered off, washed with dichloromethane, 1M aqueous sodium hydroxide solution and 1M aqueous hydrochloric acid solution to afford 2.12 g (93%) of the title compound.

$^1$H NMR (DMSO): 10.31 (1H, s), 7.98 (2H, d, J 8.7 Hz), 7.73 (2H, d, J 8.8 Hz), 7.61 (2H, d, J 8.8 Hz), 7.28 (2H, d, J 8.8 Hz), 2.47 (3H, s)

Method 33 (Compound XXX)

4-Chloro-N-(4-(methylthio)phenyl)benzothioamide

A suspension of 4-chloro-N-(4-(methylthio)phenyl)benzamide (1 g, 3.60 mmol) and Lawesson's reagent (875 mg, 2.16 mmol) in toluene (25 mL) was heated to 110° C. for 16 h. After cooling, toluene was removed in vacuo and the resulting solid was purified by column chromatography eluting using a gradient (hexanes to ethyl acetate/hexanes 30:70 v/v) to afford 503 mg (48%) of the title compound.

LCMS RT=6.98 min, MH$^+$ 294.1; $^1$H NMR (DMSO): 11.80 (1H, s), 7.85 (2H, d, J 8.6 Hz), 7.78 (2H, d, J 8.7 Hz), 7.54 (2H, d, J 8.6 Hz), 7.33 (2H, d, J 8.7 Hz)

Method 34 (Compound XXXI)

2-(4-Chlorophenyl)-6-(methylthio)benzo[d]thiazole

To a solution of potassium hexacyanoferrate(III) (670 mg, 2.04 mmol) in water (5 mL) at 90° C. was added dropwise over 5 minutes a solution of 4-chloro-N-(4-(methylthio)phenyl)benzothioamide (150 mg, 0.51 mmol) in ethanol (2 mL) and 3M aqueous sodium hydroxide solution (1.4 mL, 4.08 mmol). The resulting mixture was heated at 90° C. for 30 minutes. After cooling, the precipitate formed was filtered off and washed with water to give a yellow solid. The yellow solid was purified by column chromatography eluting using a gradient (hexanes to ethyl acetate/hexanes 5:95 v/v) to afford 100 mg (67%) of the title compound (LCMS RT=9.37 min, MH$^+$ 292.2)

$^1$H NMR (DMSO); 8.11-8.06 (3H, m), 7.98 (1H, d, J 8.6 Hz), 7.65 (2H, d, J 8.7 Hz), 7.45 (1H, dd, J 8.6 1.9 Hz), 2.58 (3H, s)

Method 35 (Compound XXXII)

2-(4-Chlorophenyl)-6-(methylsulfonyl)benzo[d]thiazole

To a solution of 2-(4-chlorophenyl)-6-(methylthio)benzo[d]thiazole (240 mg, 0.82 mmol) in dichloromethane (20 mL) was added 3-chloroperoxybenzoic acid (77% in water, 710 mg, 4.11 mmol) over 5 min. The resulting mixture was stirred at room temperature for 3 h. 1M aqueous sodium hydroxide solution was added carefully, and the mixture was then stirred for 5 min. The organic layer was then washed with 1M aqueous sodium hydroxide solution, dried over anhydrous MgSO$_4$ and evaporated. The resulting solid was recrystallised from hot ethyl acetate to afford 125 mg (47%) of the title compound (LCMS RT=6.81 min, MH$^+$ 324.0)

$^1$H NMR (CDCl$_3$): 8.61 (1H, dd, J 1.8 0.4 Hz), 8.26 (1H, dd, J 8.6 0.5 Hz), 8.14-8.09 (3H, m), 7.57 (2H, d, J 8.6 Hz), 3.19 (3H, s)

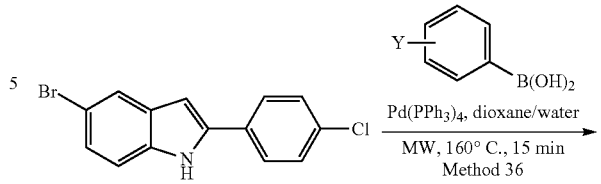

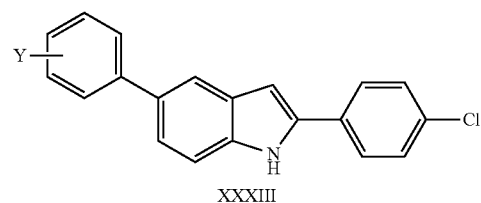

Method 36 (Compounds XXXIII)

2-(4-Chlorophenyl)-5-phenyl-1H-indole

To a suspension of 5-bromo-2-(4-chlorophenyl)-1H-indole (200 mg, 0.65 mmol) in dioxane/water 4:1 v/v (5 mL) was added phenylboronic acid (87 mg, 0.72 mmol) and a few milligrams of tetrakis(triphenylphosphine)palladium(0). The resulting suspension was heated in the microwave at 160° C. for 15 min. After cooling, the reaction was poured into water to give a precipitate, which was filtered off and washed with water. The resulting solid was purified by column chromatography eluting using a gradient (hexanes to ethyl acetate/hexanes 30:70 v/v), followed by a recrystallisation from hot ethyl acetate to afford 21 mg (11%) of the title compound (LCMS RT=8.54 min, MH$^+$304.1)

$^1$H NMR (DMSO): 11.68 (1H, s), 7.91 (2H, d, J 8.6 Hz), 7.81 (1H, d, J 1.1 Hz), 7.70-7.66 (2H, m), 7.55 (2H, d, J 8.6 Hz), 7.50-7.41 (4H, m), 7.33-7.28 (1H, m), 7.01 (1H, d, J 1.2 Hz)

The compound below was prepared following the same general method.

N-(4-(2-(4-Chlorophenyl)-1H-indol-5-yl)phenyl)acetamide

LCMS RT=6.69 min, MH$^+$ 361.0; $^1$H NMR (DMSO): 11.64 (1H, s), 9.98 (1H, s), 7.91 (2H, d, J 8.6 Hz), 7.77 (1H, d, J 1.0 Hz), 7.68-7.60 (4H, m), 7.54 (2H, d, J 8.6 Hz), 7.46 (1H, d, J 8.3 Hz), 7.41 (1H, dd, J 8.5 1.6 Hz), 6.99 (1H, d, J 1.5 Hz), 2.07 (3H, s)

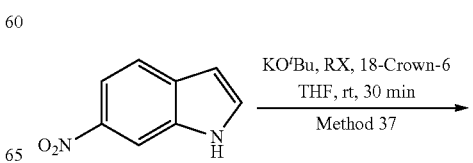

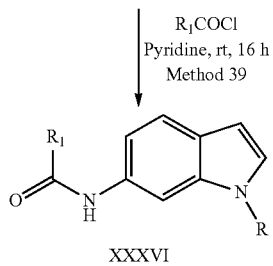

Method 37 (Compound XXXIV)

1-Methyl-6-nitro-1H-indole

To a solution of 6-nitro-1H-indole (100 mg, 0.62 mmol) and 18-Crown-6 (180 mg, 0.68 mmol) in anhydrous tetrahydrofuran (2 mL) at room temperature was slowly added potassium tert-butoxide (76 mg, 0.68 mmol) followed by methyl iodide (42 μL, 0.68 mmol). The solution was stirred at room temperature for 30 min. Tetrahydrofuran was removed in vacuo. Ethyl acetate was added, and the organic layer was washed with water and then brine. The combined organic layers were dried over anhydrous MgSO$_4$ and evaporated to afford 91 mg (84%) of the title compound.

$^1$H NMR (CDCl$_3$): 8.16 (1H, d, J 1.8 Hz), 7.85 (1H, dd, J 8.7 1.9 Hz), 7.49 (1H, d, J 8.7 Hz), 7.19 (1H, d, J 3.1 Hz), 6.43 (1H, dd, J 3.1 0.9 Hz), 3.74 (3H, s)

Method 38 (Compound XXXV)

1-Methyl-1H-indol-6-amine 1-methyl-6-nitro-1H-indole (90 mg, 0.51 mmol), ammonium chloride (55 mg, 1.02 mmol) and iron powder (143 mg, 2.55 mmol) were suspended in ethanol/water (2 mL/1 mL) and heated at 70° C. for 2 h. After cooling, the solution was filtrated through a pad of Celite®, which was washed with ethanol. Ethyl acetate was added to the filtrate and the organic layer was washed with water twice. The combined organic layers were dried over anhydrous MgSO$_4$ and evaporated to afford 30 mg (37%) of the title compound $^1$H NMR (DMSO): 7.17 (1H, d, J 8.4 Hz), 6.93 (1H, d, J 3.1 Hz), 6.51-6.49 (1H, m), 6.41 (1H, dd, J 8.3 1.9 Hz), 6.16 (1H, d, J 3.1 Hz), 4.76 (2H, s), 3.60 (3H, s)

Method 39 (Compounds XXXVI)

N-(1H-indol-6-yl)isobutyramide

To a solution of 1-methyl-1H-indol-6-amine (45 mg, 0.31 mmol) in pyridine (2 mL) at room temperature was added isobutyryl chloride (35 μL, 0.34 mmol). The resulting mixture was stirred at room temperature for 16 h. Ethyl acetate was added and the organic layer was washed three times with brine. The combined organic layers were dried over anhydrous MgSO$_4$ and evaporated to afford 24.3 mg (36%) of the title compound (LCMS RT=5.73 min, MH$^+$ 217.2)

$^1$H NMR (DMSO): 9.78 (1H, s), 7.96 (1H, m), 7.44 (1H, d, J 8.4 Hz), 7.24 (1H, d, J 3.1 Hz), 7.08 (1H, dd, J 8.4 1.7 Hz), 6.35 (1H, dd, J 3.0 0.7 Hz), 3.73 (3H, s), 2.68-2.61 (1H, m), 1.13 (6H, d, J 6.9 Hz)

The compound below was prepared following the same general method.

N-(1-Benzyl-1H-indol-6-yl)isobutyramide

LCMS RT=6.36 min, MH$^+$ 293.2; $^1$H NMR (DMSO): 9.73 (1H, s), 7.90 (1H, m), 7.45 (1H, d, J 8.5 Hz), 7.41 (1H, d, J 3.1 Hz), 7.34-7.24 (3H, m), 7.14-7.10 (3H, m), 6.42 (1H, d, J 3.2 Hz), 5.35 (2H, s), 1.08 (6H, d, J 6.8 Hz)

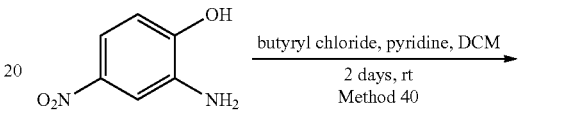

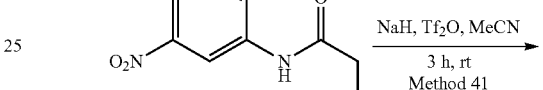

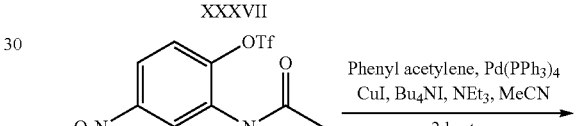

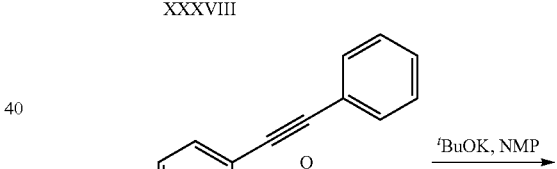

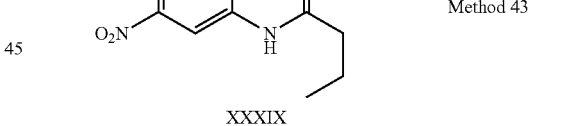

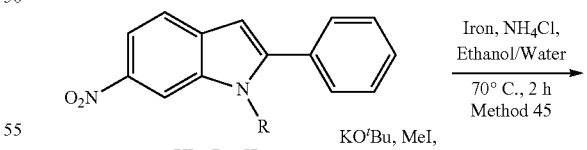

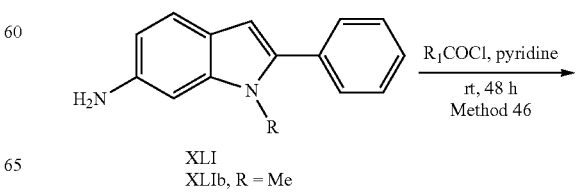

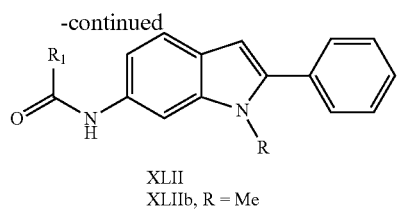

XLII
XLIIb, R = Me

Method 40 (Compound XXXVII)

N-(2-Hydroxy-5-nitrophenyl)butyramide

To a solution of 2-amino-4-nitrophenol (10 g, 64.9 mmol) in dichloromethane (250 mL) under nitrogen at 0° C. was added pyridine (10.5 mL, 129.9 mmol) followed by butyryl chloride (7.05 mL, 68.2 mmol) over a period of 5 min. After 30 min at 0° C., the solution was left warming up to room temperature for 2 days. The organic layer was washed with aqueous copper sulfate solution and brine. Insoluble material from the aqueous layer was filtered off and washed with water to afford 4.95 g (34%) of the title compound.

$^1$H NMR (DMSO): 11.64 (1H, br), 9.37 (1H, s), 8.95 (1H, d, J 2.8 Hz), 7.89 (1H, dd, J 8.9 2.8 Hz), 7.02 (1H, d, J 8.9 Hz), 2.43 (2H, t, J 7.4 Hz), 1.67-1.55 (2H, m), 0.92 (3H, t, J 7.5 Hz)

Method 41 (Compound XXXVIII)

2-Butyramido-4-nitrophenyl trifluoromethanesulfonate

To a solution of sodium hydride (220 mg, 5.58 mmol) in dry acetonitrile (40 mL) at 0° C. under nitrogen was added a solution of N-(2-hydroxy-5-nitrophenyl)butyramide (1 g, 4.46 mmol) in dry acetonitrile (90 mL). The solution was then stirred at 0° C. for 30 min. Trifluoromethanesulfonic anhydride (825 µL, 4.90 mmol) was added dropwise at 0° C. over a period of 10 min. After 3 h at 0° C., the solution was stirred at room temperature for 3 h. Water was added, and the aqueous layer was extracted with ethyl acetate. The organic layer was then washed with dilute aqueous hydrochloric acid, aqueous sodium bicarbonate and brine. The combined organic layers were dried over anhydrous MgSO$_4$ and evaporated. The resulting oil was purified by column chromatography eluting using a gradient (hexanes to ethyl acetate/hexanes 25:75 v/v) to afford 860 mg (54%) of the title compound.

$^1$H NMR (CDCl$_3$): 9.37 (1H, d, J 2.8 Hz), 8.09 (1H, dd, J 9.1 2.8 Hz), 7.53 (2H, d, J 9.1 Hz), 2.50 (2H, t, J 7.6 Hz), 1.91-1.78 (2H, m), 1.09 (3H, t, J 7.5 Hz)

Method 42 (Compound XXXIX)

N-(5-Nitro-2-(phenylethynyl)phenyl)butyramide

To a solution of 2-butyramido-4-nitrophenyl trifluoromethanesulfonate (860 mg, 2.42 mmol) in dry acetonitrile (30 mL) under nitrogen was added tetrabutylammonium iodide (1.34 g, 3.62 mmol), tetrakis(triphenylphosphine)palladium(0) (280 mg, 0.24 mmol) and copper iodide (140 mg, 0.72 mmol). Triethylamine (6 mL) was then added, followed by phenyl acetylene (530 µL, 4.83 mmol). The resulting solution was stirred at room temperature for 2 h. Ammonium chloride was then added to quench the reaction, and the aqueous layer was extracted with ethyl acetate. The organic layer was washed with brine. The combined organic layers were dried over anhydrous MgSO$_4$ and evaporated. The resulting solid was purified by column chromatography eluting using a gradient (hexanes to ethyl acetate) to afford 580 mg (78%) of the title compound.

$^1$H NMR (DMSO): 9.81 (1H, s), 8.74 (1H, d, J 2.3 Hz), 8.01 (1H, dd, J 8.6 2.4 Hz), 7.83 (1H, d, J 8.6 Hz), 7.70-7.67 (2H, m), 7.52-7.49 (3H, m), 1.73-1.61 (2H, m), 0.96 (3H, t, J 7.5 Hz)

Method 43 (Compound XLa)

6-Nitro-2-phenyl-1H-indole

To a solution of N-(5-nitro-2-(phenylethynyl)phenyl)butyramide (580 mg, 1.88 mmol) in 1-Methyl-2-pyrrolidinone (20 mL) under nitrogen was added potassium tert-butoxide (243 mg, 2.16 mmol). The resulting solution was heated at 70° C. for 6 h, and then left at room temperature for 16 h. Water was added and the aqueous layer was extracted several times with ethyl acetate. The combined organic layers were washed 10 times with water, 3 times with brine, dried over anhydrous MgSO$_4$ and evaporated. The resulting material was purified by column chromatography eluting with ethyl acetate/hexanes 15:85 v/v to afford 175 mg (39%) of the title compound.

$^1$H NMR (DMSO): 12.35 (1H, s), 8.30 (1H, d, J 2.1 Hz), 7.97-7.90 (3H, m), 7.73 (1H, d, J 8.9 Hz), 7.57-7.52 (2H, m), 7.47-7.42 (1H, m), 7.17 (1H, dd, J 2.0 0.8 Hz)

Method 44 (Compound XLb)

1-Methyl-6-nitro-2-phenyl-1H-indole

To a solution of 6-nitro-2-phenyl-1H-indole (106 mg, 0.44 mmol) and 18-Crown-6 (130 mg, 0.49 mmol) in anhydrous tetrahydrofuran (2 mL) at room temperature was added potassium tert-butoxide (55 mg, 0.49 mmol) followed by methyl iodide (31 µL, 0.49 mmol). The solution was stirred at room temperature for 30 min. Tetrahydrofuran was removed in vacuo. Ethyl acetate was added, and the organic layer was washed with water and then brine. The combined organic layers were dried over anhydrous MgSO$_4$ and evaporated to afford 110 mg (98%) of the title compound.

$^1$H NMR (DMSO): 8.60 (1H, d, J 2.1 Hz), 8.03 (1H, dd, J 8.8 2.1 Hz), 7.82 (1H, d, J 8.7 Hz), 7.74-7.71 (2H, m), 7.67-7.57 (3H, m), 6.87 (1H, d, J 0.8 Hz), 3.95 (3H, s)

Method 45 (Compound XLI)

2-Phenyl-1H-indol-6-amine

6-Nitro-2-phenyl-1H-indole (175 mg, 0.73 mmol), ammonium chloride (80 mg, 1.47 mmol) and iron powder (205 mg, 3.68 mmol) were suspended in ethanol/water (4 mL/2 mL) and heated at 70° C. for 2 h. After cooling, the solution was filtrated through a pad of Celite®, which was washed with ethanol. The organic layer was evaporated into vacuo to obtain a solid, which was purified by column chromatography eluting using a gradient (ethyl acetate/hexanes 10:90 v/v to ethyl acetate/hexanes 50:50 v/v) to afford 54 mg (35%) of the title compound.

$^1$H NMR (DMSO): 10.88 (1H, s), 7.76-7.72 (2H, m), 7.39 (2H, t, J 7.9 Hz), 7.23-7.16 (2H, m), 6.67 (1H, dd, J 2.0 0.7 Hz), 6.59-6.57 (1H, m), 6.39 (1H, dd, J 8.4 2.0 Hz), 4.82 (2H, s)

Method 46 (Compounds XLII)

N-(2-Phenyl-1H-indol-6-yl)isobutyramide

To a solution of 2-phenyl-1H-indol-6-amine (54 mg, 0.26 mmol) in pyridine (2 mL) at room temperature was added isobutyryl chloride (30 µL, 0.29 mmol). The resulting mixture was stirred at room temperature for 2 days. When water was added, a precipitate was formed. This solid was recrystallised from hot ethyl acetate to afford 15 mg (21%) of the title compound (LCMS RT=6.27 min, MH+ 279.0).

$^1$H NMR (DMSO): 11.40 (1H, s), 9.74 (1H, s), 8.02 (1H, s), 7.82 (2H, d, J 7.5 Hz), 7.47-7.40 (3H, m), 7.28 (1H, t, J 7.3 Hz), 7.07 (1H, dd, J 8.5 1.6 Hz), 6.83 (1H, d, J 1.1 Hz), 2.67-2.60 (1H, m), 1.13 (6H, d, J 6.7 Hz)

The compound below was prepared following the same general method.

N-(1-Methyl-2-phenyl-1H-indol-6-yl)isobutyramide

LCMS RT=6.66 min, MH+ 293.2; $^1$H NMR (DMSO): 9.83 (1H, s), 8.02 (1H, s), 7.61-7.39 (6H, m), 7.13 (1H, dd, 1 8.5 1.7 Hz), 6.50 (1H, d, J 0.5 Hz), 3.69 (3H, s), 2.69-2.60 (1H, m), 1.13 (6H, d, J 6.8 Hz)

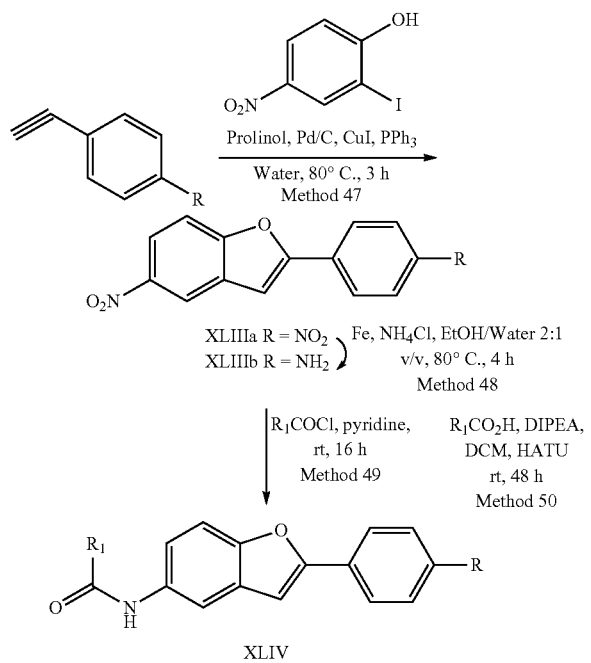

Method 47 (Compound XLIIIa)

5-Nitro-2-phenylbenzofuran

A solution of 2-iodo-4-nitrophenol (500 mg, 1.89 mmol), prolinol (573 mg, 5.66 mmol), palladium on carbon (60 mg, 0.06 mmol), triphenylphosphine (59.4 mg, 0.226 mmol) and copper iodide (22 mg, 0.113 mmol) in water (6 mL) was stirred for 1 h at room temperature. Ethynylbenzene (482 mg, 4.72 mmol) was slowly added, and the resulting mixture was heated at 80° C. for 3 h. After cooling, ethyl acetate was added, and the mixture was passed through a pad of Celite®. The filtrate was washed with water; the combined organic layers were dried over anhydrous MgSO$_4$ and evaporated. The resulting material was purified by column chromatography eluting with ethyl acetate/hexanes 1:40 v/v to afford 134 mg (30%) of the title compound.

$^1$H NMR (DMSO): 8.62 (1H, d, J 2.4 Hz), 8.23 (1H, dd, J 9.1 2.5 Hz), 8.00-7.96 (2H, m), 7.89 (1H, d, J 9.0 Hz), 7.66 (1H, d, J 0.4 Hz), 7.60-7.46 (3H, m)

Method 48 (Compound XLIIIb)

2-Phenylbenzofuran-5-amine

To 5-Nitro-2-phenylbenzofuran (250 mg, 1.04 mmol) in ethanol/water 2:1 v/v (12 mL) at 80° C. was added ammonium chloride (112 mg, 2.09 mmol) and iron powder (292 mg, 5.23 mmol). The resulting mixture was heated at 80° C. for 4 h. After cooling, the solution was filtrated through a pad of Celite®, which was washed with ethanol. The organic layer was evaporated into vacuo to obtain a solid, which was then taken up in ethyl acetate and washed with water. The combined organic layers were dried over anhydrous MgSO$_4$ and evaporated to afford 211 mg (96%) of the title compound.

$^1$H NMR (DMSO): 7.87-7.83 (2H, m), 7.50-7.44 (2H, m), 7.40-7.34 (1H, m), 7.28 (1H, d, J 8.7 Hz), 7.20 (1H, d, J 0.7 Hz), 6.74 (1H, d, J 2.2 Hz), 6.60 (1H, dd, J 8.7 2.3 Hz), 4.88 (2H, s)

Method 49 (Compounds XLIV)

N-(2-Phenylbenzofuran-5-yl)isobutyramide

To a solution of 2-phenylbenzofuran-5-amine (210 mg, 1.00 mmol) in pyridine (5 mL) at room temperature was added isobutyryl chloride (120 µL, 1.10 mmol). The resulting mixture was stirred at room temperature for 16 h. Ethyl acetate was added and the organic layer was washed with saturated aqueous copper sulfate solution followed by saturated aqueous potassium carbonate solution. The combined organic layers were dried over anhydrous MgSO$_4$ and evaporated. The resulting material was purified by column chromatography eluting using a gradient (ethyl acetate/hexanes 1:3 v/v to ethyl acetate/hexanes 1:2 v/v) to afford 134 mg (48%) of the title compound (LCMS RT=6.81 min, MH+ 280.1)

$^1$H NMR (DMSO): 9.87 (1H, s), 8.05 (1H, s), 7.91 (2H, d, J 7.4 Hz), 7.58-7.48 (3H, m), 7.45-7.38 (3H, m), 2.66-2.54 (1H, m), 1.13 (6H, d, J 6.8 Hz)

The compound below was prepared following the same general method.

2-(4'-Chlorophenyl)-5-isobutyramido-benzofuran

LCMS RT=7.41 min, MH+ 314.2; $^1$H NMR (DMSO): 9.88 (1H, s), 8.06 (1H, d, J 1.9 Hz), 7.92 (2H, d, J 8.7 Hz), 7.59-7.53 (3H, m), 7.49 (1H, d, J 0.8 Hz), 7.43 (1H, dd, J 9.0 2.2 Hz), 2.66-2.56 (1H, m), 1.13 (6H, d, J 6.8 Hz)

Method 50 (Compound XLIV)

2-Phenyl-5-(3',3',3'-trifluoropropanamido)benzofuran

To 3,3,3-trifluoropropanoic acid (136 mg, 1.06 mmol) in dry dichloromethane (10 mL) was added HATU (468 mg, 1.23 mmol) and diisopropylethylamine (580 µL, 3.35 mmol). The mixture was then stirred at room temperature for 10 min. 2-phenylbenzofuran-5-amine (234 mg, 1.12 mmol) was then added and the resulting mixture was stirred at room temperature for 48 h. Ethyl acetate was added and the organic layer was washed once with saturated aqueous water. The combined organic layers were dried over anhydrous MgSO$_4$ and evaporated. The resulting solid was purified by column chromatography eluting using a gradient (ethyl acetate/hexanes 1:3 v/v to ethyl acetate/hexanes 1:1 v/v) followed by trituration in ethyl acetate to afford 99.3 mg (28%) of the title compound (LCMS RT=6.62 min)

$^1$H NMR (DMSO): 10.37 (1H, s), 8.01 (1H, d, J 2.0 Hz), 7.92 (2H, dd, J 7.5 1.5 Hz), 7.61 (1H, d, J 8.8 Hz), 7.55-7.41 (4H, m), 7.38 (1H, dd, J 8.9 2.2 Hz), 3.53 (2H, q, J 11.2 Hz)

The compounds listed in Table 2, can be prepared by analogues methods to those described above, or by literature methods known or adapted by the persons skilled in the art.

Synergistic Effect of Combinations with Prednisone

The effect of combinations of a compound of formula (1) with a corticosteroid (prednisolone) was examined by measuring fatigue induced by a forced exercise regime in mdx mice.

Four to five week-old male mdx mice were forced to exercise (30 min running on horizontal treadmill at 12 m/min twice a week on the same day and at the same time) over a five week treatment course. Each treatment group included 6 mice.

At the end of the treatment course, exhaustion was induced by running on a horizontal treadmill at 5 m/min for 5 min, with incremental speed increases of 1 m/min each minute until exhaustion. The total distance run was then measured.

Treatment included dosing (ip) with 50 mg/kg 5-(ethylsulfonyl)-2-(naphthalen-2-yl)benzo[d]oxazole daily for 5 weeks, alone and in combination with prednisolone. Sedentary and vehicle only groups acted as negative controls.

The results are shown in FIG. 4. They show that prednisolone (PDN) and 5-(ethylsulfonyl)-2-(naphthalen-2-yl)benzo[d]oxazole (CMPD1) can act in synergy to reduce exercise-induced fatigue in the mdx mouse.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A combination comprising the compound 5-(ethylsulfonyl)-2-(naphthalen-2-yl)benzo[d]oxazole and a corticosteroid.

2. The combination of claim 1 wherein the corticosteroid is selected from prednisone, prednisolone, and deflazacort.

3. The combination of claim 1 wherein the corticosteroid and the compound 5-(ethylsulfonyl)-2-(naphthalen-2-yl)benzo[d]oxazole are physically associated; or the corticosteroid and the compound 5-(ethylsulfonyl)-2-(naphthalen-2-yl)benzo[d]oxazole are non-physically associated; or the corticosteroid and the compound 5-(ethylsulfonyl)-2-(naphthalen-2-yl)benzo[d]oxazole are
  a) in admixture;
  b) chemically/physicochemically linked;
  c) chemically/physicochemically co-packaged; or
  d) unmixed but co-packaged or co-presented.

4. The combination of claim 2 wherein the corticosteroid and the compound 5-(ethylsulfonyl)-2-(naphthalen-2-yl)benzo[d]oxazole are physically associated; or the corticosteroid and the compound 5-(ethylsulfonyl)-2-(naphthalen-2-yl)benzo[d]oxazole are non-physically associated; or the corticosteroid and the compound 5-(ethylsulfonyl)-2-(naphthalen-2-yl)benzo[d]oxazole are
  a) in admixture;
  b) chemically/physicochemically linked;
  c) chemically/physicochemically co-packaged; or
  d) unmixed but co-packaged or co-presented.

5. A pharmaceutical pack, kit or patient pack comprising the combination of claim 1.

6. A pharmaceutical pack, kit or patient pack comprising the combination of claim 2.

* * * * *

UNITED STATES PATENT AND TRADEMARK OFFICE
CERTIFICATE OF CORRECTION

| | | |
|---|---|---|
| PATENT NO. | : 8,501,713 B2 | Page 1 of 1 |
| APPLICATION NO. | : 12/600242 | |
| DATED | : August 6, 2013 | |
| INVENTOR(S) | : Wynne et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 521 days.

Signed and Sealed this
Eleventh Day of November, 2014

Michelle K. Lee
*Deputy Director of the United States Patent and Trademark Office*